(12) United States Patent
Dolente et al.

(10) Patent No.: US 9,828,385 B2
(45) Date of Patent: Nov. 28, 2017

(54) SPIRO-OXAZOLONES

(71) Applicant: Hoffmann-La Roche Inc., Little Falls, NJ (US)

(72) Inventors: Cosimo Dolente, Allschwil (CH); Bernhard Fasching, Basel (CH); Valerie Runtz-Schmitt, Rixheim (FR); Patrick Schnider, Bottmingen (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/240,705

(22) Filed: Aug. 18, 2016

(65) Prior Publication Data

US 2016/0355522 A1     Dec. 8, 2016

Related U.S. Application Data

(63) Continuation of application No. PCT/EP2015/053246, filed on Feb. 17, 2015.

(30) Foreign Application Priority Data

Feb. 20, 2014  (EP) .................... 14155965

(51) Int. Cl.
| | |
|---|---|
| *C07D 487/10* | (2006.01) |
| *C07D 491/107* | (2006.01) |
| *C07D 491/20* | (2006.01) |
| *C07D 495/10* | (2006.01) |
| *C07D 519/00* | (2006.01) |
| *C07F 7/18* | (2006.01) |

(52) U.S. Cl.
CPC ....... *C07D 491/107* (2013.01); *C07D 491/20* (2013.01); *C07D 495/10* (2013.01); *C07D 519/00* (2013.01); *C07F 7/1856* (2013.01)

(58) Field of Classification Search
USPC ................................ 514/183, 277, 359, 374
See application file for complete search history.

(56) References Cited

U.S. PATENT DOCUMENTS

2017/0008901 A1 * 1/2017 Runtz-Schmitt ..... C07D 491/10

FOREIGN PATENT DOCUMENTS

| EP | 1566384 A1 * | 8/2005 | ........... C07D 405/04 |
|---|---|---|---|
| WO | 2006/123242 A1 | 11/2006 | |
| WO | 2008/084005 A1 | 7/2008 | |
| WO | 2012/077655 A1 | 6/2012 | |

OTHER PUBLICATIONS

ISR for PCT/EP2015/053246 dated Apr. 7, 2015.

* cited by examiner

*Primary Examiner* — Pancham Bakshi
(74) *Attorney, Agent, or Firm* — Robert C. Hall

(57) ABSTRACT

The present invention provides spiro-oxazolones, which act as V1a receptor modulators, and in particular as V1a receptor antagonists, their manufacture, pharmaceutical compositions containing them and their use as medicaments. The present compounds are useful as therapeutics acting peripherally and centrally in the conditions of inappropriate secretion of vasopressin, anxiety, depressive disorders, obsessive compulsive disorder, autistic spectrum disorders, schizophrenia, aggressive behavior and phase shift sleep disorders, in particular jetlag.

14 Claims, No Drawings

SPIRO-OXAZOLONES

CROSS REFERENCE TO RELATED APPLICATIONS

This application is a continuation of International Application No. PCT/EP2015/053246 having an international filing date of Feb. 17, 2015 and which claims benefit under 35 U.S.C. §119 to European Patent Application Serial No. 14155965.8 filed on Feb. 20, 2014, the disclosure of which is incorporated herein by reference in their entirety.

The present invention provides spiro-oxazolones, which act as V1a receptor modulators, and in particular as V1a receptor antagonists, their manufacture, pharmaceutical compositions containing them and their use as medicaments. The present compounds are useful as therapeutics acting peripherally and centrally in the conditions of inappropriate secretion of vasopressin, anxiety, depressive disorders, obsessive compulsive disorder, autistic spectrum disorders, schizophrenia, aggressive behavior and phase shift sleep disorders, in particular jetlag.

TECHNICAL FIELD

The present invention provides a compound of formula I,

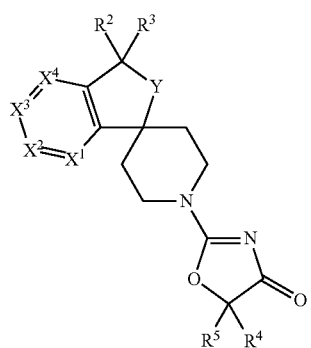

wherein the substituents and variables are as described below and in the claims, or a pharmaceutically acceptable salt thereof.

The present compounds are V1a receptor antagonists, useful for the treatment of autistic spectrum disorders.

BACKGROUND ART

Three vasopressin receptors, all belonging to the class I G-protein coupled receptors, are known. The V1a receptor is expressed in the brain, liver, vascular smooth muscle, lung, uterus and testis, the V1b or V3 receptor is expressed in the brain and pituitary gland, the V2 receptor is expressed in the kidney where it regulates water reabsorption and mediates the antidiuretic effects of vasopressin (Robben, et al.)[1]. Compounds with activity at the V2 receptor can therefore cause side-effects on blood homeostasis.

The oxytocin receptor is related to the Vasopressin receptor family and mediates the effects of the neurohormone oxytocin in the brain and the periphery. Oxytocin is believed to have central anxiolytic effects (Neumann)[2]. Central oxytocin receptor antagonism might therefore lead to anxiogenic effects, which are regarded as undesired side-effects.

In the brain vasopressin acts as a neuromodulator and is elevated in the amygdala during stress (Ebner, et al.)[3]. It is known that stressful life events can trigger major depression and anxiety (Kendler, et al.)[4] and that both have very high comorbidity, with anxiety often preceding major depression (Regier, et al.)[5]. The V1a receptor is extensively expressed in the brain and particularly in limbic areas like the amygdala, lateral septum and hippocampus which are playing an important role in the regulation of anxiety. Indeed V1a knock-out mice show a reduction in anxious behavior in the plus-maze, open field and light-dark box (Bielsky, et al.)[6]. The down-regulation of the Via receptor using anti-sense oligonucleotide injection in the septum also causes a reduction in anxious behavior (Landgraf, et al.)[7]. Vasopressin or the V1a receptor are also implicated in other neuropsychological disorders: genetic studies linked sequence polymorphism in the promoter of the human V1a receptor to autistic spectrum disorders (Yirmiya, et al.)[8], intranasal administration of vasopressin was shown to influence aggression in human males (Thompson, et al.)[9] and vasopressin levels were found to be elevated in schizophrenic patients (Raskind, et al.)[10] and patients with obsessive-compulsive disorder (Altemus, et al.)[11].

Autistic Spectrum Disorders (ASD) are a clinically heterogeneous condition characterized by defects in socialization and language. ASD include a wide range of abnormalities including a genuine incapacity to organize affective relations, behavioral anomalies in reciprocal social interactions, verbal and non-verbal communication, limited interest in the surrounding environment associated with stereotyped movements and repetitive plays (Bourreau et al, 2009)[12]. Research to date indicates that a genetic predisposition can be involved, but also environmental factors have to be taken into consideration (Bourgeron, 2009)[13]. There is at present no efficient biological/pharmaceutical treatment to ASD.

The suprachiasmatic nucleus (SCN) is the endogenous clock of the body regulating circadian rhythmicity and is known to be rich in vasopressin neurons (Kalsbeek et al. 2010)[14], producing and releasing vasopressin with a 24 h circadian rhythm (Schwartz et al. 1983)[15]. A major regulatory effect of vasopressin on circadian rhythm could not be demonstrated by the prior art. The Brattleboro rat, a rat strain naturally lacking vasopressin due to a point mutation, has no obvious defect in its circadian rhythm (Groblewski et al. 1981)[16]. Injection of vasopressin directly in the hamster SCN had no effect on circadian phase shift (Albers et al. 1984)[17]. In contrast, the vasopressin receptors were shown to modulate the circadian clock in a more subtle way. Yamaguchi et al (2013)[18] demonstrated that Via knock-out and V1a/V1b double knock-out mice show faster reentrainment to the new light/dark cycle after a circadian phase advance or a phase delay, an experiment mimicking jet-lag in humans. The same result was obtained after chronic administration of a mixture of V1a and V1b small molecule antagonists through a minipump directly on the SCN.

DETAILED DESCRIPTION OF THE INVENTION

Object of the present invention is a compound of formula I and their pharmaceutically acceptable salts thereof, the preparation of the above mentioned compounds, medicaments containing them and their manufacture as well as the use of the above mentioned compounds in the therapeutic and/or prophylactic treatment of diseases and disorders which are associated with modulation of the V1a receptor, and in particular with V1a receptor antagonism. A further object of the invention is to provide selective inhibitors of the V1a receptor, since selectivity for the Via receptor is expected to afford a low potential to cause unwanted off-target related side effects such as discussed above.

The following definitions of the general terms used in the present description apply irrespectively of whether the terms in question appear alone or in combination with other groups.

The term "$C_{1-6}$-alkyl", alone or in combination with other groups, stands for a hydrocarbon radical which can be linear or branched, with single or multiple branching, wherein the alkyl group in general comprises 1 to 6 carbon atoms, for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl, 1,2-dimethyl-propyl and the like. Particular "$C_{1-6}$-alkyl" groups have 1 to 4 carbon atoms ("$C_{1-4}$-alkyl"). A specific group is methyl.

The term "aryl-$C_{1-6}$-alkyl", alone or in combination with other groups, refers to $C_{1-6}$-alkyl as defined herein, which is substituted by one aryl group as defined herein.

The term "hydroxy-$C_{1-6}$-alkyl", alone or in combination with other groups, refers to $C_{1-6}$-alkyl as defined herein, which is substituted by one hydroxy group as defined herein.

The term "halogen-$C_{1-6}$-alkyl", alone or in combination with other groups, refers to $C_{1-6}$-alkyl as defined herein, which is substituted by one or multiple halogen, in particular 1-5 halogen, more particular 1-3 halogen ("halogen-$C_{1-3}$-alkyl"), specific 1 halogen or 3 halogen. Particular halogen is fluoro. Particular "halogen-$C_{1-6}$-alkyl" is "fluoro-$C_{1-6}$-alkyl". Examples are $CH_2F$, $CHF_2$ and $CF_3$.

The term "$C_{3-10}$-cycloalkyl-$C_{1-6}$-alkyl", alone or in combination with other groups, refers to $C_{1-6}$-alkyl as defined herein, which is substituted by one $C_{3-10}$-cycloalkyl group as defined herein.

The term "heteroaryl-$C_{1-6}$-alkyl", alone or in combination with other groups, refers to $C_{1-6}$-alkyl as defined herein, which is substituted by one heteroaryl-$C_{1-6}$-alkyl group as defined herein.

The term "heterocyclyl-$C_{1-6}$-alkyl", alone or in combination with other groups, refers to $C_{1-6}$-alkyl as defined herein, which is substituted by one heterocyclyl-$C_{1-6}$-alkyl group as defined herein.

The term "$C_{2-6}$-alkenyl" denotes a monovalent linear or branched hydrocarbon group of 2 to 6 carbon atoms, in particular 2 to 4 carbon atoms, with at least one double bond. Examples of alkenyl include ethenyl, propenyl, prop-2-enyl, n-butenyl and t-butenyl and the like. Particular "$C_{2-6}$-alkenyl" groups are prop-2-enyl and 2-methylprop-2-enyl.

The term "halogen-$C_{2-6}$-alkenyl", alone or in combination with other groups, refers to $C_{2-6}$-alkenyl as defined herein, which is substituted by one or multiple halogen, in particular 1-5 halogen, more particular 1-3 halogen ("halogen-$C_{2-6}$-alkenyl"), specific 1 halogen or 3 halogen. Particular halogen is fluoro. Particular "halogen-$C_{2-6}$-alkenyl" is "fluoro-$C_{2-6}$-alkenyl". Examples are 2-(trifluoromethyl)prop-2-enyl.

The term "$C_{2-6}$-alkynyl" denotes a monovalent linear or branched saturated hydrocarbon group of 2 to 6 carbon atoms, in particular from 2 to 4 carbon atoms, and comprising one, two or three triple bonds. Examples of alkynyl include ethynyl, propynyl, prop-2-ynyl, but-2-ynyl and the like. Particular "$C_{2-6}$-alkynyl" groups are prop-2-ynyl and but-2-ynyl.

The term "hydroxy", alone or in combination with other groups, refers to —OH.

The term "halogen", alone or in combination with other groups, denotes chloro (Cl), iodo (I), fluoro (F) and bromo (Br).

The term "oxo", alone or in combination with other groups, refers to =O.

The term "indanyl", alone or in combination with other groups, refers to a group

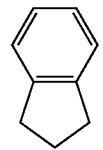

The term "benzyl", alone or in combination with other groups, refers to phenyl-$CH_2$—.

The term "$C_{1-6}$-alkyl-COO—", alone or in combination with other groups, refers to $C_{1-6}$-alkyl-(C=O)—O—.

The term "$C_{1-6}$-alkyl-OOC—", alone or in combination with other groups, refers to $C_{1-6}$-alkyl-O—(C=O)—.

The term "($C_{1-6}$-alkyl)$_3$SiO—", alone or in combination with other groups, refers to Si independently substituted by 3 $C_{1-6}$-alkyl groups as defined herein and linked via —O—. An example is [tert-butyl(dimethyl)Si]—O—.

The term "$C_{1-6}$-alkoxy", alone or in combination with other groups, stands for an —O—$C_{1-6}$-alkyl radical which can be linear or branched, with single or multiple branching, wherein the alkyl group in general comprises 1 to 6 carbon atoms, for example, methoxy (OMe, MeO), ethoxy (OEt), propoxy, isopropoxy (i-propoxy) and the like. Particular "$C_{1-6}$-alkoxy" groups have 1 to 4 carbon atoms ("$C_{1-4}$-alkoxy"). A specific group is OMe.

The term "aryl", alone or in combination with other groups, refers to an aromatic carbocyclic group comprising 6 to 14, preferably 6 to 10, carbon atoms and having one aromatic ring or multiple condensed rings in which all rings are aromatic. Examples of "aryl" include biphenyl, naphthyl, phenyl (Ph) and the like. Particular "aryl" is phenyl.

The term "$C_{3-10}$-cycloalkyl", alone or in combination with other groups, denotes a monovalent saturated monocyclic or bicyclic hydrocarbon group of 3 to 10 ring carbon atoms, particularly a monovalent saturated monocyclic hydrocarbon group of 3 to 7 ring carbon atoms ("$C_{3-7}$-cycloalkyl"). A bicyclic $C_{3-10}$-cycloalkyl can comprise 2 rings fused together, wherein at least one such ring is saturated and the other one can be un-saturated, in particular can be phenyl. Particular cycloalkyl groups are monocyclic. Examples for monocyclic cycloalkyl are cyclopropyl, cyclobutanyl (cyclobutyl), cyclopentyl, cyclohexyl or cycloheptyl. Examples for bicyclic cycloalkyl are indanyl, bicyclo[3.1.0]hexanyl, 1,2,3,3a,4,5,6,6a-octahydropentalenyl, 2,3,3a,4,5,6,7,7a-octahydro-1H-indenyl, 1,2,3,3a,4,5,6,7,8,8a-decahydroazulenyl, and the like.

The term "$C_{3-10}$-cycloalkenyl", alone or in combination with other groups, denotes a monocyclic partly saturated hydrocarbon group of 3 to 10 ring carbon atoms, particularly of 5 ring carbon atoms, wherein at least one ring is partly saturated and the other one can be saturated. Particular $C_{3-10}$-cycloalkenyl are rings with one double bond, for example cyclopentenyl. A bicyclic $C_{3-10}$-cycloalkenyl is 1,2,3,3a,4,5-hexahydropentalenyl, and the like.

The terms "heterocycloalkyl" or "heterocyclyl", alone or in combination with other groups, refers to a 3 to 10, in particular 5 to 7, membered saturated monocyclic or bicyclic ring containing one, two or three heteroatoms selected from N, O or S. A bicyclic heterocycloalkyl can comprise 2 rings fused together, wherein at least one such ring is saturated and contains a heteroatom as a ring atom (i.e., nitrogen, oxygen, or sulfur). Examples for heterocycloalkyl moieties are azetidinyl, oxetanyl, tetrahydrofuranyl, tetrahydropyranyl, tetrahydrothiopyranyl, pyrrolidinyl, pyrazolidinyl, morpholinyl, thiomorpholinyl, piperidinyl, piperazinyl, 2,3,4,5-tetrahydro-1H-2-benzazepinyl, 3,4a,5,6,7,7a-hexahydro-2H-cyclopenta[b][1,4]dioxinyl, 4,5,6,6a-tetrahydro-3aH-cyclopenta[d][1,3,2]dioxathiolyl, 3,3a,4,5,6,6a-hexahydro-1H-cyclopenta[c]furanyl and the like. Particular heterocycloalkyl are tetrahydrofuranyl, tetrahydropyranyl, tetrahydrothiopyranyl, pyrrolidinyl, piperidinyl, 2,3,4,5-tetrahydro-1H-2-benzazepinyl, 3,4a,5,6,7,7a-hexahydro-2H-cyclopenta[b][1,4]dioxinyl, 4,5,6,6a-tetrahydro-3aH-cyclopenta[d][1,3,2]dioxathiolyl and 3,3a,4,5,6,6a-hexahydro-1H-cyclopenta[c]furanyl.

The term "oxo" when referring to substituents on heterocycloalkyl means that an oxygen atom is attached to the heterocycloalkyl ring. Thereby, the "oxo" can either replace two hydrogen atoms on a carbon atom, or it can simply be attached to sulfur, so that the sulfur exists in oxidized form, i.e. bearing one or two oxygen like a group $-SO_2$.

The term "heteroaryl", alone or in combination with other groups, refers to an aromatic carbocyclic group of having a single 4 to 8 membered ring or multiple condensed rings comprising 6 to 14, more preferably 6 to 10, ring atoms and containing 1, 2 or 3 heteroatoms individually selected from N, O and S, in particular N and O, in which group all heterocyclic rings are aromatic. Examples of "heteroaryl" include pyridinyl, pyrimidinyl, pyridazinyl, thiophenyl and the like. Particular "heteroaryl" are pyridinyl and thiophenyl.

The term "pharmaceutically acceptable salts" refers to salts that are suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid, sulphuric acid, tartaric acid, trifluoroacetic acid and the like. Particular acids are formic acid, trifluoroacetic acid and hydrochloric acid. Particular are hydrochloric acid, trifluoroacetic acid and fumaric acid.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. In particular it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values ($-\log IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant (Ki) using the Cheng-Prusoff equation (Biochem. Pharmacol. (1973) 22:3099). The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values ($-\log K_i$), in which higher values indicate exponentially greater potency.

The term "antagonist" denotes a compound that diminishes or prevents the action of another compound as defined e.g. in Goodman and Gilman's "The Pharmacological Basis of Therapeutics, 7th ed." in page 35, Macmillan Publ. Company, Canada, 1985. In particular, antagonists refer to a compound that attenuates the effect of an agonist. A "competitive antagonist" binds to the same site of a receptor as the agonist but does not activate the receptor, thus blocks the agonist's action. A "non-competitive antagonist" binds to an allosteric (non-agonist) site on the receptor to prevent activation of the receptor. A "reversible antagonist" binds non-covalently to the receptor, therefore can be "washed out". An "irreversible antagonist" binds covalently to the receptor and cannot be displaced by either competing ligands or washing.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as preferred, more preferred and most preferred definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product can not necessarily result directly from the combination of two reagents which were initially added, i.e., there can be one or more intermediates which are produced in the mixture which ultimately leads to the formation of the indicated and/or the desired product.

The term "aromatic" denotes the conventional idea of aromaticity as defined in the literature, in particular in IUPAC[19].

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

The terms "Autistic Spectrum" and "Autistic Spectrum Disorders" summarize conditions classified as pervasive developmental disorders, which include but are not limited to autism, Asperger syndrome, pervasive developmental disorder not otherwise specified (PDD-NOS), childhood disintegrative disorder, Rett syndrome and Fragile X, in particular autism. These disorders are typically characterized by social deficits, communication difficulties, stereotyped or repetitive behaviors and interests, and cognitive delays.

The term "phase shift sleep disorders" summarizes conditions classified as disturbances in the circadian rhythm, i.e. the approximately 24-hour cycles that are generated by an organism, e.g. a human being. Phase shift sleep disorders include, but are not limited to transient disorders like jetlag or a changed sleep schedule due to work, social responsibilities, or illness, as well as chronic disorders like delayed sleep-phase syndrome (DSPS), delayed sleep-phase type (DSPT), advanced sleep-phase syndrome (ASPS), and irregular sleep-wake cycle.

In detail, the present invention provides compounds of the general formula I

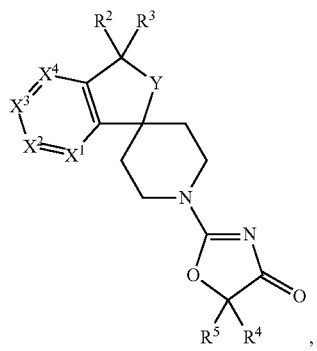

wherein
$X^1$ C—$R^1$ or N;
$X^2$ C—$R^1$ or N;
$X^3$ C—$R^1$ or N;
$X^4$ C—$R^1$ or N;
whereby only one of $X^1$, $X^2$, $X^3$ and $X^4$ is N or all of $X^1$, $X^2$, $X^3$ and $X^4$ are C—$R^1$;
Y is O or $S(O)_m$;
m is 0, 1 or 2;
$R^1$ each separately is selected from the group consisting of hydrogen, halogen, hydroxy, $C_{1-6}$-alkyl- and $C_{1-6}$-alkoxy-;
$R^2$ is selected from the group consisting of H and $C_{1-6}$-alkyl-;
$R^3$ is selected from the group consisting of H and $C_{1-6}$-alkyl-;
or $R^2$ and $R^3$ together are =O;
$R^4$ is selected from the group consisting of
  i) aryl-$C_{1-6}$-alkyl-, wherein the aryl moiety can be optionally substituted by halogen,
  ii) $C_{1-6}$-alkoxy-$CH_2$—,
  iii) $C_{1-6}$-alkyl-,
  iv) $C_{2-6}$-alkenyl-$CH_2$—,
  v) $C_{2-6}$-alkynyl-$CH_2$—,
  vi) halogen-$C_{1-6}$-alkyl-,
  vii) halogen-$C_{2-6}$-alkenyl-$CH_2$—, and
  viii) hydrogen;
$R^5$ is selected from the group consisting of
  i) aryl-,
  ii) aryl-$C_{1-6}$-alkyl-, wherein
    the aryl moiety can be optionally substituted by $C_{1-6}$-alkyl, halogen-$C_{1-6}$-alkyl or halogen, and
    the $C_{1-6}$-alkyl moiety can optionally be substituted by $C_{1-6}$-alkyl-COO—, halogen or hydroxy,
  iii) $C_{3-10}$-cycloalkyl-$C_{1-6}$-alkyl-,
  iv) halogen-$C_{1-6}$-alkyl-,
  v) heteroaryl-$C_{1-6}$-alkyl-, wherein the heteroaryl moiety can be optionally substituted by halogen,
  vi) heterocycloalkyl-$C_{1-6}$-alkyl-,
  vii) $C_{1-6}$-alkyl-,
  viii) $C_{2-6}$-alkenyl-$CH_2$— that is optionally substituted by halogen, $(C_{1-6}$-alkyl$)_3$SiO—, $C_{1-6}$-alkyl-COO— or $C_{1-6}$-alkyl-OOC—,
  ix) $C_{1-6}$-alkoxy-$CH_2$—, and
  x) $C_{2-6}$-alkynyl-$CH_2$—;
or $R^4$ and $R^5$ together are selected from the group consisting of
  i) $C_{3-10}$-cycloalkyl that is optionally substituted by $C_{1-6}$-alkyl, $C_{1-6}$-alkoxy, $C_{1-6}$-alkyl-OOC—, $C_{1-6}$-alkyl-COO—, halogen, halogen-$C_{1-6}$-alkyl, hydroxy-$C_{1-6}$-alkyl or oxo;
  ii) heterocycloalkyl that is optionally substituted by benzyl, $C_{1-6}$-alkyl, $C_{1-6}$-alkyl-OOC—, halogen-$C_{1-6}$-alkyl or oxo;
  iii) $C_{3-10}$-cycloalkenyl that is optionally substituted by $C_{1-6}$-alkyl, $C_{1-6}$-alkyl-OOC—, halogen-$C_{1-6}$-alkyl, $(C_{1-6}$-alkyl$)_3$SiO—$C_{1-6}$-alkyl- or hydroxy-$C_{1-6}$-alkyl, and
  iv) indanyl when Y is $SO_2$;
or pharmaceutically acceptable salts thereof.

A certain embodiment of this invention refers to a compound of formula I as described herein, wherein
$X^1$ C—$R^1$ or N;
$X^2$ C—$R^1$ or N;
$X^3$ C—$R^1$ or N;
$X^4$ C—$R^1$ or N;
whereby only one of $X^1$, $X^2$, $X^3$ and $X^4$ is N or all of $X^1$, $X^2$, $X^3$ and $X^4$ are C—$R^1$;
Y is O;
$R^1$ each separately is selected from the group consisting of hydrogen, halogen, hydroxy, $C_{1-6}$-alkyl- and $C_{1-6}$-alkoxy-;
$R^2$ is selected from the group consisting of H and $C_{1-6}$-alkyl-;
$R^3$ is selected from the group consisting of H and $C_{1-6}$-alkyl-;
or $R^2$ and $R^3$ together are =O;
$R^4$ is selected from the group consisting of
  i) aryl-$C_{1-6}$-alkyl-, wherein the aryl moiety can be optionally substituted by halogen,
  ii) $C_{1-6}$-alkyl-,
  iii) $C_{2-6}$-alkenyl-$CH_2$—,
  iv) $C_{2-6}$-alkynyl-$CH_2$—,
  v) halogen-$C_{2-6}$-alkenyl-$CH_2$—, and
  vi) hydrogen;
$R^5$ is selected from the group consisting of
  i) aryl-,
  ii) aryl-$C_{1-6}$-alkyl-, wherein
    the aryl moiety can be optionally substituted by $C_{1-6}$-alkyl, halogen-$C_{1-6}$-alkyl or halogen, and
    the $C_{1-6}$-alkyl moiety can optionally be substituted by $C_{1-6}$-alkyl-COO—, halogen or hydroxy,
  iii) $C_{3-10}$-cycloalkyl-$C_{1-6}$-alkyl-,
  iv) heteroaryl-$C_{1-6}$-alkyl-, wherein the heteroaryl moiety can be optionally substituted by halogen,
  v) heterocycloalkyl-$C_{1-6}$-alkyl-,
  vi) $C_{1-6}$-alkyl-,
  vii) $C_{2-6}$-alkenyl-$CH_2$— that is optionally substituted by halogen, $(C_{1-6}$-alkyl$)_3$SiO—, $C_{1-6}$-alkyl-COO— or $C_{1-6}$-alkyl-OOC—,
  viii) $C_{1-6}$-alkoxy-$CH_2$—, and
  ix) $C_{2-6}$-alkynyl-$CH_2$—;
or $R^4$ and $R^5$ together are selected from the group consisting of i) $C_{3-10}$-cycloalkyl that is optionally substituted by $C_{1-6}$-alkyl, $C_{1-6}$-alkoxy, $C_{1-6}$-alkyl-OOC—, $C_{1-6}$-alkyl-COO—, halogen, halogen-$C_{1-6}$-alkyl, hydroxy-$C_{16}$-alkyl or oxo;

ii) heterocycloalkyl that is optionally substituted by benzyl, $C_{1-6}$-alkyl, $C_{1-6}$-alkyl-OOC—, halogen-$C_{1-6}$-alkyl or oxo; and iii) $C_{3-10}$-cycloalkenyl that is optionally substituted by $C_{1-6}$-alkyl, $C_{1-6}$-alkyl-OOC—, halogen-$C_{1-6}$-alkyl, $(C_{1-6}$-alkyl$)_3$SiO—$C_{1-6}$-alkyl- or hydroxy-$C_{1-6}$-alkyl.

A certain embodiment of this invention refers to a compound of formula I as described herein, wherein $X^1$, $X^2$, $X^3$ and $X^4$ is each C—H, Y is O, $R^2$ and $R^3$ are each separately H, methyl or together =O, $R^4$ is hydrogen or methyl and $R^5$ is butyl, benzyl or cyclopentyl-$CH_2$—.

A certain embodiment of this invention refers to a compound of formula I as described herein, wherein $X^1$, $X^2$, $X^3$ and $X^4$ is each C—H, Y is O, $R^2$ and $R^3$ are each separately H, methyl or together =O and $R^4$ and $R^5$ together are $C_{3-10}$-cycloalkyl that is optionally substituted by halogen, heterocycloalkyl that is optionally substituted by $C_{1-6}$-alkyl or $C_{3-10}$-cycloalkenyl that is optionally substituted by halogen-$C_{1-6}$-alkyl.

A certain embodiment of this invention refers to a compound of formula I as described herein, wherein $X^1$, $X^2$, $X^3$ and $X^4$ is each C—H, Y is $SO_2$, $R^2$ and $R^3$ are each separately H, methyl or together =O and $R^4$ and $R^5$ together are indanyl.

A certain embodiment of this invention refers to a compound of formula I as described herein, wherein $X^1$, $X^2$, $X^3$ and $X^4$ is each C—H, Y is O, $R^2$ and $R^3$ are =O, $R^4$ is hydrogen or methyl and $R^5$ is butyl, benzyl, 4-Chlorophenyl)(hydroxy)methyl or cyclopentyl-$CH_2$.

A certain embodiment of this invention refers to a compound of formula I as described herein, wherein $X^1$, $X^2$, $X^3$ and $X^4$ is each C—$R^1$, and each $R^1$ is separately is selected from the group consisting of hydrogen, halogen, and $C_{1-6}$-alkoxy.

A certain embodiment of this invention refers to a compound of formula I as described herein, wherein $X^1$, $X^2$, $X^3$ and $X^4$ is each CH.

A certain embodiment of this invention refers to a compound of formula I as described herein, wherein $R^1$ is hydrogen.

A certain embodiment of this invention refers to a compound of formula I as described herein, wherein Y is O.

A certain embodiment of this invention refers to a compound of formula I as described herein, wherein Y is $SO_2$ and $R^4$ and $R^5$ together are indanyl.

A certain embodiment of this invention refers to a compound of formula I as described herein, wherein Y is $SO_2$.

A certain embodiment of this invention refers to a compound of formula I as described herein, wherein $R^2$ is hydrogen.

A certain embodiment of this invention refers to a compound of formula I as described herein, wherein $R^3$ is hydrogen.

A certain embodiment of this invention refers to a compound of formula I as described herein, wherein $R^2$ and $R^3$ are =O.

A certain embodiment of this invention refers to a compound of formula I as described herein, wherein $R^4$ is hydrogen or $C_{1-6}$-alkyl.

A certain embodiment of this invention refers to a compound of formula I as described herein, wherein $R^4$ is hydrogen or methyl.

A certain embodiment of this invention refers to a compound of formula I as described herein, wherein $R^4$ is hydrogen.

A certain embodiment of this invention refers to a compound of formula I as described herein, wherein $R^4$ is methyl.

A certain embodiment of this invention refers to a compound of formula I as described herein, wherein $R^5$ is benzyl or $C_{3-10}$-cycloalkyl-$C_{1-6}$-alkyl-.

A certain embodiment of this invention refers to a compound of formula I as described herein, wherein $R^5$ is benzyl or cyclopentyl-$CH_2$—.

A certain embodiment of this invention refers to a compound of formula I as described herein, wherein $R^4$ and $R^5$ together are i) $C_{3-10}$-cycloalkyl that is optionally substituted by halogen;

ii) heterocycloalkyl that is optionally substituted by $C_{1-6}$-alkyl;

iii) $C_{3-10}$-cycloalkenyl that is optionally substituted by halogen-$C_{1-6}$-alkyl, and iv) indanyl when Y is $SO_2$;

A certain embodiment of this invention refers to a compound of formula I as described herein, wherein $R^4$ and $R^5$ together are cyclopentenyl that is optionally substituted by halogen-$C_{1-6}$-alkyl, cyclohexyl that is optionally substituted by halogen or 2,3,4,5-tetrahydro-1H-2-benzazepinyl that is optionally substituted by $C_{1-6}$-alkyl.

A certain embodiment of this invention refers to a compound of formula I as described herein, wherein $R^4$ and $R^5$ together are cyclopentenyl that is optionally substituted by $CF_3$, cyclohexyl that is optionally substituted by fluoro or 2,3,4,5-tetrahydro-1H-2-benzazepinyl that is optionally substituted by methyl.

A certain embodiment of this invention refers to a compound of formula I as described herein, selected from the group consisting of (−)-(5 S)-5-Benzyl-2-(1'H,3H-spiro[2-benzofuran-1,4'-piperidin]-1'-yl)-1,3-oxazol-4(5H)-one, (−)-5-(Cyclopentylmethyl)-5-methyl-2-(1'H,3H-spiro[2-benzofuran-1,4'-piperidin]-1'-yl)-1,3-oxazol-4(5H)-one, (−)-5-(Ethoxymethyl)-5-methyl-2-(1'H,3H-spiro[2-benzofuran-1,4'-piperidin]-1'-yl)-1,3-oxazol-4(5H)-one, (−)-5-[(4-Chlorophenyl)(hydroxy)methyl]-2-(1'H,3H-spiro[2-benzofuran-1,4'-piperidin]-1'-yl)-1,3-oxazol-4(5H)-one diastereomer a, (−)-5-[(4-Chlorophenyl)(hydroxy)methyl]-2-(1'H,3H-spiro[2-benzofuran-1,4'-piperidin]-1'-yl)-1,3-oxazol-4(5H)-one diastereomer b, (−)-5-[(5-Chlorothiophen-2-yl)methyl]-5-methyl-2-(1'H,3H-spiro[2-benzofuran-1,4'-piperidin]-1'-yl)-1,3-oxazol-4(5H)-one, (−)-5-[(6-Chloropyridin-3-yl)methyl]-5-methyl-2-(1'H,3H-spiro[2-benzofuran-1,4'-piperidin]-1'-yl)-1,3-oxazol-4(5H)-one, (−)-5-Benzyl-5-methyl-2-(1'H,3H-spiro[2-benzofuran-1,4'-piperidin]-1'-yl)-1,3-oxazol-4(5H)-one, (−)-5-Butyl-2-(1'H,3H-spiro[2-benzofuran-1,4'-piperidin]-1'-yl)-1,3-oxazol-4(5H)-one, (−)-5-Butyl-5-methyl-2-(1'H,3H-spiro[2-benzofuran-1,4'-piperidin]-1'-yl)-1,3-oxazol-4(5H)-one, (−)-5-Methyl-2-(1'H,3H-spiro[2-benzofuran-1,4'-piperidin]-1'-yl)-5-(tetrahydro-2H-pyran-3-ylmethyl)-1,3-oxazol-4(5H)-one diastereomer a, (−)-5-Methyl-2-(1'H,3H-spiro[2-benzofuran-1,4'-piperidin]-1'-yl)-5-(tetrahydro-2H-pyran-3-ylmethyl)-1,3-oxazol-4(5H)-one diastereomer b, (−)-5-Methyl-5-(1-phenylethyl)-2-(1'H,3H-spiro[2-benzofuran-1,4'-piperidin]-1'-yl)-1,3-oxazol-4(5H)-one diastereomer a,
(−)-5-Methyl-5-(1-phenylethyl)-2-(1'H,3H-spiro[2-benzofuran-1,4'-piperidin]-1'-yl)-1,3-oxazol-4(5H)-one diastereomer b,
(+)-(5R)-5-Benzyl-2-(1'H,3H-spiro[2-benzofuran-1,4'-piperidin]-1'-yl)-1,3-oxazol-4(5H)-one,
(+)-5-(Cyclopentylmethyl)-5-methyl-2-(1'H,3H-spiro[2-benzofuran-1,4'-piperidin]-1'-yl)-1,3-oxazol-4(5H)-one,
(+)-5-(Ethoxymethyl)-5-methyl-2-(1'H,3H-spiro[2-benzofuran-1,4'-piperidin]-1'-yl)-1,3-oxazol-4(5H)-one,
(+)-5-[(4-Chlorophenyl)(hydroxy)methyl]-2-(1'H,3H-spiro[2-benzofuran-1,4'-piperidin]-1'-yl)-1,3-oxazol-4(5H)-one diastereomer a,
(+)-5-[(4-Chlorophenyl)(hydroxy)methyl]-2-(1'H,3H-spiro[2-benzofuran-1,4'-piperidin]-1'-yl)-1,3-oxazol-4(5H)-one diastereomer b,
(+)-5-[(5-Chlorothiophen-2-yl)methyl]-5-methyl-2-(1'H,3H-spiro[2-benzofuran-1,4'-piperidin]-1'-yl)-1,3-oxazol-4(5H)-one,
(+)-5-[(6-Chloropyridin-3-yl)methyl]-5-methyl-2-(1'H,3H-spiro[2-benzofuran-1,4'-piperidin]-1'-yl)-1,3-oxazol-4(5H)-one,
(+)-5-Benzyl-5-methyl-2-(1'H,3H-spiro[2-benzofuran-1,4'-piperidin]-1'-yl)-1,3-oxazol-4(5H)-one,
(+)-5-Butyl-2-(1'H,3H-spiro[2-benzofuran-1,4'-piperidin]-1'-yl)-1,3-oxazol-4(5H)-one,
(+)-5-Butyl-5-methyl-2-(1'H,3H-spiro[2-benzofuran-1,4'-piperidin]-1'-yl)-1,3-oxazol-4(5H)-one,
(+)-5-Methyl-2-(1'H,3H-spiro[2-benzofuran-1,4'-piperidin]-1'-yl)-5-(tetrahydro-2H-pyran-3-ylmethyl)-1,3-oxazol-4(5H)-one diastereomer a,
(+)-5-Methyl-2-(1'H,3H-spiro[2-benzofuran-1,4'-piperidin]-1'-yl)-5-(tetrahydro-2H-pyran-3-ylmethyl)-1,3-oxazol-4(5H)-one diastereomer b,
(+)-5-Methyl-5-(1-phenylethyl)-2-(1'H,3H-spiro[2-benzofuran-1,4'-piperidin]-1'-yl)-1,3-oxazol-4(5H)-one diastereomer a,
(+)-5-Methyl-5-(1-phenylethyl)-2-(1'H,3H-spiro[2-benzofuran-1,4'-piperidin]-1'-yl)-1,3-oxazol-4(5H)-one diastereomer b,
(4-Chlorophenyl)[4-oxo-2-(1'H,3H-spiro[2-benzofuran-1,4'-piperidin]-1'-yl)-4,5-dihydro-1,3-oxazol-5-yl]methyl acetate,
1'-[5-Benzyl-4-oxo-4,5-dihydro-1,3-oxazol-2-yl]-3H-spiro[2-benzofuran-1,4'-piperidin]-3-one enantiomer A,
1'-[5-Benzyl-4-oxo-4,5-dihydro-1,3-oxazol-2-yl]-3H-spiro[2-benzofuran-1,4'-piperidin]-3-one enantiomer B,
1'-(4-Oxo-1-oxa-3-azaspiro[4.5]dec-2-en-2-yl)-3H-spiro[2-benzofuran-1,4'-piperidin]-3-one,
11'-(5-Benzyl-4-oxo-4,5-dihydro-1,3-oxazol-2-yl)-4-fluoro-3H-spiro[2-benzofuran-1,4'-piperidin]-3-one,
1'-(5-Benzyl-4-oxo-4,5-dihydro-1,3-oxazol-2-yl)-5-bromo-3H-spiro[2-benzofuran-1,4'-piperidin]-3-one,
1'-(5-Benzyl-4-oxo-4,5-dihydro-1,3-oxazol-2-yl)-5-fluoro-3H-spiro[2-benzofuran-1,4'-piperidin]-3-one,
1'-(5-Benzyl-4-oxo-4,5-dihydro-1,3-oxazol-2-yl)-5-methoxy-3H-spiro[2-benzofuran-1,4'-piperidin]-3-one,
1'-(5-Butyl-5-methyl-4-oxo-4,5-dihydro-1,3-oxazol-2-yl)-3H-spiro[2-benzofuran-1,4'-piperidin]-3-one,
1'-(8,8-Difluoro-4-oxo-1-oxa-3-azaspiro[4.5]dec-2-en-2-yl)-3H-spiro[2-benzofuran-1,4'-piperidin]-3-one,
1'-[4-Oxo-8-pentyl-1-oxa-3-azaspiro[4.5]dec-2-en-2-yl]-3H-spiro[2-benzofuran-1,4'-piperidin]-3-one diastereomer a,
1'-[4-Oxo-8-pentyl-1-oxa-3-azaspiro[4.5]dec-2-en-2-yl]-3H-spiro[2-benzofuran-1,4'-piperidin]-3-one diastereomer b,
1'-[5-(4-Chlorobenzyl)-5-methyl-4-oxo-4,5-dihydro-1,3-oxazol-2-yl]-3H-spiro[2-benzofuran-1,4'-piperidin]-3-one enantiomer A,
1'-[5-(4-Chlorobenzyl)-5-methyl-4-oxo-4,5-dihydro-1,3-oxazol-2-yl]-3H-spiro[2-benzofuran-1,4'-piperidin]-3-one enantiomer B,
1'-[5-(Cyclopentylmethyl)-4-oxo-4,5-dihydro-1,3-oxazol-2-yl]-3H-spiro[2-benzofuran-1,4'-piperidin]-3-one enantiomer A,
1'-[5-(Cyclopentylmethyl)-4-oxo-4,5-dihydro-1,3-oxazol-2-yl]-3H-spiro[2-benzofuran-1,4'-piperidin]-3-one enantiomer B,
1'-[5,5-Bis(4-chlorobenzyl)-4-oxo-4,5-dihydro-1,3-oxazol-2-yl]-3H-spiro[2-benzofuran-1,4'-piperidin]-3-one,
1'-[5-Benzyl-5-methyl-4-oxo-4,5-dihydro-1,3-oxazol-2-yl]-3H-spiro[2-benzofuran-1,4'-piperidin]-3-one enantiomer A,
1'-[5-Benzyl-5-methyl-4-oxo-4,5-dihydro-1,3-oxazol-2-yl]-3H-spiro[2-benzofuran-1,4'-piperidin]-3-one enantiomer B,
1'-[5-Butyl-4-oxo-4,5-dihydro-1,3-oxazol-2-yl]-3H-spiro[2-benzofuran-1,4'-piperidin]-3-one enantiomer A,
1'-[5-Butyl-4-oxo-4,5-dihydro-1,3-oxazol-2-yl]-3H-spiro[2-benzofuran-1,4'-piperidin]-3-one enantiomer B,
1'-{5-[(4-Chlorophenyl)(hydroxy)methyl]-4-oxo-4,5-dihydro-1,3-oxazol-2-yl}-3H-spiro[2-benzofuran-1,4'-piperidin]-3-one diastereomer a, enantiomer A,
1'-{5-[(4-Chlorophenyl)(hydroxy)methyl]-4-oxo-4,5-dihydro-1,3-oxazol-2-yl}-3H-spiro[2-benzofuran-1,4'-piperidin]-3-one diastereomer a, enantiomer B,
1'-{5-[(4-Chlorophenyl)(hydroxy)methyl]-4-oxo-4,5-dihydro-1,3-oxazol-2-yl}-3H-spiro[2-benzofuran-1,4'-piperidin]-3-one diastereomer b, enantiomer A,
1'-{5-[(4-Chlorophenyl)(hydroxy)methyl]-4-oxo-4,5-dihydro-1,3-oxazol-2-yl}-3H-spiro[2-benzofuran-1,4'-piperidin]-3-one diastereomer b, enantiomer B,
1'-{5-[(4-Chlorophenyl)(hydroxy)methyl]-5-methyl-4-oxo-4,5-dihydro-1,3-oxazol-2-yl}-3H-spiro[2-benzofuran-1,4'-piperidin]-3-one,
2-(1'H,3H-Spiro[2-benzofuran-1,4'-piperidin]-1'-yl)-1,7-dioxa-3-azaspiro[4.5]dec-2-en-4-one,
2-(1'H,3H-Spiro[2-benzofuran-1,4'-piperidin]-1'-yl)-1-oxa-3-azaspiro[4.4]nona-2,7-dien-4-one,
2-(1'H,3H-Spiro[2-benzofuran-1,4'-piperidin]-1'-yl)-1-oxa-3-azaspiro[4.5]dec-2-en-4-one,
2-(1'H,3H-Spiro[2-benzofuran-1,4'-piperidin]-1'-yl)-1-oxa-8-thia-3-azaspiro[4.5]dec-2-en-4-one,
2-(1'H,3H-Spiro[2-benzofuran-1,4'-piperidin]-1'-yl)-3a',4',6',6a'-tetrahydro-1'H,4H-spiro[1,3-oxazole-5,2'-pentalene]-4,5'(3'H)-dione,
2-(1'H,3H-Spiro[2-benzofuran-1,4'-piperidin]-1'-yl)-3a',4'-dihydro-1'H,4H-spiro[1,3-oxazole-5,2'-pentalene]-4,5'(3'H)-dione,
2-(1'H,3H-Spiro[2-benzofuran-1,4'-piperidin]-1'-yl)-7-(trifluoromethyl)-1-oxa-3-azaspiro[4.4]nona-2,7-dien-4-one,
2'-(1'H,3H-Spiro[2-benzofuran-1,4'-piperidin]-1'-yl)-1,3,3a,4,5,6,7,7a-octahydro-4'H-spiro[indene-2,5'-[1,3]oxazol]-4'-one,
2-(1'H,3H-Spiro[2-benzofuran-1,4'-piperidin]-1'-yl)-1-oxa-8-thia-3-azaspiro[4.5]dec-2-en-4-one8,8-dioxide,
2'-(1'H,3H-Spiro[2-benzofuran-1,4'-piperidin]-1'-yl)-2,3,4a,5,7,7a-hexahydro-4'H-spiro[cyclopenta[b][1,4]dioxine-6,5'-[1,3]oxazol]-4'-one diastereomer b, 2'-(1'H,3H-Spiro[2-benzofuran-1,4'-piperidin]-1'-yl)-3,3a,4,
5,6,7,8,8a-octahydro-1H,4'H-spiro[azulene-2,5'-[1,3]ox-
azol]-4'-one,
2'-(1'H,3H-Spiro[2-benzofuran-1,4'-piperidin]-1'-yl)-3a,4,6,
6a-tetrahydro-1H,3H,4'H-spiro[cyclopenta[c]furan-5,5'-
[1,3]oxazol]-4'-one,
2-(1'H,3H-Spiro[2-benzofuran-1,4'-piperidin]-1'-yl)-5-[2-
(trifluoromethyl)prop-2-en-1-yl]-1,3-oxazol-4(5H)-one,
2'-(2,2-Dioxido-1'H,3H-spiro[2-benzothiophene-1,4'-pip-
eridin]-1'-yl)-1,3-dihydro-4'H-spiro[indene-2,5'-[1,3]ox-
azol]-4'-one,
2-(3H-Spiro[isobenzofuran-1,4'-piperidine]-1'-yl)-1-oxa-3-
azaspiro[4.4]non-2-en-4-one,
2-(3H-Spiro[isobenzofuran-1,4'-piperidine]-1'-yl)-5,5-bis
(2-(trifluoromethyl)allyl)oxazol-4(5H)-one,
2'-(1'H,3H-Spiro[2-benzofuran-1,4'-piperidin]-1'-yl)-1,2,3,
5-tetrahydro-4'H-spiro[2-benzazepine-4,5'-[1,3]oxazol]-
4'-one,
2'-(1'H,3H-Spiro[2-benzofuran-1,4'-piperidin]-1'-yl)-3a,4,6,
6a-tetrahydro-4'H-spiro[cyclopenta[d][1,3,2]dioxathiole-
5,5'-[1,3]oxazol]-4'-one2-oxide,
2-Methyl-2'-(1'H,3H-spiro[2-benzofuran-1,4'-piperidin]-1'-
yl)-1,2,3,5-tetrahydro-4'H-spiro[2-benzazepine-4,5'-[1,3]
oxazol]-4'-one,
4-Oxo-2-(1'H,3H-spiro[2-benzofuran-1,4'-piperidin]-1'-yl)-
1-oxa-3-azaspiro[4.4]non-2-ene-7,8-diyldiacetate diaste-
reomer a,
4-Oxo-2-(1'H,3H-spiro[2-benzofuran-1,4'-piperidin]-1'-yl)-
1-oxa-3-azaspiro[4.4]non-2-ene-7,8-diyldiacetate diaste-
reomer b,
5-((4-Chlorophenyl)fluoromethyl)-2-(1'H,3H-spiro[2-ben-
zofuran-1,4'-piperidin]-1'-yl)-1,3-oxazol-4(5H)-one
diastereomer a, enantiomer A,
5-((4-Chlorophenyl)fluoromethyl)-2-(1'H,3H-spiro[2-ben-
zofuran-1,4'-piperidin]-1'-yl)-1,3-oxazol-4(5H)-one
diastereomer a, enantiomer B,
5-((4-Chlorophenyl)fluoromethyl)-2-(1'H,3H-spiro[2-ben-
zofuran-1,4'-piperidin]-1'-yl)-1,3-oxazol-4(5H)-one
diastereomer b, enantiomer A,
5-((4-Chlorophenyl)fluoromethyl)-2-(1'H,3H-spiro[2-ben-
zofuran-1,4'-piperidin]-1'-yl)-1,3-oxazol-4(5H)-one
diastereomer b, enantiomer B,
5-(2-Bromoprop-2-en-1-yl)-5-(prop-2-en-1-yl)-2-(1'H,3H-
spiro[2-benzofuran-1,4'-piperidin]-1'-yl)-1,3-oxazol-4
(5H)-one,
5-(2-Methylprop-2-en-1-yl)-2-(1'H,3H-spiro[2-benzofuran-
1,4'-piperidin]-1'-yl)-1,3-oxazol-4(5H)-one,
5-(2-Methylpropyl)-2-(1'H,3H-spiro[2-benzofuran-1,4'-pip-
eridin]-1'-yl)-1,3-oxazol-4(5H)-one,
5-(4-Chlorobenzyl)-2-(1'H,3H-spiro[2-benzofuran-1,4'-pip-
eridin]-1'-yl)-1,3-oxazol-4(5H)-one,
5-(4-Chlorobenzyl)-5-methyl-2-(1'H,3H-spiro[2-benzo-
furan-1,4'-piperidin]-1'-yl)-1,3-oxazol-4(5H)-one,
5-(But-2-yn-1-yl)-2-(1'H,3H-spiro[2-benzofuran-1,4'-pip-
eridin]-1'-yl)-1,3-oxazol-4(5H)-one,
5-(Cyclohexylmethyl)-5-methyl-2-(1'H,3H-spiro[2-benzo-
furan-1,4'-piperidin]-1'-yl)-1,3-oxazol-4(5H)-one,
5-(Cyclopentylmethyl)-2-(1'H,3H-spiro[2-benzofuran-1,4'-
piperidin]-1'-yl)-1,3-oxazol-4(5H)-one enantiomer A,
5-(Cyclopentylmethyl)-2-(1'H,3H-spiro[2-benzofuran-1,4'-
piperidin]-1'-yl)-1,3-oxazol-4(5H)-one enantiomer B,
5-(Cyclopentylmethyl)-5-methyl-2-(1'H,3H-spiro[2-benzo-
furan-1,4'-piperidin]-1'-yl)-1,3-oxazol-4(5H)-one,
5-(Hydroxy(phenyl)methyl)-2-(1'H,3H-spiro[2-benzofuran-
1,4'-piperidin]-1'-yl)-1,3-oxazol-4(5H)-one diastereomer
a, enantiomer A,
5-(Hydroxy(phenyl)methyl)-2-(1'H,3H-spiro[2-benzofuran-
1,4'-piperidin]-1'-yl)-1,3-oxazol-4(5H)-one diastereomer
a, enantiomer B,
5-(Hydroxy(phenyl)methyl)-2-(1'H,3H-spiro[2-benzofuran-
1,4'-piperidin]-1'-yl)-1,3-oxazol-4(5H)-one diastereomer
b, enantiomer A,
5-(Hydroxy(phenyl)methyl)-2-(1'H,3H-spiro[2-benzofuran-
1,4'-piperidin]-1'-yl)-1,3-oxazol-4(5H)-one diastereomer
b, enantiomer B,
5-(Prop-2-en-1-yl)-2-(1'H,3H-spiro[2-benzofuran-1,4'-pip-
eridin]-1'-yl)-5-[2-(trifluoromethyl)prop-2-en-1-yl]-1,3-
oxazol-4(5H)-one,
5-(Prop-2-en-1-yl)-2-(1'H,3H-spiro[2-benzofuran-1,4'-pip-
eridin]-1'-yl)-1,3-oxazol-4(5H)-one,
5-(Prop-2-en-1-yl)-5-(prop-2-yn-1-yl)-2-(1'H,3H-spiro[2-
benzofuran-1,4'-piperidin]-1'-yl)-1,3-oxazol-4(5H)-one,
5,5-bis(2-Methylprop-2-en-1-yl)-2-(1'H,3H-spiro[2-benzo-
furan-1,4'-piperidin]-1'-yl)-1,3-oxazol-4(5H)-one,
5,5-bis(4-Chlorobenzyl)-2-(1'H,3H-spiro[2-benzofuran-1,
4'-piperidin]-1'-yl)-1,3-oxazol-4(5H)-one,
5,5-Di(but-2-ynyl)-2-(3H-spiro[isobenzofuran-1,4'-piperi-
dine]-1'-yl)oxazol-4(5H)-one,
5,5-Di(prop-2-en-1-yl)-2-(1'H,3H-spiro[2-benzofuran-1,4'-
piperidin]-1'-yl)-1,3-oxazol-4(5H)-one,
5-[(4-Chlorophenyl)(fluoro)methyl]-5-methyl-2-(1'H,3H-
spiro[2-benzofuran-1,4'-piperidin]-1'-yl)-1,3-oxazol-4
(5H)-one,
5-[(4-Chlorophenyl)(hydroxy)methyl]-2-(1'H,3H-spiro[2-
benzofuran-1,4'-piperidin]-1'-yl)-1,3-oxazol-4(5H)-one,
5-[(4-Chlorophenyl)(hydroxy)methyl]-5-methyl-2-(1'H,3H-
spiro[2-benzofuran-1,4'-piperidin]-1'-yl)-1,3-oxazol-4
(5H)-one,
5-[(5-Chlorothiophen-2-yl)methyl]-5-methyl-2-(1'H,3H-
spiro[2-benzofuran-1,4'-piperidin]-1'-yl)-1,3-oxazol-4
(5H)-one,
5-[(6-Chloropyridin-3-yl)methyl]-5-methyl-2-(1'H,3H-
spiro[2-benzofuran-1,4'-piperidin]-1'-yl)-1,3-oxazol-4
(5H)-one,
5-[2-({[tert-Butyl(dimethyl)silyl]oxy}methyl)prop-2-en-1-
yl]-5-(prop-2-en-1-yl)-2-(1'H,3H-spiro[2-benzofuran-1,
4'-piperidin]-1'-yl)-1,3-oxazol-4(5H)-one,
5-[Hydroxy(phenyl)methyl]-5-methyl-2-(1'H,3H-spiro[2-
benzofuran-1,4'-piperidin]-1'-yl)-1,3-oxazol-4(5H)-one,
5-{[4-(Difluoromethyl)phenyl](difluoro)methyl}-5-methyl-
2-(1'H,3H-spiro[2-benzofuran-1,4'-piperidin]-1'-yl)-1,3-
oxazol-4(5H)-one,
5',5'-Difluoro-2-(1'H,3H-spiro[2-benzofuran-1,4'-piperi-
din]-1'-yl)-3',3a',4',5',6',6a'-hexahydro-1'H,4H-spiro[1,3-
oxazole-5,2'-pentalen]-4-one,
5-Allyl-5-(2-fluoroallyl)-2-(3H-spiro[isobenzofuran-1,4'-
piperidine]-1'-yl)oxazol-4(5H)-one,
5-Allyl-5-(2-methylallyl)-2-(1'H,3H-spiro[2-benzofuran-1,
4'-piperidin]-1'-yl)-1,3-oxazol-4(5H)-one,
5-Benzyl-2-(1'H,3H-spiro[2-benzofuran-1,4'-piperidin]-1'-
yl)-1,3-oxazol-4(5H)-one,
5-Benzyl-2-(1'H,3H-spiro[2-benzothiophene-1,4'-piperi-
din]-1'-yl)-1,3-oxazol-4(5H)-one,
5-Benzyl-2-(1'H,5H-spiro[furo[3,4-b]pyridine-7,4'-piperi-
din]-1'-yl)-1,3-oxazol-4(5H)-one,
5-Benzyl-2-(1'H,7H-spiro[furo[3,4-b]pyridine-5,4'-piperi-
din]-1'-yl)-1,3-oxazol-4(5H)-one,
5-Benzyl-2-(2,2-dioxido-1'H,3H-spiro[2-benzothiophene-1,
4'-piperidin]-1'-yl)-1,3-oxazol-4(5H)-one,
5-Benzyl-2-(3,3-dimethyl-1'H,3H-spiro[2-benzofuran-1,4'-
piperidin]-1'-yl)-1,3-oxazol-4(5H)-one,
5-Benzyl-2-(3-methyl-1'H,3H-spiro[2-benzofuran-1,4'-pip-
eridin]-1'-yl)-1,3-oxazol-4(5H)-one, 5-Benzyl-2-(4-fluoro-1'H,3H-spiro[2-benzofuran-1,4'-piperidin]-1'-yl)-1,3-oxazol-4(5H)-one,
5-Benzyl-2-(6-fluoro-1'H,3H-spiro[2-benzofuran-1,4'-piperidin]-1'-yl)-1,3-oxazol-4(5H)-one,
5-Benzyl-2-(7-fluoro-1'H,3H-spiro[2-benzofuran-1,4'-piperidin]-1'-yl)-1,3-oxazol-4(5H)-one,
5-Benzyl-5-ethyl-2-(1'H,3H-spiro[2-benzofuran-1,4'-piperidin]-1'-yl)-1,3-oxazol-4(5H)-one,
5-Butyl-2-(1'H,3H-spiro[2-benzofuran-1,4'-piperidin]-1'-yl)-1,3-oxazol-4(5H)-one,
5-Butyl-5-methyl-2-(1'H,3H-spiro[2-benzofuran-1,4'-piperidin]-1'-yl)-1,3-oxazol-4(5H)-one,
5-Methyl-2-(1'H,3H-spiro[2-benzofuran-1,4'-piperidin]-1'-yl)-5-(tetrahydrofuran-3-ylmethyl)-1,3-oxazol-4(5H)-one diastereomer a,
5-Methyl-2-(1'H,3H-spiro[2-benzofuran-1,4'-piperidin]-1'-yl)-5-(tetrahydrofuran-3-ylmethyl)-1,3-oxazol-4(5H)-one diastereomer b,
5-Methyl-2-(1'H,3H-spiro[2-benzofuran-1,4'-piperidin]-1'-yl)-5-(tetrahydrofuran-2-ylmethyl)-1,3-oxazol-4(5H)-one,
5-Methyl-5-(1-phenylethyl)-2-(1'H,3H-spiro[2-benzofuran-1,4'-piperidin]-1'-yl)-1,3-oxazol-4(5H)-one diastereomer a,
5-Methyl-5-(1-phenylethyl)-2-(1'H,3H-spiro[2-benzofuran-1,4'-piperidin]-1'-yl)-1,3-oxazol-4(5H)-one diastereomer b,
5-Methyl-5-(pentafluorobenzyl)-2-(1'H,3H-spiro[2-benzofuran-1,4'-piperidin]-1'-yl)-1,3-oxazol-4(5H)-one,
5-Methyl-5-(pyrrolidin-1-ylmethyl)-2-(1'H,3H-spiro[2-benzofuran-1,4'-piperidin]-1'-yl)-1,3-oxazol-4(5H)-one,
5-Phenyl-2-(1'H,3H-spiro[2-benzofuran-1,4'-piperidin]-1'-yl)-1,3-oxazol-4(5H)-one,
5-Propyl-2-(1'H,3H-spiro[2-benzofuran-1,4'-piperidin]-1'-yl)-1,3-oxazol-4(5H)-one,
7-({[tert-Butyl(dimethyl)silyl]oxy}methyl)-2-(1'H,3H-spiro[2-benzofuran-1,4'-piperidin]-1'-yl)-1-oxa-3-azaspiro[4.4]nona-2,7-dien-4-one,
7-(Hydroxymethyl)-2-(3H-spiro[isobenzofuran-1,4'-piperidine]-1'-yl)-1-oxa-3-azaspiro[4.4]nona-2,7-dien-4-one,
7,8-Dimethoxy-2-(1'H,3H-spiro[2-benzofuran-1,4'-piperidin]-1'-yl)-1-oxa-3-azaspiro[4.4]non-2-en-4-one diastereomer a,
7,8-Dimethyl-2-(1'H,3H-spiro[2-benzofuran-1,4'-piperidin]-1'-yl)-1-oxa-3-azaspiro[4.4]nona-2,7-dien-4-one,
7-Methyl-2-(1'H,3H-spiro[2-benzofuran-1,4'-piperidin]-1'-yl)-1-oxa-3-azaspiro[4.4]nona-2,7-dien-4-one,
8-(2,2-Difluoroethyl)-2-(1'H,3H-spiro[2-benzofuran-1,4'-piperidin]-1'-yl)-1-oxa-3,8-diazaspiro[4.5]dec-2-en-4-one,
8,8-Difluoro-2-(1'H,3H-spiro[2-benzofuran-1,4'-piperidin]-1'-yl)-1-oxa-3-azaspiro[4.5]dec-2-en-4-one,
8-Benzyl-2-(1'H,3H-spiro[2-benzofuran-1,4'-piperidin]-1'-yl)-1-oxa-3,8-diazaspiro[4.5]dec-2-en-4-one,
8-Pentyl-2-(1'H,3H-spiro[2-benzofuran-1,4'-piperidin]-1'-yl)-1-oxa-3-azaspiro[4.5]dec-2-en-4-one diastereomer a,
8-Pentyl-2-(1'H,3H-spiro[2-benzofuran-1,4'-piperidin]-1'-yl)-1-oxa-3-azaspiro[4.5]dec-2-en-4-one diastereomer b,
Ethyl2-((4-oxo-5-(prop-2-ynyl)-2-(3H-spiro[isobenzofuran-1,4'-piperidine]-1'-yl)-4,5-dihydrooxazol-5-yl)methyl)acrylate,
Ethyl2-{[4-oxo-5-(prop-2-en-1-yl)-2-(1'H,3H-spiro[2-benzofuran-1,4'-piperidin]-1'-yl)-4,5-dihydro-1,3-oxazol-5-yl]methyl}prop-2-enoate,
Ethyl4'-oxo-2'-(1'H,3H-spiro[2-benzofuran-1,4'-piperidin]-1'-yl)-4'H-spiro[bicyclo[3.1.0]hexane-3,5'-[1,3]oxazole]-6-carboxylate diastereomer a,
Ethyl4'-oxo-2'-(1'H,3H-spiro[2-benzofuran-1,4'-piperidin]-1'-yl)-4'H-spiro[bicyclo[3.1.0]hexane-3,5'-[1,3]oxazole]-6-carboxylate diastereomer b,
Ethyl4-oxo-2-(1'H,3H-spiro[2-benzofuran-1,4'-piperidin]-1'-yl)-1-oxa-3-azaspiro[4.4]nona-2,7-diene-7-carboxylate,
tert-Butyl4'-oxo-2'-(1'H,3H-spiro[2-benzofuran-1,4'-piperidin]-1'-yl)-1,5-dihydro-4'H-spiro[2-benzazepine-4,5'-[1,3]oxazole]-2(3H)-carboxylate, and
tert-Butyl4-oxo-2-(1'H,3H-spiro[2-benzofuran-1,4'-piperidin]-1'-yl)-1-oxa-3,8-diazaspiro[4.5]dec-2-ene-8-carboxylate,
or pharmaceutically acceptable salts thereof.

A certain embodiment of this invention refers to a compound of formula I as described herein, selected from the group consisting of
(+)-(5R)-5-Benzyl-2-(1'H,3H-spiro[2-benzofuran-1,4'-piperidin]-1'-yl)-1,3-oxazol-4(5H)-one,
(+)-5-(Cyclopentylmethyl)-5-methyl-2-(1'H,3H-spiro[2-benzofuran-1,4'-piperidin]-1'-yl)-1,3-oxazol-4(5H)-one,
(+)-5-Benzyl-5-methyl-2-(1'H,3H-spiro[2-benzofuran-1,4'-piperidin]-1'-yl)-1,3-oxazol-4(5H)-one,
(+)-5-Butyl-2-(1'H,3H-spiro[2-benzofuran-1,4'-piperidin]-1'-yl)-1,3-oxazol-4(5H)-one,
1'-[5-Benzyl-4-oxo-4,5-dihydro-1,3-oxazol-2-yl]-3H-spiro[2-benzofuran-1,4'-piperidin]-3-one enantiomer B,
1'-[5-(Cyclopentylmethyl)-4-oxo-4,5-dihydro-1,3-oxazol-2-yl]-3H-spiro[2-benzofuran-1,4'-piperidin]-3-one enantiomer A,
2-(1'H,3H-Spiro[2-benzofuran-1,4'-piperidin]-1'-yl)-7-(trifluoromethyl)-1-oxa-3-azaspiro[4.4]nona-2,7-dien-4-one,
2'-(2,2-Dioxido-1'H,3H-spiro[2-benzothiophene-1,4'-piperidin]-1'-yl)-1,3-dihydro-4'H-spiro[indene-2,5'-[1,3]oxazol]-4'-one,
2'-(1'H,3H-Spiro[2-benzofuran-1,4'-piperidin]-1'-yl)-1,2,3,5-tetrahydro-4'H-spiro[2-benzazepine-4,5'-[1,3]oxazol]-4'-one,
2-Methyl-2'-(1'H,3H-spiro[2-benzofuran-1,4'-piperidin]-1'-yl)-1,2,3,5-tetrahydro-4'H-spiro[2-benzazepine-4,5'-[1,3]oxazol]-4'-one,
5-(Cyclopentylmethyl)-2-(1'H,3H-spiro[2-benzofuran-1,4'-piperidin]-1'-yl)-1,3-oxazol-4(5H)-one enantiomer A,
5-(Cyclopentylmethyl)-5-methyl-2-(1'H,3H-spiro[2-benzofuran-1,4'-piperidin]-1'-yl)-1,3-oxazol-4(5H)-one,
5-Benzyl-2-(1'H,3H-spiro[2-benzofuran-1,4'-piperidin]-1'-yl)-1,3-oxazol-4(5H)-one,
5-Benzyl-2-(1'H,5H-spiro[furo[3,4-b]pyridine-7,4'-piperidin]-1'-yl)-1,3-oxazol-4(5H)-one,
5-Benzyl-2-(3,3-dimethyl-1'H,3H-spiro[2-benzofuran-1,4'-piperidin]-1'-yl)-1,3-oxazol-4(5H)-one,
5-Benzyl-2-(3-methyl-1'H,3H-spiro[2-benzofuran-1,4'-piperidin]-1'-yl)-1,3-oxazol-4(5H)-one,
5-Butyl-2-(1'H,3H-spiro[2-benzofuran-1,4'-piperidin]-1'-yl)-1,3-oxazol-4(5H)-one, and
8,8-Difluoro-2-(1'H,3H-spiro[2-benzofuran-1,4'-piperidin]-1'-yl)-1-oxa-3-azaspiro[4.5]dec-2-en-4-one.

A certain embodiment of this invention refers to a compound of formula I as described herein, whenever prepared by a process as defined herein.

A certain embodiment of this invention refers to a compound of formula I as described herein for use as therapeutically active substance.

A certain embodiment of this invention refers to a compound of formula I as described herein for the use as therapeutically active substance for the therapeutic and/or prophylactic treatment of diseases and disorders which are associated with V1a receptor antagonism.

A certain embodiment of this invention refers to a compound of formula I as described herein for the use as therapeutically active substance acting peripherally and centrally in the conditions of inappropriate secretion of vasopressin, anxiety, depressive disorders, obsessive compulsive disorder, autistic spectrum disorders, schizophrenia, aggressive behavior and phase shift sleep disorders, in particular jetlag.

A certain embodiment of this invention refers to a pharmaceutical composition comprising a compound of formula I as described herein and a pharmaceutically acceptable carrier and/or a pharmaceutically acceptable auxiliary substance.

A certain embodiment of this invention refers to the use of a compound of formula I as described herein for the manufacture of a medicament for acting peripherally and centrally in the conditions of inappropriate secretion of vasopressin, anxiety, depressive disorders, obsessive compulsive disorder, autistic spectrum disorders, schizophrenia, aggressive behavior and phase shift sleep disorders, in particular jetlag.

A certain embodiment of this invention refers to a method for the use of a compound as described herein, which is acting peripherally and centrally in the conditions of inappropriate secretion of vasopressin, anxiety, depressive disorders, obsessive compulsive disorder, autistic spectrum disorders, schizophrenia, aggressive behavior and phase shift sleep disorders, in particular jetlag, which method comprises administering said compound of formula I to a human being or animal.

Furthermore, the invention includes all optical isomers, i.e. diastereoisomers, diastereomeric mixtures, racemic mixtures, all their corresponding enantiomers and/or tautomers as well as their solvates of the compounds of formula I.

The compounds of formula I can contain one or more asymmetric centers and can therefore occur as racemates, racemic mixtures, single enantiomers, diastereomeric mixtures and individual diastereomers. Additional asymmetric centers can be present depending upon the nature of the various substituents on the molecule. Each such asymmetric centre will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations can be achieved as known in the art by appropriate modification of the methodology disclosed herein. Their absolute stereochemistry can be determined by the x-ray crystallography of crystalline products or crystalline intermediates which are derivatized, if necessary, with a reagent containing an asymmetric centre of known absolute configuration. If desired, racemic mixtures of the compounds can be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

Compounds of formula 1 can be prepared according to the following processes.

Compounds of formula (I) can be prepared according to the following processes. The processes are described in more detail with the following general schemes A to N and general procedures I to XI.

Scheme 1: General scheme A

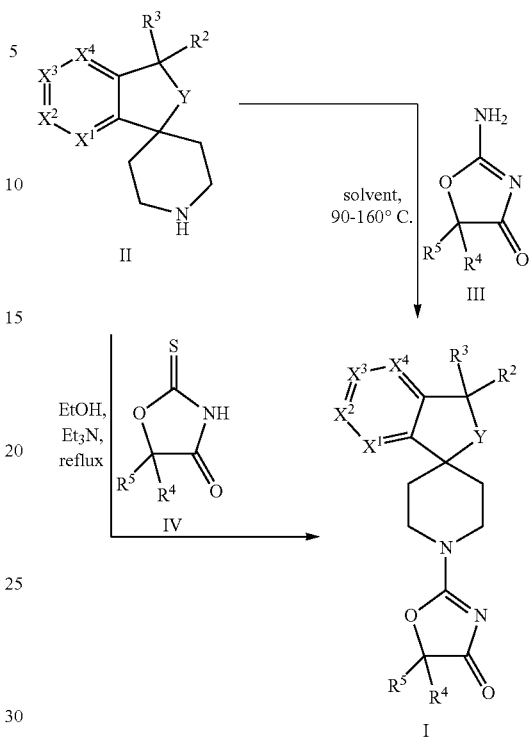

Compounds of formula (I) can be prepared by thermal condensation of a secondary amine of formula (II) and an 2-amino-oxazol-4-one of formula (III). Secondary amines of formula (II) are either commercially available or can be prepared by methods known in the art or described hereinafter in the general schemes M and N. 2-Amino-oxazol-4-ones of formula (III) can be prepared by methods known in the art or described hereinafter in the general scheme H. Compounds of formula (I) can alternatively be prepared by thermal condensation of a secondary amine of formula (II) and a 2-thioxo-oxazolidin-4-one of formula (IV). 2-Thioxo-oxazolidin-4-ones of formula (IV) are either commercially available or prepared as described hereinafter in the general scheme I. General scheme A is hereinafter further illustrated by the general procedure VI.

Scheme 2: General scheme B

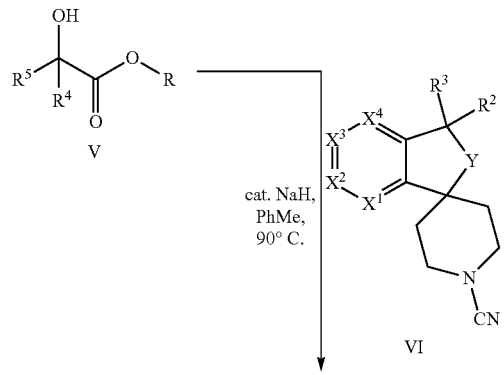

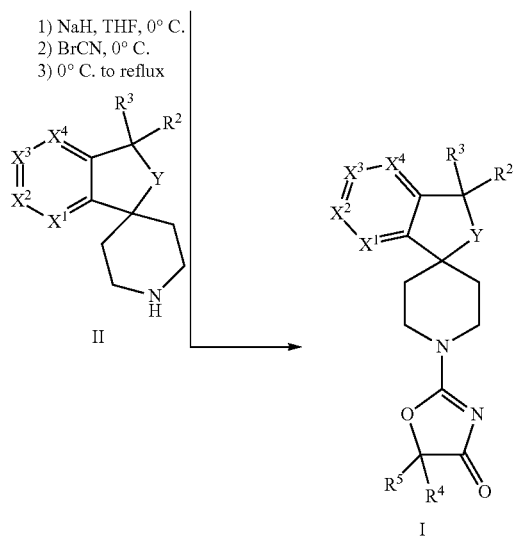

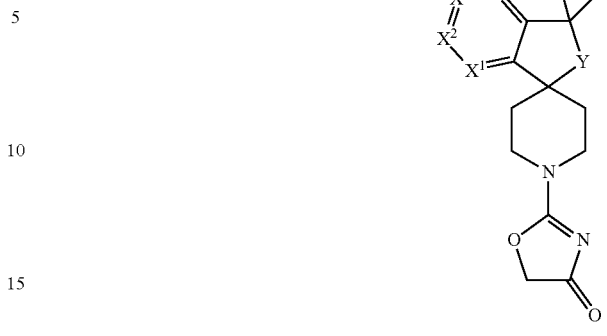

Compounds of formula (I) can be prepared by thermal condensation of a secondary cyanamide of formula (VI) and an alpha-hydroxy ester intermediate of formula (V) in a solvent such as toluene at 90° C. using a catalytic amount of a base such sodium hydride. Cyanamides of formula (VI) can be obtained by methods and from starting materials well known in the art e.g., by treatment of a compound of formula (II) with cyanogen bromide in a solvent such as ethanol or acetonitrile using an organic base such as triethylamine or an inorganic base such as sodium bicarbonate. Compounds of formula (I) can alternatively be prepared in a one pot procedure by stepwise treatment of an alpha-hydroxy ester of formula (V) with a base such as sodium hydride and cyanogen bromide at 0-5° C., followed by treatment of the intermediate with a secondary amine of formula (II) at 0° C. to reflux. The synthesis of intermediates of formula (V) is outlined in general schemes hereinafter. General scheme B is hereinafter further illustrated by the general procedures VII and VIII.

Compounds of formula (VIII) can be prepared by reaction of a secondary amine of formula (II) and chloroacetyl isocyanate (VII) in dichloromethane and subsequent treatment of the urea-intermediate with 1,8-diazabicyclo[5.4.0]undec-7-ene in tetrahydrofuran at room temperature.

Scheme 4: General scheme D

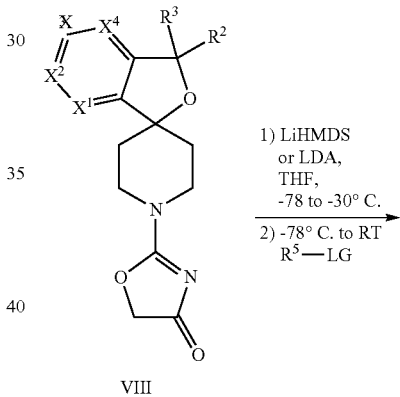

Scheme 3: General scheme C

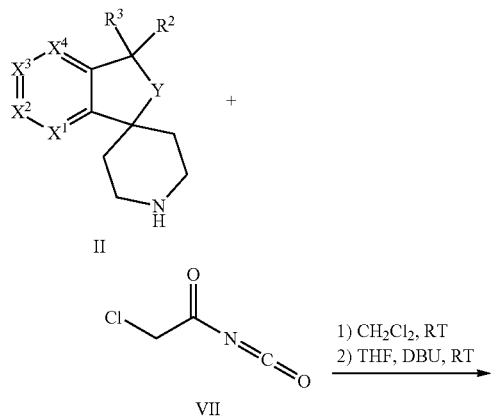

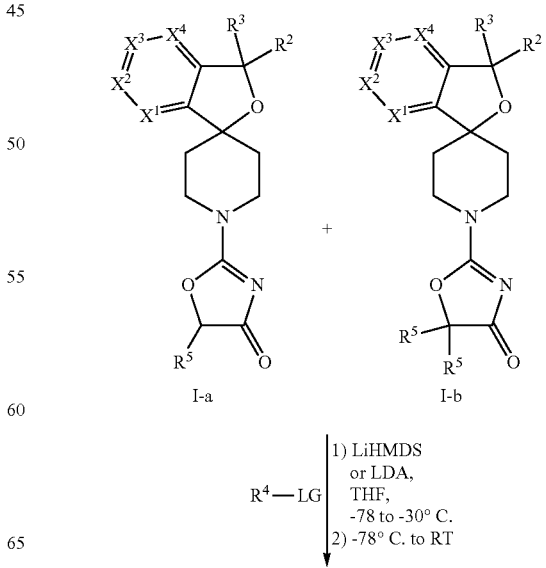

-continued

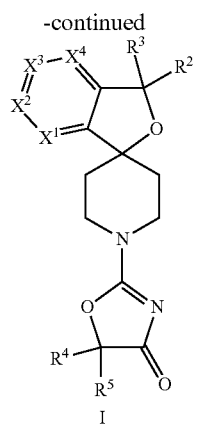

I

Compounds of formula (I) can alternatively be prepared from compounds of formula (I-a) according to methods known in the art, e.g. by consecutively treating a compound of formula (I-a) with an organic base such as lithium diisopropylamide or lithium bis(trimethylsilyl)amide and an electrophilic reactant $R^4$-LG (wherein LG is a leaving group like halide or sulfonate) which is either commercially available or easily prepared according to methods and starting materials well known in the art. Compounds of formula (I-a) and (I-b) are obtained according to methods known in the art, e.g. by consecutive treatment of a compound of formula (VIII) with an organic base such as lithium diisopropylamide or lithium bis(trimethylsilyl)amide and an electrophilic reactant $R^5$-LG (wherein LG is a leaving group like halide or sulfonate) which is either commercially available or easily prepared according to methods and starting materials well known in the art. General scheme D is hereinafter further illustrated by the general procedure IX.

Scheme 5: General scheme E

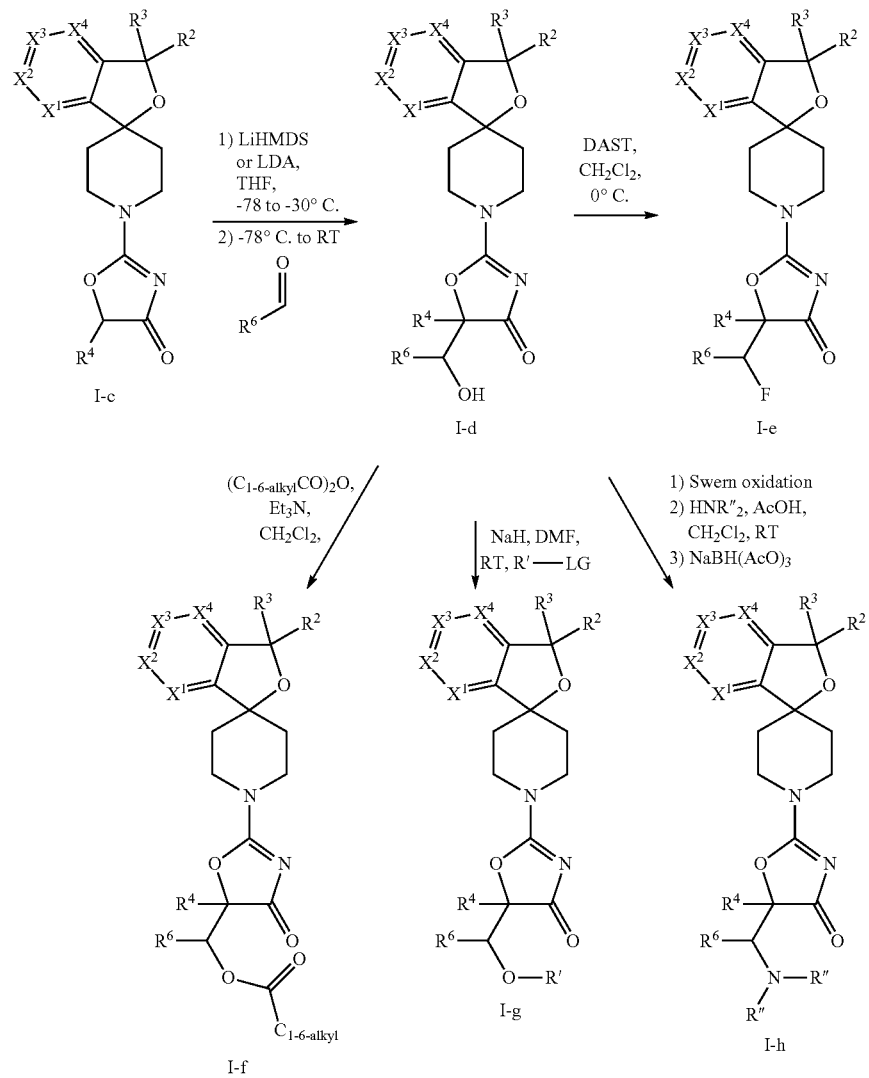

$R^6$ = aryl, optionally substituted by $C_{1-6}$-alkyl, halogen-$C_{1-6}$-alkyl or halogen
$R'$ = $C_{1-6}$-alkyl
$HNR''_2$ = cyclic secondary amine, e.g. pyrrolidine Compounds of formula (I-d) can be obtained by treatment a compound of formula (I-c) with an organic base such as lithium diisopropylamide or lithium bis(trimethylsilyl)amide and condensation of an aldehyde which is either commercially available or easily prepared according to methods and starting materials well known in the art. Compounds of formula (I-e) are prepared by treatment of compounds of formula (I-d) with a fluorinating reagent such as diethylaminosulfur trifluoride or [bis(2-methoxyethyl)amino]sulfur trifluoride in dichloromethane. Compounds of formula (I-f) are prepared by treatment of compounds of formula (I-d) with an activated acid derivative such as an acid anhydride or an acid chloride in a solvent such as dichloromethane using a standard base such triethylamine and a catalytical amount of 4-(N,N-dimethylamino)-pyridine. Compounds of formula (I-g) are prepared by treatment of compounds of formula (I-d) with sodium hydride in a solvent such as N,N-dimethylformamide, followed by alkylation with an electrophilic reactant R'-LG (wherein LG is a leaving group like halide or sulfonate) which is either commercially available or easily prepared according to methods and starting materials well known in the art. Compounds of formula (I-h) are prepared as described hereinafter: Swern oxidation of a compound of formula (I-d) with oxalyl chloride and dimethylsulfoxide in dichloromethane at −55° C. to −78° C. gives rise to an oxo-intermediate. Reductive alkylation of the oxo-intermediate by methods well known in the art, e.g. by treatment with an amine in a solvent such as dichloromethane and a catalyst such as acetic acid and reduction of the iminium intermediate with a reducing agent such as sodium triacetoxyborohydride gives a compound of formula (I-h). General scheme E is hereinafter further illustrated by the general procedure X.

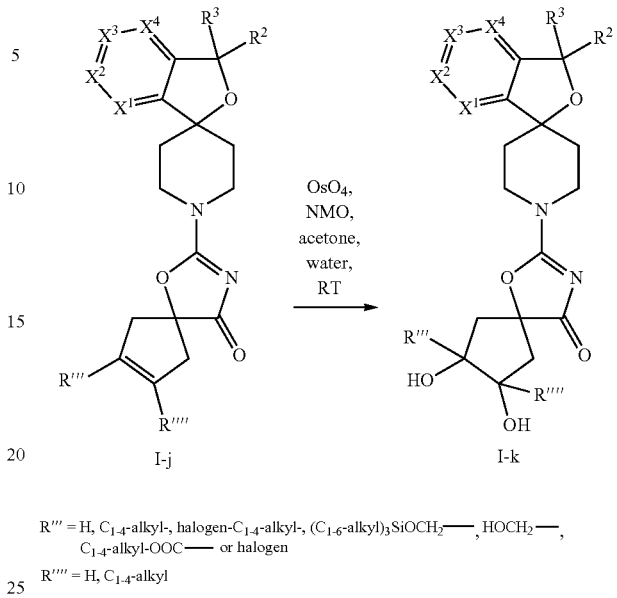

$R''' =$ H, $C_{1-4}$-alkyl-, halogen-$C_{1-4}$-alkyl-, $(C_{1-6}$-alkyl$)_3$SiOCH$_2$—, HOCH$_2$—, $C_{1-4}$-alkyl-OOC— or halogen $R'''' =$ H, $C_{1-4}$-alkyl Compounds of formula (I-j) can be prepared by ring closing metathesis of a compound of formula (I-i) with a Grubbs II catalyst in a solvent such as dichloromethane between room temperature and reflux. Compounds of formula (I-i) with R''' and R'''' equal H can be further transformed into compounds of formula (I-k) by the methods well known in the art, e.g. cis-dihydroxylation with osmium (VIII) tetraoxide and N-methylmorpholine-N-oxide in acetone/water mixtures at room temperature. General scheme F is hereinafter further illustrated by the general procedure XI.

Scheme 6: General scheme F

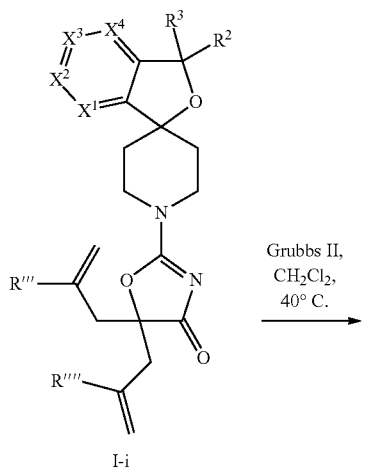

Scheme 7: General scheme G

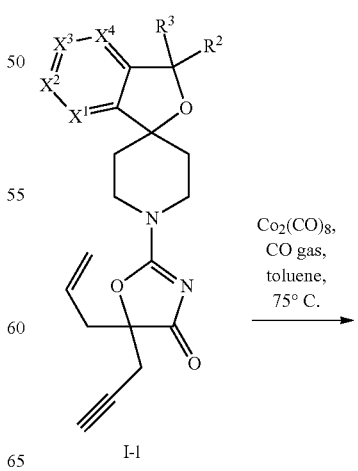

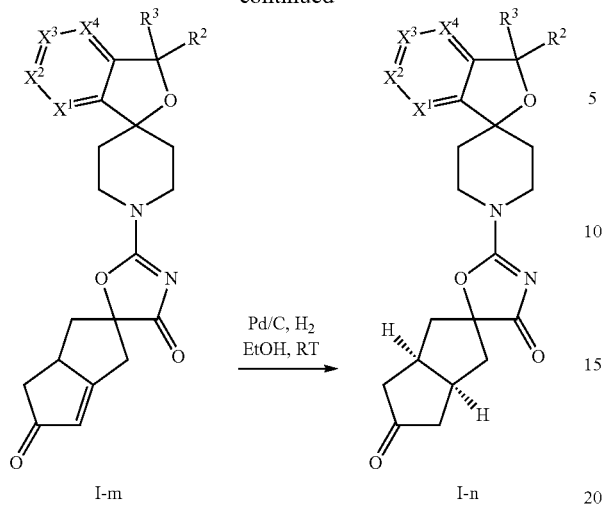

Compounds of formula (I-m) can be prepared by cyclization of a compound of formula (I-l) with carbon monoxide in a solvent such as toluene at 75° C. in the presence of a catalyst such as dicobalt octacarbonyl. Compounds of formula (I-m) can be further transformed into compounds of formula (I-n) by methods well known in the art, e.g. by palladium-catalyzed hydrogenolytic reduction.

Scheme 8: General scheme H

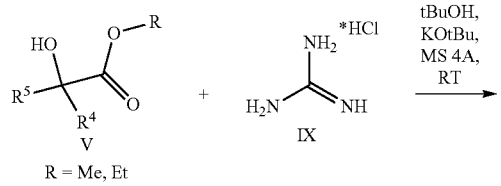

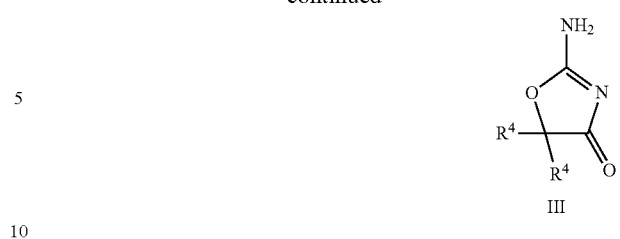

2-Amino-oxazol-4-one intermediates of formula (III) can be prepared by cyclization of an alpha-hydroxy ester of formula (V) with guanidinium hydrochloride (IX) in an alcohol such as tert-butanol using a base such as potassium tert-butoxide and a drying agent such as molecular sieves 4 A. General scheme H is hereinafter further illustrated by the general procedure V.

Scheme 9: General scheme I

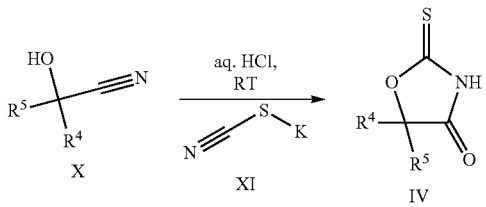

2-Thioxo-oxazolidin-4-one intermediates of formula (IV) can be prepared by treatment of a cyanohydrin intermediate of formula (X) which is either commercially available or easily prepared according to methods and starting materials well known in the art, with potassium rhodanide (XI) under aqueous acidic conditions.

Scheme 10: General Scheme J

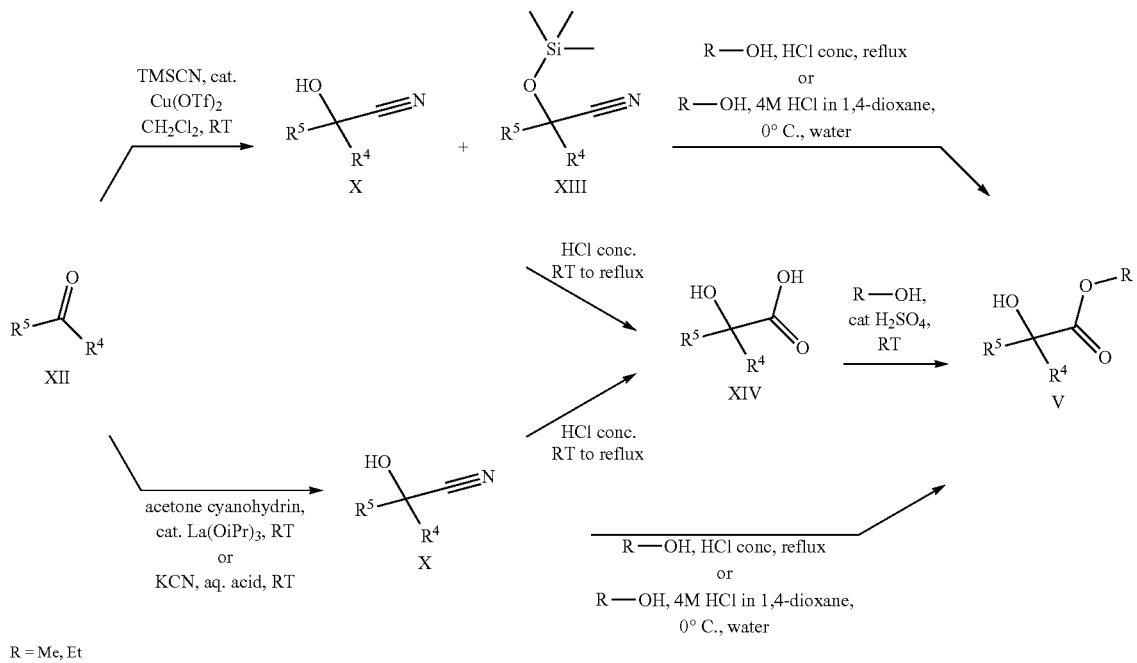

Alpha-hydroxy ester intermediates of formula (V) can be prepared by treatment of cyanohydrin intermediates of formula (X), (XIII) or a mixture of both, which are commercially available or prepared according to methods and starting materials well known in the art, under standard conditions like stirring in a mixture of an alcohol like methanol or ethanol and concentrated hydrochloric acid. Alternatively, intermediates of formula (V) can be obtained by treatment of a compound of formula (X), (XIII) or a mixture of both under Pinner conditions followed by treatment of the imidate intermediate with water. Cyanohydrins of formula (X) and (XIII) can be prepared by methods and starting materials well known in the art, e.g. by treating a ketone of formula (XII) with trimethylsilyl cyanide in dichloromethane at room temperature using a catalyst such as copper(II) triflate. Alternatively intermediates of formula (X) can be prepared by treating a ketone of formula (XII) with acetone cyanohydrin in a solvent such as tetrahydrofuran at room temperature using a catalyst such as lanthanum(III) triisopropoxide or with hydrogen cyanide, which can be prepared in situ from a cyanide salt such as potassium or sodium cyanide and an acid such as hydrochloric acid. Alpha-hydroxy acid intermediates of formula (XIV) can be prepared by treating a cyanohydrin of formula (X), (XIII) or a mixture of both in an acid such as concentrated hydrochloric acid. Alpha-hydroxy ester intermediates of formula (V) can be prepared by treatment of an alpha-hydroxy acid intermediate of formula (XIV) by esterification in an alcohol such as methanol or ethanol and a catalytic amount of an acid such as concentrated sulfuric acid. General scheme J is hereinafter further illustrated by general procedures I to IV.

Scheme 11: General Scheme K

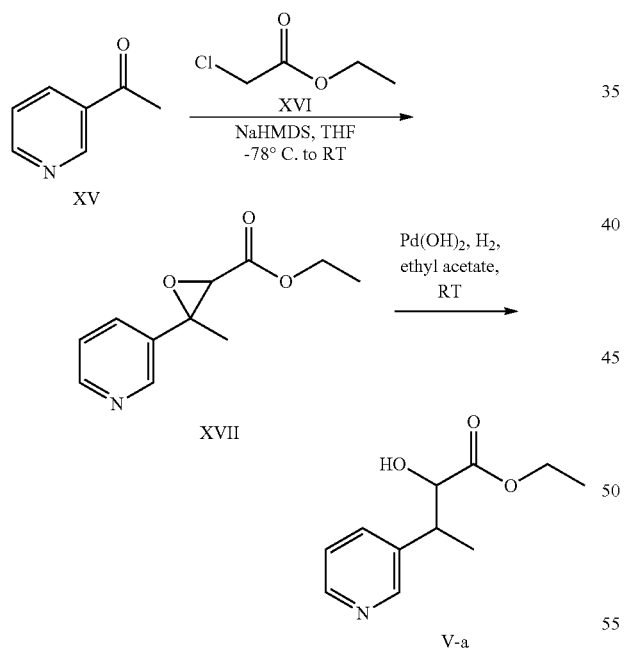

The alpha-hydroxy ester intermediate of formula (V-a) can be obtained by treatment of an epoxide intermediate of formula (XVII) under hydrogenolytic conditions, e.g. using hydrogen gas in the presence of palladium hydroxide in a solvent such as ethyl acetate. The epoxide intermediate of formula (XVII) can be obtained by treatment of ethyl chloro acetate (XVI) with a base such as sodium bis(trimethylsilyl) amide followed by the addition of 1-(pyridin-3-yl)ethanone (XV) in a solvent such as tetrahydrofuran at −78° C. to room temperature.

Scheme 12: General Scheme L

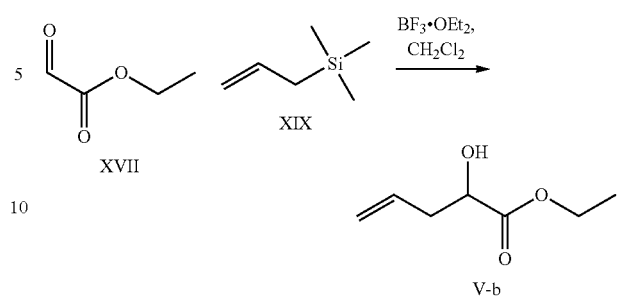

The alpha-hydroxy ester intermediate of formula (V-b) can be prepared by a Sakurai reaction of ethyl 2-oxoacetate (XVIII) with allyltrimethylsilane (XIX) in dichloromethane at reflux using borontrifluoride etherate complex.

Scheme 13: General Scheme M

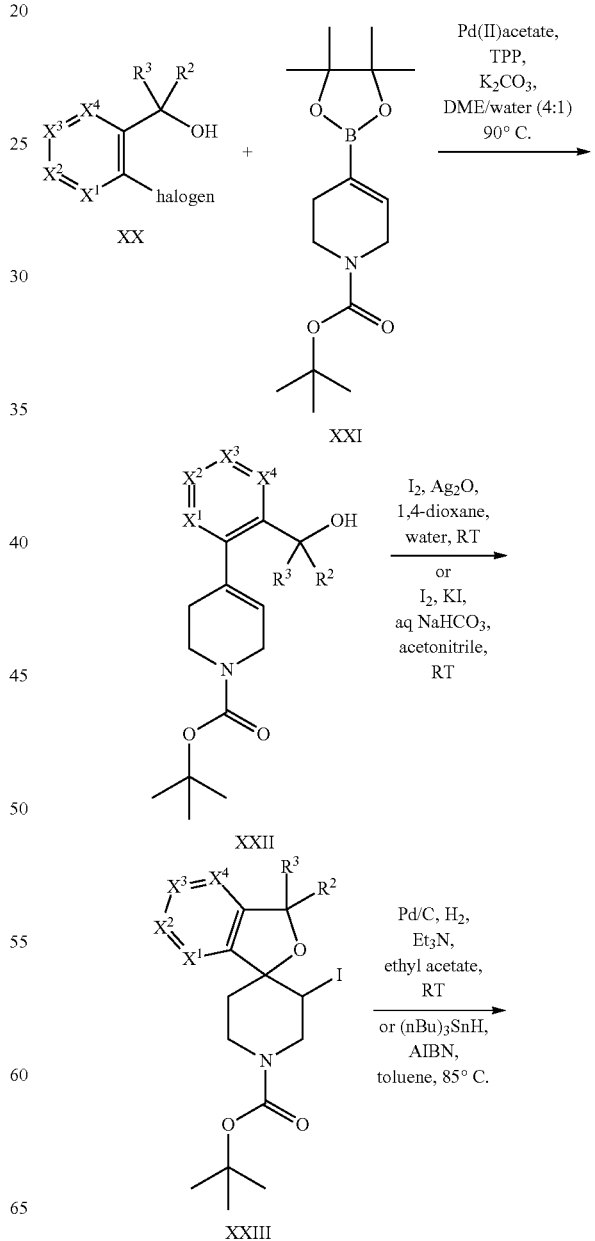

-continued

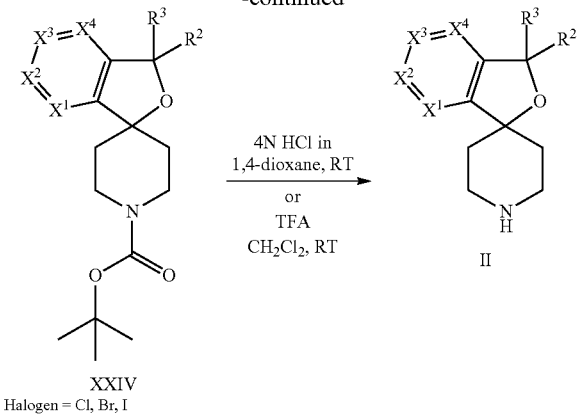

XXIV
Halogen = Cl, Br, I

Amine intermediates of formula (II) can be prepared as described hereinafter: Cross coupling of an aromatic halide of formula (XX), which is commercially available or prepared by methods known in the art, with boronic acid ester of formula (XXI) in the presence of a palladium catalyst, e.g. formed in situ from palladium acetate and triphenylphosphine, and an inorganic base such as potassium carbonate gives a tetrahydropyridine derivative of formula (XXII). Compounds of formula (XXII) can be cyclized with iodine and silver(I) oxide in a 1,4-dioxane/water mixture or with iodine and potassium iodide in a water/acetonitrile mixture to give spiro iodo-piperidines of formula (XXIII). Compounds of formula (XXIV) can be obtained under hydrogenolytic conditions, e.g. using hydrogen gas in the presence of palladium on charcoal and an organic base such as triethyl amine, or using tri-n-butyltin hydride and a radical starter such as azobisisobutyronitrile. N—BOC-deprotection of compounds of formula (XXIV) under acidic conditions, e.g. hydrogen chloride in 1,4-dioxane or trifluoroacetic acid in dichloromethane, gives amine intermediates of formula (II).

Scheme 14: General Scheme N

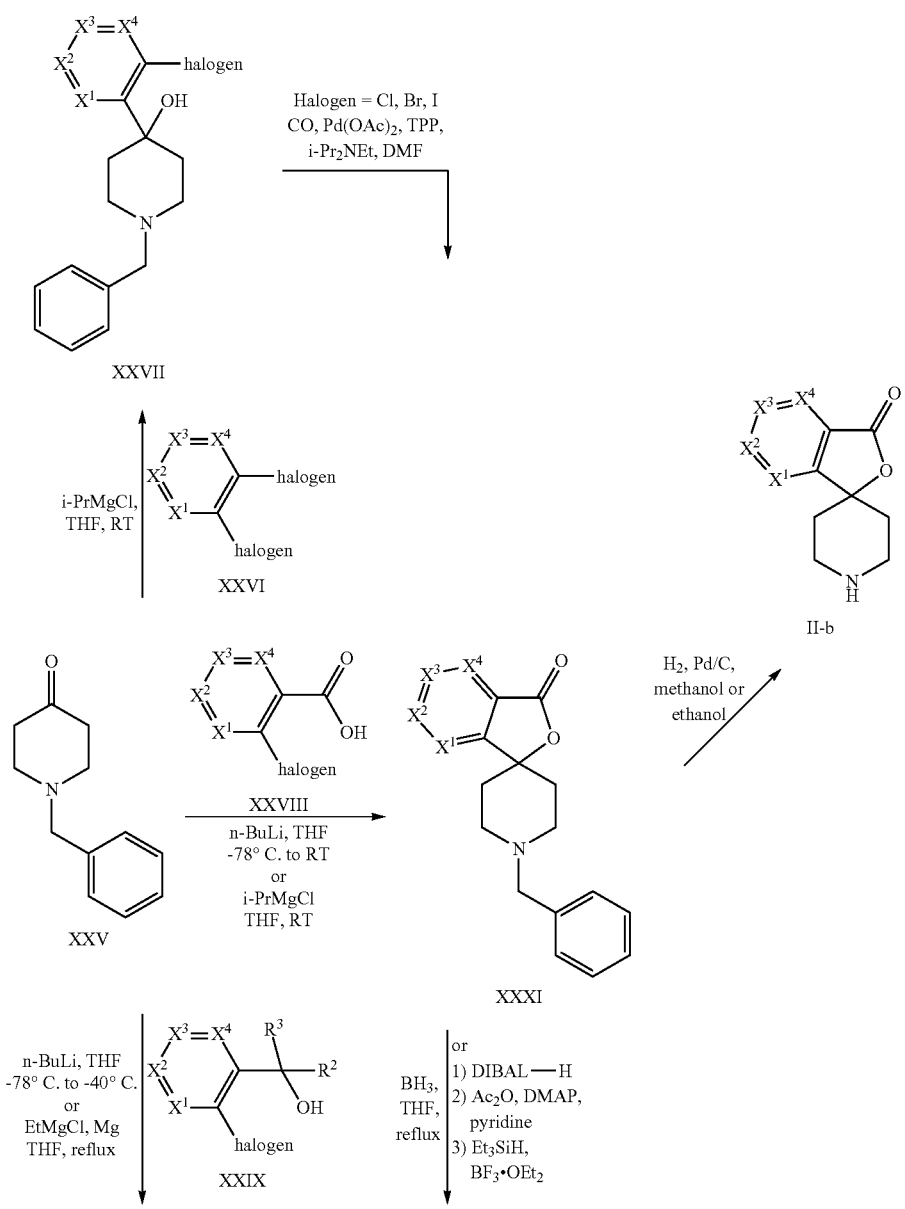

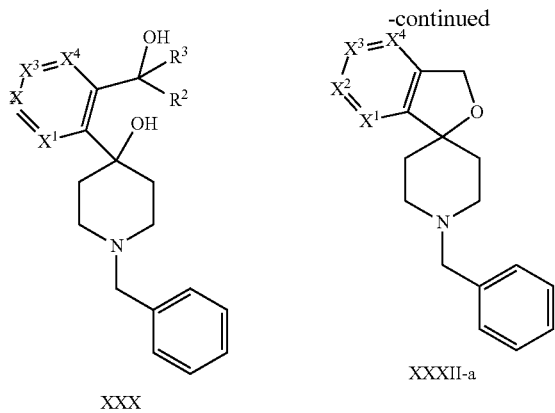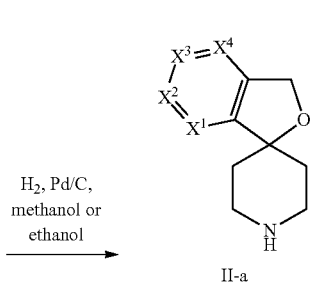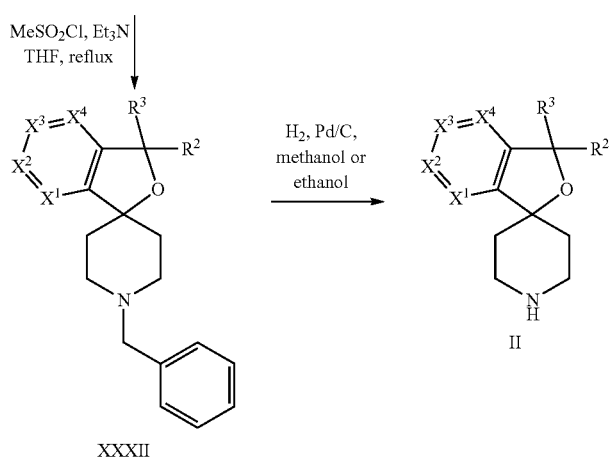

Amine intermediates of formulas (II), (II-a) and (II-b) can be prepared as described hereinafter: Double-lithiation of an o-halo-carboxylic acid derivative of formula (XXVIII) via O-deprotonation and bromine-lithium exchange with an alkyllithium reagent and subsequent addition to N-benzyl piperidone (XXV) leads to a spirolactone derivative of formula (XXXI). Compounds of formula (XXXI) can be reduced either directly with borane or using a stepwise procedure by consecutive treatment with diisopropylaluminum hydride, acetic anhydride in the presence of pyridine and 4-N,N-dimethylaminopyridine, and triethylsilane in the presence of boron trifluoride to yield compounds of formula (XXXII). Double-metallation of a compound of formula (XXIX), which is commercially available or prepared by methods known in the art, via O-deprotonation and bromine-metal exchange with magnesium, or a Grignard or alkyllithium reagent, and subsequent addition to N-benzylpiperidone (XXV) leads to a diol derivative of formula (XXX). Cyclization of the diol derivatives of formula (XXX) with methanesulfonyl chloride using a base such as triethylamine leads to spiro derivatives of formula (XXXII). Treatment of compounds of formula (XXVI), which are commercially available or prepared by methods known in the art, with isopropyl magnesium chloride leads to the formation of a Grignard reagent which is added to the carbonyl moiety of 1-benzyl-4-piperidone (XXV) to form compounds of formula (XXVII). Treatment of a compound of formula (XXVII) with carbon monoxide in the presence of a palladium catalyst e.g. formed in situ from palladium acetate and triphenylphosphine, and an amine base gives spirolactone compounds of formula (XXXI). Amine derivatives of formulas (II), (II-a) and (II-b) are obtained by palladium-catalyzed hydrogenolytic N-debenzylation of compounds of formulas (XXXI), (XXXII) and (XXXII-a), respectively.

The corresponding pharmaceutically acceptable salts with acids can be obtained by standard methods known to the person skilled in the art, e.g. by dissolving the compound of formula I in a suitable solvent such as e.g. dioxane or THF and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilization.

Insofar as their preparation is not described in the examples, the compounds of formula I as well as all intermediate products can be prepared according to analogous methods or according to the methods set forth herein. Starting materials are commercially available, known in the art or can be prepared by methods known in the art or in analogy thereto.

It will be appreciated that the compounds of general formula I in this invention can be derivatised at functional groups to provide derivatives which are capable of conversion back to the parent compound in vivo.

Pharmacological Tests

The human V1a receptor was cloned by RT-PCR from total human liver RNA. The coding sequence was subcloned in an expression vector after sequencing to confirm the identity of the amplified sequence. To demonstrate the affinity of the compounds from the present invention to the human V1a receptor binding studies were performed. Cell membranes were prepared from HEK293 cells transiently transfected with the expression vector and grown in 20 liter fermenters with the following protocol.

50 g of cells are re-suspended in 30 ml freshly prepared ice cold Lysis buffer (50 mM HEPES, 1 mM EDTA, 10 mM $MgCl_2$ adjusted to pH=7.4+complete cocktail of protease inhibitor (Roche Diagnostics)). Homogenized with Polytron for 1 min and sonicated on ice for 2×2 minutes at 80% intensity (Vibracell sonicator). The preparation is centrifuged 20 min at 500 g at 4° C., the pellet is discarded and the supernatant centrifuged 1 hour at 43'000 g at 4° C. (19'000 rpm). The pellet is re-suspended in 12.5 ml Lysis buffer+12.5 ml Sucrose 20% and homogenized using a Polytron for 1-2 min. The protein concentration is determined by the Bradford method and aliquots are stored at −80° C. until use. For binding studies 60 mg Yttrium silicate SPA beads (Amersham) are mixed with an aliquot of membrane in binding buffer (50 mM Tris, 120 mM NaCl, 5 mM KCl, 2 mM $CaCl_2$, 10 mM $MgCl_2$) for 15 minutes with mixing. 50 µl of bead/membrane mixture is then added to each well of a 96 well plate, followed by 50 µl of 4 nM 3H-Vasopressin (American Radiolabeled Chemicals). For total binding measurement 100 µl of binding buffer are added to the respective wells, for non-specific binding 100 µl of 8.4 mM cold vasopressin and for compound testing 100 µl of a serial dilution of each compound in 2% DMSO. The plate is incubated 1 h at room temperature, centrifuged 1 min at 1000 g and counted on a Packard Top-Count. Non-specific binding counts are subtracted from each well and data is normalized to the maximum specific binding set at 100%. To calculate an IC 50 the curve is fitted using a non-linear regression model (XLfit) and the $K_i$ is calculated using the Cheng-Prussoff equation.

The following representative data show the antagonistic activity against human $V_{1a}$ receptor of compounds according to present invention:

TABLE 1 pKi values of selected examples

| Ex. | Structure | Name | $pK_i$ $hV_{1a}$ |
|---|---|---|---|
| 1 | 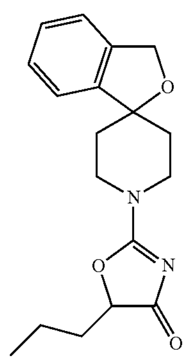 [SMILES: CCCC1OC(N2CCC3(CC2)OCc2ccccc23)=NC1=O] | 5-Propyl-2-(1'H,3H-spiro[2-benzofuran-1,4'-piperidin]-1'-yl)-1,3-oxazol-4(5H)-one | 7.1 |
| 2 | 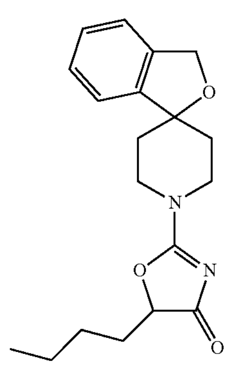 [SMILES: CCCCC1OC(N2CCC3(CC2)OCc2ccccc23)=NC1=O] | 5-Butyl-2-(1'H,3H-spiro[2-benzofuran-1,4'-piperidin]-1'-yl)-1,3-oxazol-4(5H)-one | 8.3 |

TABLE 1-continued pKi values of selected examples

| Ex. | Structure | Name | pK$_i$ hV$_{1a}$ |
|---|---|---|---|
| 3 | 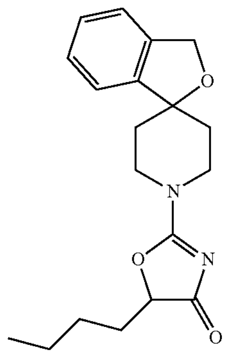 [SMILES: CCCCC1OC(N2CCC3(CC2)OCc2ccccc23)=NC1=O] | (−)-5-Butyl-2-(1'H,3H-spiro[2-benzofuran-1,4'-piperidin]-1'-yl)-1,3-oxazol-4(5H)-one | 7.3 |
| 4 | 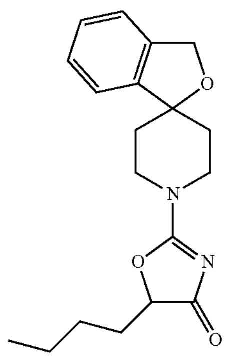 [SMILES: CCCCC1OC(N2CCC3(CC2)OCc2ccccc23)=NC1=O] | (+)-5-Butyl-2-(1'H,3H-spiro[2-benzofuran-1,4'-piperidin]-1'-yl)-1,3-oxazol-4(5H)-one | 8.3 |
| 5 | 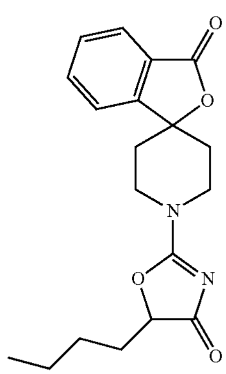 [SMILES: CCCCC1OC(N2CCC3(CC2)OC(=O)c2ccccc23)=NC1=O] | 1'-[5-Butyl-4-oxo-4,5-dihydro-1,3-oxazol-2-yl]-3H-spiro[2-benzofuran-1,4'-piperidin]-3-one enantiomer A | 6.6 |
| 6 | 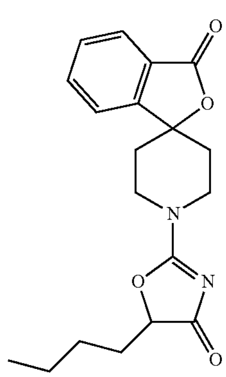 [SMILES: CCCCC1OC(N2CCC3(CC2)OC(=O)c2ccccc23)=NC1=O] | 1'-[5-Butyl-4-oxo-4,5-dihydro-1,3-oxazol-2-yl]-3H-spiro[2-benzofuran-1,4'-piperidin]-3-one enantiomer B | 7.7 |

TABLE 1-continued pKi values of selected examples

| Ex. | Structure | Name | pK$_i$ hV$_{1a}$ |
|---|---|---|---|
| 7 | 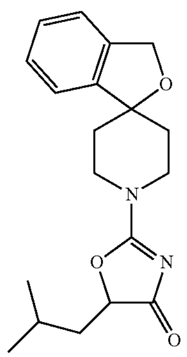 [SMILES: CC(C)CC1OC(N2CCC3(CC2)OCc2ccccc23)=NC1=O] | 5-(2-Methylpropyl)-2-(1'H,3H-spiro[2-benzofuran-1,4'-piperidin]-1'-yl)-1,3-oxazol-4(5H)-one | 7.7 |
| 8 | 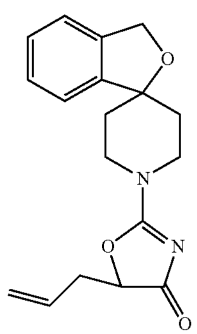 [SMILES: C=CCC1OC(N2CCC3(CC2)OCc2ccccc23)=NC1=O] | 5-(Prop-2-en-1-yl)-2-(1'H,3H-spiro[2-benzofuran-1,4'-piperidin]-1'-yl)-1,3-oxazol-4(5H)-one | 6.8 |
| 9 | 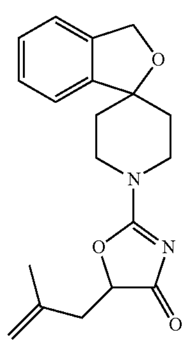 [SMILES: C=C(C)CC1OC(N2CCC3(CC2)OCc2ccccc23)=NC1=O] | 5-(2-Methylprop-2-en-1-yl)-2-(1'H,3H-spiro[2-benzofuran-1,4'-piperidin]-1'-yl)-1,3-oxazol-4(5H)-one | 8.7 |
| 10 | 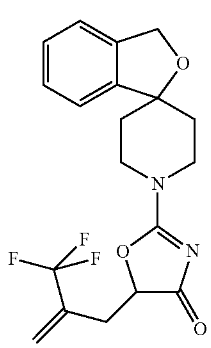 [SMILES: C=C(CC1OC(N2CCC3(CC2)OCc2ccccc23)=NC1=O)C(F)(F)F] | 2-(1'H,3H-Spiro[2-benzofuran-1,4'-piperidin]-1'-yl)-5-[2-(trifluoromethyl)prop-2-en-1-yl]-1,3-oxazol-4(5H)-one | 8.4 |

TABLE 1-continued pKi values of selected examples

| Ex. | Structure | Name | pK$_i$ hV$_{1a}$ |
|---|---|---|---|
| 11 | 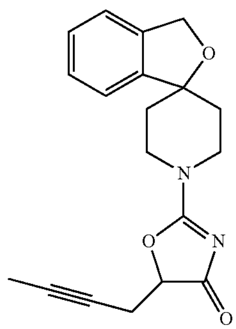 [SMILES: CC#CCC1OC(N2CCC3(CC2)OCc2ccccc23)=NC1=O] | 5-(But-2-yn-1-yl)-2-(1'H,3H-spiro[2-benzofuran-1,4'-piperidin]-1'-yl)-1,3-oxazol-4(5H)-one | 7.3 |
| 12 | 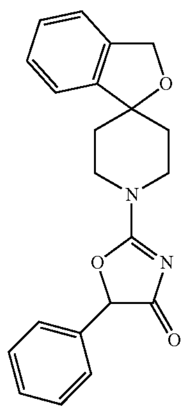 [SMILES: O=C1N=C(N2CCC3(CC2)OCc2ccccc23)OC1c1ccccc1] | 5-Phenyl-2-(1'H,3H-spiro[2-benzofuran-1,4'-piperidin]-1'-yl)-1,3-oxazol-4(5H)-one | 6.5 |
| 13 | 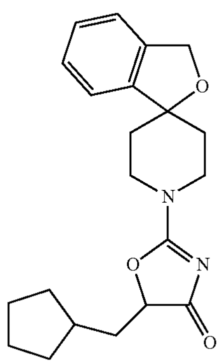 [SMILES: O=C1N=C(N2CCC3(CC2)OCc2ccccc23)OC1CC1CCCC1] | 5-(Cyclopentylmethyl)-2-(1'H,3H-spiro[2-benzofuran-1,4'-piperidin]-1'-yl)-1,3-oxazol-4(5H)-one enantiomer A | 9.1 |
| 14 | 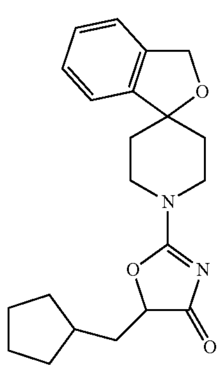 [SMILES: O=C1N=C(N2CCC3(CC2)OCc2ccccc23)OC1CC1CCCC1] | 5-(Cyclopentylmethyl)-2-(1'H,3H-spiro[2-benzofuran-1,4'-piperidin]-1'-yl)-1,3-oxazol-4(5H)-one enantiomer B | 8.6 |

TABLE 1-continued pKi values of selected examples

| Ex. | Structure | Name | pK$_i$ hV$_{1a}$ |
|---|---|---|---|
| 15 | 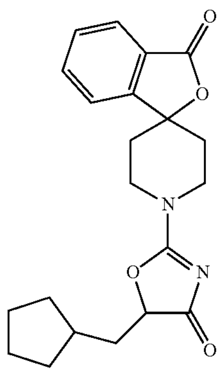 [SMILES: O=C1OC2(CCN(C3=NC(=O)C(CC4CCCC4)O3)CC2)c2ccccc21] | 1'-[5-(Cyclopentylmethyl)-4-oxo-4,5-dihydro-1,3-oxazol-2-yl]-3H-spiro[2-benzofuran-1,4'-piperidin]-3-one enantiomer A | 8.6 |
| 16 | 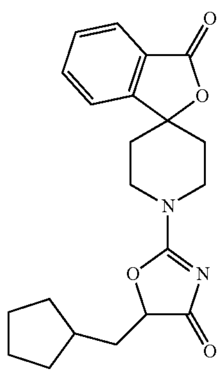 [SMILES: O=C1OC2(CCN(C3=NC(=O)C(CC4CCCC4)O3)CC2)c2ccccc21] | 1'-[5-(Cyclopentylmethyl)-4-oxo-4,5-dihydro-1,3-oxazol-2-yl]-3H-spiro[2-benzofuran-1,4'-piperidin]-3-one enantiomer B | 7.9 |
| 17 | 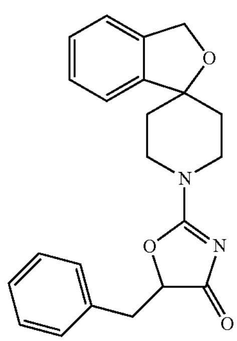 [SMILES: O=C1N=C(N2CCC3(CC2)OCc2ccccc23)OC1Cc1ccccc1] | 5-Benzyl-2-(1'H,3H-spiro[2-benzofuran-1,4'-piperidin]-1'-yl)-1,3-oxazol-4(5H)-one | 8.4 |
| 18 | 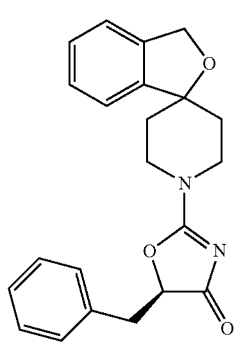 [SMILES: O=C1N=C(N2CCC3(CC2)OCc2ccccc23)O[C@@H]1Cc1ccccc1] | (+)-(5R)-5-Benzyl-2-(1'H,3H-spiro[2-benzofuran-1,4'-piperidin]-1'-yl)-1,3-oxazol-4(5H)-one | 8.8 |

TABLE 1-continued pKi values of selected examples

| Ex. | Structure | Name | pK$_i$ hV$_{1a}$ |
| --- | --- | --- | --- |
| 19 | 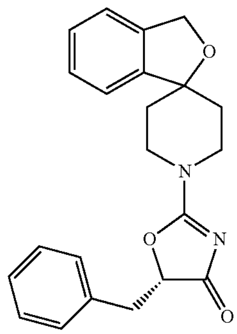 [SMILES: O=C1N=C(N2CCC3(CC2)OCc2ccccc23)O[C@H]1Cc1ccccc1] | (−)-(5S)-5-Benzyl-2-(1'H,3H-spiro[2-benzofuran-1,4'-piperidin]-1'-yl)-1,3-oxazol-4(5H)-one | 7.6 |
| 20 | 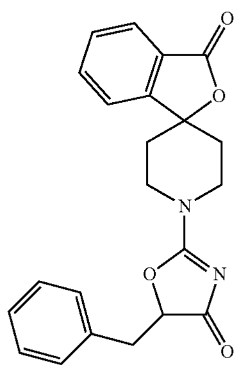 [SMILES: O=C1OC2(CCN(C3=NC(=O)C(Cc4ccccc4)O3)CC2)c2ccccc21] | 1'-[5-Benzyl-4-oxo-4,5-dihydro-1,3-oxazol-2-yl]-3H-spiro[2-benzofuran-1,4'-piperidin]-3-one enantiomer A | 6.6 |
| 21 | 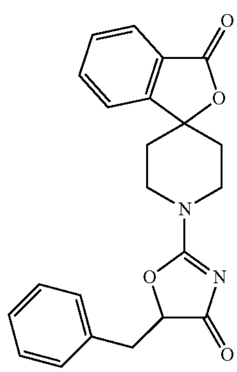 [SMILES: O=C1OC2(CCN(C3=NC(=O)C(Cc4ccccc4)O3)CC2)c2ccccc21] | 1'-[5-Benzyl-4-oxo-4,5-dihydro-1,3-oxazol-2-yl]-3H-spiro[2-benzofuran-1,4'-piperidin]-3-one enantiomer B | 8.3 |
| 22 | 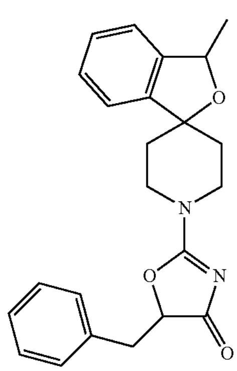 [SMILES: CC1OC2(CCN(C3=NC(=O)C(Cc4ccccc4)O3)CC2)c2ccccc21] | 5-Benzyl-2-(3-methyl-1'H,3H-spiro[2-benzofuran-1,4'-piperidin]-1'-yl)-1,3-oxazol-4(5H)-one | 8.9 |

TABLE 1-continued
pKi values of selected examples
| Ex. | Structure | Name | pK$_i$ hV$_{1a}$ |
|---|---|---|---|
| 23 | 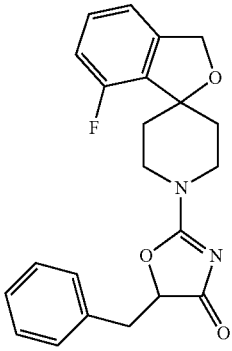 [SMILES: O=C1N=C(N2CCC3(CC2)OCc2cccc(F)c23)OC1Cc1ccccc1] | 5-Benzyl-2-(7-fluoro-1'H,3H-spiro[2-benzofuran-1,4'-piperidin]-1'-yl)-1,3-oxazol-4(5H)-one | 8.6 |
| 24 | 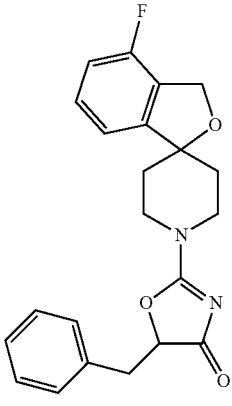 [SMILES: O=C1N=C(N2CCC3(CC2)OCc2c(F)cccc23)OC1Cc1ccccc1] | 5-Benzyl-2-(4-fluoro-1'H,3H-spiro[2-benzofuran-1,4'-piperidin]-1'-yl)-1,3-oxazol-4(5H)-one | 8.2 |
| 25 | 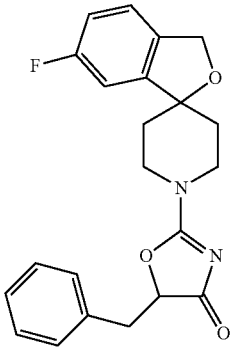 [SMILES: O=C1N=C(N2CCC3(CC2)OCc2ccc(F)cc23)OC1Cc1ccccc1] | 5-Benzyl-2-(6-fluoro-1'H,3H-spiro[2-benzofuran-1,4'-piperidin]-1'-yl)-1,3-oxazol-4(5H)-one | 8.2 |
| 26 | 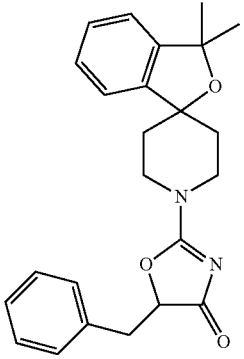 [SMILES: CC1(C)OC2(CCN(C3=NC(=O)C(Cc4ccccc4)O3)CC2)c2ccccc21] | 5-Benzyl-2-(3,3-dimethyl-1'H,3H-spiro[2-benzofuran-1,4'-piperidin]-1'-yl)-1,3-oxazol-4(5H)-one | 9.2 |

TABLE 1-continued pKi values of selected examples

| Ex. | Structure | Name | pK$_i$ hV$_{1a}$ |
|---|---|---|---|
| 27 | 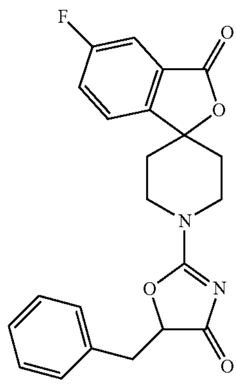 [SMILES: O=C1OC2(CCN(C3=NC(=O)C(Cc4ccccc4)O3)CC2)c2ccc(F)cc21] | 1'-(5-Benzyl-4-oxo-4,5-dihydro-1,3-oxazol-2-yl)-5-fluoro-3H-spiro[2-benzofuran-1,4'-piperidin]-3-one | 7.8 |
| 28 | 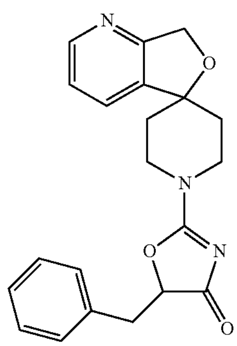 [SMILES: O=C1N=C(N2CCC3(CC2)OCc2ncccc23)OC1Cc1ccccc1] | 5-Benzyl-2-(1'H,7H-spiro[furo[3,4-b]pyridine-5,4'-piperidin]-1'-yl)-1,3-oxazol-4(5H)-one | 7.1 |
| 29 | 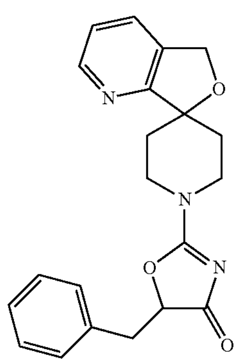 [SMILES: O=C1N=C(N2CCC3(CC2)OCc2cccnc23)OC1Cc1ccccc1] | 5-Benzyl-2-(1'H,5H-spiro[furo[3,4-b]pyridine-7,4'-piperidin]-1'-yl)-1,3-oxazol-4(5H)-one | 8.0 |
| 30 | 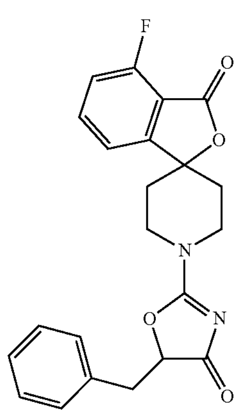 [SMILES: O=C1OC2(CCN(C3=NC(=O)C(Cc4ccccc4)O3)CC2)c2cccc(F)c21] | 1'-(5-Benzyl-4-oxo-4,5-dihydro-1,3-oxazol-2-yl)-4-fluoro-3H-spiro[2-benzofuran-1,4'-piperidin]-3-one | 6.7 |

TABLE 1-continued pKi values of selected examples

| Ex. | Structure | Name | pK$_i$ hV$_{1a}$ |
|---|---|---|---|
| 31 | 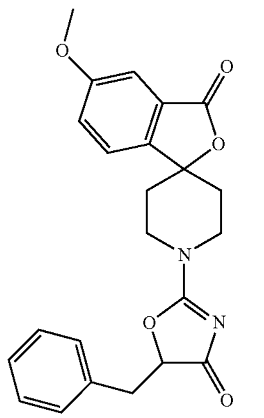 [SMILES: COc1ccc2c(c1)C(=O)OC21CCN(C2=NC(=O)C(Cc3ccccc3)O2)CC1] | 1'-(5-Benzyl-4-oxo-4,5-dihydro-1,3-oxazol-2-yl)-5-methoxy-3H-spiro[2-benzofuran-1,4'-piperidin]-3-one | 7.0 |
| 32 | 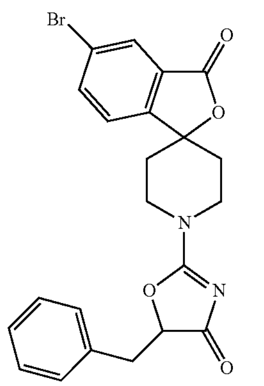 [SMILES: O=C1OC2(CCN(C3=NC(=O)C(Cc4ccccc4)O3)CC2)c2ccc(Br)cc21] | 1'-(5-Benzyl-4-oxo-4,5-dihydro-1,3-oxazol-2-yl)-5-bromo-3H-spiro[2-benzofuran-1,4'-piperidin]-3-one | 7.2 |
| 33 | 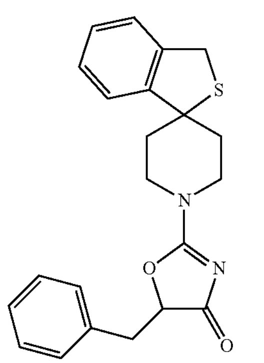 [SMILES: O=C1N=C(N2CCC3(CC2)SCc2ccccc23)OC1Cc1ccccc1] | 5-Benzyl-2-(1'H,3H-spiro[2-benzothiophene-1,4'-piperidin]-1'-yl)-1,3-oxazol-4(5H)-one | 7.9 |
| 34 | 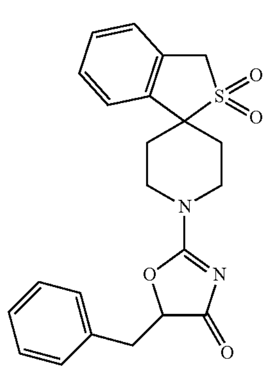 [SMILES: O=C1N=C(N2CCC3(CC2)c2ccccc2CS3(=O)=O)OC1Cc1ccccc1] | 5-Benzyl-2-(2,2-dioxido-1'H,3H-spiro[2-benzothiophene-1,4'-piperidin]-1'-yl)-1,3-oxazol-4(5H)-one | 8.0 |

TABLE 1-continued

| Ex. | Structure | Name | pK$_i$ hV$_{1a}$ |
|---|---|---|---|
| 35 | 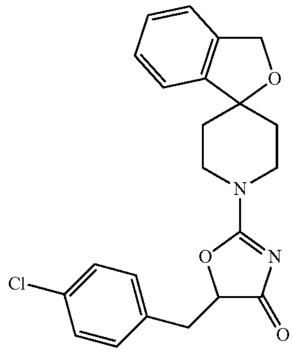 [SMILES: O=C1N=C(N2CCC3(CC2)OCc2ccccc23)OC1Cc1ccc(Cl)cc1] | 5-(4-Chlorobenzyl)-2-(1'H,3H-spiro[2-benzofuran-1,4'-piperidin]-1'-yl)-1,3-oxazol-4(5H)-one | 8.7 |
| 36 | 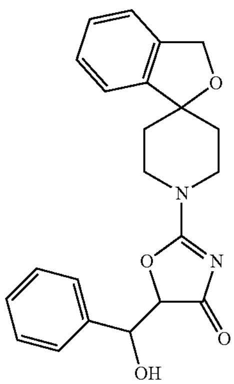 [SMILES: O=C1N=C(N2CCC3(CC2)OCc2ccccc23)OC1C(O)c1ccccc1] | 5-(Hydroxy(phenyl)methyl)-2-(1'H,3H-spiro[2-benzofuran-1,4'-piperidin]-1'-yl)-1,3-oxazol-4(5H)-one diastereomer a, enantiomer A | 7.5 |
| 37 | 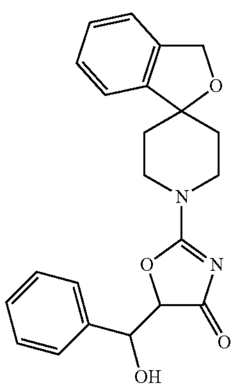 [SMILES: O=C1N=C(N2CCC3(CC2)OCc2ccccc23)OC1C(O)c1ccccc1] | 5-(Hydroxy(phenyl)methyl)-2-(1'H,3H-spiro[2-benzofuran-1,4'-piperidin]-1'-yl)-1,3-oxazol-4(5H)-one diastereomer a, enantiomer B | 6.9 |
| 38 | 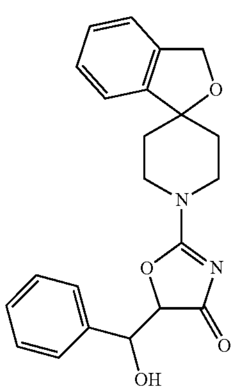 [SMILES: O=C1N=C(N2CCC3(CC2)OCc2ccccc23)OC1C(O)c1ccccc1] | 5-(Hydroxy(phenyl)methyl)-2-(1'H,3H-spiro[2-benzofuran-1,4'-piperidin]-1'-yl)-1,3-oxazol-4(5H)-one diastereomer b, enantiomer A | 6.1 |

TABLE 1-continued pKi values of selected examples

| Ex. | Structure | Name | pK$_i$ hV$_{1a}$ |
|---|---|---|---|
| 39 | 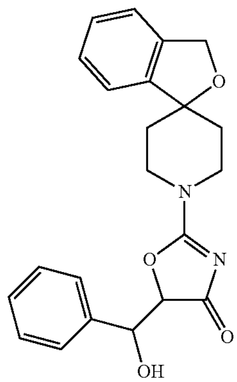 [SMILES: O=C1N=C(N2CCC3(CC2)OCc2ccccc23)OC1C(O)c1ccccc1] | 5-(Hydroxy(phenyl)methyl)-2-(1'H,3H-spiro[2-benzofuran-1,4'-piperidin]-1'-yl)-1,3-oxazol-4(5H)-one diastereomer b, enantiomer B | 6.9 |
| 40 | 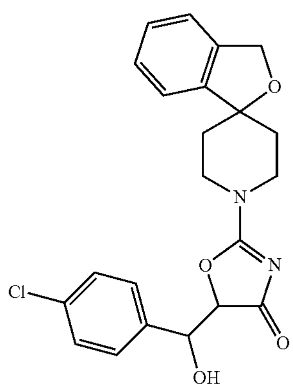 [SMILES: O=C1N=C(N2CCC3(CC2)OCc2ccccc23)OC1C(O)c1ccc(Cl)cc1] | 5-[(4-Chlorophenyl)(hydroxy)methyl]-2-(1'H,3H-spiro[2-benzofuran-1,4'-piperidin]-1'-yl)-1,3-oxazol-4(5H)-one | 8.4 |
| 41 | 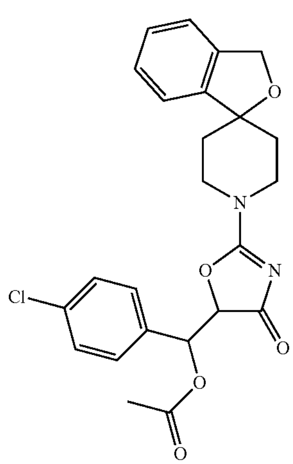 [SMILES: CC(=O)OC(c1ccc(Cl)cc1)C1OC(N2CCC3(CC2)OCc2ccccc23)=NC1=O] | (4-Chlorophenyl)[4-oxo-2-(1'H,3H-spiro[2-benzofuran-1,4'-piperidin]-1'-yl)-4,5-dihydro-1,3-oxazol-5-yl]methyl acetate | 7.5 |

TABLE 1-continued pKi values of selected examples

| Ex. | Structure | Name | pK$_i$ hV$_{1a}$ |
|---|---|---|---|
| 42 | 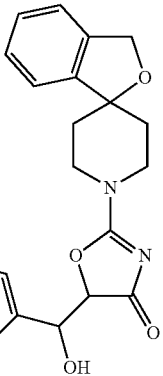 | (−)-5-[(4-Chlorophenyl)(hydroxy)methyl]-2-(1'H,3H-spiro[2-benzofuran-1,4'-piperidin]-1'-yl)-1,3-oxazol-4(5H)-one diastereomer a | 8.5 |
| 43 | 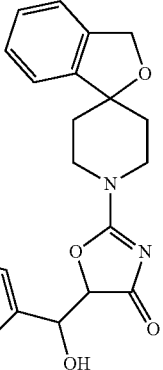 | (+)-5-[(4-Chlorophenyl)(hydroxy)methyl]-2-(1'H,3H-spiro[2-benzofuran-1,4'-piperidin]-1'-yl)-1,3-oxazol-4(5H)-one diastereomer a | 7.8 |
| 44 | 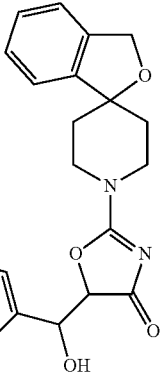 | (−)-5-[(4-Chlorophenyl)(hydroxy)methyl]-2-(1'H,3H-spiro[2-benzofuran-1,4'-piperidin]-1'-yl)-1,3-oxazol-4(5H)-one diastereomer b | 6.9 |
| 45 | 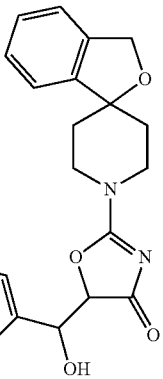 | (+)-5-[(4-Chlorophenyl)(hydroxy)methyl]-2-(1'H,3H-spiro[2-benzofuran-1,4'-piperidin]-1'-yl)-1,3-oxazol-4(5H)-one diastereomer b | 7.8 |

TABLE 1-continued

| pKi values of selected examples |||| 
|---|---|---|---|
| Ex. | Structure | Name | pK$_i$ hV$_{1a}$ |
| 46 | | 5-((4-Chlorophenyl)fluoromethyl)-2-(1'H,3H-spiro[2-benzofuran-1,4'-piperidin]-1'-yl)-1,3-oxazol-4(5H)-one diastereomer a, enantiomer A | 7.5 |
| 47 | | 5-((4-Chlorophenyl)fluoromethyl)-2-(1'H,3H-spiro[2-benzofuran-1,4'-piperidin]-1'-yl)-1,3-oxazol-4(5H)-one diastereomer a, enantiomer B | 7.7 |
| 48 | | 5-((4-Chlorophenyl)fluoromethyl)-2-(1'H,3H-spiro[2-benzofuran-1,4'-piperidin]-1'-yl)-1,3-oxazol-4(5H)-one diastereomer b, enantiomer A | 7.4 |
| 49 | | 5-((4-Chlorophenyl)fluoromethyl)-2-(1'H,3H-spiro[2-benzofuran-1,4'-piperidin]-1'-yl)-1,3-oxazol-4(5H)-one diastereomer b, enantiomer B | 8.7 |

TABLE 1-continued pKi values of selected examples

| Ex. | Structure | Name | pK$_i$ hV$_{1a}$ |
|---|---|---|---|
| 50 | 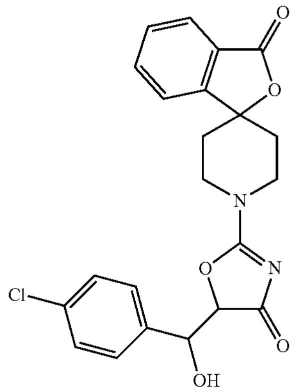 [SMILES: O=C1OC2(CCN(C3=NC(=O)C(C(O)c4ccc(Cl)cc4)O3)CC2)c2ccccc21] | 1'-{-5-[(4-Chlorophenyl)(hydroxy)methyl]-4-oxo-4,5-dihydro-1,3-oxazol-2-yl}-3H-spiro[2-benzofuran-1,4'-piperidin]-3-one diastereomer a, enantiomer A | 7.7 |
| 51 | 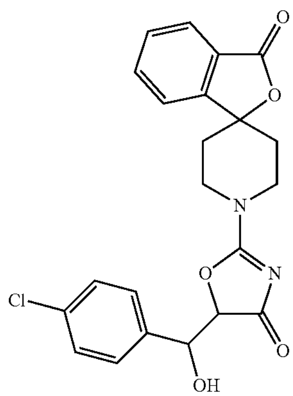 [SMILES: O=C1OC2(CCN(C3=NC(=O)C(C(O)c4ccc(Cl)cc4)O3)CC2)c2ccccc21] | 1'-{-5-[(4-Chlorophenyl)(hydroxy)methyl]-4-oxo-4,5-dihydro-1,3-oxazol-2-yl}-3H-spiro[2-benzofuran-1,4'-piperidin]-3-one diastereomer a, enantiomer B | 6.8 |
| 52 | 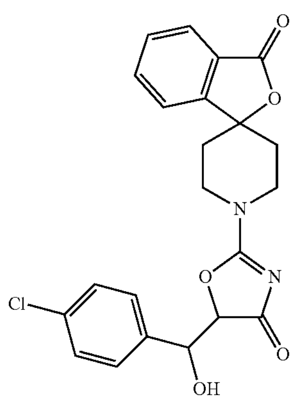 [SMILES: O=C1OC2(CCN(C3=NC(=O)C(C(O)c4ccc(Cl)cc4)O3)CC2)c2ccccc21] | 1'-{-5-[(4-Chlorophenyl)(hydroxy)methyl]-4-oxo-4,5-dihydro-1,3-oxazol-2-yl}-3H-spiro[2-benzofuran-1,4'-piperidin]-3-one diastereomer b, enantiomer A | 6.2 |
| 53 | 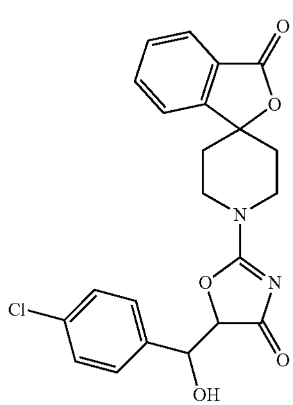 [SMILES: O=C1OC2(CCN(C3=NC(=O)C(C(O)c4ccc(Cl)cc4)O3)CC2)c2ccccc21] | 1'-{-5-[(4-Chlorophenyl)(hydroxy)methyl]-4-oxo-4,5-dihydro-1,3-oxazol-2-yl}-3H-spiro[2-benzofuran-1,4'-piperidin]-3-one diastereomer b, enantiomer B | 6.8 |

TABLE 1-continued pKi values of selected examples

| Ex. | Structure | Name | pK$_i$ hV$_{1a}$ |
|---|---|---|---|
| 54 | 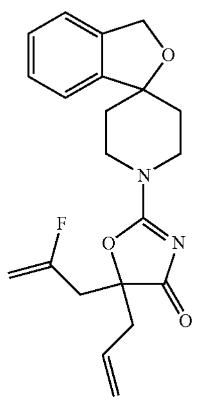 [SMILES: C=CCC1(CC(=C)F)OC(N2CCC3(CC2)OCc2ccccc23)=NC1=O] | 5-Allyl-5-(2-fluoroallyl)-2-(3H-spiro[isobenzofuran-1,4'-piperidine]-1'-yl)oxazol-4(5H)-one | 6.2 |
| 55 | 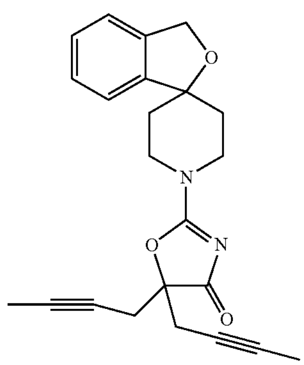 [SMILES: CC#CCC1(CC#CC)OC(N2CCC3(CC2)OCc2ccccc23)=NC1=O] | 5,5-Di(but-2-ynyl)-2-(3H-spiro[isobenzofuran-1,4'-piperidine]-1'-yl)oxazol-4(5H)-one | 8.3 |
| 56 | 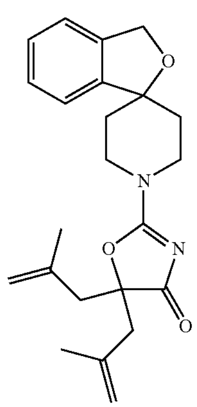 [SMILES: C=C(C)CC1(CC(=C)C)OC(N2CCC3(CC2)OCc2ccccc23)=NC1=O] | 5,5-bis(2-Methylprop-2-en-1-yl)-2-(1'H,3H-spiro[2-benzofuran-1,4'-piperidin]-1'-yl)-1,3-oxazol-4(5H)-one | 7.8 |
| 57 | 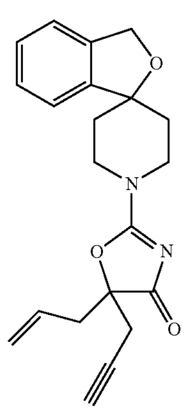 [SMILES: C#CCC1(CC=C)OC(N2CCC3(CC2)OCc2ccccc23)=NC1=O] | 5-(Prop-2-en-1-yl)-5-(prop-2-yn-1-yl)-2-(1'H,3H-spiro[2-benzofuran-1,4'-piperidin]-1'-yl)-1,3-oxazol-4(5H)-one | 7.4 |

TABLE 1-continued pKi values of selected examples

| Ex. | Structure | Name | pK$_i$ hV$_{1a}$ |
|---|---|---|---|
| 58 | 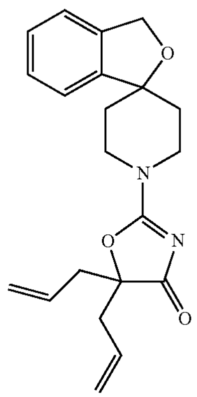 [SMILES: C=CCC1(CC=C)OC(N2CCC3(CC2)OCc2ccccc23)=NC1=O] | 5,5-Di(prop-2-en-1-yl)-2-(1'H,3H-spiro[2-benzofuran-1,4'-piperidin]-1'-yl)-1,3-oxazol-4(5H)-one | 7.3 |
| 59 | 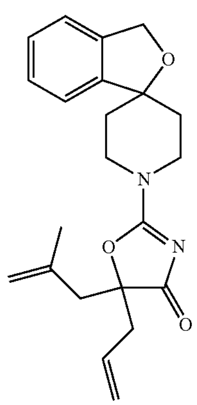 [SMILES: C=CCC1(CC(=C)C)OC(N2CCC3(CC2)OCc2ccccc23)=NC1=O] | 5-Allyl-5-(2-methylallyl)-2-(1'H,3H-spiro[2-benzofuran-1,4'-piperidin]-1'-yl)-1,3-oxazol-4(5H)-one | 8.0 |
| 60 | 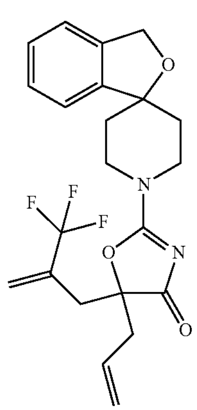 [SMILES: C=CCC1(CC(=C)C(F)(F)F)OC(N2CCC3(CC2)OCc2ccccc23)=NC1=O] | 5-(Prop-2-en-1-yl)-2-(1'H,3H-spiro[2-benzofuran-1,4'-piperidin]-1'-yl)-5-[2-(trifluoromethyl)prop-2-en-1-yl]-1,3-oxazol-4(5H)-one | 7.6 |

TABLE 1-continued pKi values of selected examples

| Ex. | Structure | Name | pK$_i$ hV$_{1a}$ |
|---|---|---|---|
| 61 | 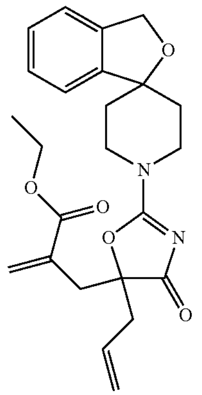 [SMILES: C=CCC1(CC(=C)C(=O)OCC)OC(N2CCC3(CC2)OCc2ccccc23)=NC1=O] | Ethyl 2-{[4-oxo-5-(prop-2-en-1-yl)-2-(1'H,3H-spiro[2-benzofuran-1,4'-piperidin]-1'-yl)-4,5-dihydro-1,3-oxazol-5-yl]methyl}prop-2-enoate | 6.1 |
| 62 | 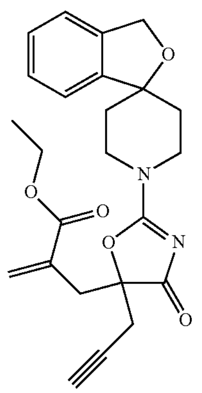 [SMILES: C#CCC1(CC(=C)C(=O)OCC)OC(N2CCC3(CC2)OCc2ccccc23)=NC1=O] | Ethyl 2-((4-oxo-5-(prop-2-ynyl)-2-(3H-spiro[isobenzofuran-1,4'-piperidine]-1'-yl)-4,5-dihydrooxazol-5-yl)methyl)acrylate | 6.2 |
| 63 | 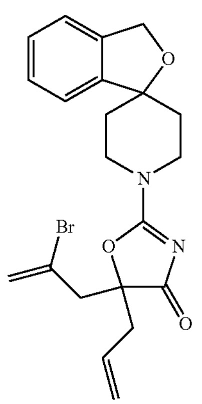 [SMILES: C=CCC1(CC(=C)Br)OC(N2CCC3(CC2)OCc2ccccc23)=NC1=O] | 5-(2-Bromoprop-2-en-1-yl)-5-(prop-2-en-1-yl)-2-(1'H,3H-spiro[2-benzofuran-1,4'-piperidin]-1'-yl)-1,3-oxazol-4(5H)-one | 7.9 |

TABLE 1-continued

| Ex. | Structure | Name | pK$_i$ hV$_{1a}$ |
|---|---|---|---|
| 64 | 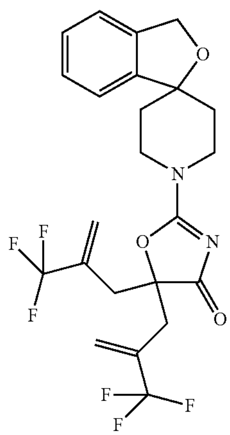 [SMILES: C=C(CC1(CC(=C)C(F)(F)F)OC(N2CCC3(CC2)OCc2ccccc23)=NC1=O)C(F)(F)F] | 2-(3H-Spiro[isobenzofuran-1,4'-piperidine]-1'-yl)-5,5-bis(2-(trifluoromethyl)allyl)oxazol-4(5H)-one | 7.9 |
| 65 | 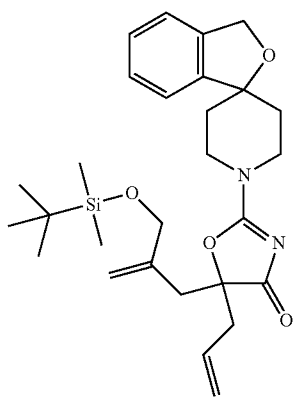 [SMILES: C=CCC1(CC(=C)CO[Si](C)(C)C(C)(C)C)OC(N2CCC3(CC2)OCc2ccccc23)=NC1=O] | 5-[2-({[tert-Butyl(dimethyl)silyl]oxy}methyl)prop-2-en-1-yl]-5-(prop-2-en-1-yl)-2-(1'H,3H-spiro[2-benzofuran-1,4'-piperidin]-1'-yl)-1,3-oxazol-4(5H)-one | 7.2 |
| 66 | 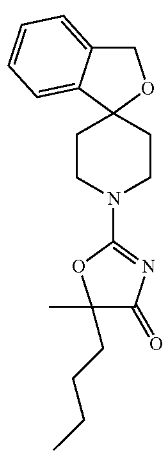 [SMILES: CCCCC1(C)OC(N2CCC3(CC2)OCc2ccccc23)=NC1=O] | 5-Butyl-5-methyl-2-(1'H,3H-spiro[2-benzofuran-1,4'-piperidin]-1'-yl)-1,3-oxazol-4(5H)-one | 7.4 |

TABLE 1-continued pKi values of selected examples

| Ex. | Structure | Name | pK$_i$ hV$_{1a}$ |
|---|---|---|---|
| 67 | 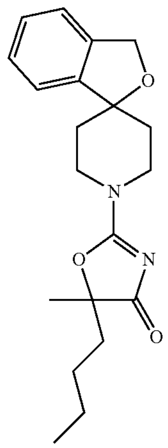 [SMILES: CCCCC1(C)OC(N2CCC3(CC2)OCc2ccccc23)=NC1=O] | (+)-5-Butyl-5-methyl-2-(1'H,3H-spiro[2-benzofuran-1,4'-piperidin]-1'-yl)-1,3-oxazol-4(5H)-one | 7.6 |
| 68 | 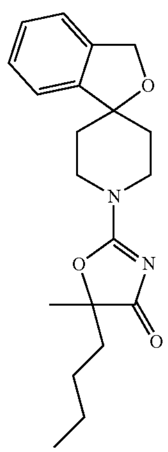 [SMILES: CCCCC1(C)OC(N2CCC3(CC2)OCc2ccccc23)=NC1=O] | (−)-5-Butyl-5-methyl-2-(1'H,3H-spiro[2-benzofuran-1,4'-piperidin]-1'-yl)-1,3-oxazol-4(5H)-one | 6.7 |
| 69 | 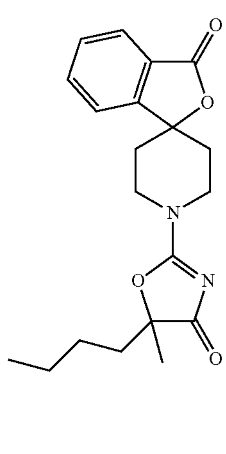 [SMILES: CCCCC1(C)OC(N2CCC3(CC2)OC(=O)c2ccccc23)=NC1=O] | 1'-(5-Butyl-5-methyl-4-oxo-4,5-dihydro-1,3-oxazol-2-yl)-3H-spiro[2-benzofuran-1,4'-piperidin]-3-one | 6.5 |

TABLE 1-continued

| Ex. | Structure | Name | pK$_i$ hV$_{1a}$ |
|---|---|---|---|
| 70 | 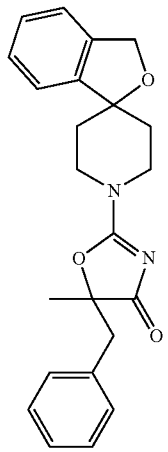 [SMILES: CC1(Cc2ccccc2)OC(N2CCC3(CC2)OCc2ccccc23)=NC1=O] | (+)-5-Benzyl-5-methyl-2-(1'H,3H-spiro[2-benzofuran-1,4'-piperidin]-1'-yl)-1,3-oxazol-4(5H)-one | 8.1 |
| 71 | 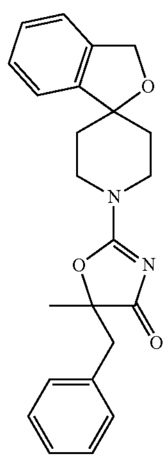 [SMILES: CC1(Cc2ccccc2)OC(N2CCC3(CC2)OCc2ccccc23)=NC1=O] | (−)-5-Benzyl-5-methyl-2-(1'H,3H-spiro[2-benzofuran-1,4'-piperidin]-1'-yl)-1,3-oxazol-4(5H)-one | 7.1 |
| 72 | 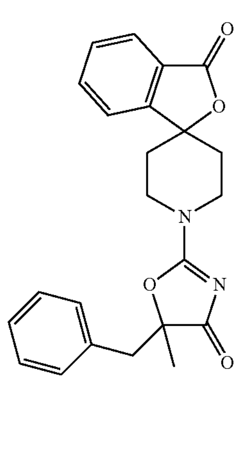 [SMILES: CC1(Cc2ccccc2)OC(N2CCC3(CC2)OC(=O)c2ccccc23)=NC1=O] | 1'-[5-Benzyl-5-methyl-4-oxo-4,5-dihydro-1,3-oxazol-2-yl]-3H-spiro[2-benzofuran-1,4'-piperidin]-3-one enantiomer A | 7.6 |

TABLE 1-continued pKi values of selected examples

| Ex. | Structure | Name | pK$_i$ hV$_{1a}$ |
|---|---|---|---|
| 73 | 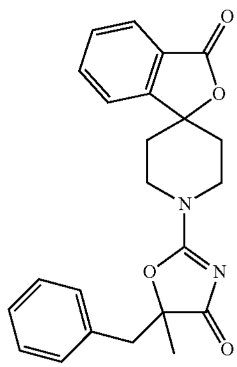 [SMILES: CC1(Cc2ccccc2)OC(N2CCC3(CC2)OC(=O)c2ccccc23)=NC1=O] | 1'-[5-Benzyl-5-methyl-4-oxo-4,5-dihydro-1,3-oxazol-2-yl]-3H-spiro[2-benzofuran-1,4'-piperidin]-3-one enantiomer B | 6.6 |
| 74 | 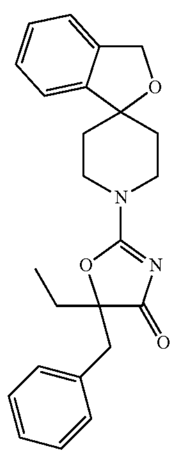 [SMILES: CCC1(Cc2ccccc2)OC(N2CCC3(CC2)OCc2ccccc23)=NC1=O] | 5-Benzyl-5-ethyl-2-(1'H,3H-spiro[2-benzofuran-1,4'-piperidin]-1'-yl)-1,3-oxazol-4(5H)-one | 8.0 |
| 75 | 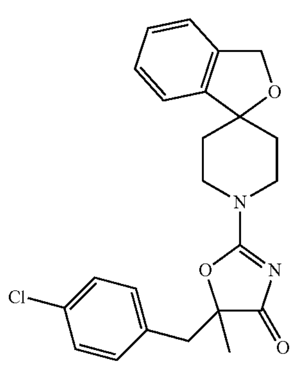 [SMILES: CC1(Cc2ccc(Cl)cc2)OC(N2CCC3(CC2)OCc2ccccc23)=NC1=O] | 5-(4-Chlorobenzyl)-5-methyl-2-(1'H,3H-spiro[2-benzofuran-1,4'-piperidin]-1'-yl)-1,3-oxazol-4(5H)-one | 8.4 |

TABLE 1-continued pKi values of selected examples

| Ex. | Structure | Name | pK$_i$ hV$_{1a}$ |
|---|---|---|---|
| 76 | 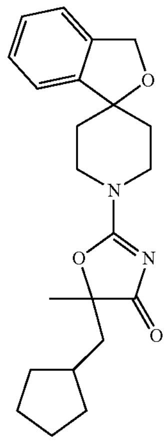 | 5-(Cyclopentylmethyl)-5-methyl-2-(1'H,3H-spiro[2-benzofuran-1,4'-piperidin]-1'-yl)-1,3-oxazol-4(5H)-one | 8.3 |
| 77 | 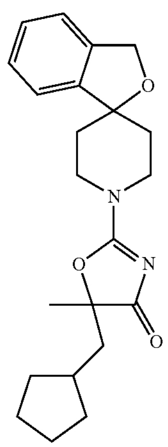 [SMILES: CC1(CC2CCCC2)OC(N2CCC3(CC2)OCc2ccccc23)=NC1=O] | (+)-5-(Cyclopentylmethyl)-5-methyl-2-(1'H,3H-spiro[2-benzofuran-1,4'-piperidin]-1'-yl)-1,3-oxazol-4(5H)-one | 8.6 |
| 78 | 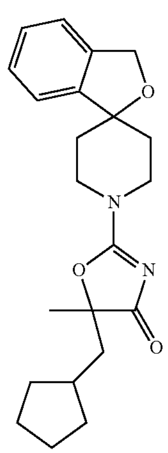 [SMILES: CC1(CC2CCCC2)OC(N2CCC3(CC2)OCc2ccccc23)=NC1=O] | (−)-5-(Cyclopentylmethyl)-5-methyl-2-(1'H,3H-spiro[2-benzofuran-1,4'-piperidin]-1'-yl)-1,3-oxazol-4(5H)-one | 7.0 |

TABLE 1-continued pKi values of selected examples

| Ex. | Structure | Name | pK$_i$ hV$_{1a}$ |
|---|---|---|---|
| 79 | 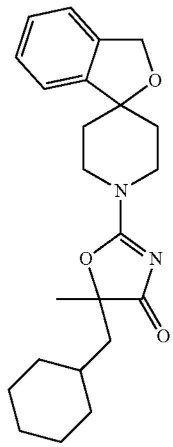 [SMILES: CC1(CC2CCCCC2)OC(N2CCC3(CC2)OCc2ccccc23)=NC1=O] | 5-(Cyclohexylmethyl)-5-methyl-2-(1'H,3H-spiro[2-benzofuran-1,4'-piperidin]-1'-yl)-1,3-oxazol-4(5H)-one | 7.7 |
| 80 | 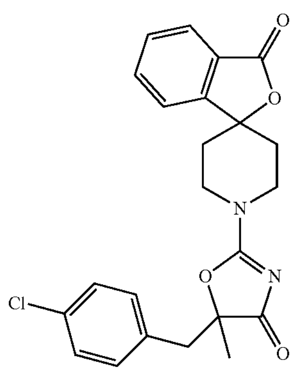 [SMILES: CC1(Cc2ccc(Cl)cc2)OC(N2CCC3(CC2)OC(=O)c2ccccc23)=NC1=O] | 1'-[5-(4-Chlorobenzyl)-5-methyl-4-oxo-4,5-dihydro-1,3-oxazol-2-yl]-3H-spiro[2-benzofuran-1,4'-piperidin]-3-one enantiomer A | 7.7 |
| 81 | 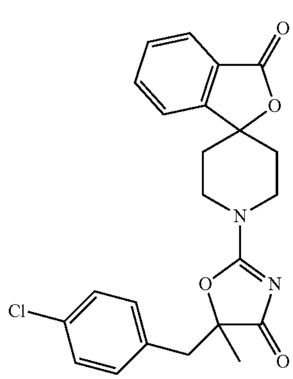 [SMILES: CC1(Cc2ccc(Cl)cc2)OC(N2CCC3(CC2)OC(=O)c2ccccc23)=NC1=O] | 1'-[5-(4-Chlorobenzyl)-5-methyl-4-oxo-4,5-dihydro-1,3-oxazol-2-yl]-3H-spiro[2-benzofuran-1,4'-piperidin]-3-one enantiomer B | 6.3 |

TABLE 1-continued pKi values of selected examples

| Ex. | Structure | Name | pK$_i$ hV$_{1a}$ |
|---|---|---|---|
| 82 | 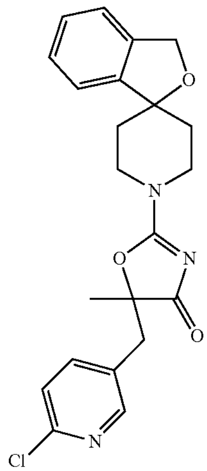 [SMILES: CC1(Cc2ccc(Cl)nc2)OC(N2CCC3(CC2)OCc2ccccc23)=NC1=O] | 5-[(6-Chloropyridin-3-yl)methyl]-5-methyl-2-(1'H,3H-spiro[2-benzofuran-1,4'-piperidin]-1'-yl)-1,3-oxazol-4(5H)-one | 7.3 |
| 83 | 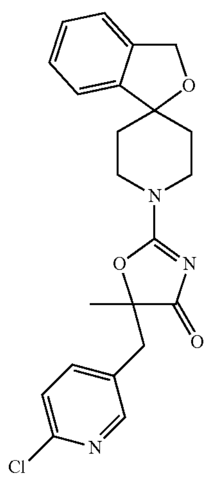 [SMILES: CC1(Cc2ccc(Cl)nc2)OC(N2CCC3(CC2)OCc2ccccc23)=NC1=O] | (−)-5-[(6-Chloropyridin-3-yl)methyl]-5-methyl-2-(1'H,3H-spiro[2-benzofuran-1,4'-piperidin]-1'-yl)-1,3-oxazol-4(5H)-one | 7.4 |
| 84 | 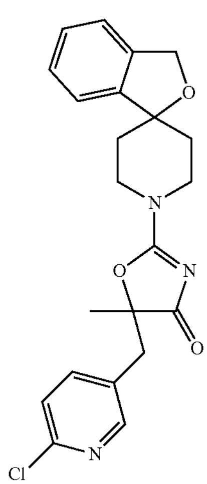 [SMILES: CC1(Cc2ccc(Cl)nc2)OC(N2CCC3(CC2)OCc2ccccc23)=NC1=O] | (+)-5-[(6-Chloropyridin-3-yl)methyl]-5-methyl-2-(1'H,3H-spiro[2-benzofuran-1,4'-piperidin]-1'-yl)-1,3-oxazol-4(5H)-one | 6.3 |

TABLE 1-continued pKi values of selected examples

| Ex. | Structure | Name | pK$_i$ hV$_{1a}$ |
|---|---|---|---|
| 85 | 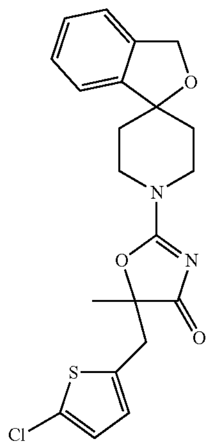 [SMILES: CC1(Cc2ccc(Cl)s2)OC(N2CCC3(CC2)OCc2ccccc23)=NC1=O] | 5-[(5-Chlorothiophen-2-yl)methyl]-5-methyl-2-(1'H,3H-spiro[2-benzofuran-1,4'-piperidin]-1'-yl)-1,3-oxazol-4(5H)-one | 8.3 |
| 86 | 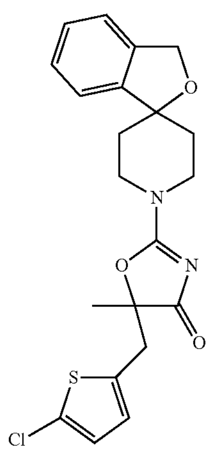 [SMILES: CC1(Cc2ccc(Cl)s2)OC(N2CCC3(CC2)OCc2ccccc23)=NC1=O] | (+)-5-[(5-Chlorothiophen-2-yl)methyl]-5-methyl-2-(1'H,3H-spiro[2-benzofuran-1,4'-piperidin]-1'-yl)-1,3-oxazol-4(5H)-one | 8.9 |
| 87 | 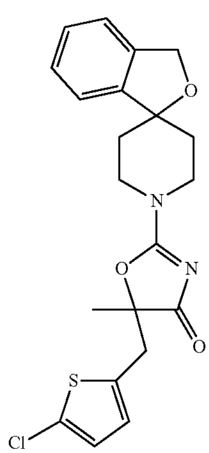 [SMILES: CC1(Cc2ccc(Cl)s2)OC(N2CCC3(CC2)OCc2ccccc23)=NC1=O] | (−)-5-[(5-Chlorothiophen-2-yl)methyl]-5-methyl-2-(1'H,3H-spiro[2-benzofuran-1,4'-piperidin]-1'-yl)-1,3-oxazol-4(5H)-one | 6.7 |

TABLE 1-continued pKi values of selected examples

| Ex. | Structure | Name | pK$_i$ hV$_{1a}$ |
|---|---|---|---|
| 88 | 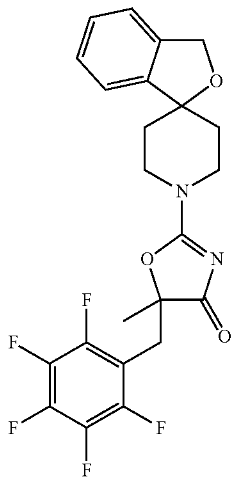 | 5-Methyl-5-(pentafluorobenzyl)-2-(1'H,3H-spiro[2-benzofuran-1,4'-piperidin]-1'-yl)-1,3-oxazol-4(5H)-one | 7.1 |
| 89 | 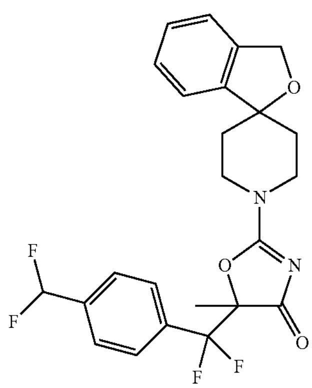 [SMILES: CC1(C(F)(F)c2ccc(C(F)F)cc2)OC(N2CCC3(CC2)OCc2ccccc23)=NC1=O] | 5-{[4-(Difluoromethyl)phenyl]difluoro)methyl}-5-methyl-2-(1'H,3H-spiro[2-benzofuran-1,4'-piperidin]-1'-yl)-1,3-oxazol-4(5H)-one | 6.8 |
| 90 | 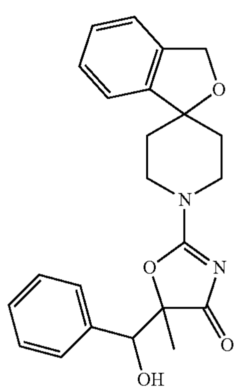 [SMILES: CC1(C(O)c2ccccc2)OC(N2CCC3(CC2)OCc2ccccc23)=NC1=O] | 5-[Hydroxy(phenyl)methyl]-5-methyl-2-(1'H,3H-spiro[2-benzofuran-1,4'-piperidin]-1'-yl)-1,3-oxazol-4(5H)-one | 6.9 |

TABLE 1-continued
| Ex. | Structure | Name | $pK_i$ $hV_{1a}$ |
|---|---|---|---|
| 91 | 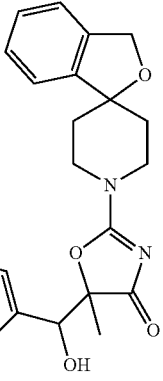 | 5-[(4-Chlorophenyl)(hydroxy)methyl]-5-methyl-2-(1'H,3H-spiro[2-benzofuran-1,4'-piperidin]-1'-yl)-1,3-oxazol-4(5H)-one | 7.6 |
| 92 | 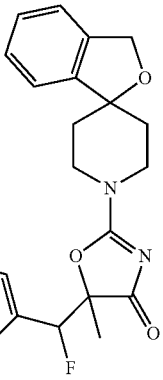 | 5-[(4-Chlorophenyl)(fluoro)methyl]-5-methyl-2-(1'H,3H-spiro[2-benzofuran-1,4'-piperidin]-1'-yl)-1,3-oxazol-4(5H)-one | 7.5 |
| 93 | 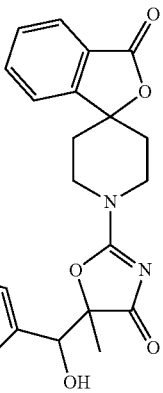 | 1'-{5-[(4-Chlorophenyl)(hydroxy)methyl]-5-methyl-4-oxo-4,5-dihydro-1,3-oxazol-2-yl}-3H-spiro[2-benzofuran-1,4'-piperidin]-3-one | 6.9 |

TABLE 1-continued pKi values of selected examples

| Ex. | Structure | Name | pK$_i$ hV$_{1a}$ |
|---|---|---|---|
| 94 | 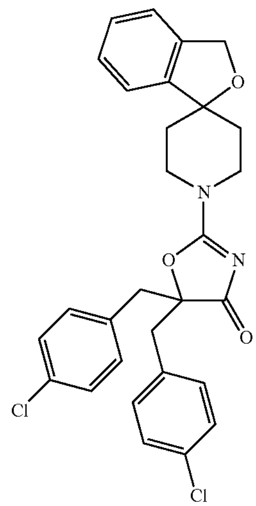 [SMILES: O=C1N=C(N2CCC3(CC2)OCc2ccccc23)OC1(Cc1ccc(Cl)cc1)Cc1ccc(Cl)cc1] | 5,5-bis(4-Chlorobenzyl)-2-(1'H,3H-spiro[2-benzofuran-1,4'-piperidin]-1'-yl)-1,3-oxazol-4(5H)-one | 9.0 |
| 95 | 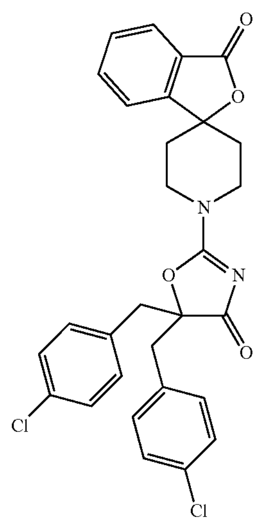 [SMILES: O=C1OC2(CCN(C3=NC(=O)C(Cc4ccc(Cl)cc4)(Cc4ccc(Cl)cc4)O3)CC2)c2ccccc21] | 1'-[5,5-Bis(4-chlorobenzyl)-4-oxo-4,5-dihydro-1,3-oxazol-2-yl]-3H-spiro[2-benzofuran-1,4'-piperidin]-3-one | 8.3 |
| 96 | 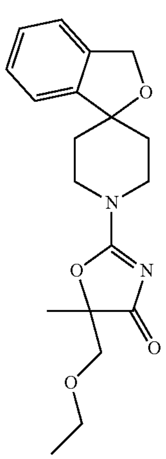 [SMILES: CCOCC1(C)OC(N2CCC3(CC2)OCc2ccccc23)=NC1=O] | (+)-5-(Ethoxymethyl)-5-methyl-2-(1'H,3H-spiro[2-benzofuran-1,4'-piperidin]-1'-yl)-1,3-oxazol-4(5H)-one | 6.6 |

TABLE 1-continued pKi values of selected examples

| Ex. | Structure | Name | pK$_i$ hV$_{1a}$ |
|---|---|---|---|
| 97 | 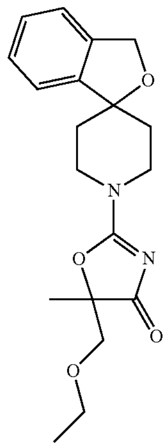 [SMILES: CCOCC1(C)OC(N2CCC3(CC2)OCc2ccccc23)=NC1=O] | (−)-5-(Ethoxymethyl)-5-methyl-2-(1'H,3H-spiro[2-benzofuran-1,4'-piperidin]-1'-yl)-1,3-oxazol-4(5H)-one | 5.8 |
| 98 | 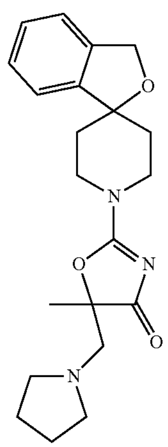 [SMILES: CC1(CN2CCCC2)OC(N2CCC3(CC2)OCc2ccccc23)=NC1=O] | 5-Methyl-5-(pyrrolidin-1-ylmethyl)-2-(1'H,3H-spiro[2-benzofuran-1,4'-piperidin]-1'-yl)-1,3-oxazol-4(5H)-one | 6.6 |
| 99 | 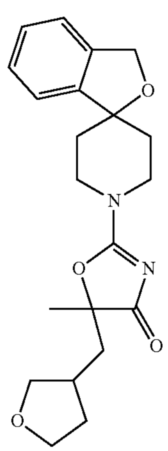 [SMILES: CC1(CC2CCOC2)OC(N2CCC3(CC2)OCc2ccccc23)=NC1=O] | 5-Methyl-2-(1'H,3H-spiro[2-benzofuran-1,4'-piperidin]-1'-yl)-5-(tetrahydrofuran-3-ylmethyl)-1,3-oxazol-4(5H)-one diastereomer a | 6.6 |

TABLE 1-continued pKi values of selected examples

| Ex. | Structure | Name | pK$_i$ hV$_{1a}$ |
|---|---|---|---|
| 100 | 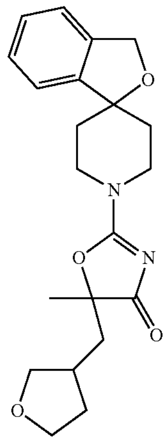 [SMILES: CC1(CC2CCOC2)OC(N2CCC3(CC2)OCc2ccccc23)=NC1=O] | 5-Methyl-2-(1'H,3H-spiro[2-benzofuran-1,4'-piperidin]-1'-yl)-5-(tetrahydrofuran-3-ylmethyl)-1,3-oxazol-4(5H)-one diastereomer b | 6.9 |
| 101 | 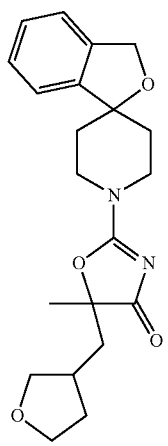 [SMILES: CC1(CC2CCOC2)OC(N2CCC3(CC2)OCc2ccccc23)=NC1=O] | 5-Methyl-2-(1'H,3H-spiro[2-benzofuran-1,4'-piperidin]-1'-yl)-5-(tetrahydrofuran-2-ylmethyl)-1,3-oxazol-4(5H)-one | 6.7 |
| 102 | 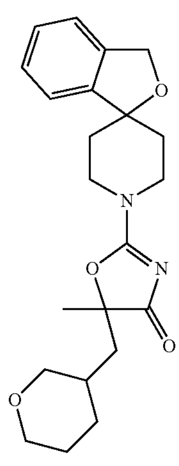 [SMILES: CC1(CC2CCCOC2)OC(N2CCC3(CC2)OCc2ccccc23)=NC1=O] | (+)-5-Methyl-2-(1'H,3H-spiro[2-benzofuran-1,4'-piperidin]-1'-yl)-5-(tetrahydro-2H-pyran-3-ylmethyl)-1,3-oxazol-4(5H)-one diastereomer a | 7.7 |

TABLE 1-continued

| Ex. | Structure | Name | pK$_i$ hV$_{1a}$ |
|---|---|---|---|
| 103 | 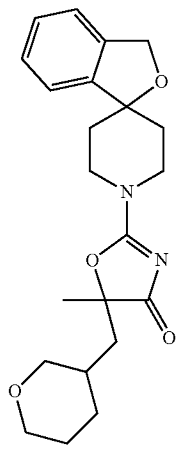 [SMILES: CC1(CC2CCCOC2)OC(N2CCC3(CC2)OCc2ccccc23)=NC1=O] | (−)-5-Methyl-2-(1'H,3H-spiro[2-benzofuran-1,4'-piperidin]-1'-yl)-5-(tetrahydro-2H-pyran-3-ylmethyl)-1,3-oxazol-4(5H)-one diastereomer a | 8.0 |
| 104 | 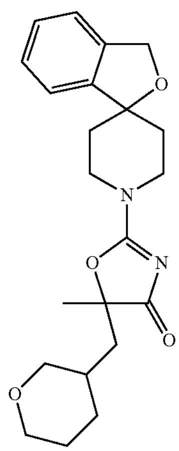 [SMILES: CC1(CC2CCCOC2)OC(N2CCC3(CC2)OCc2ccccc23)=NC1=O] | (+)-5-Methyl-2-(1'H,3H-spiro[2-benzofuran-1,4'-piperidin]-1'-yl)-5-(tetrahydro-2H-pyran-3-ylmethyl)-1,3-oxazol-4(5H)-one diastereomer b | 7.3 |
| 105 | 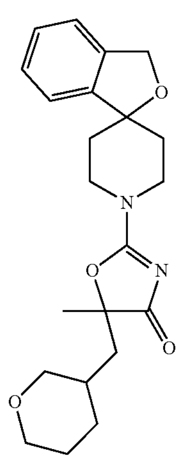 [SMILES: CC1(CC2CCCOC2)OC(N2CCC3(CC2)OCc2ccccc23)=NC1=O] | (−)-5-Methyl-2-(1'H,3H-spiro[2-benzofuran-1,4'-piperidin]-1'-yl)-5-(tetrahydro-2H-pyran-3-ylmethyl)-1,3-oxazol-4(5H)-one diastereomer b | 6.3 |

TABLE 1-continued pKi values of selected examples

| Ex. | Structure | Name | pK$_i$ hV$_{1a}$ |
|---|---|---|---|
| 106 | 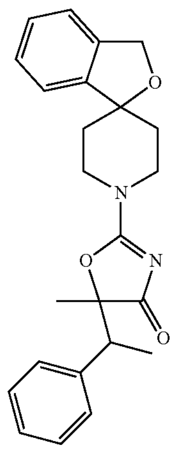 [SMILES: CC(c1ccccc1)C1(C)OC(N2CCC3(CC2)OCc2ccccc23)=NC1=O] | 5-Methyl-5-(1-phenylethyl)-2-(1'H,3H-spiro[2-benzofuran-1,4'-piperidin]-1'-yl)-1,3-oxazol-4(5H)-one diastereomer a | 7.8 |
| 107 | 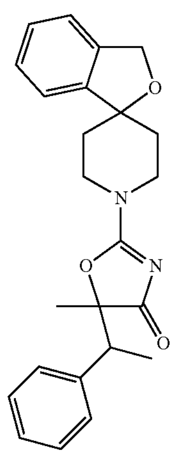 [SMILES: CC(c1ccccc1)C1(C)OC(N2CCC3(CC2)OCc2ccccc23)=NC1=O] | 5-Methyl-5-(1-phenylethyl)-2-(1'H,3H-spiro[2-benzofuran-1,4'-piperidin]-1'-yl)-1,3-oxazol-4(5H)-one diastereomer b | 8.0 |
| 108 | 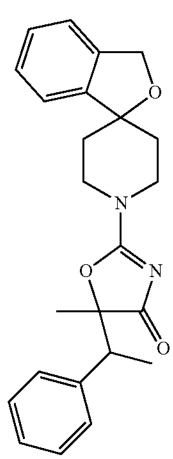 [SMILES: CC(c1ccccc1)C1(C)OC(N2CCC3(CC2)OCc2ccccc23)=NC1=O] | (+)-5-Methyl-5-(1-phenylethyl)-2-(1'H,3H-spiro[2-benzofuran-1,4'-piperidin]-1'-yl)-1,3-oxazol-4(5H)-one diastereomer a | 7.9 |

TABLE 1-continued

| Ex. | Structure | Name | pK$_i$ hV$_{1a}$ |
|---|---|---|---|
| 109 | 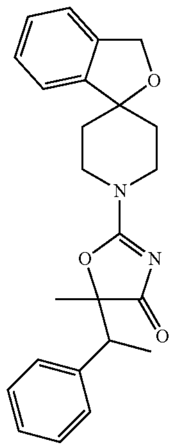 [SMILES: CC(c1ccccc1)C1(C)OC(N2CCC3(CC2)OCc2ccccc23)=NC1=O] | (−)-5-Methyl-5-(1-phenylethyl)-2-(1'H,3H-spiro[2-benzofuran-1,4'-piperidin]-1'-yl)-1,3-oxazol-4(5H)-one diastereomer a | 7.3 |
| 110 | 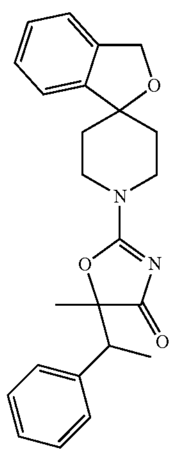 [SMILES: CC(c1ccccc1)C1(C)OC(N2CCC3(CC2)OCc2ccccc23)=NC1=O] | (−)-5-Methyl-5-(1-phenylethyl)-2-(1'H,3H-spiro[2-benzofuran-1,4'-piperidin]-1'-yl)-1,3-oxazol-4(5H)-one diastereomer b | 8.2 |
| 111 | 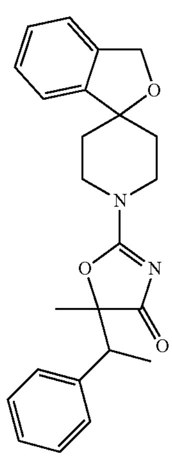 [SMILES: CC(c1ccccc1)C1(C)OC(N2CCC3(CC2)OCc2ccccc23)=NC1=O] | (+)-5-Methyl-5-(1-phenylethyl)-2-(1'H,3H-spiro[2-benzofuran-1,4'-piperidin]-1'-yl)-1,3-oxazol-4(5H)-one diastereomer b | 6.6 |

TABLE 1-continued

| | | pKi values of selected examples | |
|---|---|---|---|
| Ex. | Structure | Name | pK$_i$ hV$_{1a}$ |
| 112 | | 2-(3H-Spiro[isobenzofuran-1,4'-piperidine]-1'-yl)-1-oxa-3-azaspiro[4.4]non-2-en-4-one | 6.8 |
| 113 | | 2-(1'H,3H-Spiro[2-benzofuran-1,4'-piperidin]-1'-yl)-1-oxa-3-azaspiro[4.4]nona-2,7-dien-4-one | 7.0 |
| 114 | | 7-Methyl-2-(1'H,3H-spiro[2-benzofuran-1,4'-piperidin]-1'-yl)-1-oxa-3-azaspiro[4.4]nona-2,7-dien-4-one | 7.9 |
| 115 | | 7,8-Dimethyl-2-(1'H,3H-spiro[2-benzofuran-1,4'-piperidin]-1'-yl)-1-oxa-3-azaspiro[4.4]nona-2,7-dien-4-one | 8.0 |

TABLE 1-continued pKi values of selected examples

| Ex. | Structure | Name | pK$_i$ hV$_{1a}$ |
|---|---|---|---|
| 116 | 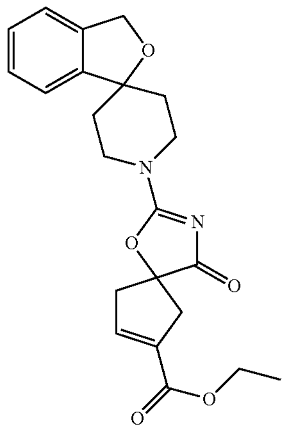 [SMILES: CCOC(=O)C1=CCC2(C1)OC(N1CCC3(CC1)OCc1ccccc13)=NC2=O] | Ethyl 4-oxo-2-(1'H,3H-spiro[2-benzofuran-1,4'-piperidin]-1'-yl)-1-oxa-3-azaspiro[4.4]nona-2,7-diene-7-carboxylate | 6.9 |
| 117 | 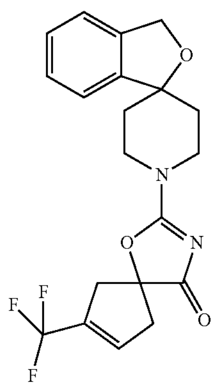 [SMILES: O=C1N=C(N2CCC3(CC2)OCc2ccccc23)OC12CC=C(C(F)(F)F)C2] | 2-(1'H,3H-Spiro[2-benzofuran-1,4'-piperidin]-1'-yl)-7-(trifluoromethyl)-1-oxa-3-azaspiro[4.4]nona-2,7-dien-4-one | 8.9 |
| 118 | 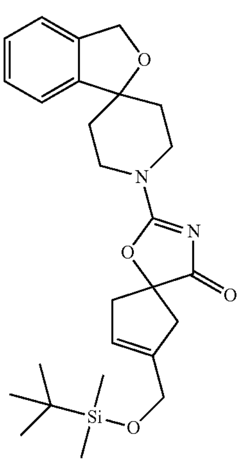 [SMILES: CC(C)(C)[Si](C)(C)OCC1=CCC2(C1)OC(N1CCC3(CC1)OCc1ccccc13)=NC2=O] | 7-({[tert-Butyl(dimethyl)silyl]oxy}methyl)-2-(1'H,3H-spiro[2-benzofuran-1,4'-piperidin]-1'-yl)-1-oxa-3-azaspiro[4.4]nona-2,7-dien-4-one | 6.5 |

TABLE 1-continued

| Ex. | Structure | Name | pK$_i$ hV$_{1a}$ |
|---|---|---|---|
| 119 | 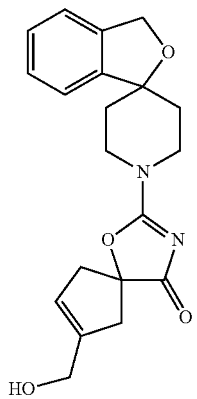 [SMILES: O=C1N=C(N2CCC3(CC2)OCc2ccccc23)OC12CC=C(CO)C2] | 7-(Hydroxymethyl)-2-(3H-spiro[isobenzofuran-1,4'-piperidine]-1'-yl)-1-oxa-3-azaspiro[4.4]nona-2,7-dien-4-one | 6.0 |
| 120 | 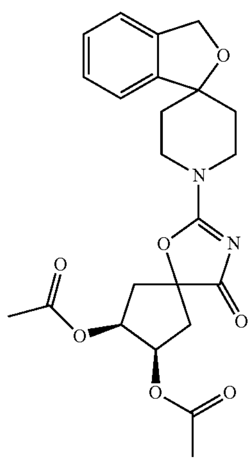 [SMILES: CC(=O)O[C@H]1CC2(C[C@H]1OC(C)=O)OC(N1CCC3(CC1)OCc1ccccc13)=NC2=O] | 4-Oxo-2-(1'H,3H-spiro[2-benzofuran-1,4'-piperidin]-1'-yl)-1-oxa-3-azaspiro[4.4]non-2-ene-7,8-diyl diacetate diastereomer a | 6.7 |
| 121 | 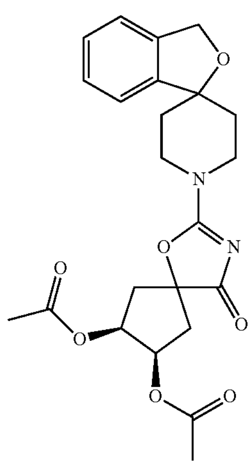 [SMILES: CC(=O)O[C@H]1CC2(C[C@H]1OC(C)=O)OC(N1CCC3(CC1)OCc1ccccc13)=NC2=O] | 4-Oxo-2-(1'H,3H-spiro[2-benzofuran-1,4'-piperidin]-1'-yl)-1-oxa-3-azaspiro[4.4]non-2-ene-7,8-diyl diacetate diastereomer b | 8.2 |

TABLE 1-continued pKi values of selected examples

| Ex. | Structure | Name | pK$_i$ hV$_{1a}$ |
|---|---|---|---|
| 122 | 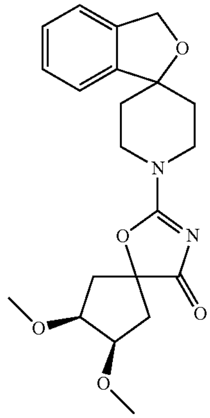 [SMILES: CO[C@H]1CC2(C[C@H]1OC)OC(N1CCC3(CC1)OCc1ccccc13)=NC2=O] | 7,8-Dimethoxy-2-(1'H,3H-spiro[2-benzofuran-1,4'-piperidin]-1'-yl)-1-oxa-3-azaspiro[4.4]non-2-en-4-one diastereomer a | 6.7 |
| 123 | 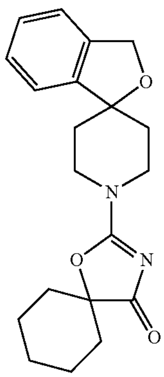 [SMILES: O=C1N=C(N2CCC3(CC2)OCc2ccccc23)OC12CCCCC2] | 2-(1'H,3H-Spiro[2-benzofuran-1,4'-piperidin]-1'-yl)-1-oxa-3-azaspiro[4.5]dec-2-en-4-one | 8.0 |
| 124 | 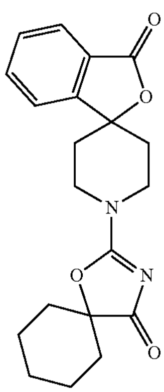 [SMILES: O=C1OC2(CCN(C3=NC(=O)C4(CCCCC4)O3)CC2)c2ccccc21] | 1'-(4-Oxo-1-oxa-3-azaspiro[4.5]dec-2-en-2-yl)-3H-spiro[2-benzofuran-1,4'-piperidin]-3-one | 6.8 |
| 125 | 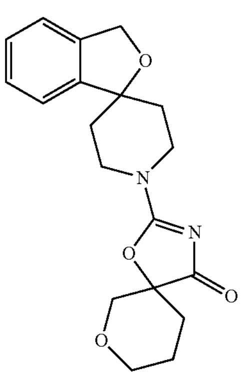 [SMILES: O=C1N=C(N2CCC3(CC2)OCc2ccccc23)OC12CCCOC2] | 2-(1'H,3H-Spiro[2-benzofuran-1,4'-piperidin]-1'-yl)-1,7-dioxa-3-azaspiro[4.5]dec-2-en-4-one | 6.7 |

TABLE 1-continued

| | pKi values of selected examples | | |
|---|---|---|---|
| Ex. | Structure | Name | pK$_i$ hV$_{1a}$ |
| 126 | | 1'-[4-Oxo-8-pentyl-1-oxa-3-azaspiro[4.5]dec-2-en-2-yl]-3H-spiro[2-benzofuran-1,4'-piperidin]-3-one diastereomer a | 7.5 |
| 127 | | 1'-[4-Oxo-8-pentyl-1-oxa-3-azaspiro[4.5]dec-2-en-2-yl]-3H-spiro[2-benzofuran-1,4'-piperidin]-3-one diastereomer b | 6.6 |
| 128 | | 8-Pentyl-2-(1'H,3H-spiro[2-benzofuran-1,4'-piperidin]-1'-yl)-1-oxa-3-azaspiro[4.5]dec-2-en-4-one diastereomer a | 7.7 |

TABLE 1-continued pKi values of selected examples

| Ex. | Structure | Name | pK$_i$ hV$_{1a}$ |
|---|---|---|---|
| 129 | 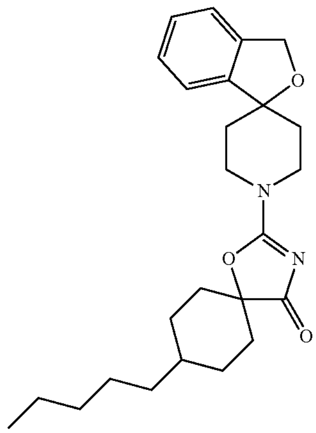 [SMILES: CCCCCC1CCC2(CC1)OC(N1CCC3(CC1)OCc1ccccc13)=NC2=O] | 8-Pentyl-2-(1'H,3H-spiro[2-benzofuran-1,4'-piperidin]-1'-yl)-1-oxa-3-azaspiro[4.5]dec-2-en-4-one diastereomer b | 6.8 |
| 130 | 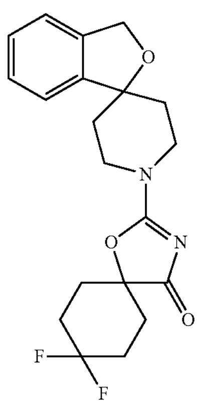 [SMILES: O=C1N=C(N2CCC3(CC2)OCc2ccccc23)OC12CCC(F)(F)CC2] | 8,8-Difluoro-2-(1'H,3H-spiro[2-benzofuran-1,4'-piperidin]-1'-yl)-1-oxa-3-azaspiro[4.5]dec-2-en-4-one | 8.2 |
| 131 | 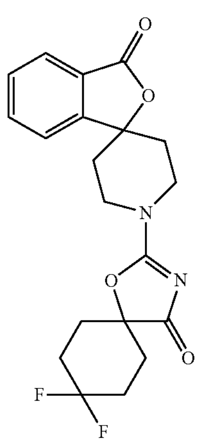 [SMILES: O=C1OC2(CCN(C3=NC(=O)C4(CCC(F)(F)CC4)O3)CC2)c2ccccc21] | 1'-(8,8-Difluoro-4-oxo-1-oxa-3-azaspiro[4.5]dec-2-en-2-yl)-3H-spiro[2-benzofuran-1,4'-piperidin]-3-one | 7.3 |

TABLE 1-continued pKi values of selected examples

| Ex. | Structure | Name | pK$_i$ hV$_{1a}$ |
|---|---|---|---|
| 132 | 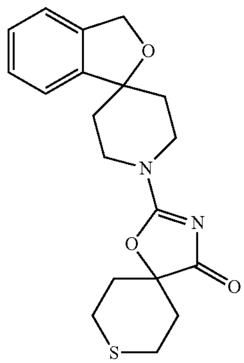 [SMILES: O=C1N=C(N2CCC3(CC2)OCc2ccccc23)OC12CCSCC2] | 2-(1'H,3H-Spiro[2-benzofuran-1,4'-piperidin]-1'-yl)-1-oxa-8-thia-3-azaspiro[4.5]dec-2-en-4-one | 7.8 |
| 133 | 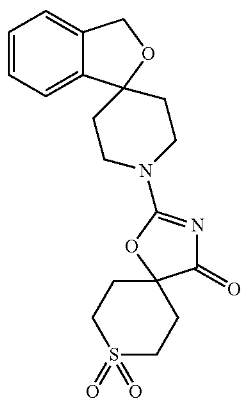 [SMILES: O=C1N=C(N2CCC3(CC2)OCc2ccccc23)OC12CCS(=O)(=O)CC2] | 2-(1'H,3H-Spiro[2-benzofuran-1,4'-piperidin]-1'-yl)-1-oxa-8-thia-3-azaspiro[4.5]dec-2-en-4-one 8,8-dioxide | 6.9 |
| 134 | 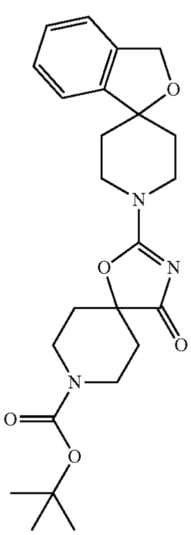 [SMILES: CC(C)(C)OC(=O)N1CCC2(CC1)OC(N1CCC3(CC1)OCc1ccccc13)=NC2=O] | tert-Butyl 4-oxo-2-(1'H,3H-spiro[2-benzofuran-1,4'-piperidin]-1'-yl)-1-oxa-3,8-diazaspiro[4.5]dec-2-ene-8-carboxylate | 6.8 |

TABLE 1-continued

| Ex. | Structure | Name | pK$_i$ hV$_{1a}$ |
|---|---|---|---|
| 135 | 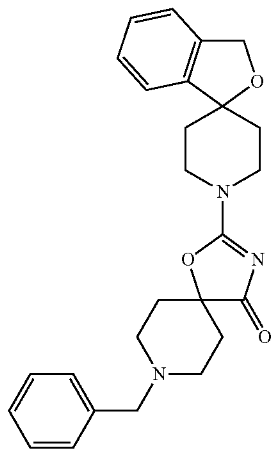 [SMILES: O=C1N=C(N2CCC3(CC2)OCc2ccccc23)OC12CCN(Cc1ccccc1)CC2] | 8-Benzyl-2-(1'H,3H-spiro[2-benzofuran-1,4'-piperidin]-1'-yl)-1-oxa-3,8-diazaspiro[4.5]dec-2-en-4-one | 6.4 |
| 136 | 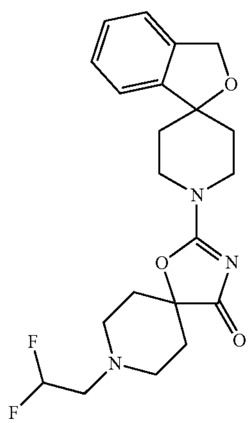 [SMILES: O=C1N=C(N2CCC3(CC2)OCc2ccccc23)OC12CCN(CC(F)F)CC2] | 8-(2,2-Difluoroethyl)-2-(1'H,3H-spiro[2-benzofuran-1,4'-piperidin]-1'-yl)-1-oxa-3,8-diazaspiro[4.5]dec-2-en-4-one | 6.5 |
| 137 | 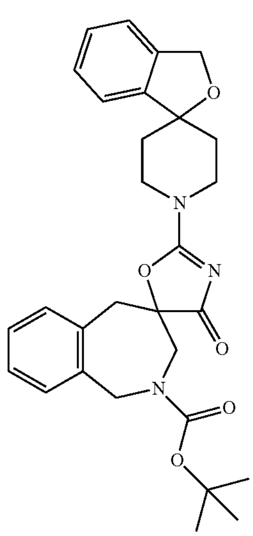 [SMILES: CC(C)(C)OC(=O)N1Cc2ccccc2CC2(C1)OC(N1CCC3(CC1)OCc1ccccc13)=NC2=O] | tert-Butyl 4'-oxo-2'-(1'H,3H-spiro[2-benzofuran-1,4'-piperidin]-1'-yl)-1,5-dihydro-4'H-spiro[2-benzazepine-4,5'-[1,3]oxazole]-2(3H)-carboxylate | 8.8 |

TABLE 1-continued pKi values of selected examples

| Ex. | Structure | Name | pK$_i$ hV$_{1a}$ |
|---|---|---|---|
| 138 | 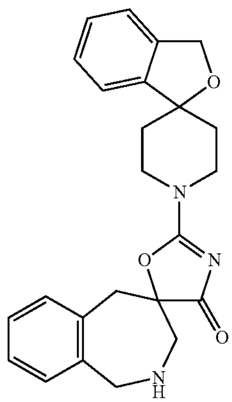 [SMILES: O=C1N=C(N2CCC3(CC2)OCc2ccccc23)OC12CNCc1ccccc1C2] | 2'-(1'H,3H-Spiro[2-benzofuran-1,4'-piperidin]-1'-yl)-1,2,3,5-tetrahydro-4'H-spiro[2-benzazepine-4,5'-[1,3]oxazol]-4'-one | 8.2 |
| 139 | 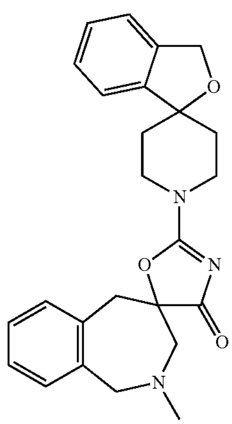 [SMILES: CN1Cc2ccccc2CC2(C1)OC(N1CCC3(CC1)OCc1ccccc13)=NC2=O] | 2-Methyl-2'-(1'H,3H-spiro[2-benzofuran-1,4'-piperidin]-1'-yl)-1,2,3,5-tetrahydro-4'H-spiro[2-benzazepine-4,5'-[1,3]oxazol]-4'-one | 8.9 |
| 140 | 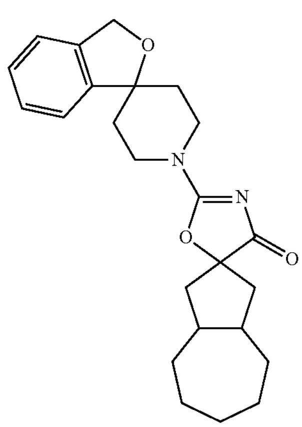 [SMILES: O=C1N=C(N2CCC3(CC2)OCc2ccccc23)OC12CC1CCCCCC1C2] | 2'-(1'H,3H-Spiro[2-benzofuran-1,4'-piperidin]-1'-yl)-3,3a,4,5,6,7,8,8a-octahydro-1H,4'H-spiro[azulene-2,5'-[1,3]oxazol]-4'-one | 9.2 |

TABLE 1-continued pKi values of selected examples

| Ex. | Structure | Name | pK$_i$ hV$_{1a}$ |
|---|---|---|---|
| 141 | 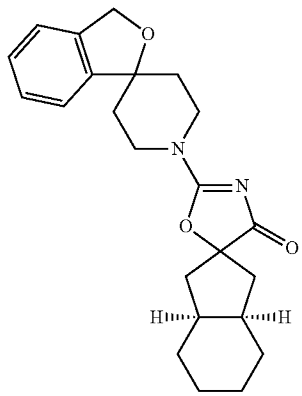 [SMILES: O=C1N=C(N2CCC3(CC2)OCc2ccccc23)OC12C[C@H]1CCCC[C@H]1C2] | 2'-(1'H,3H-Spiro[2-benzofuran-1,4'-piperidin]-1'-yl)-1,3,3a,4,5,6,7,7a-octahydro-4'H-spiro[indene-2,5'-[1,3]oxazol]-4'-one | 9.3 |
| 142 | 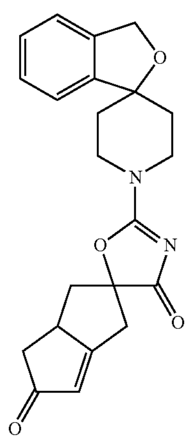 [SMILES: O=C1C=C2CC3(CC2C1)OC(N1CCC2(CC1)OCc1ccccc12)=NC3=O] | 2-(1'H,3H-Spiro[2-benzofuran-1,4'-piperidin]-1'-yl)-3a',4'-dihydro-1'H,4H-spiro[1,3-oxazole-5,2'-pentalene]-4,5'(3'H)-dione | 6.8 |
| 143 | 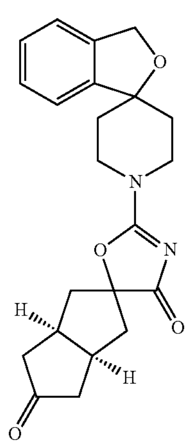 [SMILES: O=C1C[C@@H]2CC3(C[C@@H]2C1)OC(N1CCC2(CC1)OCc1ccccc12)=NC3=O] | 2-(1'H,3H-Spiro[2-benzofuran-1,4'-piperidin]-1'-yl)-3a',4',6',6a'-tetrahydro-1'H,4H-spiro[1,3-oxazole-5,2'-pentalene]-4,5'(3'H)-dione | 7.0 |

TABLE 1-continued pKi values of selected examples

| Ex. | Structure | Name | pK$_i$ hV$_{1a}$ |
|---|---|---|---|
| 144 | 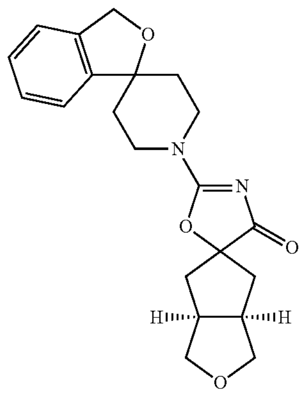 [SMILES: O=C1N=C(N2CCC3(CC2)OCc2ccccc23)OC12C[C@H]1COC[C@H]1C2] | 2'-(1'H,3H-Spiro[2-benzofuran-1,4'-piperidin]-1'-yl)-3a,4,6,6a-tetrahydro-1H,3H,4'H-spiro[cyclopenta[c]furan-5,5'-[1,3]oxazol]-4'-one | 7.1 |
| 145 | 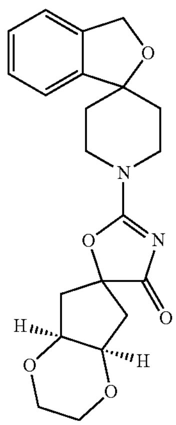 [SMILES: O=C1N=C(N2CCC3(CC2)OCc2ccccc23)OC12C[C@@H]1OCCO[C@@H]1C2] | 2'-(1'H,3H-Spiro[2-benzofuran-1,4'-piperidin]-1'-yl)-2,3,4a,5,7,7a-hexahydro-4'H-spiro[cyclopenta[b][1,4]dioxine-6,5'-[1,3]oxazol]-4'-one diastereomer b | 7.3 |
| 146 | 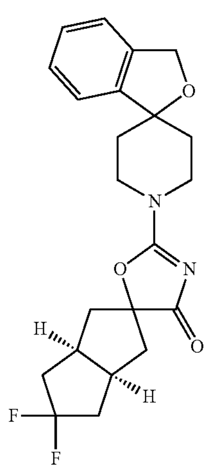 [SMILES: O=C1N=C(N2CCC3(CC2)OCc2ccccc23)OC12C[C@H]1CC(F)(F)C[C@H]1C2] | 5',5'-Difluoro-2-(1'H,3H-spiro[2-benzofuran-1,4'-piperidin]-1'-yl)-3',3a',4',5',6',6a'-hexahydro-1'H,4H-spiro[1,3-oxazole-5,2'-pentalen]-4-one | 8.4 |

TABLE 1-continued pKi values of selected examples

| Ex. | Structure | Name | pK$_i$ hV$_{1a}$ |
|---|---|---|---|
| 147 | 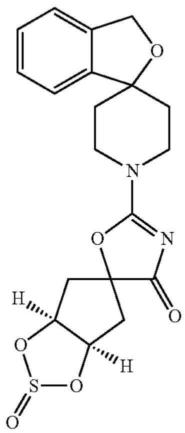 [SMILES: O=C1N=C(N2CCC3(CC2)OCc2ccccc23)OC12C[C@@H]1OS(=O)O[C@@H]1C2] | 2'-(1'H,3H-Spiro[2-benzofuran-1,4'-piperidin]-1'-yl)-3a,4,6,6a-tetrahydro-4'H-spiro[cyclopenta[d][1,3,2]dioxathiole-5,5'-[1,3]oxazol]-4'-one 2-oxide | 6.8 |
| 148 | 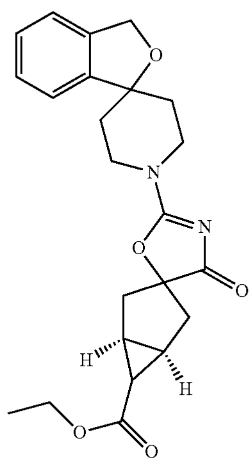 [SMILES: CCOC(=O)C1[C@H]2CC3(C[C@@H]12)OC(N1CCC2(CC1)OCc1ccccc12)=NC3=O] | Ethyl 4'-oxo-2'-(1'H,3H-spiro[2-benzofuran-1,4'-piperidin]-1'-yl)-4'H-spiro[bicyclo[3.1.0]hexane-3,5'-[1,3]oxazole]-6-carboxylate diastereomer a | 6.0 |
| 149 | 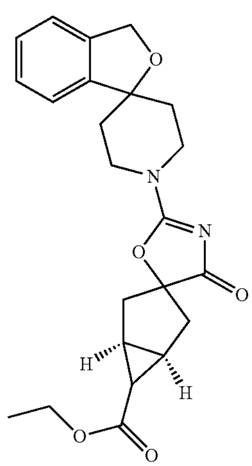 [SMILES: CCOC(=O)C1[C@H]2CC3(C[C@@H]12)OC(N1CCC2(CC1)OCc1ccccc12)=NC3=O] | Ethyl 4'-oxo-2'-(1'H,3H-spiro[2-benzofuran-1,4'-piperidin]-1'-yl)-4'H-spiro[bicyclo[3.1.0]hexane-3,5'-[1,3]oxazole]-6-carboxylate diastereomer b | 6.7 |

TABLE 1-continued pKi values of selected examples

| Ex. | Structure | Name | $pK_i\ hV_{1a}$ |
|---|---|---|---|
| 150 | 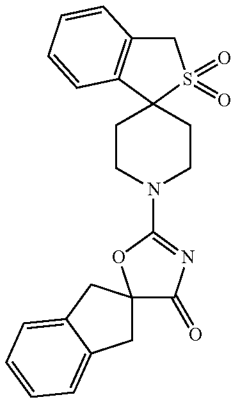 [SMILES: O=C1N=C(N2CCC3(CC2)c2ccccc2CS3(=O)=O)OC12Cc1ccccc1C2] | 2'-(2,2-Dioxido-1'H,3H-spiro[2-benzothiophene-1,4'-piperidin]-1'-yl)-1,3-dihydro-4'H-spiro[indene-2,5'-[1,3]oxazol]-4'-one | 9.6 |

Pharmaceutical Compositions

The compounds of formula I and the pharmaceutically acceptable salts can be used as therapeutically active substances, e.g. in the form of pharmaceutical preparations. The pharmaceutical preparations can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and the pharmaceutically acceptable salts thereof can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also provided by the present invention, as is a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, in particular 1-100 mg, of a compound of formula I. Examples of compositions according to the invention are:

Example A

Tablets of the Following Composition are Manufactured in the Usual Manner

TABLE 2 possible tablet composition

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure

1. Mix ingredients 1, 2, 3 and 4 and granulate with purified water.

2. Dry the granules at 50° C.

3. Pass the granules through suitable milling equipment.

4. Add ingredient 5 and mix for three minutes; compress on a suitable press.

Example B-1

Capsules of the Following Composition are Manufactured

TABLE 3 possible capsule ingredient composition

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure

1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Example B-2

Soft Gelatin Capsules of the Following Composition are Manufactured

TABLE 4 possible soft gelatin capsule ingredient composition

| ingredient | mg/capsule |
|---|---|
| Compound of formula I | 5 |
| Yellow wax | 8 |
| Hydrogenated Soya bean oil | 8 |
| Partially hydrogenated plant oils | 34 |
| Soya bean oil | 110 |
| Total | 165 |

TABLE 5 possible soft gelatin capsule composition

| ingredient | mg/capsule |
|---|---|
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

Example C

Suppositories of the Following Composition are Manufactured

TABLE 6 possible suppository composition

| ingredient | mg/supp. |
|---|---|
| Compound of formula I | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

Example D

Injection Solutions of the Following Composition are Manufactured

TABLE 7 possible injection solution composition

| ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the Following Composition are Manufactured

TABLE 8 possible sachet composition

| ingredient | mg/sachet |
|---|---|
| Compound of formula I | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.
The following table lists abbreviations used within the present document.

TABLE 9 list with abbreviations

| | |
|---|---|
| AIBN | azobisisobutyronitrile |
| brine | saturated sodium chloride solution in water |
| BF$_3$*OEt$_2$ | borontrifluoride diethyl etherate |
| BrCN | cyanogen bromide |
| CH$_2$Cl$_2$ | dichloromethane |
| CSO | (10-camphorsulfonyl)oxaziridine |
| Cu(OTf)$_2$ | copper(II) trifluoromethanesulfonate |
| DAST | diethylaminosulfur trifluoride |
| DBU | 1,8-diazabicyclo[5.4.0]undec-7-ene |
| DIBAL-H | diisobutylaluminium hydride |
| DMAP | 4-(N,N-dimethylamino)-pyridine |
| DME | 1,2-dimethoxyethane |
| DMF | N,N-dimethylformamide |
| DMSO | dimethylsulfoxide |
| ee | enantiomeric excess |
| Et$_3$N | triethylamine |
| Grubbs II | [1,3-bis-(2,4,6-trimethylphenyl)-2-imidazolidinylidene]dichloro(phenylmethylene)(tricyclohexylphosphine)ruthenium |
| LDA | lithium diisopropylamide |
| LiHMDS | lithium bis(trimethylsilyl)amide |
| NaHMDS | sodium bis(trimethylsilyl)amide |
| LG | leaving group |
| MeOH | methanol |
| MS 4A | molecular sieves 4Angstrom |
| NaH | sodium hydride |
| NaOH | sodium hydroxide |
| n-BuLi | n-butyllithium |
| n-BuOH | n-butanol |
| NMO | N-methylmorpholine-N-oxide |
| PhMe | toluene |
| RT | room temperature |
| TBDMS | tert-butyl-dimethylsilyl |
| t-BuOK, KOtBu | potassium tert-butanolate |
| TFA | trifluoroacetic acid |
| THF | tetrahydrofuran |
| TMSCN | trimethylsilyl cyanide |
| TPP | triphenylphosphine |

Experimental Part

The following examples are provided for illustration of the invention. They should not be considered as limiting the scope of the invention, but merely as being representative thereof.

Intermediate of Formula (VI)

1'H,3H-Spiro[2-benzofuran-1,4'-piperidine]-1'-carbonitrile

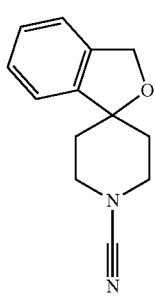

To a solution of 3H-spiro[isobenzofuran-1,4'-piperidine] (5.0 g, 26 mmol) and triethylamine (5.9 g, 8.1 ml, 58 mmol) in ethanol (50 ml) was drop wise added in approximately 30 minutes 5 M cyanic bromide solution in acetonitrile (5.6 ml, 28 mmol) at 0-5° C. Stirring was continued for 30 minutes. The solids were removed by filtration. The filtrate was partitioned between tert-butyl methyl ether (200 ml) and a 2 M aqueous sodium carbonate solution (200 ml)/water (100 ml) mixture. The layers were separated. The aqueous layer was extracted with one 100-ml portion of tert-butyl methyl ether. The combined organic layers were washed with one 100-ml portion of saturated ammonium chloride solution, dried over anhydrous sodium sulfate and concentrated in vacuo. Flash-chromatography with n-heptane/ethyl acetate gave the title compound (4.1 g, 72%) as white solid. MS m/e: 214 (M$^+$).

Intermediate of Formula (XII)

(3a,6a)-5,5-Difluorohexahydropentalen-2(1H)-one

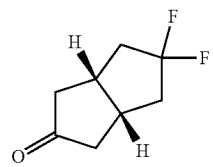 [SMILES: O=C1C[C@@H]2CC(F)(F)C[C@@H]2C1]

a) (3a"R, 6a"S)-3a",4",6",6a"-Tetrahydro-1"H-dispiro[fluorene-9, 5'-[1,3]dioxane-2',2"-pentalen]-5"(3"H)-one A mixture of (3a,6a)-tetrahydropentalene-2,5(1H,3H)-dione (8.3 g, 60 mmol), (9H-fluorene-9,9-diyl)dimethanol (14.0 g, 60 mmol) and p-toluensulfonic acid (0.060 g, 0.32 mmol) in toluene (75 ml) was refluxed for 2 hour with a water separator. The solvent was evaporated. The residue was partitioned between dichloromethane (300 ml) and 5% aqueous sodium bicarbonate solution (50 ml). The layers were separated. The organic layer was dried over magnesium sulfate, filtrated and concentrated in vacuo. Purification by flash chromatography with n-heptane/dichloromethane as eluent gave the mono-protected intermediate (10.5 g, 51%).

b) (3a"R, 6a"S)-5",5"-Difluoro-3",3a",4",5",6",6a"-hexahydro-1"H-dispiro[fluorene-9, 5'-[1,3]dioxane-2',2"-pentalene]

To a solution of the above prepared mono-protected intermediate (1.5 g, 4.3 mmol) in dichloromethane (15 ml) at 0-5° C., was added diethylaminosulfur trifluoride (1.4 g, 1.1 ml, 8.7 mmol). The mixture was stirred at 0-5° C. for 2 h and overnight at room temperature. A further portion of diethylaminosulfur trifluoride (1.4 g, 1.1 ml, 8.7 mmol) was added to the reaction and stirring was continued for 6 h. The reaction mixture was partitioned between dichloromethane and 5% aqueous sodium bicarbonate solution. The layers were separated. The aqueous layer was extracted with dichloromethane. The organic layers were washed with 5% aqueous sodium bicarbonate solution, dried over anhydrous sodium sulfate, filtered and concentrated in vacuo. Purification by flash chromatography with n-heptane/ethyl acetate as eluent gave the intermediate difluorinated acetal (0.63 g, 40%) as off-white solid.

c) (3a,6a)-5,5-Difluorohexahydropentalen-2(1H)-one

To a suspension of the above prepared difluorinated acetal (0.50 g, 1.4 mmol) in methanol (5 ml), 1,4-dioxane (5 ml) and water (2.5 mL) was added p-toluensulfonic acid (0.026 g, 0.14 mmol). The mixture was heated at 70° C. and stirred for 10 h. The reaction mixture was partitioned between diethyl ether and water. The layers were separated. The aqueous layer was extracted with diethyl ether. The organic layers were dried over anhydrous sodium sulfate, filtered and concentrated in vacuo. Purification by flash chromatography with dichloromethane as eluent gave the title compound (0.19 g, 89%) as a colorless liquid. MS m/e: 160 ([M]$^+$)

Cyanohydrin Intermediates of Formula (X) and Trimethylsilyl Cyanohydrin Intermediates of Formula (XIII)

General Procedure I: Copper Catalyzed

A solution of a ketone intermediate of formula (XII), trimethylsilyl cyanide (2.6 eq) and copper(II) trifluoromethanesulfonate (0.01 eq) in dichloromethane (0.5-1.0 M) is stirred at room temperature for 15-24 h. The reaction mixture is concentrated to dryness to give a trimethylsilyl cyanohydrin intermediate of formula (XIII). The crude compound of formula (XIII) is partitioned between an organic solvent such as dichloromethane and water. The layers are separated. The aqueous layer is extracted with one or two portions of organic solvent. The combined organic layers are washed with one portion of brine, dried over anhydrous sodium sulfate and concentrated to dryness to give an intermediate of formula (XIII). During the work-up the trimethylsilyl group of the resulting trimethylsilyl cyanohydrin may be partially or completely cleaved to give a cyanohydrin intermediate of formula (X).

General Procedure II: Lanthanum Catalyzed

A solution of a ketone intermediate of formula (XII), 2-hydroxy-2-methylpropanenitrile (1.5 eq) and lanthanum (III) isopropoxide (0.1 eq) in tetrahydrofuran (0.5-1.0 M) is stirred at room temperature for 15-24 h. The reaction mixture is partitioned between an organic solvent such as ethyl acetate or tert-butyl methyl ether and saturated aqueous ammonium chloride solution. The layers are separated. The aqueous layer is extracted with one or two portions of organic solvent. The combined organic layers are washed with one portion of brine, dried over anhydrous sodium sulfate and concentrated to dryness. Purification by flash-chromatography gives a cyanohydrin intermediate of formula (X).

Cyanohydrin 1

1-Hydroxycyclohexanecarbonitrile

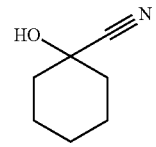

The title compound was obtained as off-white waxy solid in 81% yield according to the general procedure II from cyclohexanone and 2-hydroxy-2-methylpropanenitrile. MS m/e: 124 ([M–H]$^+$)

Cyanohydrin 2

4-Hydroxytetrahydro-2H-thiopyran-4-carbonitrile

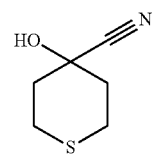

The title compound was obtained as white solid in 78% yield according to the general procedure II from tetrahydro-4H-thiopyran-4-one and 2-hydroxy-2-methylpropanenitrile. MS m/e: 143 (M$^+$)

Cyanohydrin 3

3-Hydroxytetrahydro-2H-pyran-3-carbonitrile

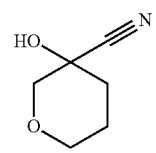

The title compound was obtained as light yellow oil in 55% yield according to the general procedure II from dihydro-pyran-3-one and 2-hydroxy-2-methylpropanenitrile.

Cyanohydrin 4

4,4-Difluoro-1-[(trimethylsilyl)oxy]cyclohexanecarbonitrile

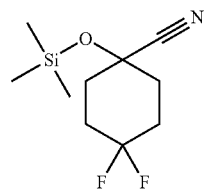

The title compound was obtained as light yellow oil in quantitative yield according to the general procedure I from 4,4-difluorocyclohexan-4-one and trimethylsilyl cyanide.

Cyanohydrin 5 tert-Butyl 4-cyano-4-hydroxy-1,3,4,5-tetrahydro-2H-2-benzazepine-2-carboxylate

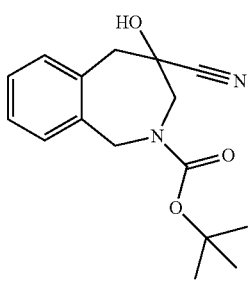 [SMILES: CC(C)(C)OC(=O)N1Cc2ccccc2CC(O)(C#N)C1]

The title compound was obtained as white solid in 47% yield according to the general procedure II from tert-butyl 4-oxo-4,5-dihydro-1H-benzo[c]azepine-2(3H)-carboxylate and 2-hydroxy-2-methylpropanenitrile. MS m/e: 289.5 ([M+H]$^+$)

Cyanohydrin 6

(3a,7a)-2-[(Trimethylsilyl)oxy]octahydro-1H-indene-2-carbonitrile

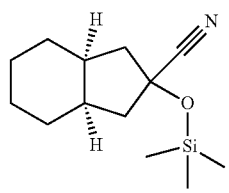 [SMILES: C[Si](C)(C)OC1(C#N)C[C@H]2CCCC[C@H]2C1]

The title compound was obtained as yellow oil in quantitative yield according to the general procedure I from hexahydro-1H-inden-2(3H)-one and trimethylsilyl cyanide.

Cyanohydrin 7

2-[(Trimethylsilyl)oxy]decahydroazulene-2-carbonitrile

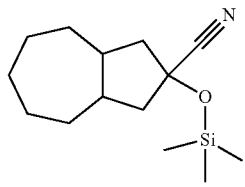 [SMILES: C[Si](C)(C)OC1(C#N)CC2CCCCCC2C1]

The title compound was obtained as yellow oil in 81% yield according to the general procedure I from octahydroazulen-2(1H)-one and trimethylsilyl cyanide.

Cyanohydrin 8

(2s,3a,6a)-5,5-Difluoro-2-[(trimethylsilyl)oxy]octahydropentalene-2-carbonitrile

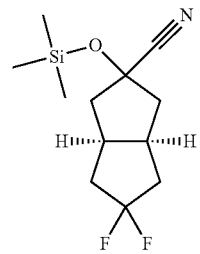 [SMILES: C[Si](C)(C)OC1(C#N)C[C@H]2CC(F)(F)C[C@H]2C1]

The title compound was obtained as colorless oil in 59% yield according to the general procedure I from 5,5-difluorohexahydropentalen-2(1H)-one and trimethylsilyl cyanide. MS m/e: 259 ([M]$^+$)

Cyanohydrin 9

(3a,5,6a)-5-[(Trimethylsilyl)oxy]hexahydro-1H-cyclopenta[c]furan-5-carbonitrile

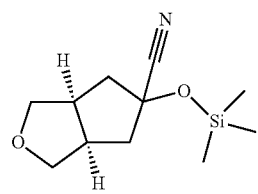

The title compound was obtained as light brown oil in 66% yield according to the general procedure I from (3aR,6aS)-tetrahydro-1H-cyclopenta[c]furan-5(3H)-one and trimethylsilyl cyanide.

Cyanohydrin 10

2-[(Trimethylsilyl)oxy]-2,3-dihydro-1H-indene-2-carbonitrile

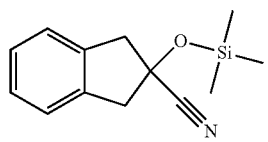 [SMILES: C[Si](C)(C)OC1(C#N)Cc2ccccc2C1]

The title compound was obtained as light brown oil in quantitative yield according to the general procedure I from 2-indanone and trimethylsilyl cyanide. MS m/e: 231 (M+)

Alpha-Hydroxy Intermediates of Formula (V)

General Procedure III: Cyanohydrin Hydrolysis with Concentrated Hydrochloric Acid A solution of a cyanohydrin intermediate of formula (X) or a trimethylsilyl cyanohydrin intermediate of formula (XIII) in an alcohol such as methanol or ethanol (0.3 M) and concentrated hydrochloric acid (20 eq) is refluxed for 6-24 h. The reaction mixture is partitioned between an organic solvent such as ethyl acetate or tert-butyl methyl ether and water. The layers are separated. The aqueous layer is extracted with one or two portions of organic solvent. The combined organic layers are washed with one portion of brine, dried over anhydrous sodium sulfate and concentrated to dryness. Purification by flash-chromatography gives an alpha-hydroxy ester intermediate of formula (V).

General Procedure IV: Pinner-Type Cyanohydrin Hydrolysis

A solution of a cyanohydrin intermediate of formula (X) or a trimethylsilyl cyanohydrin intermediate of formula (XIII) and an alcohol such as methanol or ethanol (1 eq) in 4 M hydrochloric acid in 1,4-dioxane (4-10 eq) is stored overnight in the freezer or alternatively stirred overnight at −10 to −5° C. Water is added to the reaction mixture and stirring is continued for 1-4 h. The reaction mixture is partitioned between an organic solvent such as ethyl acetate or tert-butyl methyl ether and water. The layers are separated. The aqueous layer is extracted with one or two portions of organic solvent. The combined organic layers are washed with one portion of brine, dried over anhydrous sodium sulfate and concentrated to dryness. Purification by flash-chromatography gives an alpha-hydroxy intermediate of formula (V).

Alpha-Hydroxy Ester 1

Ethyl 2-hydroxypent-4-enoate

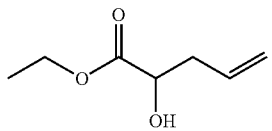

To a solution of ethyl 2-oxoacetate (50.0 g, 245 mmol) and allyltrimethylsilane (50.4 g, 441 mmol) in dichloromethane (700 ml) was added borontrifluoride diethyl etherate (52.1 g, 46.5 ml, 367 mmol) at room temperature. Stirring was continued for 3 h at reflux. The reaction mixture was poured into 500 ml saturated aqueous sodium bicarbonate solution. The layers were separated. The aqueous layer was extracted with two 500-ml portions of dichloromethane. The organic layers were dried over anhydrous sodium sulfate, filtrated and concentrated in vacuo to give the crude title compound (35.8 g, quantitative) as colorless oil, which was used in the next step without further purifications.

Alpha-Hydroxy Ester 2

Ethyl 2-hydroxy-2-methyl-3-phenylpropanoate

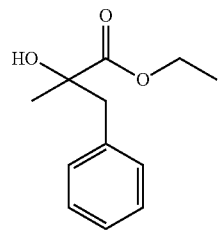

To a solution of (RS)-2-hydroxy-2-methyl-3-phenylpropanoic acid (2.9 g, 16 mmol) in ethanol (81 ml) was added a catalytic amount of sulfuric acid. The reaction mixture was stirred at room temperature for 3 d. The solvent was concentrated in vacuo. The residue was partitioned between ethyl acetate (50 ml) and 1 M aqueous sodium carbonate (50 ml). The layers were separated. The aqueous layer was extracted with two 50-ml portions of ethyl acetate. The combined organic layers were dried over anhydrous sodium sulfate, filtered and concentrated in vacuo to give the title compound (3.0 g, 88%) as colorless oil. MS m/e: 223 ([M+H]$^+$).

Alpha-Hydroxy Ester 3

Ethyl 2-benzyl-2-hydroxybutanoate

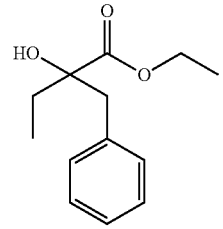

A mixture of (RS)-2-benzyl-2-hydroxybutanenitrile (1.3 g, 7.4 mmol) in 6 M aqueous hydrogen chloride (37 ml, 223 mmol) was heated at reflux for 15 h. The reaction mixture was extracted with two 75-ml portions of ethyl acetate. The combined organic layers were washed with one 30-ml portion of brine, dried over anhydrous sodium sulfate and concentrated in vacuo. Flash-chromatography with n-heptane/ethyl acetate gave (RS)-2-benzyl-2-hydroxybutanoic acid (0.45 g, 31%). To a solution of 2-benzyl-2-hydroxybutanoic acid in ethanol (4.6 ml) was added a catalytic amount of sulfuric acid. The reaction mixture was heated at reflux for 20 h. The solvent was evaporated. The residue was partitioned between ethyl acetate (75 ml) and brine (25 ml). The layers were separated. The aqueous layer was extracted with one 75-ml portion of ethyl acetate. The combined organic layers were dried over anhydrous sodium sulfate, filtered and concentrated in vacuo to give the title compound (0.42 g, 82%) as colorless oil. MS m/e: 209 ([M+H]$^+$).

Alpha-Hydroxy Ester 4

Ethyl 2-hydroxy-3-(pyridin-3-yl)butanoate

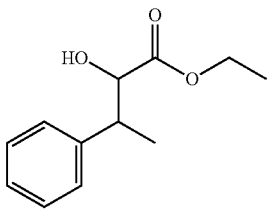

a) Ethyl 3-methyl-3-(pyridin-3-yl)oxirane-2-carboxylate

To a solution of ethyl 2-chloroacetate (1.2 g, 1.1 ml, 10 mmol) and 1-(pyridin-3-yl)ethanone (1.2 g, 1.1 ml, 10 mmol) in tetrahydrofuran (16 ml) was added 1 M sodium bis(trimethylsilyl)amide solution in tetrahydrofuran (9.5 ml, 9.5 mmol) at −78° C. The cooling bath was removed after 30 minutes and the reaction mixture was allowed to warm to room temperature. The reaction mixture was quenched with water and concentrated under reduced pressure. The residue was partitioned between water (10 ml) and diethyl ether (20 ml). The layers were separated. The organic layer was washed with water and brine, dried over anhydrous sodium sulfate, filtered and concentrated in vacuo to give the crude epoxide intermediate, which was used in the next step without further purifications.

b) Ethyl 2-hydroxy-3-(pyridin-3-yl) butanoate

To a solution of ethyl 3-methyl-3-(pyridin-3-yl)oxirane-2-carboxylate (2.1 g, 10 mmol) in ethyl acetate (20 ml) was added palladium(II) hydroxide (0.28 g, 2.0 mmol). The flask was filled with hydrogen (1 bar) and stirred for 48 h at room temperature. The catalyst was removed by filtration. The filtrate was concentrated in vacuo to give the title compound (2.6 g, quantitative) as light yellow oil.

Alpha-Hydroxy Ester 5

Ethyl 1-hydroxycyclopentanecarboxylate

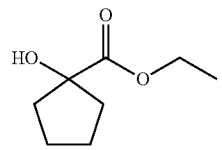

To a solution of 1-hydroxycyclopentanecarboxylic acid (0.98 g, 7.5 mmol) in ethanol (3.8 ml) was added a cat amount of sulfuric acid. The reaction mixture was stirred for 3 d at room temperature. The solvent was concentrated in vacuo. The residue was partitioned between ethyl acetate (75-ml) and brine (25-ml). The layers were separated. The aqueous layer was extracted with one 75-ml portion of ethyl acetate. The combined organic layers were dried over anhydrous sodium sulfate and concentrated in vacuo to give the title compound (1.13 g, 95%) as light brown oil. MS m/e: 159 ([M+H]$^+$)

Alpha-Hydroxy Ester 6

Methyl 1-hydroxycyclohexanecarboxylate

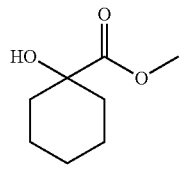

The title compound was obtained as light yellow liquid in 64% yield according to the general procedure IV from 1-hydroxycyclohexanecarbonitrile. MS m/e: 159 ([M+H]$^+$)

Alpha-Hydroxy Ester 7

Cis/Trans-Methyl 1-hydroxy-4-pentylcyclohexanecarboxylate

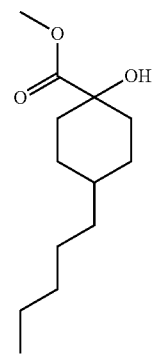 [SMILES: CCCCCC1CCC(O)(C(=O)OC)CC1]

The title compound was obtained as yellow waxy solid in 77% yield as a mixture of the cis/trans methyl ester and the acid according to the general procedure IV from 1-hydroxy-4-pentylcyclohexanecarbonitrile. MS m/e: 229 ([M+H]$^+$)

Alpha-Hydroxy Ester 8

Methyl 4,4-difluoro-1-hydroxycyclohexanecarboxylate

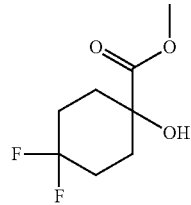

The title compound was obtained as yellow oil with a purity of 83% in 45% yield according to the general procedure III from 4,4-difluoro-1-[(trimethylsilyl)oxy]cyclohexanecarbonitrile. MS m/e: 194 (M$^+$)

Alpha-Hydroxy Ester 9

Ethyl 4-hydroxytetrahydro-2H-thiopyran-4-carboxylate

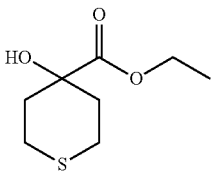

The title compound was obtained as colorless liquid in 39% yield according to the general procedure IV from 4-hydroxytetrahydro-2H-thiopyran-4-carbonitrile. MS m/e: 191 ([M+H]$^+$)

137

Alpha-Hydroxy Ester 10

Ethyl 3-hydroxytetrahydro-2H-pyran-3-carboxylate

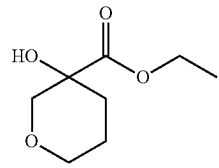

The title compound was obtained as colorless liquid with a purity of 82% in 8% yield according to the general procedure IV from 3-hydroxytetrahydro-2H-pyran-3-carbonitrile. MS m/e: 174 (M$^+$).

Alpha-Hydroxy Ester 11

2-tert-Butyl 4-methyl 4-hydroxy-1,3,4,5-tetrahydro-2H-2-benzazepine-2,4-dicarboxylate

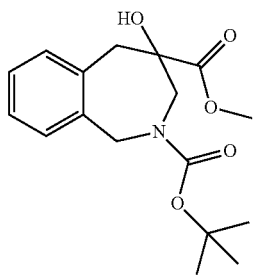 [SMILES: COC(=O)C1(O)Cc2ccccc2CN(C(=O)OC(C)(C)C)C1]

To a solution of tert-butyl 4-cyano-4-hydroxy-4,5-dihydro-1H-benzo[c]azepine-2(3H)-carboxylate (0.078 g, 0.27 mmol) in methanol (1.1 ml) was added concentrated hydrochloric acid (0.45 ml, 5.4 mmol) at room temperature. The reaction mixture was stirred for 5 minutes and then heated at 80° C. for 15 h. The reaction mixture was concentrated in vacuo. Residual water was removed by evaporation of one 50-ml portion of toluene. To a solution of the crude intermediate mixture in methanol (5 ml) was added a catalytic amount of sulfuric acid at room temperature. The reaction mixture was heated at reflux for 3 h. The reaction mixture was concentrated in vacuo. To a solution of the crude alpha hydroxy ester in dichloromethane (5 ml) was added di-tert-butyl dicarbonate (0.089 g, 0.41 mmol) and triethylamine (0.082 g, 0.11 ml, 0.81 mmol) at room temperature. The reaction mixture was stirred for 2 h and then partitioned between ethyl acetate (30 ml) and saturated ammonium chloride solution (30 ml). The layers were separated. The aqueous layer was extracted with two 30-ml portions of ethyl acetate. The combined organic layers were washed with one 30-ml portion of brine, dried over anhydrous sodium sulfate, filtered and concentrated in vacuo. Purification by flash-chromatography with n-heptane/ethyl acetate as eluent gave the title compound (0.06 g, 69%) as brown viscous oil. MS m/e: 322 ([M+H]$^+$).

138

Alpha-Hydroxy Ester 12

Methyl (3a,7a)-2-hydroxyoctahydro-1H-indene-2-carboxylate

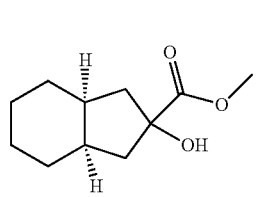

The title compound was obtained as light yellow oil in 65% yield according to the general procedure IV from 2-[(trimethylsilyl)oxy]-2,3-dihydro-1H-indene-2-carbonitrile.

Alpha-Hydroxy Ester 13

Methyl 2-hydroxydecahydroazulene-2-carboxylate

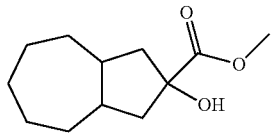

The title compound was obtained as light yellow oil in 17% yield according to the general procedure IV from (3a,7a)-2-[(trimethylsilyl)oxy]octahydro-1H-indene-2-carbonitrile.

Alpha-Hydroxy Ester 14

Methyl (2,3a,6a)-5,5-difluoro-2-hydroxyoctahydropentalene-2-carboxylate

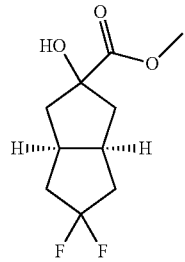

The title compound was obtained as colorless oil in quantitative yield according to the general procedure IV from (2,3a,6a)-5,5-difluoro-2-[(trimethylsilyl)oxy]octahydropentalene-2-carbonitrile. MS m/e: 220 ([M]$^+$)

Alpha-Hydroxy Ester 15

Methyl (3a,6a)-5-hydroyhexahydro-1H-cyclopenta[c]furan-5-carboxylate

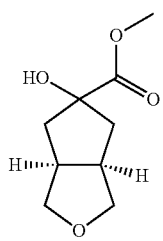

The title compound was obtained as yellow oil in 87% yield according to the general procedure IV from (3a,5,6a)-5-[(trimethylsilyl)oxy]hexahydro-1H-cyclopenta[c]furan-5-carbonitrile.

Alpha-Hydroxy Ester 16

Ethyl 2-hydroxy-2,3-dihydro-1H-indene-2-carboxylate a) 2-Hydroxy-2,3-dihydro-1H-indene-2-carboxylate

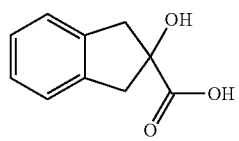 [SMILES: O=C(O)C1(O)Cc2ccccc2C1]

A slurry of 2-(trimethylsilyloxy)-2,3-dihydro-1H-indene-2-carbonitrile (21 g, 91 mmol) and concentrated hydrochloric acid (76 ml, 908 mmol) was stirred for 1 h at room temperature and for 4 h at 100° C. The reaction mixture was diluted with one 50-ml portion of water. The heating bath was removed and stirring was continued for 15 h. The precipitate was collected by filtration and washed with two 50-ml portions of 1 M aqueous hydrogen chloride solution. The wet precipitate was partitioned between ethyl acetate (150 ml) and 1 M aqueous sodium hydroxide solution (150 ml). The layers were separated. The organic layer was extracted with two 200-ml portions of 0.5 M aqueous sodium hydroxide solution. The combined aqueous layers were extracted with one 150-ml portion of ethyl acetate. The combined aqueous layers were acidified by addition of concentrated hydrochloric acid (35 ml). The aqueous layer was extracted with two 150-ml portions of ethyl acetate. The combined ethyl acetate layers from the acidic extraction were washed with one 50-ml portion of brine, dried over anhydrous sodium sulfate, filtered and concentrated in vacuo. The residue was triturated in diethyl ether (100 ml) for 3 h at room temperature. The precipitate was collected by filtration, washed with diethyl ether and dried in vacuo to give the title compound as off-white solid. Crystallization from hot ethyl acetate (90 ml) afforded the title compound (7.0 g, 43%) as white solid. MS m/e: 177 ([M–H]).

b) Ethyl 2-hydroxy-2,3-dihydro-1H-indene-2-carboxylate

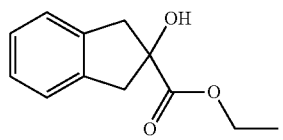

To a solution of 2-hydroxy-2,3-dihydro-1H-indene-2-carboxylic acid (4.0 g, 22 mmol) in ethanol (75 ml) was added a catalytic amount (3 drops) of sulfuric acid at room temperature. The reaction mixture was stirred for 48 h. The solvent was evaporated in vacuo. The residue was partitioned between ethyl acetate (150 ml) and 1 M sodium carbonate (50 ml). The layers were separated. The organic layer was washed with one 50-ml portion of brine, dried over anhydrous sodium sulfate, filtered and concentrated in vacuo to give the title compound (4.5 g, 97%) as white solid.

Intermediate of Formula (IV)

5-Methyl-2-thioxo-1,3-oxazolidin-4-one

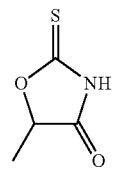

To a solution of potassium thiocyanate (6.49 g, 66.8 mmol, Eq: 1.00) and 2-hydroxypropanenitrile (5.0 g, 5.1 ml, 67 mmol, Eq: 1.00) in water (30 ml) was added drop wise concentrated hydrochloric acid (28 ml, 334 mmol, Eq: 5) in approximately 35 minutes. Stirring was continued for 24 h. The reaction mixture was partitioned between ethyl acetate (100 ml) and crushed ice/water (100 ml). The layers were separated. The aqueous layer was extracted with three 100-ml portions of ethyl acetate. The combined organic layers were washed with one 50-ml portion of brine, dried over anhydrous sodium sulfate, filtrated and concentrated in vacuo. The residue was triturated in warm toluene (50-ml). The precipitate was removed by filtration over Decalite. The filtrate was concentrated in vacuo. The residue was triturated in warm n-heptane (50 ml). The precipitate was collected by filtration, washed with n-heptane and dried in vacuo to give the title compound (5.6 g, 64%) as light yellow solid. MS m/e: 131 ($M^+$).

2-Amino-oxazol-4-ones Intermediate of Formula (III)

General Procedure V

A mixture of molecular sieves 4 A, guanidine hydrochloride (1.6-7 eq) and potassium tert-butoxide in tert-butanol is stirred at room temperature for 2-24 h. Addition of an alpha-hydroxy ester intermediate of formula (V) is followed by stirring for 2-24 h. The reaction mixture is diluted with a solvent mixture such as ethyl acetate/2-propanol (4:1) or isopropyl acetate/2-propanol (4:1). The solids are removed by filtration. The filtrate is washed with water. The layers are separated. The aqueous layer is extracted with one or two portions of organic solvent mixture. The combined organic layers are washed with one portion of brine, dried over anhydrous sodium sulfate and concentrated to dryness. Trituration from a solvent such as ethyl acetate or isopropyl acetate gives a 2-amino-oxazol-4-one intermediate of formula (III).

2-Amino-oxazol-4-one 1

2-Amino-5-(prop-2-en-1-yl)-1,3-oxazol-4(5H)-one

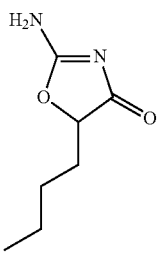

The title compound was obtained as white solid in quantitative yield according to the general procedure V from ethyl 2-hydroxyhexanoate. MS m/e: 157 ([M+H]$^+$)

2-Amino-oxazol-4-one 2

2-Amino-5-(prop-2-en-1-yl)-1,3-oxazol-4(5H)-one

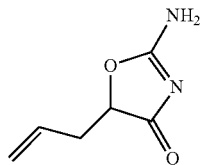

The title compound was obtained as white solid in 58% yield according to the general procedure V from ethyl 2-hydroxypent-4-enoate.

2-Amino-oxazol-4-one 3

2-Amino-5-(cyclopentylmethyl)-1,3-oxazol-4(5H)-one

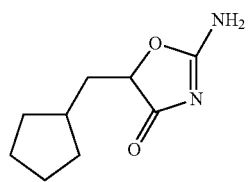 [SMILES: NC1=NC(=O)C(CC2CCCC2)O1]

The title compound was obtained as white gum in 91% yield according to the general procedure V from methyl 3-cyclopentyl-2-hydroxypropanoate. MS m/e: 183 ([M+H]$^+$)

2-Amino-oxazol-4-one 4

2-Amino-5-benzyl-1,3-oxazol-4(5H)-one

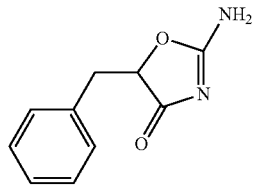 [SMILES: NC1=NC(=O)C(Cc2ccccc2)O1]

The title compound was obtained as a white solid in 74% yield according to the general procedure V from methyl 2-hydroxy-3-phenylpropanoate. MS m/e: 191 ([M+H]$^+$)

2-Amino-oxazol-4-one 5

2-Amino-1-oxa-3-azaspiro[4.5]dec-2-en-4-one

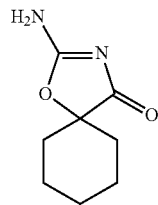 [SMILES: NC1=NC(=O)C2(CCCCC2)O1]

The title compound was obtained as white solid in 70% yield according to the general procedure V from methyl 1-hydroxycyclohexanecarboxylate. MS m/e: 169 ([M+H]$^+$)

2-Amino-oxazol-4-one 6

Cis/Trans-2-Amino-8-pentyl-1-oxa-3-azaspiro[4.5]dec-2-en-4-one

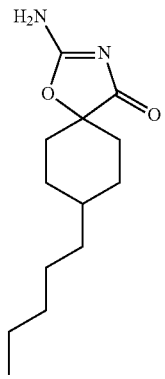 [SMILES: CCCCCC1CCC2(CC1)OC(N)=NC2=O]

The title compound was obtained as white solid in 47% yield according to the general procedure V from cis/trans-methyl 1-hydroxy-4-pentylcyclohexanecarboxylate. MS m/e: 239 ([M+H]$^+$)

2-Amino-oxazol-4-one 7

2-Amino-8,8-difluoro-1-oxa-3-azaspiro[4.5]dec-2-en-4-one

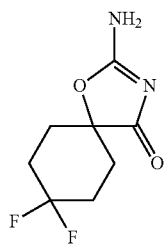

The title compound was obtained as light yellow solid in 66% yield according to the general procedure V from methyl 4,4-difluoro-1-hydroxycyclohexanecarboxylate. MS m/e: 205 ([M+H]$^+$)

2-Amino-oxazol-4-one 8 tert-Butyl 2-amino-4-oxo-1-oxa-3,8-diazaspiro[4.5]dec-2-ene-8-carboxylate

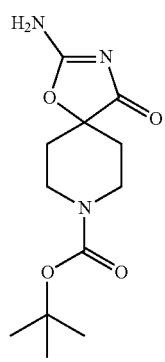 [SMILES: CC(C)(C)OC(=O)N1CCC2(CC1)OC(N)=NC2=O]

The title compound was obtained as white solid in 83% yield according to the general procedure V from 1-tert-butyl 4-ethyl 4-hydroxypiperidine-1,4-dicarboxylate. MS m/e: 270 ([M+H]$^+$)

2-Amino-oxazol-4-one 9

(2r,3a,7a)-2'-Amino-1,3,3a,4,5,6,7,7a-octahydro-4'H-spiro[indene-2,5'-[1,3]oxazol]-4'-one

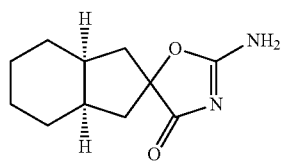 [SMILES: NC1=NC(=O)C2(C[C@H]3CCCC[C@H]3C2)O1]

The title compound was obtained as light brown solid in 82% yield according to the general procedure V from methyl (3a,7a)-2-hydroxyoctahydro-1H-indene-2-carboxylate. MS m/e: 209 ([M+H]$^+$)

2-Amino-oxazol-4-one 10

2'-Amino-3,3a,4,5,6,7,8,8a-octahydro-1H,4'H-spiro[azulene-2,5'-[1,3]oxazol]-4'-one

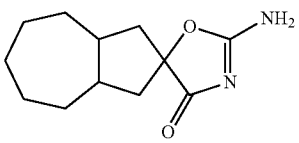 [SMILES: NC1=NC(=O)C2(CC3CCCCCC3C2)O1]

The title compound was obtained as brown solid in 50% yield according to the general procedure V from methyl 2-hydroxydecahydroazulene-2-carboxylate. MS m/e: 209 ([M+H]$^+$)

2-Amino-oxazol-4-one 11

(3a',5,6a')-2-Amino-5',5'-difluoro-3',3a',4',5',6',6a'-hexahydro-1'H,4H-spiro[1,3-oxazole-5,2'-pentalen]-4-one

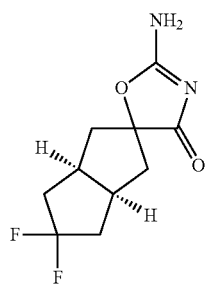

The title compound was obtained as white solid in 65% yield according to the general procedure V from methyl (2s,3a,6a)-5,5-difluoro-2-hydroxyoctahydropentalene-2-carboxylate. MS m/e: 231 ([M+H]$^+$)

2-Amino-oxazol-4-one 12

2'-Amino-3a,4,6,6a-tetrahydro-1H,3H,4'H-spiro[cyclopenta[c]furan-5,5'-[1,3]oxazol]-4'-one

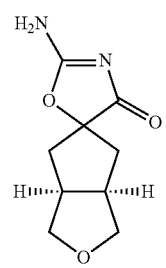

The title compound was obtained as light yellow solid in quantitative yield according to the general procedure V from methyl (3a,6a)-5-hydroxyhexahydro-1H-cyclopenta[c]furan-5-carboxylate. MS m/e: 196 ([M+H]$^+$)

2-Amino-oxazol-4-one 13

2'-Amino-1,3-dihydro-4'H-spiro[indene-2,5'-[1,3]oxazol]-4'-one

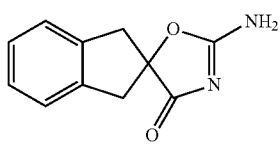 [SMILES: NC1=NC(=O)C2(Cc3ccccc3C2)O1]

The title compound was obtained as white solid in 75% yield according to the general procedure V from ethyl 2-hydroxy-2,3-dihydro-1H-indene-2-carboxylate. MS m/e: 203 ([M+H]$^+$)

Intermediate of Formula (VIII)

2-(1'H,3H-Spiro[2-benzofuran-1,4'-piperidin]-1'-yl)-1,3-oxazol-4(5H)-one

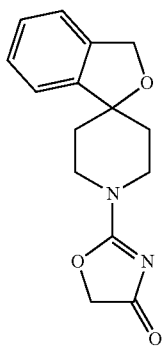 [SMILES: O=C1COC(N2CCC3(CC2)OCc2ccccc23)=N1]

A mixture of 3H-spiro[isobenzofuran-1,4'-piperidine] (7.9 g, 42 mmol) and 2-chloroacetyl isocyanate (5.0 g, 42 mmol) in dichloromethane (250 ml) was stirred for 1 h. The reaction mixture was poured into 250 ml water and extracted with two 200-ml portions of dichloromethane. The organic layers were dried over anhydrous sodium sulfate, filtered and concentrated in vacuo. The residue was dissolved in tetrahydrofuran (500 ml) to give a colorless solution. 1,8-Diazabicyclo[5.4.0]undec-7-ene (13 ml, 83 mmol) was added. The reaction mixture was stirred at RT for 30 minutes. The reaction mixture was poured into 400 ml aqueous 1 M hydrogen chloride solution and extracted with one 500-ml portion of ethyl acetate and two 300-ml portions of dichloromethane. The combined organic layers were dried over anhydrous sodium sulfate, filtered and concentrated in vacuo. The light yellow solid crude product was purified by precipitation from dichloromethane with ethyl acetate yielding the title compound (5.7 g, 50% yield) as a white solid. MS m/e: 273 ([M+H]$^+$)

Intermediate of Formula (I-c)

5-Methyl-2-(1'H,3H-spiro[2-benzofuran-1,4'-piperidin]-1'-yl)-1,3-oxazol-4(5H)-one

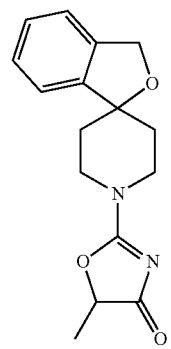 [SMILES: CC1OC(N2CCC3(CC2)OCc2ccccc23)=NC1=O]

A solution of 5-methyl-2-thioxooxazolidin-4-one (0.71 g, 5.4 mmol, Eq: 1.0),3H-spiro[isobenzofuran-1,4'-piperidine] (1.0 g, 5.4 mmol, Eq: 1.0) and triethylamine (0.75 ml, 5.4 mmol, Eq: 1.0) in ethanol (27 ml) was heated at reflux for 20 h. The heating bath was removed and stirring was continued for 90 minutes. The precipitate was collected by filtration, washed with cold ethanol and dried in vacuo to give the title compound (1.1 g, 71%) as white solid. MS m/e: 287 ([M+H]$^+$)

EXAMPLES

General Procedure VI: Aminolysis

A mixture of a spiropiperidine of formula (II) as free base and a 2-amino-oxazol-4-one intermediate of formula (III) in a solvent such as ethanol, n-butanol, tert-butanol, 1,4-dioxane or tetrahydrofuran (0.1-0.3 M) is heated at 90° C. to reflux for (6-72 h). Alternatively a mixture of a spiropiperidine of formula (II) as hydrochloride salt (1-1.5 eq), an organic base such as Huenig's Base or triethylamine (1-1.5 eq) and a 2-amino-oxazol-4-one intermediate of formula (III) in a solvent such as ethanol, n-butanol, tert-butanol, 1,4-dioxane or tetrahydrofuran (0.1-0.3 M) is heated at 90° C. to reflux for (6-72 h). The mixture can alternatively be heated under microwave irradiation at 130-160° C. for 10-30 minutes. After cooling to room temperature the reaction mixture is partitioned between an organic solvent such as ethyl acetate or dichloromethane and aqueous saturated ammonium chloride solution. The layers are separated. The aqueous layer is extracted with one or two portions of organic solvent. The combined organic layers are washed with one portion of brine, dried over anhydrous sodium sulfate and concentrated to dryness. Purification by flash-chromatography or crystallization from a suitable solvent gives a compound of formula (I).

General Procedure VII: One Pot Reaction with Amines

To a solution of an alpha-hydroxy ester intermediate of formula (V) in a solvent such as 1,2-dimethoxyethane or tetrahydrofuran (0.2 M) is added sodium hydride (1.0 eq, 50% in oil), at 0-5° C. Stirring for 20-30 minutes is followed by addition of 5.0 M cyanogen bromide solution in acetonitrile (1.0 eq). The reaction mixture is stirred for 30-60 minutes. An amine intermediate of formula (II) is added, and stirring is continued at room temperature for 30 minutes and at reflux for 6-24 h. The reaction mixture is partitioned between an organic solvent such as ethyl acetate or tert-butyl methyl ether and saturated aqueous ammonium chloride solution. The layers are separated. The aqueous layer is extracted with one or two portions of organic solvent. The combined organic layers are washed with one portion of brine, dried over anhydrous sodium sulfate and concentrated to dryness. Purification by flash-chromatography gives a compound of formula (I).

General Procedure VIII: One Pot Reaction with Piperidine-1-Carbonitriles

A mixture of an alpha-hydroxy ester intermediate of formula (V) in toluene (0.1-0.3 M) and sodium hydride (1.0 eq, 50% in oil), is stirred for 5-30 minutes at 0-5° C. A cyanamide intermediate of formula (VI) is added, and stirring is continued for 6-24 h at 90° C. After cooling to room temperature the reaction mixture is partitioned between an organic solvent such as ethyl acetate or tert-butyl methyl ether and saturated aqueous ammonium chloride solution. The layers are separated. The aqueous layer is extracted with one or two portions of organic solvent. The combined organic layers are washed with one portion of brine, dried over anhydrous sodium sulfate and concentrated to dryness. Purification by flash-chromatography gives a compound of formula (I).

General Procedure IX: Alkylation of Oxazolones with Alkyl Halides

To a solution of a compound of formula (VIII) or (I-a) in tetrahydrofuran (0.1 M) is added 1.0 M lithium bis(trimethylsilyl)amide solution in tetrahydrofuran (1.1 eq) at 0-5° C. The reaction mixture is stirred for 30-60 minutes. An alkyl halide (1.2-2.0 eq) is added, and stirring is continued for 2-24 h. The reaction mixture is partitioned between an organic solvent such as ethyl acetate or tert-butyl methyl ether and 1 M aqueous hydrogen chloride solution. The layers are separated. The aqueous layer is extracted with one or two portions of organic solvent. The combined organic layers are washed with one portion of brine, dried over anhydrous sodium sulfate and concentrated to dryness. Purification by flash-chromatography gives a compound of formula (I), (I-a) or (I-b) respectively.

General Procedure X: Condensation of Oxazolones with Aldehydes or Ketones

To a solution of a compound of formula (VIII) or (I-c) in tetrahydrofuran (0.1 M) is added 1.0 M lithium diisopropyl amide solution in tetrahydrofuran (1.2 eq) at −78° C. The reaction mixture is stirred for 30-60 minutes. An aldehyde or ketone (1.2) is added, and stirring is continued for 2-24 h. The reaction mixture is partitioned between an organic solvent such as ethyl acetate or tert-butyl methyl ether and water. The layers are separated. The aqueous layer is extracted with one or two portions of organic solvent. The combined organic layers are washed with one portion of brine, dried over anhydrous sodium sulfate and concentrated to dryness. Purification by flash-chromatography gives a compound of formula (I-d).

General Procedure XI: Ring-Closing Metathesis

To a solution of an intermediate of formula (I-l) in dichloromethane or toluene (0.005-0.01 M) at room temperature is added Grubbs $2^{nd}$ generation catalyst (0.1 to 1.0 eq). Stirring is continued at 40-110° C. for 1-24 h. The reaction mixture is concentrated to dryness. Purification by flash-chromatography gives a compound of formula (I-m).

Example 1

5-Propyl-2-(1'H,3H-spiro[2-benzofuran-1,4'-piperidin]-1'-yl)-1,3-oxazol-4(5H)-one The title compound was obtained as off-white solid in 54% yield according to the general procedure VIII from 1'H,3H-spiro[2-benzofuran-1,4'-piperidine]-1'-carbonitrile and ethyl 2-hydroxypentanoate. MS m/e: 315 ([M+H]$^+$)

Example 2

5-Butyl-2-(1'H,3H-spiro[2-benzofuran-1,4'-piperidin]-1'-yl)-1,3-oxazol-4(5H)-one The title compound was obtained as white solid in 60% yield from 2-amino-5-butyloxazol-4(5H)-one and 3H-spiro[isobenzofuran-1,4'-piperidine] according to the general procedure VI. MS m/e: 329 ([M+H]$^+$)

Example 3

(−)-5-Butyl-2-(1'H,3H-spiro[2-benzofuran-1,4'-piperidin]-1'-yl)-1,3-oxazol-4(5H)-one and Example 4

(+)-5-Butyl-2-(1'H,3H-spiro[2-benzofuran-1,4'-piperidin]-1'-yl)-1,3-oxazol-4(5H)-one (−)-5-Butyl-2-(1'H,3H-spiro[2-benzofuran-1,4'-piperidin]-1'-yl)-1,3-oxazol-4(5H)-one and (+)-5-butyl-2-(1'H,3H-spiro[2-benzofuran-1,4'-piperidin]-1'-yl)-1,3-oxazol-4(5H)-one were obtained from 5-butyl-2-(1'H,3H-spiro[2-benzofuran-1,4'-piperidin]-1'-yl)-1,3-oxazol-4(5H)-one by chiral HPLC separation on a Chiralcel OD column with n-heptane/ethanol as eluent.

(−)-5-Butyl-2-(1'H,3H-spiro[2-benzofuran-1,4'-piperidin]-1'-yl)-1,3-oxazol-4(5H)-one was obtained as white solid in 43% yield. MS m/e: 329 ([M+H]$^+$), $[\alpha]D=-31.03$ (c=0.680, CHCl$_3$, 20° C.).

(+)-5-Butyl-2-(1'H,3H-spiro[2-benzofuran-1,4'-piperidin]-1'-yl)-1,3-oxazol-4(5H)-one was obtained as white solid in 33% yield. MS m/e: 329 ([M+H]$^+$), $[\alpha]D=+20.49$ (c=0.576, CHCl$_3$, 20° C.).

Example 5

1'-[5-Butyl-4-oxo-4,5-dihydro-1,3-oxazol-2-yl]-3H-spiro[2-benzofuran-1,4'-piperidin]-3-one enantiomer A and Example 6

1'-[5-Butyl-4-oxo-4,5-dihydro-1,3-oxazol-2-yl]-3H-spiro[2-benzofuran-1,4'-piperidin]-3-one enantiomer B The title compounds were obtained according to the general procedure VI from 2-amino-5-(prop-2-en-1-yl)-1,3-oxazol-4(5H)-one and 3H-spiro[isobenzofuran-1,4'-piperidin]-3-one after separation by chiral HPLC on a Chiralcel OD (OD-H) column with n-heptane/ethanol (7:3) as eluent. The rotational sense was determined during the separation with a chiral detector from IBZ Messtechnik at 426 nm. The compounds are cited in the order of elution:

1'-[5-Butyl-4-oxo-4,5-dihydro-1,3-oxazol-2-yl]-3H-spiro[2-benzofuran-1,4'-piperidin]-3-one enantiomer A was obtained as white solid in 7% yield. MS m/e: 343 ([M+H]$^+$). Rotational sense: (−)

1'-[5-Butyl-4-oxo-4,5-dihydro-1,3-oxazol-2-yl]-3H-spiro[2-benzofuran-1,4'-piperidin]-3-one enantiomer B was obtained as white solid in 7% yield. MS m/e: 343 ([M+H]$^+$). Rotational sense: (+)

Example 7

5-(2-Methylpropyl)-2-(1'H,3H-spiro[2-benzofuran-1,4'-piperidin]-1'-yl)-1,3-oxazol-4(5H)-one The title compound was obtained as light yellow solid in 10% yield according to the general procedure VIII from 1'H,3H-spiro[2-benzofuran-1,4'-piperidine]-1'-carbonitrile and isopropyl 2-hydroxy-4-methylpentanoate. MS m/e: 329 ([M+H]$^+$)

Example 8

5-(Prop-2-en-1-yl)-2-(1'H,3H-spiro[2-benzofuran-1,4'-piperidin]-1'-yl)-1,3-oxazol-4(5H)-one The title compound was obtained as white solid in 55% yield according to the general procedure VI from 2-amino-5-(prop-2-en-1-yl)-1,3-oxazol-4(5H)-one and 3H-spiro[isobenzofuran-1,4'-piperidine]. MS m/e: 313 ([M+H]$^+$)

Example 9

5-(2-Methylprop-2-en-1-yl)-2-(1'H,3H-spiro[2-benzofuran-1,4'-piperidin]-1'-yl)-1,3-oxazol-4(5H)-one The title compound was obtained as off-white solid in 7% yield according to the general procedure IX from 2-(1'H,3H-spiro[2-benzofuran-1,4'-piperidin]-1'-yl)-1,3-oxazol-4(5H)-one and 3-bromo-2-methylprop-1-ene. MS m/e: 326 ([M+]$^+$)

Example 10

2-(1'H,3H-Spiro[2-benzofuran-1,4'-piperidin]-1'-yl)-5-[2-(trifluoromethyl)prop-2-en-1-yl]-1,3-oxazol-4(5H)-one The title compound was obtained as light yellow solid in 44% yield according to the general procedure IX from 2-(1'H,3H-spiro[2-benzofuran-1,4'-piperidin]-1'-yl)-1,3-oxazol-4(5H)-one and 2-(bromomethyl)-3,3,3-trifluoroprop-1-ene. MS m/e: 381 ([M+H]$^+$)

Example 11

5-(But-2-yn-1-yl)-2-(1'H,3H-spiro[2-benzofuran-1,4'-piperidin]-1'-yl)-1,3-oxazol-4(5H)-one The title compound was obtained as light yellow solid in 38% yield according to the general procedure IX from 2-(1'H,3H-spiro[2-benzofuran-1,4'-piperidin]-1'-yl)-1,3-oxazol-4(5H)-one and 1-bromobut-2-yne. MS m/e: 325 ([M+H]$^+$)

Example 12

5-Phenyl-2-(1'H,3H-spiro[2-benzofuran-1,4'-piperidin]-1'-yl)-1,3-oxazol-4(5H)-one The title compound was obtained as white solid in 33% yield according to the general procedure VIII from 1'H,3H-spiro[2-benzofuran-1,4'-piperidine]-1'-carbonitrile and methyl 2-hydroxy-2-phenylacetate.

Example 13

5-(Cyclopentylmethyl)-2-(1'H,3H-spiro[2-benzofuran-1,4'-piperidin]-1'-yl)-1,3-oxazol-4(5H)-one enantiomer A and Example 14

5-(Cyclopentylmethyl)-2-(1'H,3H-spiro[2-benzofuran-1,4'-piperidin]-1'-yl)-1,3-oxazol-4(5H)-one enantiomer B 5-(Cyclopentylmethyl)-2-(1'H,3H-spiro[2-benzofuran-1,4'-piperidin]-1'-yl)-1,3-oxazol-4(5H)-one enantiomer A and 5-(cyclopentylmethyl)-2-(1'H,3H-spiro[2-benzofuran-1,4'-piperidin]-1'-yl)-1,3-oxazol-4(5H)-one enantiomer B were obtained according to the general procedure VI from 2-amino-5-(cyclopentylmethyl)-1,3-oxazol-4(5H)-one and 3H-spiro[isobenzofuran-1,4'-piperidine] after separation by chiral HPLC on a Chiralpak AD column with n-heptane/ethanol (3:1) as eluent. The rotational sense was determined during the separation with a chiral detector from IBZ Messtechnik at 426 nm. The compounds are cited in order of elution:

5-(Cyclopentylmethyl)-2-(1'H,3H-spiro[2-benzofuran-1,4'-piperidin]-1'-yl)-1,3-oxazol-4(5H)-one enantiomer A (0.005 g, 2%) was obtained as light yellow solid. MS m/e: 355 ([M+H]$^+$). Rotational sense: (+)

5-(Cyclopentylmethyl)-2-(1'H,3H-spiro[2-benzofuran-1,4'-piperidin]-1'-yl)-1,3-oxazol 4(5H)-one enantiomer B (0.009 g, 4%) was obtained as light yellow solid. MS m/e: 355 ([M+H]$^+$). Rotational sense: (−)

Example 15

1'-[5-(Cyclopentylmethyl)-4-oxo-4,5-dihydro-1,3-oxazol-2-yl]-3H-spiro[2-benzofuran-1,4'-piperidin]-3-one enantiomer A and Example 16

1'-[5-(Cyclopentylmethyl)-4-oxo-4,5-dihydro-1,3-oxazol-2-yl]-3H-spiro[2-benzofuran-1,4'-piperidin]-3-one enantiomer B The title compounds were obtained according to the general procedure VI from 2-amino-5-(cyclopentylmethyl)-1,3-oxazol-4(5H)-one and 3H-spiro[isobenzofuran-1,4'-piperidin]-3-one by chiral HPLC separation on a Chiralpak AD column with n-heptane/ethanol (3:2) as eluent. The rotational sense was determined during the separation with a chiral detector from IBZ Messtechnik at 426 nm. The compounds are cited in order of elution:

1'-[5-(Cyclopentylmethyl)-4-oxo-4,5-dihydro-1,3-oxazol-2-yl]-3H-spiro[2-benzofuran-1,4'-piperidin]-3-one enantiomer A was obtained as light yellow solid in 3% yield. MS m/e: 369 ([M+H]$^+$). Rotational sense: (+)

1'-[5-(Cyclopentylmethyl)-4-oxo-4,5-dihydro-1,3-oxazol-2-yl]-3H-spiro[2-benzofuran-1,4'-piperidin]-3-one enantiomer B was obtained as white solid in 6% yield. MS m/e: 369 ([M+H]$^+$). Rotational sense: (−)

Example 17

5-Benzyl-2-(1'H,3H-spiro[2-benzofuran-1,4'-piperidin]-1'-yl)-1,3-oxazol-4(5H)-one The title compound was obtained as white solid in 10% yield from 2-amino-5-benzyl-1,3-oxazol-4(5H)-one and 3H-spiro[isobenzofuran-1,4'-piperidine] according to the general procedure VI. MS m/e: 363 ([M+H]$^+$)

Example 18

(+)-(5R)-5-Benzyl-2-(1'H,3H-spiro[2-benzofuran-1,4'-piperidin]-1'-yl)-1,3-oxazol-4(5H)-one and Example 19

(−)-(5S)-5-Benzyl-2-(1'H,3H-spiro[2-benzofuran-1,4'-piperidin]-1'-yl)-1,3-oxazol-4(5H)-one The title compounds were obtained from 5-benzyl-2-(1'H,3H-spiro[2-benzofuran-1,4'-piperidin]-1'-yl)-1,3-oxazol-4(5H)-one by chiral HPLC separation on a Chiralpak AD column with n-heptane/isopropanol as eluent. Another batch of (−)-(5S)-5-benzyl-2-(1'H,3H-spiro[2-benzofuran-1,4'-piperidin]-1'-yl)-1,3-oxazol-4(5H)-one with an enantiomeric excess of 95% was prepared from (S)-benzyl 2-hydroxy-3-phenylpropanoate, cyanogen bromide and 3H-spiro[isobenzofuran-1,4'-piperidine] according to the general procedure VII.

(+)-(5R)-5-Benzyl-2-(1'H,3H-spiro[2-benzofuran-1,4'-piperidin]-1'-yl)-1,3-oxazol-4(5H)-one: (MS m/e: 363 ([M+H]$^+$), [α]D=+46.68 (c=0.512, CHCl$_3$, 20° C.)

(−)-(5S)-5-Benzyl-2-(1'H,3H-spiro[2-benzofuran-1,4'-piperidin]-1'-yl)-1,3-oxazol-4(5H)-one: (MS m/e: 363 ([M+H]$^+$), [α]D=−48.02 (c=1.004, CHCl$_3$, 20° C.)

(−)-(5S)-5-Benzyl-2-(1'H,3H-spiro[2-benzofuran-1,4'-piperidin]-1'-yl)-1,3-oxazol-4(5H)-one (95% ee) from procedure VII: (MS m/e: 363 ([M+H]$^+$), [α]D=−33.20 (c=1.000, CHCl$_3$, 20° C.)

Example 20

1'-[5-Benzyl-4-oxo-4,5-dihydro-1,3-oxazol-2-yl]-3H-spiro[2-benzofuran-1,4'-piperidin]-3-one enantiomer A and Example 21

1'-[5-Benzyl-4-oxo-4,5-dihydro-1,3-oxazol-2-yl]-3H-spiro[2-benzofuran-1,4'-piperidin]-3-one enantiomer B The title compounds were obtained according to the general procedure VI from 2-amino-5-benzyl-1,3-oxazol-4(5H)-one and 3H-spiro[isobenzofuran-1,4'-piperidin]-3-one after separation by chiral HPLC separation on a Reprosil Chiral-NR column with n-heptane/ethanol (3:2) as eluent. The rotational sense was determined during the separation with a chiral detector from IBZ Messtechnik at 426 nm. The compounds are cited in order of elution:

1'-[5-Benzyl-4-oxo-4,5-dihydro-1,3-oxazol-2-yl]-3H-spiro[2-benzofuran-1,4'-piperidin]-3-one enantiomer A was obtained as white solid in 18% yield. MS m/e: 377 ([M+H]$^+$). Rotational sense: (−)

1'-[5-Benzyl-4-oxo-4,5-dihydro-1,3-oxazol-2-yl]-3H-spiro[2-benzofuran-1,4'-piperidin]-3-one enantiomer B was obtained as colorless oil in 14% yield. MS m/e: 377 ([M+H]$^+$). Rotational sense: (+)

Example 22

5-Benzyl-2-(3-methyl-1'H,3H-spiro[2-benzofuran-1,4'-piperidin]-1'-yl)-1,3-oxazol-4(5H)-one The title compound was obtained as white semisolid in 37% yield according to the general procedure VI from 3-methyl-3H-spiro[isobenzofuran-1,4'-piperidine]-one and 2-amino-5-benzyl-1,3-oxazol-4(5H)-one. MS m/e: 377 ([M+H]$^+$)

Example 23

5-Benzyl-2-(7-fluoro-1'H,3H-spiro[2-benzofuran-1,4'-piperidin]-1'-yl)-1,3-oxazol-4(5H)-one The title compound was obtained as white semisolid in 40% yield according to the general procedure VI from 7-fluoro-3H-spiro[isobenzofuran-1,4'-piperidine] and 2-amino-5-benzyl-1,3-oxazol-4(5H)-one. MS m/e: 381 ([M+H]$^+$)

Example 24

5-Benzyl-2-(4-fluoro-1'H,3H-spiro[2-benzofuran-1,4'-piperidin]-1'-yl)-1,3-oxazol-4(5H)-one The title compound was obtained as light yellow semisolid in 19% yield according to the general procedure VI from 2-amino-5-benzyl-1,3-oxazol-4(5H)-one and 4-fluoro-3H-spiro[isobenzofuran-1,4'-piperidine]. MS m/e: 381 ([M+H]$^+$)

Example 25

5-Benzyl-2-(6-fluoro-1'H,3H-spiro[2-benzofuran-1,4'-piperidin]-1'-yl)-1,3-oxazol-4(5H)-one The title compound was obtained as white solid in 45% yield according to the general procedure VI from 2-amino-5-benzyl-1,3-oxazol-4(5H)-one and 6-fluoro-3H-spiro[isobenzofuran-1,4'-piperidine]. MS m/e: 381 ([M+H]$^+$)

Example 26

5-Benzyl-2-(3,3-dimethyl-1'H,3H-spiro[2-benzofuran-1,4'-piperidin]-1'-yl)-1,3-oxazol-4(5H)-one The title compound was obtained as white solid in 39% yield from 2-amino-5-benzyl-1,3-oxazol-4(5H)-one and 3,3-dimethyl-3H-spiro[isobenzofuran-1,4'-piperidine] according to the general procedure VI. MS m/e: 391 ([M+H]$^+$)

Example 27

1'-(5-Benzyl-4-oxo-4,5-dihydro-1,3-oxazol-2-yl)-5-fluoro-3H-spiro[2-benzofuran-1,4'-piperidin]-3-one The title compound was obtained as white solid in 49% yield according to the general procedure VI from 2-amino- 5-benzyl-1,3-oxazol-4(5H)-one and 5-fluoro-3H-spiro [isobenzofuran-1,4'-piperidin]-3-one. MS m/e: 395 ([M+H]$^+$)

Example 28

5-Benzyl-2-(1'H,7H-spiro[furo[3,4-b]pyridine-5,4'-piperidin]-1'-yl)-1,3-oxazol-4(5H)-one The title compound was obtained as colorless oil in 18% yield according to the general procedure VI from 2-amino-5-benzyl-1,3-oxazol-4(5H)-one and 7H-spiro[furo[3,4-b]pyridine-5,4'-piperidine]. MS m/e: 364 ([M+H]$^+$)

Example 29

5-Benzyl-2-(1'H,5H-spiro[furo[3,4-b]pyridine-7,4'-piperidin]-1'-yl)-1,3-oxazol-4(5H)-one The title compound was obtained as white semisolid in 8% yield according to the general procedure VI from 2-amino-5-benzyl-1,3-oxazol-4(5H)-one and 5H-spiro[furo[3,4-b]pyridine-7,4'-piperidine]. MS m/e: 364 ([M+H]$^+$)

Example 30

1'-(5-Benzyl-4-oxo-4,5-dihydro-1,3-oxazol-2-yl)-4-fluoro-3H-spiro[2-benzofuran-1,4'-piperidin]-3-one The title compound was obtained as yellow oil in 4% yield according to the general procedure VI from 2-amino-5-benzyl-1,3-oxazol-4(5H)-one and 4-fluoro-3H-spiro[isobenzofuran-1,4'-piperidin]-3-one. MS m/e: 395 ([M+H]$^+$)

Example 31

1'-(5-Benzyl-4-oxo-4,5-dihydro-1,3-oxazol-2-yl)-5-methoxy-3-spiro[2-benzofuran-1,4'-piperidin]-3-one The title compound was obtained as yellow oil in 6% yield according to the general procedure VI from 2-amino-5-benzyl-1,3-oxazol-4(5H)-one and 5-methoxy-3H-spiro[isobenzofuran-1,4'-piperidin]-3-one. MS m/e: 407 ([M+H]$^+$)

Example 32

1'-(5-Benzyl-4-oxo-4,5-dihydro-1,3-oxazol-2-yl)-5-bromo-3H-spiro[2-benzofuran-1,4'-piperidin]-3-one The title compound was obtained as white solid in 21% yield according to the general procedure VI from 2-amino-5-benzyl-1,3-oxazol-4(5H)-one and 5-bromo-3H-spiro[isobenzofuran-1,4'-piperidin]-3-one. MS m/e: 457 ([M+H]$^+$)

Example 33

5-Benzyl-2-(1'H,3H-spiro[2-benzothiophene-1,4'-piperidin]-1'-yl)-1,3-oxazol-4(5H)-one The title compound was obtained as yellow gum in 38% yield according to the general procedure VI from 2-amino-5-benzyl-1,3-oxazol-4(5H)-one and 3H-spiro[benzo[α]thiophene-1,4'-piperidine] hydrochloride using sodium bicarbonate. MS m/e: 379 ([M+H]$^+$)

Example 34

5-Benzyl-2-(2,2-dioxido-1'H,3H-spiro[2-benzothiophene-1,4'-piperidin]-1'-yl)-1,3-oxazol-4(5H)-one The title compound was obtained as white gum in 33% yield according to the general procedure VI from 2-amino-5-benzyl-1,3-oxazol-4(5H)-one and spiro[1H-2-benzothiophene-3,4'-piperidine] 2,2-dioxide hydrochloride using sodium bicarbonate. MS m/e: 411 ([M+H]$^+$)

Example 35

5-(4-Chlorobenzyl)-2-(1'H,3H-spiro[2-benzofuran-1,4'-piperidin]-1'-yl)-1,3-oxazol-4(5H)-one The title compound was obtained as white solid in 12% yield according to the general procedure IX from 2-(1'H,3H-spiro[2-benzofuran-1,4'-piperidin]-1'-yl)-1,3-oxazol-4(5H)-one and 1-(bromomethyl)-4-chlorobenzene. MS m/e: 397 ([M+H]$^+$)

Example 36

5-(Hydroxy(phenyl)methyl)-2-(1'H,3H-spiro[2-benzofuran-1,4'-piperidin]-1'-yl)-1,3-oxazol-4(5H)-one diastereomer a, enantiomer A and

Example 37

5-(Hydroxy(phenyl)methyl)-2-(1'H,3H-spiro[2-benzofuran-1,4'-piperidin]-1'-yl)-1,3-oxazol-4(5H)-one diastereomer a, enantiomer B and

Example 38

5-(Hydroxy(phenyl)methyl)-2-(1'H,3H-spiro[2-benzofuran-1,4'-piperidin]-1'-yl)-1,3-oxazol-4(5H)-one diastereomer b, enantiomer A and

Example 39

5-(Hydroxy(phenyl)methyl)-2-(1'H,3H-spiro[2-benzofuran-1,4'-piperidin]-1'-yl)-1,3-oxazol-4(5H)-one diastereomer b, enantiomer B The title compounds were obtained according to the general procedure X from 2-(1'H,3H-spiro[2-benzofuran-1,4'-piperidin]-1'-yl)-1,3-oxazol-4(5H)-one and benzaldehyde after chiral HPLC separation on a Reprosil Chiral NR column with n-heptane/ethanol (4:1) as eluent. The rotational sense was determined during the separation with a chiral detector from IBZ Messtechnik at 426 nm. The compounds are cited in the order of elution:

5-(Hydroxy(phenyl)methyl)-2-(1'H,3H-spiro[2-benzofuran-1,4'-piperidin]-1'-yl)-1,3-oxazol-4(5H)-one 3-one diastereomer a, enantiomer A was obtained as white waxy solid in 4% yield. MS m/e: 379 ([M+H]$^+$). Rotational sense: (−)

5-(Hydroxy(phenyl)methyl)-2-(1'H,3H-spiro[2-benzofuran-1,4'-piperidin]-1'-yl)-1,3-oxazol-4(5H)-one diastereomer a, enantiomer B was obtained as white waxy solid in 4% yield. MS m/e: 379 ([M+H]$^+$). Rotational sense: (+)

5-(Hydroxy(phenyl)methyl)-2-(1'H,3H-spiro[2-benzofuran-1,4'-piperidin]-1'-yl)-1,3-oxazol-4(5H)-one diastereomer b, enantiomer A was obtained as white waxy solid in 3% yield. MS m/e: 379 ([M+H]$^+$). Rotational sense: (−)

5-(Hydroxy(phenyl)methyl)-2-(1'H,3H-spiro[2-benzofuran-1,4'-piperidin]-1'-yl)-1,3-oxazol-4(5H)-one diastereomer b, enantiomer B was obtained as white waxy solid in 4% yield. MS m/e: 379 ([M+H]$^+$). Rotational sense: (+)

Example 40

5-[(4-Chlorophenyl)(hydroxy)methyl]-2-(1'H,3H-spiro[2-benzofuran-1,4'-piperidin]-1'-yl)-1,3-oxazol-4(5H)-one The title compound was obtained as yellow solid in 40% yield according to the general procedure X from 2-(1'H,3H-spiro[2-benzofuran-1,4'-piperidin]-1'-yl)-1,3-oxazol-4(5H)-one and 4-chlorobenzaldehyde. MS m/e: 413 ([M+H]$^+$)

Example 41

(4-Chlorophenyl)[4-oxo-2-(1'H,3H-spiro[2-benzofuran-1,4'-piperidin]-1'-yl)-4,5-dihydro-1,3-oxazol-5-yl]methyl acetate To a suspension of 5-[(4-chlorophenyl)(hydroxy)methyl]-2-(1'H,3H-spiro[2-benzofuran-1,4'-piperidin]-1'-yl)-1,3-oxazol-4(5H)-one (0.030 g, 0.073 mmol) and triethylamine (0.011 ml, 0.076 mmol) in dichloromethane (0.30 ml) was added acetic anhydride (0.0080 ml, 0.080 mmol). Stirring was continued for 4 h. The reaction mixture was partitioned between saturated aqueous sodium bicarbonate solution and dichloromethane. The layers were separated. The aqueous layer was extracted with dichloromethane. The combined organic layers were washed with saturated aqueous sodium bicarbonate solution, dried over anhydrous sodium sulfate, filtered and concentrated in vacuo. Purification by flash chromatography with n-heptane/ethyl acetate as eluent gave the title compound (0.006 g, 18%) as a white solid. MS m/e: 455 ([M+H]$^+$)

Example 42

(−)-5-[(4-Chlorophenyl)(hydroxy)methyl]-2-(1'H,3H-spiro[2-benzofuran-1,4'-piperidin]-1'-yl)-1,3-oxazol-4(5H)-one diastereomer a and Example 43

(+)-5-[(4-Chlorophenyl)(hydroxy)methyl]-2-(1'H,3H-spiro[2-benzofuran-1,4'-piperidin]-1'-yl)-1,3-oxazol-4(5H)-one diastereomer a and Example 44

(−)-5-[(4-Chlorophenyl)(hydroxy)methyl]-2-(1'H,3H-spiro[2-benzofuran-1,4'-piperidin]-1'-yl)-1,3-oxazol-4(5H)-one diastereomer b and Example 45

(+)-5-[(4-Chlorophenyl)(hydroxy)methyl]-2-(1'H,3H-spiro[2-benzofuran-1,4'-piperidin]-1'-yl)-1,3-oxazol-4(5H)-one diastereomer b The four stereoisomers were obtained from 5-[(4-chlorophenyl)(hydroxy)methyl]-2-(1'H,3H-spiro[2-benzofuran-1,4'-piperidin]-1'-yl)-1,3-oxazol-4(5H)-one by chiral HPLC separation on a Reprosil Chiral-NR column with n-heptane/ethanol as eluent.

(−)-5-[(4-Chlorophenyl)(hydroxy)methyl]-2-(1'H,3H-spiro[2-benzofuran-1,4'-piperidin]-1'-yl)-1,3-oxazol-4(5H)-one diastereomer a, enantiomer A was obtained as light yellow solid in 20% yield. MS m/e: 363 ([M+H]$^+$), [α]D= −71.81 (c=0.996, CHCl$_3$, 20° C.)

(+)-5-[(4-Chlorophenyl)(hydroxy)methyl]-2-(1'H,3H-spiro[2-benzofuran-1,4'-piperidin]-1'-yl)-1,3-oxazol-4(5H)-one diastereomer a, enantiomer B was obtained as light yellow solid in 21% yield. MS m/e: 363 ([M+H]$^+$), [α]D=66.45 (c=1.002, CHCl$_3$, 20° C.)

(−)-5-[(4-Chlorophenyl)(hydroxy)methyl]-2-(1'H,3H-spiro[2-benzofuran-1,4'-piperidin]-1'-yl)-1,3-oxazol-4(5H)-one diastereomer b, enantiomer A was obtained as light yellow solid in 11% yield. MS m/e: 363 ([M+H]$^+$), [α]D= −2.80 (c=0.786, CHCl$_3$, 20° C.)

(+)-5-[(4-Chlorophenyl)(hydroxy)methyl]-2-(1'H,3H-spiro[2-benzofuran-1,4'-piperidin]-1'-yl)-1,3-oxazol-4(5H)-one diastereomer b, enantiomer B was obtained as light yellow solid in 13% yield. MS m/e: 363 ([M+H]$^+$), [α]D= +4.828 (c=0.746, CHCl$_3$, 20° C.)

Example 46

5-((4-Chlorophenyl)fluoromethyl)-2-(1'H,3H-spiro[2-benzofuran-1,4'-piperidin]-1'-yl)-1,3-oxazol-4(5H)-one diastereomer a, enantiomer A Example 47

5-((4-Chlorophenyl)fluoromethyl)-2-(1'H,3H-spiro[2-benzofuran-1,4'-piperidin]-1'-yl)-1,3-oxazol-4(5H)-one diastereomer a, enantiomer B Example 48

5-((4-Chlorophenyl)fluoromethyl)-2-(1'H,3H-spiro[2-benzofuran-1,4'-piperidin]-1'-yl)-1,3-oxazol-4(5H)-one diastereomer b, enantiomer A Example 49

5-((4-Chlorophenyl)fluoromethyl)-2-(1'H,3H-spiro[2-benzofuran-1,4'-piperidin]-1'-yl)-1,3-oxazol-4(5H)-one diastereomer b, enantiomer B To a suspension of 5-[(4-chlorophenyl)(hydroxy)methyl]-2-(1'H,3H-spiro[2-benzofuran-1,4'-piperidin]-1'-yl)-1,3-oxazol-4(5H)-one (30 mg, 0.073 mmol) in dichloromethane (0.60 ml) at 0-5° C. was added diethylaminosulfur trifluoride (0.010 ml, 0.073 mmol). Stirring was continued for 30 minutes. The reaction mixture was partitioned between dichloromethane and saturated aqueous sodium bicarbonate solution. The layers were separated. The aqueous layer was extracted with two 10-ml portions of dichloromethane. The combined organic layers were washed with saturated aqueous sodium bicarbonate solution, dried over anhydrous sodium sulfate, filtered and concentrated in vacuo. The title compounds were obtained by chiral HPLC separation on a Reprosil Chiral-NR column with n-heptane/ethanol as eluent:

5-((4-Chlorophenyl)fluoromethyl)-2-(1'H,3H-spiro[2-benzofuran-1,4'-piperidin]-1'-yl)-1,3-oxazol-4(5H)-one diastereomer a, enantiomer A was obtained as light yellow solid in 7% yield. MS m/e: 416 ([M+H]$^+$)

5-((4-Chlorophenyl)fluoromethyl)-2-(1'H,3H-spiro[2-benzofuran-1,4'-piperidin]-1'-yl)-1,3-oxazol-4(5H)-one diastereomer a, enantiomer B was obtained as light yellow solid in 10% yield. MS m/e: 416 ([M+H]$^+$)

5-((4-Chlorophenyl)fluoromethyl)-2-(1'H,3H-spiro[2-benzofuran-1,4'-piperidin]-1'-yl)-1,3-oxazol-4(5H)-one diastereomer b, enantiomer A was obtained as light yellow solid in 7% yield. MS m/e: 416 ([M+H]$^+$)

5-((4-Chlorophenyl)fluoromethyl)-2-(1'H,3H-spiro[2-benzofuran-1,4'-piperidin]-1'-yl)-1,3-oxazol-4(5H)-one diastereomer b, enantiomer B was obtained as light yellow solid in 20% yield. MS m/e: 416 ([M+H]$^+$)

Example 50

1'-{-5-[(4-Chlorophenyl)(hydroxy)methyl]-4-oxo-4,5-dihydro-1,3-oxazol-2-yl}-3H-spiro[2-benzofuran-1,4'-piperidin]-3-one diastereomer a, enantiomer A
and Example 51

1'-{-5-[(4-Chlorophenyl)(hydroxy)methyl]-4-oxo-4,5-dihydro-1,3-oxazol-2-yl}-3H-spiro[2-benzofuran-1,4'-piperidin]-3-one diastereomer a, enantiomer B
and Example 52

1'-{-5-[(4-Chlorophenyl)(hydroxy)methyl]-4-oxo-4,5-dihydro-1,3-oxazol-2-yl}-3H-spiro[2-benzofuran-1,4'-piperidin]-3-one diastereomer b, enantiomer A
and Example 53

1'-{-5-[(4-Chlorophenyl)(hydroxy)methyl]-4-oxo-4,5-dihydro-1,3-oxazol-2-yl}-3H-spiro[2-benzofuran-1,4'-piperidin]-3-one diastereomer b, enantiomer B The title compounds were obtained according to the general procedure X from 1'-(4-oxo-4, 5-dihydrooxazol-2-yl)-3H-spiro[isobenzofuran-1,4'-piperidin]-3-one and 4-chlorobenzaldehyde after separation by chiral HPLC on a Reprosil Chiral NR column with n-heptane/ethanol as eluent. The compounds are cited in the order of elution:

1' '-{-5-[(4-Chlorophenyl)(hydroxy)methyl]-4-oxo-4,5-dihydro-1,3-oxazol-2-yl}-3H-spiro[2-benzofuran-1,4'-piperidin]-3-one diastereomer a, enantiomer A was obtained as yellow solid in 9% yield. MS m/e: 428 ([M+H]$^+$)

1'-{-5-[(4-Chlorophenyl)(hydroxy)methyl]-4-oxo-4,5-dihydro-1,3-oxazol-2-yl}-3H-spiro[2-benzofuran-1,4'-piperidin]-3-one diastereomer a, enantiomer B was obtained as yellow solid in 9% yield. MS m/e: 428 ([M+H]$^+$)

1'-{-5-[(4-Chlorophenyl)(hydroxy)methyl]-4-oxo-4,5-dihydro-1,3-oxazol-2-yl}-3H-spiro[2-benzofuran-1,4'-piperidin]-3-one diastereomer b, enantiomer A was obtained as yellow solid in 7% yield. MS m/e: 428 ([M+H]$^+$)

1'-{-5-[(4-Chlorophenyl)(hydroxy)methyl]-4-oxo-4,5-dihydro-1,3-oxazol-2-yl}-3H-spiro[2-benzofuran-1,4'-piperidin]-3-one diastereomer b, enantiomer B was obtained as yellow solid in 9% yield. MS m/e: 428 ([M+H]$^+$)

Example 54

5-Allyl-5-(2-fluoroallyl)-2-(3H-spiro[isobenzofuran-1,4'-piperidine]-1'-yl)oxazol-4(5H)-one The title compound was obtained as yellow oil in 1% yield from according to the general procedure IX from 5-(prop-2-en-1-yl)-2-(1'H,3H-spiro[2-benzofuran-1,4'-piperidin]-1'-yl)-1,3-oxazol-4(5H)-one and 3-chloro-2-fluoroprop-1-ene. MS m/e: 371 ([M+H]$^+$)

Example 55

5,5-Di(but-2-ynyl)-2-(3H-spiro[isobenzofuran-1,4'-piperidine]-1'-yl)oxazol-4(5H)-one The title compound was obtained as brown solid in 11% yield according to the general procedure IX from 2-(1'H,3H-spiro[2-benzofuran-1,4'-piperidin]-1'-yl)-1,3-oxazol-4(5H)-one and 1-bromobut-2-yne. MS m/e: 377 ([M+H]$^+$)

Example 56

5,5-Bis(2-ethylprop-2-en-1-yl)-2-(1'H,3H-spiro[2-benzofuran-1,4'-piperidin]-1'-yl)-1,3-oxazol-4(5H)-one The title compound was obtained as white solid in 53% yield from 2-(1'H,3H-spiro[2-benzofuran-1,4'-piperidin]-1'-yl)-1,3-oxazol-4(5H)-one and 3-bromo-2-methylprop-1-ene according to the general procedure IX. MS m/e: 381 ([M+H]$^+$)

Example 57

5-(Prop-2-en-1-yl)-5-(prop-2-yn-1-yl)-2-(1'H,3H-spiro[2-benzofuran-1,4'-piperidin]-1'-yl)-1,3-oxazol-4(5H)-one The title compound was obtained as light yellow foam in 69% yield according to the general procedure IX from 5-(prop-2-en-1-yl)-2-(1'H,3H-spiro[2-benzofuran-1,4'-piperidin]-1'-yl)-1,3-oxazol-4(5H)-one and with 3-bromoprop-1-yne. MS m/e: 351 ([M+H]$^+$)

Example 58

5,5-Di(prop-2-en-1-yl)-2-(1'H,3H-spiro[2-benzofuran-1,4'-piperidin]-1'-yl)-1,3-oxazol-4(5H)-one The title compound was obtained as orange oil in quantitative yield according to the general procedure IX from 5-(prop-2-en-1-yl)-2-(1'H,3H-spiro[2-benzofuran-1,4'-piperidin]-1'-yl)-1,3-oxazol-4(5H)-one and allyl bromide. MS m/e: 353 ([M+H]$^+$)

Example 59

5-Allyl-5-(2-methylallyl)-2-(1'H,3H-spiro[2-benzofuran-1,4'-piperidin]-1'-yl)-1,3-oxazol-4(5H)-one The title compound was obtained as colorless oil in 76% yield according to the general procedure IX from 5-(prop-2-en-1-yl)-2-(1'H,3H-spiro[2-benzofuran-1,4'-piperidin]-1'-yl)-1,3-oxazol-4(5H)-one and 3-bromo-2-methylprop-1-ene. MS m/e: 367 ([M+H]$^+$)

Example 60

5-(Prop-2-en-1-yl)-2-(1'H,3H-spiro[2-benzofuran-1,4'-piperidin]-1'-yl)-5-[2-(trifluoromethyl)prop-2-en-1-yl]-1,3-oxazol-4(5H)-one The title compound was obtained as orange oil in 98% yield according to the general procedure IX from 5-(prop- 2-en-1-yl)-2-(1'H,3H-spiro[2-benzofuran-1,4'-piperidin]-1'-yl)-1,3-oxazol-4(5H)-one and with 2-(bromomethyl)-3,3,3-trifluoroprop-1-ene. MS m/e: 421 ([M+H]$^+$)

Example 61

Ethyl 2-{[4-oxo-5-(prop-2-en-1-yl)-2-(1'H,3H-spiro[2-benzofuran-1,4'-piperidin]-1'-yl)-4,5-dihydro-1,3-oxazol-5-yl]methyl}prop-2-enoate The title compound was obtained as light yellow oil in 60% yield according to the general procedure IX from 5-(prop-2-en-1-yl)-2-(1'H,3H-spiro[2-benzofuran-1,4'-piperidin]-1'-yl)-1,3-oxazol-4(5H)-one and ethyl 2-(bromomethyl)acrylate. MS m/e: 426 ([M+H]$^+$)

Example 62

Ethyl 2-((4-oxo-5-(prop-2-ynyl)-2-(3H-spiro[isobenzofuran-1,4'-piperidine]-1'-yl)-4,5-dihydrooxazol-5-yl)methyl)acrylate The title compound was obtained as light yellow solid in 54% yield according to the general procedure IX from 5-(prop-2-ynyl)-2-(3H-spiro[isobenzofuran-1,4'-piperidine]-1'-yl)oxazol-4(5H)-one and ethyl 2-(bromomethyl)acrylate. MS m/e: 423 ([M+H]$^+$)

Example 63

5-(2-Bromoprop-2-en-1-yl)-5-(prop-2-en-1-yl)-2-(1'H,3H-spiro[2-benzofuran-1,4'-piperidin]-1'-yl)-1,3-oxazol-4(5H)-one The title compound was obtained as orange oil in 92% yield according to the general procedure IX from 5-(prop-2-en-1-yl)-2-(1'H,3H-spiro[2-benzofuran-1,4'-piperidin]-1'-yl)-1,3-oxazol-4(5H)-one and 2,3-dibromoprop-1-ene. MS m/e: 433 ([M+H]$^+$)

Example 64

2-(3H-Spiro[isobenzofuran-1,4'-piperidine]-1'-yl)-5,5-bis(2-(trifluoromethyl)allyl)oxazol-4(5H)-one The title compound was obtained as yellow oil in 9% yield according to the general procedure IX from 2-(1'H,3H-spiro[2-benzofuran-1,4'-piperidin]-1'-yl)-1,3-oxazol-4(5H)-one and 2-(bromomethyl)-3,3,3-trifluoroprop-1-ene. MS m/e: 489 ([M+H]$^+$)

Example 65

5-[2-({[tert-Butyl(dimethyl)silyl]oxy}methyl)prop-2-en-1-yl]-5-(prop-2-en-1-yl)-2-(1'H,3H-spiro[2-benzofuran-1,4'-piperidin]-1'-yl)-1,3-oxazol-4(5H)-one The title compound was obtained as colorless oil in 77% yield according to the general procedure IX from 5-(prop-2-en-1-yl)-2-(1'H,3H-spiro[2-benzofuran-1,4'-piperidin]-1'-yl)-1,3-oxazol-4(5H)-one and (2-(bromomethyl)allyloxy)(tert-butyl)dimethylsilane. MS m/e: 497 ([M+H]$^+$)

Example 66

5-Butyl-5-methyl-2-(1'H,3H-spiro[2-benzofuran-1,4'-piperidin]-1'-yl)-1,3-oxazol-4(5H)-one The title compound was obtained as white solid in 60% yield from 5-methyl-2-(1'H,3H-spiro[2-benzofuran-1,4'-piperidin]-1'-yl)-1,3-oxazol-4(5H)-one and 1-iodobutane according to the general procedure IX. MS m/e: 343 ([M+H]$^+$)

Example 67

(+)-5-Butyl-5-methyl-2-(1'H,3H-spiro[2-benzofuran-1,4'-piperidin]-1'-yl)-1,3-oxazol-4(5H)-one and

Example 68

(−)-5-Butyl-5-methyl-2-(1'H,3H-spiro[2-benzofuran-1,4'-piperidin]-1'-yl)-1,3-oxazol-4(5H)-one (+)-5-Butyl-5-methyl-2-(1'H,3H-spiro[2-benzofuran-1,4'-piperidin]-1'-yl)-1,3-oxazol-4(5H)-one and (−)-5-butyl-5-methyl-2-(1'H,3H-spiro[2-benzofuran-1,4'-piperidin]-1'-yl)-1,3-oxazol-4(5H)-one were obtained from 5-butyl-5-methyl-2-(1'H,3H-spiro[2-benzofuran-1,4'-piperidin]-1'-yl)-1,3-oxazol-4(5H)-one by chiral HPLC separation on a Chiralpak AD column with n-heptane/isopropanol (85:15) as eluent.

(+)-5-Butyl-5-methyl-2-(1'H,3H-spiro[2-benzofuran-1,4'-piperidin]-1'-yl)-1,3-oxazol-4(5H)-one (0.047 g, 20%) was obtained as off-white solid. (MS m/e: 343 ([M+H]$^+$) racemate, [α]D=+11.38 (c=0.536, CHCl$_3$, 20° C.)

(−)-5-Butyl-5-methyl-2-(1'H,3H-spiro[2-benzofuran-1,4'-piperidin]-1'-yl)-1,3-oxazol-4(5H)-one (0.051 g, 21%) was obtained as off-white solid. (MS m/e: 343 ([M+H]$^+$) racemate, [α]D=−11.11 (c=0.504, CHCl$_3$, 20° C.)

Example 69

1'-(5-Butyl-5-methyl-4-oxo-4,5-dihydro-1,3-oxazol-2-yl)-3H-spiro[2-benzofuran-1,4'-piperidin]-3-one The title compound was obtained as orange oil in 12% yield according to the general procedure IX from 5-methyl-2-(1'H,3H-spiro[2-benzofuran-1,4'-piperidin]-1'-yl)-1,3-oxazol-4(5H)-one and 1-iodobutane. MS m/e: 357 ([M+H]$^+$)

Example 70

(+)-5-Benzyl-5-methyl-2-(1'H,3H-spiro[2-benzofuran-1,4'-piperidin]-1'-yl)-1,3-oxazol-4(5H)-one and

Example 71

(−)-5-Benzyl-5-methyl-2-(1'H,3H-spiro[2-benzofuran-1,4'-piperidin]-1'-yl)-1,3-oxazol-4(5H)-one The title compounds were obtained from (RS)-ethyl 2-hydroxy-2-methyl-3-phenylpropanoate and 3H-spiro[isobenzofuran-1,4'-piperidine] according to the general procedure VII after separation by chiral HPLC separation on a Reprosil Chiral NR column with n-heptane/ethanol as eluent.

(+)-5-Benzyl-5-methyl-2-(1'H,3H-spiro[2-benzofuran-1,4'-piperidin]-1'-yl)-1,3-oxazol-4(5H)-one (0.27 g, 18%) was obtained as off-white solid with an ee-purity of 99.4%. MS m/e: 377 (racemate) ([M+H]$^+$). [α]D=+9.279 (c=1.002, CHCl$_3$, 20° C.)

(−)-5-Benzyl-5-methyl-2-(1'H,3H-spiro[2-benzofuran-1,4'-piperidin]-1'-yl)-1,3-oxazol-4(5H)-one (0.26 g, 18%) was obtained as off-white solid with an ee-purity of 96.8%. MS m/e: 377 (racemate) ([M+H]$^+$). [α]D=−8.719 (c=0.998, CHCl$_3$, 20° C.)

Example 72

1'-[5-Benzyl-5-methyl-4-oxo-4,5-dihydro-1,3-oxazol-2-yl]-3H-spiro[2-benzofuran-1,4'-piperidin]-3-one enantiomer A and Example 73

1'-[5-Benzyl-5-methyl-4-oxo-4,5-dihydro-1,3-oxazol-2-yl]-3H-spiro[2-benzofuran-1,4'-piperidin]-3-one enantiomer B The title compounds were obtained according to the general procedure IX from 1'-(5-methyl-4-oxo-4,5-dihydrooxazol-2-yl)-3H-spiro[isobenzofuran-1,4'-piperidin]-3-one and 1-(bromomethyl)benzene after separation by chiral HPLC on a Reprosil Chiral NR column with n-heptane/ethanol as eluent. The compounds are cited in the order of elution:

1'-[5-Benzyl-5-methyl-4-oxo-4,5-dihydro-1,3-oxazol-2-yl]-3H-spiro[2-benzofuran-1,4'-piperidin]-3-one enantiomer A was obtained as colorless oil in 6% yield. MS m/e: 391 ([M+H]$^+$)

1'-[5-Benzyl-5-methyl-4-oxo-4,5-dihydro-1,3-oxazol-2-yl]-3H-spiro[2-benzofuran-1,4'-piperidin]-3-one enantiomer B was obtained as light yellow solid in 10% yield. MS m/e: 391 ([M+H]$^+$)

Example 74

5-Benzyl-5-ethyl-2-(1'H,3H-spiro[2-benzofuran-1,4'-piperidin]-1'-yl)-1,3-oxazol-4(5H)-one The title compound was obtained as off-white solid in 34% yield from (RS)-ethyl 2-benzyl-2-hydroxybutanoate and 3H-spiro[isobenzofuran-1,4'-piperidine] according to the general procedure VII. MS m/e: 391 ([M+H]$^+$)

Example 75

5-(4-Chlorobenzyl)-5-methyl-2-(1'H,3H-spiro[2-benzofuran-1,4'-piperidin]-1'-yl)-1,3-oxazol-4(5H)-one The title compound was obtained as white solid in 60% yield from 5-methyl-2-(1'H,3H-spiro[2-benzofuran-1,4'-piperidin]-1'-yl)-1,3-oxazol-4(5H)-one and 1-(bromomethyl)-4-chlorobenzene according to the general procedure IX. MS m/e: 411 ([M+H]$^+$)

Example 76

5-(Cyclopentylmethyl)-5-methyl-2-(1'H,3-spiro[2-benzofuran-1,4'-piperidin]-1'-yl)-1,3-oxazol-4(5H)-one The title compound was obtained as yellow solid in 47% yield from 5-methyl-2-(1'H,3H-spiro[2-benzofuran-1,4'-piperidin]-1'-yl)-1,3-oxazol-4(5H)-one and (iodomethyl)cyclopentane according to the general procedure IX. MS m/e: 369 ([M+H]$^+$)

Example 77

(+)-5-(Cyclopentylmethyl)-5-methyl-2-(1'H,3H-spiro[2-benzofuran-1,4'-piperidin]-1'-yl)-1,3-oxazol-4(5H)-one and Example 78

(−)-5-(Cyclopentylmethyl)-5-methyl-2-(1'H,3H-spiro[2-benzofuran-1,4'-piperidin]-1'-yl)-1,3-oxazol-4(5H)-one (+)-5-(Cyclopentylmethyl)-5-methyl-2-(1'H,3H-spiro[2-benzofuran-1,4'-piperidin]-1'-yl)-1,3-oxazol-4(5H)-one and (−)-5-(cyclopentylmethyl)-5-methyl-2-(1'H,3H-spiro[2-benzofuran-1,4'-piperidin]-1'-yl)-1,3-oxazol-4(5H)-one were obtained from 5-(cyclopentylmethyl)-5-methyl-2-(1'H,3H-spiro[2-benzofuran-1,4'-piperidin]-1'-yl)-1,3-oxazol-4(5H)-one by chiral HPLC separation on a Reprosil Chiral NR column with n-heptane/isopropanol as eluent.

(+)-5-(Cyclopentylmethyl)-5-methyl-2-(1'H,3H-spiro[2-benzofuran-1,4'-piperidin]-1'-yl)-1,3-oxazol-4(5H)-one (0.053 g, 21%) was obtained as white solid. (MS m/e: 369 ([M+H]$^+$) racemate, [α]D=+14.35 (c=0.745, CHCl$_3$, 20° C.)

(−)-5-(Cyclopentylmethyl)-5-methyl-2-(1'H,3H-spiro[2-benzofuran-1,4'-piperidin]-1'-yl)-1,3-oxazol-4(5H)-one (0.039 g, 15%) was obtained as white solid. (MS m/e: 369 ([M+H]$^+$) racemate, [α]D=−13.84 (c=0.831, CHCl$_3$, 20° C.)

Example 79

5-(Cyclohexylmethyl)-5-methyl-2-(1'11'H,3H-spiro[2-benzofuran-1,4'-piperidin]-1'-yl)-1,3-oxazol-4(5H)-one The title compound was obtained as colorless oil in 20% yield from 5-methyl-2-(1'H,3H-spiro[2-benzofuran-1,4'-piperidin]-1'-yl)-1,3-oxazol-4(5H)-one and (bromomethyl)cyclohexane according to the general procedure IX. MS m/e: 383 ([M+H]$^+$)

Example 80

1'-[5-(4-Chlorobenzyl)-5-methyl-4-oxo-4,5-dihydro-1,3-oxazol-2-yl]-3H-spiro[2-benzofuran-1,4'-piperidin]-3-one enantiomer A and Example 81

1'-[5-(4-Chlorobenzyl)-5-methyl-4-oxo-4,5-dihydro-1,3-oxazol-2-yl]-3H-spiro[2-benzofuran-1,4'-piperidin]-3-one enantiomer B The title compounds were obtained according to the general procedure IX from 1'-(5-methyl-4-oxo-4,5-dihydrooxazol-2-yl)-3H-spiro[isobenzofuran-1,4'-piperidin]-3-one and 1-(bromomethyl)-4-chlorobenzene after separation by chiral HPLC on a Reprosil Chiral NR column with n-heptane/ethanol as eluent. The compounds are cited in the order of elution:

1'-[5-(4-Chlorobenzyl)-5-methyl-4-oxo-4,5-dihydro-1,3-oxazol-2-yl]-3H-spiro[2-benzofuran-1,4'-piperidin]-3-one enantiomer A was obtained as yellow oil in 14% yield. MS m/e: 425 ([M+H]$^+$)

1'-[5-(4-Chlorobenzyl)-5-methyl-4-oxo-4,5-dihydro-1,3-oxazol-2-yl]-3H-spiro[2-benzofuran-1,4'-piperidin]-3-one enantiomer B was obtained as yellow oil in 12% yield. MS m/e: 425 ([M+H]$^+$)

Example 82

5-[(6-Chloropyridin-3-yl)methyl]-5-methyl-2-(1'H,3H-spiro[2-benzofuran-1,4'-piperidin]-1'-yl)-1,3-oxazol-4(5H)-one The title compound was obtained as white solid in 17% yield from (RS)-5-methyl-2-(1'H,3H-spiro[2-benzofuran-1,4'-piperidin]-1'-yl)-1,3-oxazol-4(5H)-one and 2-chloro-5-(chloromethyl)-pyridine according to the general procedure IX. MS m/e: 412 ([M+H]$^+$)

Example 83

(−)-5-[(6-Chloropyridin-3-yl)methyl]-5-methyl-2-(1'H,3H-spiro[2-benzofuran-1,4'-piperidin]-1'-yl)-1,3-oxazol-4(5H)-one and Example 84

(+)-5-[(6-Chloropyridin-3-yl)methyl]-5-methyl-2-(1'H,3H-spiro[2-benzofuran-1,4'-piperidin]-1'-yl)-1,3-oxazol-4(5H)-one (−)-5-[(6-Chloropyridin-3-yl)methyl]-5-methyl-2-(1'H,3H-spiro[2-benzofuran-1,4'-piperidin]-1'-yl)-1,3-oxazol-4(5H)-one and (+)-5-[(6-chloropyridin-3-yl)methyl]-5-methyl-2-(1'H,3H-spiro[2-benzofuran-1,4'-piperidin]-1'-yl)-1,3-oxazol-4(5H)-one were obtained from 5-[(6-chloropyridin-3-yl)methyl]-5-methyl-2-(1'H,3H-spiro[2-benzofuran-1,4'-piperidin]-1'-yl)-1,3-oxazol-4(5H)-one by chiral HPLC separation on a Chiralpak AD column with n-heptane/isopropanol as eluent.

(−)-5-[(6-Chloropyridin-3-yl)methyl]-5-methyl-2-(1'H,3H-spiro[2-benzofuran-1,4'-piperidin]-1'-yl)-1,3-oxazol-4(5H)-one (0.023 g, 6%) was obtained as white solid. [α]D=−110.2 (c=0.999, CHCl$_3$, 20° C.)

(+)-5-[(6-Chloropyridin-3-yl)methyl]-5-methyl-2-(1'H,3H-spiro[2-benzofuran-1,4'-piperidin]-1'-yl)-1,3-oxazol-4(5H)-one (0.026 g, 7%) was obtained as white solid. [α]D=+80.12 (c=1.000, CHCl$_3$, 20° C.)

Example 85

5-[(5-Chlorothiophen-2-yl)methyl]-5-methyl-2-(1'H,3H-spiro[2-benzofuran-1,4'-piperidin]-1'-yl)-1,3-oxazol-4(5H)-one The title compound was obtained as light yellow solid in 44% yield from (RS)-5-methyl-2-(1'H,3H-spiro[2-benzofuran-1,4'-piperidin]-1'-yl)-1,3-oxazol-4(5H)-one and 2-chloro-5-(chloromethyl)-thiophene according to the general procedure IX. MS m/e: 417 ([M+H]$^+$)

Example 86

(+)-5-[(5-Chlorothiophen-2-yl)methyl]-5-methyl-2-(1'H,3H-spiro[2-benzofuran-1,4'-piperidin]-1'-yl)-1,3-oxazol-4(5H)-one and Example 87

(−)-5-[(5-Chlorothiophen-2-yl)methyl]-5-methyl-2-(1'H,3H-spiro[2-benzofuran-1,4'-piperidin]-1'-yl)-1,3-oxazol-4(5H)-one (+)-5-[(5-Chlorothiophen-2-yl)methyl]-5-methyl-2-(1'H,3H-spiro[2-benzofuran-1,4'-piperidin]-1'-yl)-1,3-oxazol-4(5H)-one and (−)-5-[(5-chlorothiophen-2-yl)methyl]-5-methyl-2-(1'H,3H-spiro[2-benzofuran-1,4'-piperidin]-1'-yl)-1,3-oxazol-4(5H)-one were obtained from 5-[(5-chlorothiophen-2-yl)methyl]-5-methyl-2-(1'H,3H-spiro[2-benzofuran-1,4'-piperidin]-1'-yl)-1,3-oxazol-4(5H)-one by chiral HPLC separation on a Chiralpak AD column with n-heptane/ethanol as eluent.

(+)-5-[(5-Chlorothiophen-2-yl)methyl]-5-methyl-2-(1'H,3H-spiro[2-benzofuran-1,4'-piperidin]-1'-yl)-1,3-oxazol-4(5H)-one (0.059 g, 16%) was obtained as off-white solid. MS m/e: 417 ([M+H]$^+$) (racemate). [α]D=+22.19 (c=0.586, CHCl$_3$, 20° C.)

(−)-5-[(5-Chlorothiophen-2-yl)methyl]-5-methyl-2-(1'H,3H-spiro[2-benzofuran-1,4'-piperidin]-1'-yl)-1,3-oxazol-4(5H)-one (0.060 g, 17%) was obtained as off-white solid. MS m/e: 417 ([M+H]$^+$) (racemate). [α]D=−23.44 (c=0.742, CHCl$_3$, 20° C.)

Example 88

5-Methyl-5-(pentafluorobenzyl)-2-(1'H,3H-spiro[2-benzofuran-1,4'-piperidin]-1'-yl)-1,3-oxazol-4(5H)-one The title compound was obtained as white foam in 36% yield from (RS)-5-methyl-2-(1'H,3H-spiro[2-benzofuran-1,4'-piperidin]-1'-yl)-1,3-oxazol-4(5H)-one and 2,3,4,5,6-pentafluorobenzyl bromide according to the general procedure IX. MS m/e: 467 ([M+H]$^+$)

Example 89

5-{[4-(Difluoromethyl)phenyl](difluoro)methyl}-5-methyl-2-(1'H,3H-spiro[2-benzofuran-1,4'-piperidin]-1'-yl)-1,3-oxazol-4(5H)-one The title compound was obtained as yellow oil in 28% yield according to the general procedure IX from 5-methyl-2-(1'H,3H-spiro[2-benzofuran-1,4'-piperidin]-1'-yl)-1,3-oxazol-4(5H)-one and 1-(bromodifluoromethyl)-4-(difluoromethyl)benzene. MS m/e: 463 ([M+H]$^+$)

Example 90

5-[Hydroxy(phenyl)methyl]-5-methyl-2-(1'H,3H-spiro[2-benzofuran-1,4'-piperidin]-1'-yl)-1,3-oxazol-4(5H)-one The title compound was obtained as colorless oil in 85% yield according to the general procedure X from 5-methyl- 2-(1'H,3H-spiro[2-benzofuran-1,4'-piperidin]-1'-yl)-1,3-oxazol-4(5H)-one and benzaldehyde. MS m/e: 393 ([M+H]$^+$)

Example 91

5-[(4-Chlorophenyl)(hydroxy)methyl]-5-methyl-2-(1'H,3H-spiro[2-benzofuran-1,4'-piperidin]-1'-yl)-1,3-oxazol-4(5H)-one The title compound was obtained as white solid in 39% yield according to the general procedure X from 5-methyl-2-(1'H,3H-spiro[2-benzofuran-1,4'-piperidin]-1'-yl)-1,3-oxazol-4(5H)-one and 4-chlorobenzaldehyde. MS m/e: 427 ([M+H]$^+$)

Example 92

5-[(4-Chlorophenyl)(fluoro)methyl]-5-methyl-2-(1'H,3H-spiro[2-benzofuran-1,4'-piperidin]-1'-yl)-1,3-oxazol-4(5H)-one To a suspension of 5-[(4-chlorophenyl)(hydroxy)methyl]-5-methyl-2-(1'H,3H-spiro[2-benzofuran-1,4'-piperidin]-1'-yl)-1,3-oxazol-4(5H)-one (0.050 g, 0.12 mmol) in dichloromethane (1.0 ml) was added diethylaminosulfur trifluoride (0.016 ml, 0.12 mmol) at 0-5° C. Stirring was continued for 30 minutes. The reaction mixture was partitioned between dichloromethane and saturated aqueous sodium bicarbonate solution. The layers were separated. The aqueous layer was extracted with dichloromethane. The combined organic layers were washed with saturated aqueous sodium bicarbonate solution, dried over anhydrous sodium sulfate, filtered and concentrated in vacuo. Purification by flash chromatography with n-heptane/ethyl acetate as eluent gave the title compound (0.010 g, 18%) as a white foam. MS m/e: 429 ([M+H]$^+$)

Example 93

1'-{5-[(4-Chlorophenyl)(hydroxy)methyl]-5-methyl-4-oxo-4,5-dihydro-1,3-oxazol-2-yl}-3H-spiro[2-benzofuran-1,4'-piperidin]-3-one The title compound was obtained as white solid in 51% yield according to the general procedure X from 1'-(5-methyl-4-oxo-4,5-dihydrooxazol-2-yl)-3H-spiro[isobenzofuran-1,4'-piperidin]-3-one and 4-chlorobenzaldehyde. MS m/e: 441 ([M+H]$^+$)

Example 94

5,5-bis(4-Chlorobenzyl)-2-(1'H,3H-spiro[2-benzofuran-1,4'-piperidin]-1'-yl)-1,3-oxazol-4(5H)-one The title compound was obtained as yellow oil in 10% yield according to the general procedure IX from 2-(1'H,3H-spiro[2-benzofuran-1,4'-piperidin]-1'-yl)-1,3-oxazol-4(5H)-one and 1-(bromomethyl)-4-chlorobenzene. MS m/e: 521 ([M+H]$^+$)

Example 95

1'-[5,5-Bis(4-chlorobenzyl)-4-oxo-4,5-dihydro-1,3-oxazol-2-yl]-3H-spiro[2-benzofuran-1,4'-piperidin]-3-one The title compound was obtained as white solid in 6% yield from 1'-(4-oxo-4,5-dihydrooxazol-2-yl)-3H-spiro[isobenzofuran-1,4'-piperidin]-3-one and 1-(bromomethyl)-4-chlorobenzene according to the general procedure IX. MS m/e: 535 ([M+H]$^+$)

Example 96

(+)-5-(Ethoxymethyl)-5-methyl-2-(1'H,3H-spiro[2-benzofuran-1,4'-piperidin]-1'-yl)-1,3-oxazol-4(5H)-one and

Example 97

(−)-5-(Ethoxymethyl)-5-methyl-2-(1'H,3H-spiro[2-benzofuran-1,4'-piperidin]-1'-yl)-1,3-oxazol-4(5H)-one a) 5-(Hydroxymethyl)-5-methyl-2-(1'H,3H-spiro[2-benzofuran-1,4'-piperidin]-1'-yl)-1,3-oxazol-4(5H)-one To a mixture of 5-methyl-2-(3H-spiro[isobenzofuran-1,4'-piperidine]-1'-yl)oxazol-4(5H)-one (0.96 g, 3.4 mmol) in tetrahydrofuran (34 ml) was added lithium bis(trimethylsilyl)amide (3.7 ml, 3.7 mmol) at 0-5° C. The reaction mixture was stirred for 30 minutes. Paraformaldehyde (0.40 g, 13 mmol) was added in one portion. The ice bath was removed after 30 minutes and stirring was continued for 15 h at room temperature. Quenching with 2 M aqueous hydrogen chloride solution (5 ml) was followed by stirring for 15 minutes. The reaction mixture was partitioned between ethyl acetate (50 ml) and saturated ammonium chloride solution (50 ml). The layers were separated. The aqueous layer was extracted with two 50-ml portions of ethyl acetate. The combined organic layers were washed with one 30-ml portion of brine, dried over anhydrous sodium sulfate and concentrated in vacuo. Purification by flash chromatography with n-heptane/isopropanol as eluent gave the title compound (0.83 g, 78%) as off-white solid. MS m/e: 317 ([M+H]$^+$)

b) 5-(Ethoxymethyl)-5-methyl-2-(1',3H-spiro[2-benzofuran-1,4'-piperidin]-1'-yl)-1,3-oxazol-4(5H)-one To a solution of 5-(hydroxymethyl)-5-methyl-2-(1'H,3H-spiro[2-benzofuran-1,4'-piperidin]-1'-yl)-1,3-oxazol-4(5H)-one (0.20 g, 0.63 mmol) in N,N-dimethylformamide (6.3 ml) was added sodium hydride (0.032 g, 0.67 mmol) at room temperature. The reaction mixture was stirred for 15 minutes. Iodoethane (0.12 g, 0.061 ml, 0.76 mmol) was added at 0-5° C. The ice bath was removed after 10 minutes and stirring was continued for 15 h. The reaction mixture was partitioned between ethyl acetate (50 ml) and 0.5 M aqueous hydrogen chloride solution (30 ml). The layers were separated. The aqueous layer was extracted with one 50-ml portion of ethyl acetate. The combined organic layers were washed with one 30-ml portion of brine, dried over anhydrous sodium sulfate and concentrated in vacuo. Flash-chromatography with n-heptane/isopropanol gave 5-(ethoxymethyl)-5-methyl-2-(1'H,3H-spiro[2-benzofuran-1,4'-piperidin]-1'-yl)-1,3-oxazol-4(5H)-one.

(+)-5-(Ethoxymethyl)-5-methyl-2-(1'H,3H-spiro[2-benzofuran-1,4'-piperidin]-1'-yl)-1,3-oxazol-4(5H)-one and (−)-5-(ethoxymethyl)-5-methyl-2-(1'H,3H-spiro[2-benzofuran-1,4'-piperidin]-1'-yl)-1,3-oxazol-4(5H)-one were obtained from 5-(ethoxymethyl)-5-methyl-2-(1'H,3H-spiro[2-benzofuran-1,4'-piperidin]-1'-yl)-1,3-oxazol-4(5H)-one by chiral HPLC separation on a Reprosil Chiral NR column with n-heptane/ethanol as eluent.

(+)-5-(Ethoxymethyl)-5-methyl-2-(1'H,3H-spiro[2-benzofuran-1,4'-piperidin]-1'-yl)-1,3-oxazol-4(5H)-one (0.031 g, 14%) was obtained as white solid. MS m/e: 345 ([M+H]$^+$) (racemate). [α]D=+9.277 (c=0.981, CHCl$_3$, 20° C.)

(−)-5-(Ethoxymethyl)-5-methyl-2-(1'H,3H-spiro[2-benzofuran-1,4'-piperidin]-1'-yl)-1,3-oxazol-4(5H)-one (0.037 g, 17%) was obtained as white solid. MS m/e: 345 ([M+H]$^+$) (racemate). [α]D=−9.909 (c=0.999, CHCl$_3$, 20° C.)

Example 98

5-Methyl-5-(pyrrolidin-1-ylmethyl)-2-(1'H,3H-spiro[2-benzofuran-1,4'-piperidin]-1'-yl)-1,3-oxazol-4(5H)-one a) b) 5-Methyl-4-oxo-2-(1'H,3H-spiro[2-benzofuran-1,4'-piperidin]-1'-yl)-4,5-dihydro-1, 3-oxazole-5-carbaldehyde To a solution of oxalyl chloride (0.24 g, 0.17 ml, 1.9 mmol) in dry dichloromethane (11 ml) at −78° C. was slowly added dimethyl sulfoxide (0.30 g, 0.27 ml, 3.8 mmol). The cooling bath was removed and the reaction mixture was stirred for 5 minutes at −50° C. to complete the formation of S-chlorodimethylsulfonium chloride. A solution of 5-(hydroxymethyl)-5-methyl-2-(1'H,3H-spiro[2-benzofuran-1,4'-piperidin]-1'-yl)-1,3-oxazol-4(5H)-one (0.50 g, 1.6 mmol) in dichloromethane (5 ml) was added at −65° C. The reaction mixture was stirred for 30 minutes prior to add triethylamine (0.80 g, 1.1 ml, 7.9 mmol). The reaction mixture was stirred for 15 minutes. The cooling bath was removed and the mixture was stirred for 1 h at room temperature. The reaction mixture was partitioned between dichloromethane (50 ml) and 1 M aqueous hydrogen chloride solution (50 ml). The layers were separated. The aqueous layer was extracted with two 50-ml portions of dichloromethane. The combined organic layers were washed with one 30-ml portion of brine, dried over anhydrous sodium sulfate and concentrated in vacuo to give the title compound (0.48 g, 97%) as light brown solid, which was used in the next step without further purifications.

b) 5-Methyl-5-(pyrrolidin-1-ylmethyl)-2-(1'H,3H-spiro[2-benzofuran-1,4'-piperidin]-1'-yl)-1,3-oxazol-4(5H)-one To a mixture of 5-methyl-4-oxo-2-(3H-spiro[isobenzofuran-1,4'-piperidine]-1'-yl)-4,5-dihydrooxazole-5-carbaldehyde (0.17 g, 0.53 mmol) and pyrrolidine (0.047 ml, 0.58 mmol) in dichloromethane (3.5 ml) was added acetic acid (0.030 ml, 0.52 mmol) at room temperature. The mixture was stirred for 1 h. Addition of sodium triacetoxyborohydride (0.18 g, 0.84 mmol) in one portion at 0-5° C. The cooling bath was removed after 5 minutes and stirring was continued for 15 h. The reaction mixture was partitioned between dichloromethane (40 ml) and 0.5 M aqueous sodium hydroxide solution (30 ml). The layers were separated. The aqueous layer was extracted with one 50-ml portion of dichloromethane. The combined organic layers were dried over anhydrous sodium sulfate and concentrated in vacuo. Flash-chromatography with n-heptane/isopropanol gave the title compound (0.071 g, 37%) as off-white solid. MS m/e: 370 ([M+H]$^+$)

Example 99

5-Methyl-2-(1'1H,3H-spiro[2-benzofuran-1,4'-piperidin]-1'-yl)-5-(tetrahydrofuran-3-ylmethyl)-1,3-oxazol-4(5H)-one diastereomer a and Example 100

5-Methyl-2-(1'1H,3H-spiro[2-benzofuran-1,4'-piperidin]-1'-yl)-5-(tetrahydrofuran-3-ylmethyl)-1,3-oxazol-4(5H)-one diastereomer b The title compounds were obtained from 5-methyl-2-(1'H,3H-spiro[2-benzofuran-1,4'-piperidin]-1'-yl)-1,3-oxazol-4(5H)-one and 3-(bromomethyl)tetrahydrofuran according to the general procedure IX and chiral HPLC separation on a Reprosil Chiral-NR with n-heptane/ethanol as eluent.

5-Methyl-2-(1'H,3H-spiro[2-benzofuran-1,4'-piperidin]-1'-yl)-5-(tetrahydrofuran-3-ylmethyl)-1,3-oxazol-4(5H)-one diastereomer a (0.014 g, 2%) was obtained as off-white solid. MS m/e: 371.5 ([M+H]$^+$)

5-Methyl-2-(1'H,3H-spiro[2-benzofuran-1,4'-piperidin]-1'-yl)-5-(tetrahydrofuran-3-ylmethyl)-1,3-oxazol-4(5H)-one diastereomer b (0.012 g, 2%) was obtained as off-white solid. MS m/e: 371.5 ([M+H]$^+$)

Example 101

5-Methyl-2-(1'H,3H-spiro[2-benzofuran-1,4'-piperidin]-1'-yl)-5-(tetrahydrofuran-2-ylmethyl)-1,3-oxazol-4(5H)-one The title compound was obtained as off-white in 10% yield from 5-methyl-2-(1'H,3H-spiro[2-benzofuran-1,4'-piperidin]-1'-yl)-1,3-oxazol-4(5H)-one and (RS)-2-(bromomethyl)-tetrahydrofuran according to the general procedure IX. MS m/e: 371.5 ([M+H]$^+$)

Example 102

(+)-5-Methyl-2-(1'H,3H-spiro[2-benzofuran-1,4'-piperidin]-1'-yl)-5-(tetrahydro-2H-pyran-3-ylmethyl)-1,3-oxazol-4(5H)-one diastereomer a and Example 103

(−)-5-Methyl-2-(1'H,3H-spiro[2-benzofuran-1,4'-piperidin]-1'-yl)-5-(tetrahydro-2H-pyran-3-ylmethyl)-1,3-oxazol-4(5H)-one diastereomer a and Example 104

(+)-5-Methyl-2-(1'H,3H-spiro[2-benzofuran-1,4'-piperidin]-1'-yl)-5-(tetrahydro-2H-pyran-3-ylmethyl)-1,3-oxazol-4(5H)-one diastereomer b and Example 105

(−)-5-Methyl-2-(1'11'H,3H-spiro[2-benzofuran-1,4'-piperidin]-1'-yl)-5-(tetrahydro-2H-pyran-3-ylmethyl)-1,3-oxazol-4(5H)-one diastereomer b The title compounds were obtained from 5-methyl-2-(1'H,3H-spiro[2-benzofuran-1,4'-piperidin]-1'-yl)-1,3-oxazol-4(5H)-one and 3-(bromomethyl)tetrahydro-2H-pyran according to the general procedure IX and chiral HPLC separation on a Reprosil Chiral-NR with n-heptane/ethanol as eluent.

(+)-5-Methyl-2-(1'H,3H-spiro[2-benzofuran-1,4'-piperidin]-1'-yl)-5-(tetrahydro-2H-pyran-3-ylmethyl)-1,3-oxazol-4(5H)-one diastereomer a (0.127 g, 16%) was obtained as off-white solid with an ee-purity of 86%. [α]D=+4.187 (c=1.003, CHCl$_3$, 20° C.)

(−)-5-Methyl-2-(1'H,3H-spiro[2-benzofuran-1,4'-piperidin]-1'-yl)-5-(tetrahydro-2H-pyran-3-ylmethyl)-1,3-oxazol-4(5H)-one diastereomer a (0.131 g, 16%) was obtained as off-white solid with an ee-purity of 95%. MS m/e: 385 ([M+H]$^+$). [α]D=−4.093 (c=1.002, CHCl$_3$, 20° C.)

(+)-5-Methyl-2-(1'H,3H-spiro[2-benzofuran-1,4'-piperidin]-1'-yl)-5-(tetrahydro-2H-pyran-3-ylmethyl)-1,3-oxazol-4(5H)-one diastereomer b (0.0.35 g, 4%) was obtained as off-white solid. [α]D=+16.82 (c=0.648, CHCl$_3$, 20° C.)

(−)-5-Methyl-2-(1'H,3H-spiro[2-benzofuran-1,4'-piperidin]-1'-yl)-5-(tetrahydro-2H-pyran-3-ylmethyl)-1,3-oxazol-4(5H)-one diastereomer b (0.040 g, 5%) was obtained as off-white solid. MS m/e: 385 ([M+H]$^+$). [α]D=−12.01 (c=0.616, CHCl$_3$, 20° C.)

Example 106

5-Methyl-5-(1-phenylethyl)-2-(1'H,3H-spiro[2-benzofuran-1,4'-piperidin]-1'-yl)-1,3-oxazol-4(5H)-one diastereomer a and Example 107

5-Methyl-5-(1-phenylethyl)-2-(1'H,3H-spiro[2-benzofuran-1,4'-piperidin]-1'-yl)-1,3-oxazol-4(5H)-one diastereomer b The title compounds were obtained from 5-methyl-2-(1'H,3H-spiro[2-benzofuran-1,4'-piperidin]-1'-yl)-1,3-oxazol-4(5H)-one and (RS)-(1-bromoethyl)benzene according to the general procedure IX.

5-Methyl-5-(1-phenylethyl)-2-(1'H,3H-spiro[2-benzofuran-1,4'-piperidin]-1'-yl)-1,3-oxazol-4(5H)-one diastereomer a (0.087 g, 16%) was obtained as white solid.

5-Methyl-5-(1-phenylethyl)-2-(1'H,3H-spiro[2-benzofuran-1,4'-piperidin]-1'-yl)-1,3-oxazol-4(5H)-one diastereomer b (0.110 g, 20%) was obtained as white solid.

Example 108

(+)-5-Methyl-5-(1-phenylethyl)-2-(1'H,3-spiro[2-benzofuran-1,4'-piperidin]-1'-yl)-1,3-oxazol-4(5H)-one diastereomer a and Example 109

(−)-5-Methyl-5-(1-phenylethyl)-2-(1'H,3H-spiro[2-benzofuran-1,4'-piperidin]-1'-yl)-1,3-oxazol-4(5H)-one diastereomer a The title compounds were obtained from 5-methyl-5-(1-phenylethyl)-2-(1'H,3H-spiro[2-benzofuran-1,4'-piperidin]-1'-yl)-1,3-oxazol-4(5H)-one diastereomer a by chiral HPLC separation on a Chiralpak AD column with n-heptane/isopropanol as eluent.

(+)-5-Methyl-5-(1-phenylethyl)-2-(1'H,3H-spiro[2-benzofuran-1,4'-piperidin]-1'-yl)-1,3-oxazol-4(5H)-one diastereomer a (0.024 g, 4%) was obtained as white solid. MS m/e: 391 ([M+H]$^+$). [α]D=+99.74 (c=0.384, CHCl$_3$, 20° C.)

(−)-5-Methyl-5-(1-phenylethyl)-2-(1'H,3H-spiro[2-benzofuran-1,4'-piperidin]-1'-yl)-1,3-oxazol-4(5H)-one diastereomer a (0.033 g, 6%) was obtained as white solid. [α]D=−87.77 (c=0.376, CHCl$_3$, 20° C.)

Example 110

(−)-5-Methyl-5-(1-phenylethyl)-2-(1'H,3H-spiro[2-benzofuran-1,4'-piperidin]-1'-yl)-1,3-oxazol-4(5H)-one diastereomer b and Example 111

(+)-5-Methyl-5-(1-phenylethyl)-2-(1'H,3-spiro[2-benzofuran-1,4'-piperidin]-1'-yl)-1,3-oxazol-4(5H)-one diastereomer b The title compounds were obtained from 5-methyl-5-(1-phenylethyl)-2-(1'H,3H-spiro[2-benzofuran-1,4'-piperidin]-1'-yl)-1,3-oxazol-4(5H)-one diastereomer b by chiral HPLC separation on a Reprosil Chiral NR column with n-heptane/ethanol as eluent.

(−)-5-Methyl-5-(1-phenylethyl)-2-(1'H,3H-spiro[2-benzofuran-1,4'-piperidin]-1'-yl)-1,3-oxazol-4(5H)-one diastereomer b (0.053 g, 10%) was obtained as white solid. MS m/e: 391 ([M+H]$^+$). [α]D=−36.63 (c=0.409, CHCl$_3$, 20° C.)

(+)-5-Methyl-5-(1-phenylethyl)-2-(1'H,3H-spiro[2-benzofuran-1,4'-piperidin]-1'-yl)-1,3-oxazol-4(5H)-one diastereomer b (0.046 g, 8%) was obtained as white solid. [α]D=+43.03 (c=0.421, CHCl$_3$, 20° C.)

Example 112

2-(3H-Spiro[isobenzofuran-1,4'-piperidine]-1'-yl)-1-oxa-3-azaspiro[4.4]non-2-en-4-one The title compound was obtained as off-white solid in 42% yield from ethyl 1-hydroxycyclopentanecarboxylate and 3H-spiro[isobenzofuran-1,4'-piperidine] according to the general procedure VII. MS m/e: 327 ([M+H]$^+$)

Example 113

2-(1'H,3H-Spiro[2-benzofuran-1,4'-piperidin]-1'-yl)-1-oxa-3-azaspiro[4.4]nona-2,7-dien-4-one The title compound was obtained as grey solid in 91% yield according to the general procedure XI from 5,5-di(prop-2-en-1-yl)-2-(1'H,3H-spiro[2-benzofuran-1,4'-piperidin]-1'-yl)-1,3-oxazol-4(5H)-one and Grubbs 2nd generation catalyst. MS m/e: 325 ([M+H]$^+$)

Example 114

7-Methyl-2-(1'H,3H-spiro[2-benzofuran-1,4'-piperidin]-1'-yl)-1-oxa-3-azaspiro[4.4]nona-2,7-dien-4-one The title compound was obtained as brown solid in 62% yield according to the general procedure XI from 5-allyl-5-(2-methylallyl)-2-(1'H,3H-spiro[2-benzofuran-1,4'-piperidin]-1'-yl)-1,3-oxazol-4(5H)-one and Grubbs 2nd generation catalyst. MS m/e: 339 ([M+H]$^+$)

Example 115

7,8-Dimethyl-2-(1'H,3H-spiro[2-benzofuran-1,4'-piperidin]-1'-yl)-1-oxa-3-azaspiro[4.4]nona-2,7-dien-4-one The title compound was obtained as white foam in 72% yield according to the general procedure XI from 5,5-bis(2-methylprop-2-en-1-yl)-2-(1'H,3H-spiro[2-benzofuran-1,4'-piperidin]-1'-yl)-1,3-oxazol-4(5H)-one and Grubbs 2nd generation catalyst. MS m/e: 353 ([M+H]$^+$)

Example 116

Ethyl 4-oxo-2-(1'H,3H-spiro[2-benzofuran-1,4'-piperidin]-1'-yl)-1-oxa-3-azaspiro[4.4]nona-2,7-diene-7-carboxylate The title compound was obtained as brown solid in 28% yield according to the general procedure XI from ethyl 2-{[4-oxo-5-(prop-2-en-1-yl)-2-(1'H,3H-spiro[2-benzofuran-1,4'-piperidin]-1'-yl)-4,5-dihydro-1,3-oxazol-5-yl]methyl}prop-2-enoate and Grubbs 2nd generation catalyst. MS m/e: 397 ([M+H]$^+$)

Example 117

2-(1'H,3H-Spiro[2-benzofuran-1,4'-piperidin]-1'-yl)-7-(trifluoromethyl)-1-oxa-3-azaspiro[4.4]nona-2,7-dien-4-one The title compound was obtained as white solid in 4% yield according to the general procedure XI from 5-(prop-2-en-1-yl)-2-(1'H,3H-spiro[2-benzofuran-1,4'-piperidin]-1'-yl)-5-[2-(trifluoromethyl)prop-2-en-1-yl]-1,3-oxazol-4(5H)-one and Grubbs 2nd generation catalyst. MS m/e: 393 ([M+H]$^+$)

Example 118

7-({[tert-Butyl(dimethyl)silyl]oxy}methyl)-2-(1'H,3H-spiro[2-benzofuran-1,4'-piperidin]-1'-yl)-1-oxa-3-azaspiro[4.4]nona-2,7-dien-4-one The title compound was obtained as brown solid in 28% yield according to the general procedure XI from 5-[2-({[tert-butyl(dimethyl)silyl]oxy}methyl)prop-2-en-1-yl]-5-(prop-2-en-1-yl)-2-(1'H,3H-spiro[2-benzofuran-1,4'-piperidin]-1'-yl)-1,3-oxazol-4(5H)-one and Grubbs 2nd generation catalyst. MS m/e: 469 ([M+H]$^+$)

Example 119

7-(Hydroxymethyl)-2-(3H-spiro[isobenzofuran-1,4'-piperidine]-1'-yl)-1-oxa-3-azaspiro[4.4]nona-2,7-dien-4-one To a solution of 7-({[tert-butyl(dimethyl)silyl]oxy}methyl)-2-(1'H,3H-spiro[2-benzofuran-1,4'-piperidin]-1'-yl)-1-oxa-3-azaspiro[4.4]nona-2,7-dien-4-one (0.062 g, 0.13 mmol) in tetrahydrofuran (0.70 ml) was added 1 M tetrabutyl ammonium fluoride solution in tetrahydrofuran (0.17 ml, 0.17 mmol). Stirring was continued for 4 h. The reaction mixture was poured into saturated ammonium chloride solution (2 ml) and extracted with three 2-ml portions of ethyl acetate. The organic layers were dried over magnesium sulfate, filtered and concentrated in vacuo. Purification by flash chromatography with dichloromethane/methanol as eluent gave the title compound (0.046 g, 98%) as light brown oil. MS m/e: 355 ([M+H]$^+$)

Example 120

4-Oxo-2-(1'H,3H-spiro[2-benzofuran-1,4'-piperidin]-1'-yl)-1-oxa-3-azaspiro[4.4]non-2-ene-7,8-diyl diacetate diastereomer a and Example 121

4-Oxo-2-(1'H,3H-spiro[2-benzofuran-1,4'-piperidin]-1'-yl)-1-oxa-3-azaspiro[4.4]non-2-ene-7,8-diyl diacetate diastereomer b a) 7,8-Dihydroxy-2-(1'H,3H-spiro[2-benzofuran-1,4'-piperidin]-1'-yl)-1-oxa-3-azaspiro[4.4]non-2-en-4-one diastereomer a and 7, 8-Dihydroxy-2-(1'H,3H-spiro[2-benzofuran-1,4'-piperidin]-1'-yl)-1-oxa-3-azaspiro[4.4]non-2-en-4-one diastereomer b A mixture of 2-(3H-spiro[isobenzofuran-1,4'-piperidine]-1'-yl)-1-oxa-3-azaspiro[4.4]nona-2,7-dien-4-one (0.25 g, 0.77 mmol, Eq: 1.00), osmium tetroxide 2.5% in tert-butanol (0.078 g, 0.0077 mmol, Eq: 0.01) and N-methylmorpholine-N-oxide (0.27 g, 2.3 mmol, Eq: 3.00) in acetone (4.8 ml) and water (1.2 ml was stirred for 3 h at room temperature. The reaction mixture was quenched with saturated aqueous sodium sulfite solution and stirred for 30 minutes. Purification by flash-chromatography with dichloromethane/ethyl acetate as eluent gave the title compounds. The compounds are cited in order of elution:

7,8-Dihydroxy-2-(1'H,3H-spiro[2-benzofuran-1,4'-piperidin]-1'-yl)-1-oxa-3-azaspiro[4.4]non-2-en-4-one diastereomer a was obtained in 55% yield as a brown solid. MS m/e: 360 ([M+H]$^+$)

7,8-Dihydroxy-2-(1'H,3H-spiro[2-benzofuran-1,4'-piperidin]-1'-yl)-1-oxa-3-azaspiro[4.4]non-2-en-4-one diastereomer b was obtained in 40% yield as a brown solid. MS m/e: 360 ([M+H]$^+$)

b) 4-Oxo-2-(1'H,3H-spiro[2-benzofuran-1,4'-piperidin]-1'-yl)-1-oxa-3-azaspiro[4.4]non-2-ene-7,8-diyl diacetate diastereomer a To a solution of 7,8-dihydroxy-2-(1'H,3H-spiro[2-benzofuran-1,4'-piperidin]-1'-yl)-1-oxa-3-azaspiro[4.4]non-2-en-4-one diastereomer a (0.045 g, 0.13 mmol), triethylamine (0.049 ml, 0.35 mmol) and 4-(N,N-dimethylamino)-pyridine (0.0015 g, 0.013 mmol) in dichloromethane (2.0 ml) was added acetic anhydride (0.024 ml, 0.25 mmol) at room temperature. Stirring was continued for 5 h. The solvent was evaporated. Purification by flash chromatography with n-heptane/ethyl acetate as eluent gave the title compound (0.040 g, 72%) as colorless oil. MS m/e: 443 ([M+H]$^+$)

c) 4-Oxo-2-(1'H,3H-spiro[2-benzofuran-1,4'-piperidin]-1'-yl)-1-oxa-3-azaspiro[4.4]non-2-ene-7,8-diyl diacetate diastereomer b To a solution of 7,8-dihydroxy-2-(1'H,3H-spiro[2-benzofuran-1,4'-piperidin]-1'-yl)-1-oxa-3-azaspiro[4.4]non-2-en- 4-one diastereomer b (0.050 g, 0.14 mmol), triethylamine (0.054 ml, 0.39 mmol) and 4-(N,N-dimethylamino)-pyridine (0.0017 g, 0.014 mmol) in dichloromethane (2.0 ml) was added acetic anhydride (0.026 ml, 0.28 mmol) at room temperature. Stirring was continued for 5 h. The solvent was evaporated. Purification by flash chromatography with n-heptane/ethyl acetate as eluent gave the title compound (0.029 g, 48%) as colorless oil. MS m/e: 443 ([M+H]$^+$)

Example 122

7,8-Dimethoxy-2-(1'H,3H-spiro[2-benzofuran-1,4'-piperidin]-1'-yl)-1-oxa-3-azaspiro[4.4]non-2-en-4-one diastereomer a

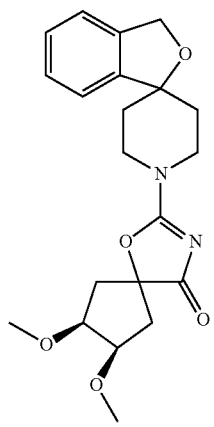 [SMILES: CO[C@H]1CC2(C[C@H]1OC)OC(N1CCC3(CC1)OCc1ccccc13)=NC2=O]

To a suspension of sodium hydride (0.012 g, 0.29 mmol) in N,N-dimethylformamide (1.0 ml) was added 7,8-dihydroxy-2-(3H-spiro[isobenzofuran-1,4'-piperidine]-1'-yl)-1-oxa-3-azaspiro[4.4]non-2-en-4-one diastereomer a (0.050 g, 0.14 mmol). The reaction mixture was stirred for 20 minutes. Iodomethane (0.059 g, 0.42 mmol) was added at 0-5° C. and stirring was continued for 10 minutes. The reaction mixture was quenched with water (2 ml) and extracted with three 5-ml portions of dichloromethane. The combined organic layers were dried over magnesium sulfate, filtered and concentrated in vacuo. Purification by flash chromatography with n-heptane/ethyl acetate as eluent gave the title compound (0.010 g, 18%) as light brown solid. MS m/e: 487 ([M+H]$^+$)

Example 123

2-(1'H,3H-Spiro[2-benzofuran-1,4'-piperidin]-1'-yl)-1-oxa-3-azaspiro[4.5]dec-2-en-4-one The title compound was obtained as off-white solid in 42% yield from ethyl 1-hydroxycyclopentanecarboxylate and 1'H,3H-spiro[2-benzofuran-1,4'-piperidine]-1'-carbonitrile according to the general procedure VIII. MS m/e: 341 ([M+H]$^+$)

Example 124

1'-(4-Oxo-1-oxa-3-azaspiro[4.5]dec-2-en-2-yl)-3H-spiro[2-benzofuran-1,4'-piperidin]-3-one The title compound was obtained as white solid in 41% yield from 2-amino-1-oxa-3-azaspiro[4.5]dec-2-en-4-one and 3H-spiro[isobenzofuran-1,4'-piperidin]-3-one hydrochloride using triethylamine according to the general procedure VI. MS m/e: 341 ([M+H]$^+$)

Example 125

2-(1'H,3H-Spiro[2-benzofuran-1,4'-piperidin]-1'-yl)-1,7-dioxa-3-azaspiro[4.5]dec-2-en-4-one The title compound was obtained as white solid in 22% yield from ethyl 3-hydroxytetrahydro-2H-pyran-3-carboxylate and 3H-spiro[isobenzofuran-1,4'-piperidine]according to the general procedure VII. MS m/e: 343 ([M+H]$^+$)

Example 126

1'-[4-Oxo-8-pentyl-1-oxa-3-azaspiro[4.5]dec-2-en-2-yl]-3H-spiro[2-benzofuran-1,4'-piperidin]-3-one diastereomer a and Example 127

1'-[4-Oxo-8-pentyl-1-oxa-3-azaspiro[4.5]dec-2-en-2-yl]-3H-spiro[2-benzofuran-1,4'-piperidin]-3-one diastereomer b The title compounds were obtained from 2-amino-8-pentyl-1-oxa-3-azaspiro[4.5]dec-2-en-4-one and 3H-spiro[isobenzofuran-1,4'-piperidin]-3-one hydrochloride according to the general procedure VI after separation by RP chromatography on a Gemini NX column using acetonitrile/water/formic acid as eluent.
1'-[4-Oxo-8-pentyl-1-oxa-3-azaspiro[4.5]dec-2-en-2-yl]-3H-spiro[2-benzofuran-1,4'-piperidin]-3-one diastereomer a (0.014 g, 16%) was obtained as white solid. MS m/e: 425 ([M+H]$^+$)
1'-[4-Oxo-8-pentyl-1-oxa-3-azaspiro[4.5]dec-2-en-2-yl]-3H-spiro[2-benzofuran-1,4'-piperidin]-3-one diastereomer b (0.006 g, 7%) was obtained as white solid. MS m/e: 425 ([M+H]$^+$)

Example 128

8-Pentyl-2-(1'H,3H-spiro[2-benzofuran-1,4'-piperidin]-1'-yl)-1-oxa-3-azaspiro[4.5]dec-2-en-4-one diastereomer a and Example 129

8-Pentyl-2-(1'H,3H-spiro[2-benzofuran-1,4'-piperidin]-1'-yl)-1-oxa-3-azaspiro[4.5]dec-2-en-4-one diastereomer b The title compounds were obtained from 2-amino-8-pentyl-1-oxa-3-azaspiro[4.5]dec-2-en-4-one and 3H-spiro[isobenzofuran-1,4'-piperidine] according to the general procedure VI by flash chromatography using n-heptane/isopropanol as eluent.
8-Pentyl-2-(1'H,3H-spiro[2-benzofuran-1,4'-piperidin]-1'-yl)-1-oxa-3-azaspiro[4.5]dec-2-en-4-one diastereomer a (0.030 g, 25%) was obtained as white solid. MS m/e: 411 ([M+H]$^+$)
8-Pentyl-2-(1'H,3H-spiro[2-benzofuran-1,4'-piperidin]-1'-yl)-1-oxa-3-azaspiro[4.5]dec-2-en-4-one diastereomer b (0.013 g, 11%) was obtained as white solid. MS m/e: 411 ([M+H]$^+$)

Example 130

8,8-Difluoro-2-(1'H,3H-spiro[2-benzofuran-1,4'-piperidin]-1'-yl)-1-oxa-3-azaspiro[4.5]dec-2-en-4-one The title compound was obtained as white solid in 59% yield from 2-amino-8,8-difluoro-1-oxa-3-azaspiro[4.5]dec-2-en-4-one and 3H-spiro[isobenzofuran-1,4'-piperidine] according to the general procedure VI. MS m/e: 377 ([M+H]$^+$)

Example 131

1'-(8,8-Difluoro-4-oxo-1-oxa-3-azaspiro[4.5]dec-2-en-2-yl)-3H-spiro[2-benzofuran-1,4'-piperidin]-3-one The title compound was obtained as white solid in 54% yield from 2-amino-8,8-difluoro-1-oxa-3-azaspiro[4.5]dec-2-en-4-one and 3H-spiro[isobenzofuran-1,4'-piperidin]-3-one hydrochloride using triethylamine according to the general procedure VI. MS m/e: 390 ([M+H]$^+$)

Example 132

2-(1'H,3H-Spiro[2-benzofuran-1,4'-piperidin]-1'-yl)-1-oxa-8-thia-3-azaspiro[4.5]dec-2-en-4-one The title compound was obtained as light yellow solid in 5% yield from ethyl 4-hydroxytetrahydro-2H-thiopyran-4-carboxylate and 3H-spiro[isobenzofuran-1,4'-piperidine]according to the general procedure VII. MS m/e: 359 ([M+H]$^+$)

Example 133

2-(1'H,3H-Spiro[2-benzofuran-1,4'-piperidin]-1'-yl)-1-oxa-8-thia-3-azaspiro[4.5]dec-2-en-4-one 8,8-dioxide To a solution of 2-(1'H,3H-spiro[2-benzofuran-1,4'-piperidin]-1'-yl)-1-oxa-8-thia-3-azaspiro[4.5]dec-2-en-4-one (0.038 g, 0.11 mmol) in methanol/water (20:1, 1.0 ml) was added in two equal portions potassium peroxymonosulfate (0.13 g, 0.21 mmol) over a period of 1 h at room temperature. The reaction mixture was partitioned between ethyl acetate (30 ml) and 1 M aqueous sodium carbonate (10 ml). The layers were separated. The aqueous layer was extracted with two 30-ml portions of ethyl acetate. The combined organic layers dried over anhydrous sodium sulfate and concentrated in vacuo. Flash chromatography on a 3-aminopropyl-functionalized silica gel column with n-heptane/ethyl acetate as eluent gave the title compound (0.014 g, 34%) as white solid. MS m/e: 391 ([M+H]$^+$)

Example 134 tert-Butyl 4-oxo-2-(1'H,3H-spiro[2-benzofuran-1,4'-piperidin]-1'-yl)-1-oxa-3,8-diazaspiro[4.5]dec-2-ene-8-carboxylate The title compound was obtained as white solid in 46% yield from tert-butyl 2-amino-4-oxo-1-oxa-3,8-diazaspiro[4.5]dec-2-ene-8-carboxylate and 3H-spiro[isobenzofuran-1,4'-piperidine] according to the general procedure VI. MS m/e: 442 ([M+H]$^+$)

Example 135

8-Benzyl-2-(1'H,3H-spiro[2-benzofuran-1,4'-piperidin]-1'-yl)-1-oxa-3,8-diazaspiro[4.5]dec-2-en-4-one a) 2-(1'H,3H-Spiro[2-benzofuran-1,4'-piperidin]-1'-yl)-1-oxa-3, 8-diazaspiro[4.5]dec-2-en-4-one To a solution of tert-butyl 4-oxo-2-(1'H,3H-spiro[2-benzofuran-1,4'-piperidin]-1'-yl)-1-oxa-3,8-diazaspiro[4.5]dec-2-ene-8-carboxylate (0.35 g, 0.79 mmol) in dichloromethane (7.9 ml) was added 2,2,2-trifluoroacetic acid (1.2 ml, 16 mmol) at 0-5° C. The ice bath was removed after 15 minutes and stirring was continued for 20 h. The reaction mixture was partitioned between dichloromethane (50 ml) and 1 M aqueous sodium hydroxide solution (30 ml). The layers were separated. The aqueous layer was extracted with two 50-ml portions of dichloromethane. The combined organic layers were dried over anhydrous sodium sulfate and concentrated in vacuo to give the title compound (0.27 g, quantitative) which was used in the next step without further purifications. MS m/e: 342 ([M+H]$^+$)

b) 8-Benzyl-2-(1'H,3H-spiro[2-benzofuran-1,4'-piperidin]-1'-yl)-1-oxa-3, 8-diazaspiro[4.5]dec-2-en-4-one A mixture of 2-(1'H,3H-spiro[2-benzofuran-1,4'-piperidin]-1'-yl)-1-oxa-3,8-diazaspiro[4.5]dec-2-en-4-one (0.073 g, 0.21 mmol, acetic acid (0.012 ml, 0.21 mmol) and benzaldehyde (0.024 ml, 0.24 mmol) in dichloromethane (2.0 ml) was stirred at room temperature for 45 minutes. Addition of sodium triacteoxyborohydride (0.073 g, 0.34 mmol) in small portions at 0-5° C. and stirring for 15 minutes was followed by stirring for 15 h at room temperature. The reaction mixture was partitioned between ethyl acetate (30 ml) and 1 M aqueous sodium hydroxide solution (20 ml). The layers were separated. The aqueous layer was extracted with one 30-ml portion of ethyl acetate. The combined organic layers were dried over anhydrous sodium sulfate and concentrated in vacuo. Flash chromatography on a 3-aminopropyl-functionalized silica gel column with n-heptane/isopropanol as eluent gave the title compound (0.053 g, 57%) as white solid. MS m/e: 432 ([M+H]$^+$)

Example 136

8-(2,2-Difluoroethyl)-2-(1'H,3H-spiro[2-benzofuran-1,4'-piperidin]-1'-yl)-1-oxa-3,8-diazaspiro[4.5]dec-2-en-4-one A solution of 2-(1'H,3H-spiro[2-benzofuran-1,4'-piperidin]-1'-yl)-1-oxa-3,8-diazaspiro[4.5]dec-2-en-4-one (0.050 g, 0.15 mmol), 2,2-difluoroethyl trifluoromethanesulfonate (0.021 ml, 0.16 mmol) and N,N-diisopropylethylamine (0.028 ml, 0.16 mmol) in acetonitrile (0.73 ml) was heated at reflux for 2 h. The reaction mixture was partitioned between dichloromethane (30 ml) and 1 M aqueous sodium hydroxide solution (20 ml). The layers were separated. The aqueous layer was extracted with two 30-ml portions of dichloromethane. The combined organic layers were dried over anhydrous sodium sulfate and concentrated in vacuo. Flash chromatography on a 3-aminopropyl-functionalized silica gel column with n-heptane/isopropanol as eluent gave the title compound (0.039 g, 66%) as white solid. MS m/e: 406 ([M+H]$^+$)

Example 137 tert-Butyl 4'-oxo-2'-(1'H,3H-spiro[2-benzofuran-1, 4'-piperidin]-1'-yl)-1,5-dihydro-4'H-spiro[2-benzazepine-4,5'-[1,3]oxazole]-2(3H)-carboxylate The title compound was obtained as off-white solid in 23% yield from 2-tert-butyl 4-methyl 4-hydroxy-4,5-dihydro-1H-benzo[α]azepine-2,4(3H)-dicarboxylate and 3H-spiro[isobenzofuran-1,4'-piperidine] according to the general procedure VII. MS m/e: 504 ([M+H]$^+$)

Example 138

2'-(1'H,3H-Spiro[2-benzofuran-1,4'-piperidin]-1'-yl)-1,2,3,5-tetrahydro-4'H-spiro[2-benzazepine-4,5'-[1,3]oxazol]-4'-one A solution of tert-butyl 4'-oxo-2'-(3H-spiro[isobenzofuran-1,4'-piperidine]-1'-yl)-3,5-dihydro-4'H-spiro[benzo[α]azepine-4,5'-oxazole]-2(1H)-carboxylate (0.020 g, 0.040 mmol) and 2,2,2-trifluoroacetic acid (0.061 ml, 0.79 mmol) in dichloromethane (2.0 ml) was stirred for 4 h at room temperature. The reaction mixture was partitioned between dichloromethane (30 ml) and 2 M aqueous sodium carbonate (20 ml). The layers were separated. The aqueous layer was extracted with two 30-ml portions of dichloromethane. The combined organic layers were dried over anhydrous sodium sulfate and concentrated in vacuo to give the crude title compound (0.016 g, quantitative) as dark brown amorphous solid which was used in the next step without further purification. MS m/e: 404 ([M+H]$^+$)

Example 139

2-Methyl-2'-(1'H,3H-spiro[2-benzofuran-1,4'-piperidin]-1'-yl)-1,2,3,5-tetrahydro-4'H-spiro[2-benzazepine-4,5'-[1,3]oxazol]-4'-one To a mixture of 2'-(3H-spiro[isobenzofuran-1,4'-piperidine]-1'-yl)-1,2,3,5-tetrahydro-4'H-spiro[benzo[α]azepine-4,5'-oxazol]-4'-one (0.014 g, 0.035 mmol), sodium acetate (0.0030 g, 0.035 mmol) and acetic acid (0.0020 ml, 0.035 mmol) in dichloromethane (0.60 ml) was added formaldehyde, 36% in water (0.0040 ml, 0.049 mmol) at room temperature. The mixture was stirred for 30 min. Addition of sodium triacetoxyborohydride (0.012 g, 0.056 mmol) in one portion at 0-5° C. The cooling bath was removed after the addition and stirring was continued for 45 minutes. The reaction mixture was partitioned between dichloromethane (30 ml) and 1 M aqueous sodium hydroxide solution (20 ml). The layers were separated. The aqueous layer was extracted with two 30-ml portions of dichloromethane. The combined organic layers were dried over anhydrous sodium sulfate and concentrated in vacuo. Flash chromatography with n-heptane/isopropanol as eluent gave the title compound (0.0070 g, 48%) as off-white solid. MS m/e: 418 ([M+H]$^+$)

Example 140

2'-(1'H,3H-Spiro[2-benzofuran-1,4'-piperidin]-1'-yl)-3,3a,4,5,6,7,8,8a-octahydro-1H,4'H-spiro[azulene-2,5'-[1,3]oxazol]-4'-one The title compound was obtained as light brown solid in 10% yield from 2'-amino-3,3a,4,5,6,7,8,8a-octahydro-1H, 4'H-spiro[azulene-2,5'-[1,3]oxazol]-4'-one and 3H-spiro[isobenzofuran-1,4'-piperidine] according to the general procedure VI. MS m/e: 395 ([M+H]$^+$)

Example 141

2'-(1'H,3H-Spiro[2-benzofuran-1,4'-piperidin]-1'-yl)-1,3,3a,4,5,6,7,7a-octahydro-4'H-spiro[indene-2,5'-[1,3]oxazol]-4'-one The title compound was obtained as off-white solid in 38% yield from (2r,3a,7a)-2'-amino-1,3,3a,4,5,6,7,7a-octahydro-4'H-spiro[indene-2,5'-[1,3]oxazol]-4'-one and 3H-spiro[isobenzofuran-1,4'-piperidine] according to the general procedure VI. MS m/e: 382 ([M+H]$^+$)

Example 142

2-(1'H,3H-Spiro[2-benzofuran-1,4'-piperidin]-1'-yl)-3a',4'-dihydro-1'H,4H-spiro[1,3-oxazole-5,2'-pentalene]-4,5' (3'H)-dione A mixture of 5-allyl-5-(prop-2-ynyl)-2-(3H-spiro[isobenzofuran-1,4'-piperidine]-1'-yl)oxazol-4(5H)-one (0.18 g, 0.51 mmol, Eq: 1.00) and dicobalt octacarbonyl (0.018 g, 0.051 mmol, Eq: 0.1) in toluene (7.0 ml) was stirred at 75° C. under an atmosphere of carbon monoxide (1 bar) for 15 h. The reaction mixture was filtered through sintered glass. The filtrate was concentrated in vacuo. Purification by flash chromatography with n-heptane/ethyl acetate as eluent gave the title compound (0.070 g, 36%) as light brown solid. MS m/e: 379 ([M+H]$^+$)

Example 143

2-(1'H,3H-Spiro[2-benzofuran-1,4'-piperidin]-1'-yl)-3a',4',6',6a'-tetrahydro-1'H,4H-spiro[1,3-oxazole-5,2'-pentalene]-4,5'(3'H)-dione To a solution of 2-(1'H,3H-spiro[2-benzofuran-1,4'-piperidin]-1'-yl)-3a',4'-dihydro-1'H,4H-spiro[1,3-oxazole-5,2'-pentalene]-4,5'(3'H)-dione (0.020 g, 0.053 mmol) in ethanol (1 ml) was added palladium 10% on activated charcoal (0.0056 g, 0.0053 mmol). The flask was filled with hydrogen (1 bar) and stirred for 8 h. The catalyst was removed by filtration over a pad of celite. The filtrate was concentrated in vacuo. Purification by flash chromatography with n-heptane/ethyl acetate as eluent gave the title compound (0.010 g, 51%) as off-white solid in 51% yield. MS m/e: 381 ([M+H]$^+$)

Example 144

2'-(1'H,3H-Spiro[2-benzofuran-1,4'-piperidin]-1'-yl)-3a,4,6,6a-tetrahydro-1H,3H,4'H-spiro[cyclopenta[c]furan-5,5'-[1,3]oxazol]-4'-one The title compound was obtained as light brown solid in 12% 2'-amino-3a,4,6,6a-tetrahydro-1H,3H,4'H-spiro[cyclopenta[c]furan-5,5'-[1,3]oxazol]-4'-one and 3H-spiro[isobenzofuran-1,4'-piperidine] according to the general procedure VI. MS m/e: 369 ([M+H]$^+$)

Example 145

2'-(1'H,3H-Spiro[2-benzofuran-1,4'-piperidin]-1'-yl)-2,3,4a,5,7,7a-hexahydro-4'H-spiro[cyclopenta[b][1,4]dioxine-6,5'-[1,3]oxazol]-4'-one diastereomer b a) 7-Hydroxy-8-(2-hydroxyethoxy)-2-(3H-spiro[isobenzofuran-1,4'-piperidine]-1'-yl)-1-oxa-3-azaspiro[4.4]non-2-en-4-one diastereomer b A mixture of 7,8-dihydroxy-2-(1'H,3H-spiro[2-benzofuran-1,4'-piperidin]-1'-yl)-1-oxa-3-azaspiro[4.4]non-2-en-4-one diastereomer b (0.20 g, 0.56 mmol, Eq: 1.00) and dibutyltin oxide (0.14 g, 0.56 mmol, Eq: 1.00) in toluene (19 ml) was heated at reflux for 6 h using a Dean-Stark trap for the removal of water. The reaction mixture was concentrated to half of the volume. Tetrabutylammonium iodide (0.21 g, 0.56 mmol, Eq: 1.00) and 2-chloroethanol (0.45 g, 5.6 mmol, Eq: 10) were added and the mixture was heated at reflux for 16 h. The solvent was evaporated. Purification by flash-chromatography with dichloromethane/methanol as eluent gave the title compound (0.22 g, 68%) as brown oil with a purity of approximately 70%. MS m/e: 403 ([M+H]$^+$)

b) 2-{[8-Hydroxy-4-oxo-2-(1'H,3H-spiro[2-benzofuran-1,4'-piperidin]-1'-yl)-1-oxa-3-azaspiro[4.4]non-2-en-7-yl]oxy}ethyl 4-methylbenzenesulfonate diastereomer b To a solution of 7-hydroxy-8-(2-hydroxyethoxy)-2-(3H-spiro[isobenzofuran-1,4'-piperidine]-1'-yl)-1-oxa-3-azaspiro[4.4]non-2-en-4-one diastereomer b (0.10 g, 0.25 mmol), p-toluenesulfonyl chloride (0.057 g, 0.30 mmol), and 4-(N,N-dimethylamino)-pyridine (0.0030 g, 0.025 mmol) in dichloromethane (3.3 ml) was added pyridine (0.098 g, 0.10 ml, 1.2 mmol) at room temperature. Stirring was continued for 15 h. The reaction mixture was partitioned between 1 M aqueous hydrogen chloride solution (2 ml) and dichloromethane (5 ml). The layers were separated. The aqueous layer was extracted with two 5-ml portions of dichloromethane. The combined organic layers were dried over magnesium sulfate, filtered and concentrated in vacuo. Purification by flash-chromatography with dichloromethane/methanol as eluent gave the title compound (0.036 g, 26%) as colorless oil. MS m/e: 558 ([M+H]$^+$)

c) 2'-(1'H,3H-Spiro[2-benzofuran-1,4'-piperidin]-1'-yl)-2,3,4a,5,7,7a-hexahydro-4'H-spiro[cyclopenta[b][1,4]dioxine-6,5'-[1,3]oxazol]-4'-one diastereomer b To a solution of 2-{[8-hydroxy-4-oxo-2-(1'H,3H-spiro[2-benzofuran-1,4'-piperidin]-1'-yl)-1-oxa-3-azaspiro[4.4]non-2-en-7-yl]oxy}ethyl 4-methylbenzenesulfonate diastereomer b (0.034 g, 0.060 mmol) in tetrahydrofuran (2.8 ml) was added sodium hydride (0.0050 g, 0.12 mmol) at room temperature. The reaction mixture was heated to 60° C. for 10 minutes. The reaction mixture was partitioned between saturated aqueous ammonium chloride solution (1 ml) and ethyl acetate (5 ml). The layers were separated. The aqueous layer was extracted with two 5-ml portions of ethyl acetate. The combined organic layers were dried over magnesium sulfate, filtered and concentrated in vacuo. Purification by flash-chromatography with dichloromethane/methanol as eluent gave the title compound (0.008 g, 36%) as colorless. MS m/e: 385 ([M+H]$^+$)

Example 146

5',5'-Difluoro-2-(1'H,3H-spiro[2-benzofuran-1,4'-piperidin]-1'-yl)-3',3a',4',5',6',6a'-hexahydro-1'H,4'H-spiro[1,3-oxazole-5,2'-pentalen]-4-one The title compound was obtained as white solid in 14% yield from (3a',5s,6a')-2-amino-5',5'-difluoro-3',3a',4',5',6',6a'-hexahydro-1'H,4'H-spiro[1,3-oxazole-5,2'-pentalen]-4-one and 3H-spiro[isobenzofuran-1,4'-piperidine] according to the general procedure VI. MS m/e: 403 ([M+H]$^+$)

Example 147

2'-(1'H,3H-Spiro[2-benzofuran-1,4'-piperidin]-1'-yl)-3a,4,6,6a-tetrahydro-4'H-spiro[cyclopenta[d][1,3,2]dioxathiole-5,5'-[1,3]oxazol]-4'-one 2-oxide To a solution of 7,8-dihydroxy-2-(1'H,3H-spiro[2-benzofuran-1,4'-piperidin]-1'-yl)-1-oxa-3-azaspiro[4.4]non-2-en-4-one diastereomer b (0.030 g, 0.084 mmol) in dichloromethane (0.32 ml) was added morpholinosulfur trifluoride (0.036 ml, 0.29 mmol) at 0-5° C. The cooling bath was removed after 5 h and stirring was continued for 12 h at room temperature. The reaction mixture was partitioned between dichloromethane and saturated aqueous sodium bicarbonate solution. The layers were separated. The aqueous layer was extracted with dichloromethane. The organic layers were washed with saturated aqueous sodium bicarbonate solution, dried over anhydrous sodium sulfate, filtered and concentrated in vacuo. Purification by reverse phase HPLC on a Gemini NX, C18 column with water/methanol as eluent gave the title compound (0.015 g, 46%) as off-white solid. MS m/e: 463 ([M+H]$^+$)

Example 148

Ethyl 4'-oxo-2'-(1'H,3H-spiro[2-benzofuran-1,4'-piperidin]-1'-yl)-4'H-spiro[bicyclo[3.1.0]hexane-3,5'-[1,3]oxazole]-6-carboxylate diastereomer a and

Example 149

Ethyl 4'-oxo-2'-(1'H,3H-spiro[2-benzofuran-1,4'-piperidin]-1'-yl)-4'H-spiro[bicyclo[3.1.0]hexane-3,5'-[1,3]oxazole]-6-carboxylate diastereomer b To a solution of 2-(1'H,3H-spiro[2-benzofuran-1,4'-piperidin]-1'-yl)-1-oxa-3-azaspiro[4.4]nona-2,7-dien-4-one (0.10 g, 0.31 mmol) in dichloromethane (2.0 ml) was added rhodium (II) acetate dimer (0.014 g, 0.031 mmol) and ethyl 2-diazoacetate (0.65 ml, 0.93 mmol) at 0-5° C. The reaction mixture was stirred for 16 h at room temperature. Further rhodium (II) acetate dimer (0.020 g, 0.046 mmol) and ethyl 2-diazoacetate (0.65 ml, 0.93 mmol) were added. Stirring was continued for 4 h. The reaction mixture was diluted with dichloromethane, washed with two portions of water, dried over anhydrous sodium sulfate and concentrated in vacuo. Purification by reverse phase HPLC on a Gemini NX 3u 50×4.6 mm column gave the title compounds. The compounds are cited in order of elution:

Ethyl 4'-oxo-2'-(1'H,3H-spiro[2-benzofuran-1,4'-piperidin]-1'-yl)-4'H-spiro[bicyclo[3.1.0]hexane-3,5'-[1,3]oxazole]-6-carboxylate diastereomer a was obtained as yellow oil in 2% yield. MS m/e: 411 ([M+H]$^+$)

Ethyl 4'-oxo-2'-(1'H,3H-spiro[2-benzofuran-1,4'-piperidin]-1'-yl)-4'H-spiro[bicyclo[3.1.0]hexane-3,5'-[1,3]oxazole]-6-carboxylate diastereomer b was obtained as yellow oil in 1% yield. MS m/e: 411 ([M+H]+)

Example 150

2'-(2,2-Dioxido-1'H,3H-spiro[2-benzothiophene-1, 4'-piperidin]-1'-yl)-1,3-dihydro-4'H-spiro[indene-2, 5'-[1,3]oxazol]-4'-one The title compound was obtained as light grey solid in 61% yield from 2'-amino-1,3-dihydro-4'H-spiro[indene-2, 5'-oxazol]-4'-one and spiro[1H-2-benzothiophene-3,4'-piperidine]2,2-dioxide hydrochloride using Huenig's base according to the general procedure VI. MS m/e: 423 ([M+H]+)

[1] Robben, et al. (2006). Am J Physiol Renal Physiol. 291, F257-70, "Cell biological aspects of the vasopressin type-2 receptor and aquaporin 2 water channel in nephrogenic diabetes insipidus"
[2] Neumann (2008). J Neuroendocrinol. 20, 858-65, "Brain oxytocin: a key regulator of emotional and social behaviours in both females and males"
[3] Ebner, et al. (2002). Eur J Neurosci. 15, 384-8., "Forced swimming triggers vasopressin release within the amygdala to modulate stress-coping strategies in rats"
[4] Kendler, et al. (2003). Arch Gen Psychiatry. 60, 789-96, "Life Event Dimensions of Loss, Humiliation, Entrapment, and Danger in the Prediction of Onsets of Major Depression and Generalized Anxiety"
[5] Regier, et al. (1998). Br J Psychiatry Suppl. 24-8, "Prevalence of anxiety disorders and their comorbidity with mood and addictive disorders"
[6] Bielsky, et al. (2004). Neuropsychopharmacology. 29, 483-93, "Profound impairment in social recognition and reduction in anxiety-like behavior in vasopressin Via receptor knockout mice" Landgraf, et al. (1995). Regul Pept. 59, 229-39., "V1 vasopressin receptor antisense oligodeoxynucleotide into septum reduces vasopressin binding, social discrimination abilities, and anxiety-related behavior in rats"
[8] Yirmiya, et al. (2006). 11, 488-94, "Association between the arginine vasopressin 1a receptor (AVPR1a) gene and autism in a family-based study: mediation by socialization skills"
[9] Thompson, et al. (2004). Psychoneuroendocrinology. 29, 35-48, "The effects of vasopressin on human facial responses related to social communication"
[10] Raskind, et al. (1987). Biol Psychiatry. 22, 453-62, "Antipsychotic drugs and plasma vasopressin in normals and acute schizophrenic patients"
[11] Altemus, et al. (1992). Arch Gen Psychiatry. 49, 9-20, "Abnormalities in the regulation of vasopressin and corticotropin releasing factor secretion in obsessive-compulsive disorder"
[12] Genes, Brain and Behavior (2011) 10: 228-235
[13] Curr. Opin. Neurobiol. 19, 231-234 (2009)
[14] Kalsbeek, A., E. Fliers, M. A. Hofman, D. F. Swaab and R. M. Buijs. 2010. Vasopressin and the output of the hypothalamic biological clock.
[15] Schwartz, W. J., R. J. Coleman and S. M. Reppert. 1983. A daily vasopressin rhythm in rat cerebrospinal fluid. Brain Res 263: 105-12
[16] Groblewski, T. A., A. A. Nunez and R. M. Gold. 1981. Circadian rhythms in vasopressin deficient rats. Brain Res Bull 6: 125-30
[17] Albers, H. E., C. F. Ferris, S. E. Leeman and B. D. Goldman. 1984. Avian pancreatic polypeptide phase shifts hamster circadian rhythms when microinjected into the suprachiasmatic region. Science 223: 833-5
[18] Yoshiaki Yamaguchi, Toru Suzuki, Yasutaka Mizoro, Hiroshi Kori, Kazuki Okada, Yulin Chen, Jean-Michel Fustin, Fumiyoshi Yamazaki, Naoki Mizuguchi, Jing Zhang, Xin Dong, Gozoh Tsujimoto, Yasushi Okuno, Masao Doi, Hitoshi Okamura. Mice Genetically Deficient in Vasopressin V1a and V1b Receptors Are Resistant to Jet Lag. (2013) Science, 342: 85-90
[19] Compendium of Chemical Terminology, 2nd, A. D. McNaught & A. Wilkinson (Eds). Blackwell Scientific Publications, Oxford (1997)

The invention claimed is:
1. A compound of formula I,

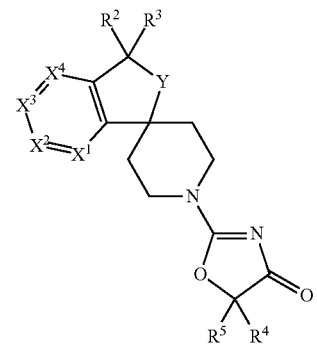

wherein
$X^1$, $X^2$, $X^3$ and $X^4$ are C—$R^1$;
Y is O or S(O)$_m$;
m is 0, 1 or 2;
$R^1$ each separately is selected from the group consisting of hydrogen, halogen, hydroxy, $C_{1-6}$-alkyl- and $C_{1-6}$-alkoxy-;
$R^2$ is selected from the group consisting of H and $C_{1-6}$-alkyl-;
$R^3$ is selected from the group consisting of H and $C_{1-6}$-alkyl-;
or $R^2$ and $R^3$ together are =O;
$R^4$ is selected from the group consisting of
  i) aryl-$C_{1-6}$-alkyl-, wherein the aryl moiety can be optionally substituted by halogen,
  ii) $C_{1-6}$-alkoxy-$CH_2$—,
  iii) $C_{1-6}$-alkyl-,
  iv) $C_{2-6}$-alkenyl-$CH_2$—,
  v) $C_{2-6}$-alkynyl-$CH_2$—,
  vi) halogen-$C_{1-6}$-alkyl-,
  vii) halogen-$C_{2-6}$-alkenyl-$CH_2$—, and
  viii) hydrogen;
$R^5$ is selected from the group consisting of
  i) aryl-,
  ii) aryl-$C_{1-6}$-alkyl-, wherein
    the aryl moiety can be optionally substituted by $C_{1-6}$-alkyl, halogen-$C_{1-6}$-alkyl or halogen, and
    the $C_{1-6}$-alkyl moiety can optionally be substituted by $C_{1-6}$-alkyl-COO—, halogen or hydroxy,
  iii) $C_{3-10}$-cycloalkyl-$C_{1-6}$-alkyl,
  iv) halogen-$C_{1-6}$-alkyl-,
  v) heteroaryl-$C_{1-6}$-alkyl-, wherein the heteroaryl moiety can be optionally substituted by halogen,
  vi) heterocycloalkyl-$C_{1-6}$-alkyl-,
  vii) $C_{1-6}$-alkyl-, viii) C$_{2-6}$-alkenyl-CH$_2$— that is optionally substituted by halogen, (C$_{1-6}$-alkyl)$_3$SiO—, C$_{1-6}$-alkyl-COO— or C$_{1-6}$-alkyl-OOC—,
ix) C$_{1-6}$-alkoxy-CH$_2$—, and
x) C$_{2-6}$-alkynyl-CH$_2$—;
or R$^4$ and R$^5$ together are selected from the group consisting of
i) C$_{3-10}$-cycloalkyl that is optionally substituted by C$_{1-6}$-alkyl, C$_{1-6}$-alkoxy, C$_{1-6}$-alkyl-OOC—, halogen, halogen-C$_{1-6}$-alkyl, hydroxy-C$_{1-6}$-alkyl or oxo;
ii) heterocycloalkyl that is optionally substituted by benzyl, C$_{1-6}$-alkyl, C$_{1-6}$-alkyl-OOC—, halogen-C$_{1-6}$-alkyl or oxo;
iii) C$_{3-10}$-cycloalkenyl that is optionally substituted by C$_{1-6}$-alkyl, C$_{1-6}$-alkyl-OOC—, halogen-C$_{1-6}$-alkyl, (C$_{1-6}$-alkyl)$_3$SiO—C$_{1-6}$-alkyl- or hydroxy-C$_{1-6}$-alkyl, and
iv) indanyl when Y is SO$_2$;
or pharmaceutically acceptable salts thereof.

2. The compound of claim 1, wherein
Y is O;
R$^4$ is selected from the group consisting of
i) aryl-C$_{1-6}$-alkyl-, wherein the aryl moiety can be optionally substituted by halogen,
ii) C$_{1-6}$-alkyl-,
iii) C$_{2-6}$-alkenyl-CH$_2$—,
iv) C$_{2-6}$-alkynyl-CH$_2$—,
v) halogen-C$_{2-6}$-alkenyl-CH$_2$—, and
vi) hydrogen;
R$^5$ is selected from the group consisting of
i) aryl-,
ii) aryl-C$_{1-6}$-alkyl-, wherein
the aryl moiety can be optionally substituted by C$_{1-6}$-alkyl, halogen-C$_{1-6}$-alkyl or halogen, and
the C$_{1-6}$-alkyl moiety can optionally be substituted by C$_{1-6}$-alkyl-COO—, halogen or hydroxy,
iii) C$_{3-10}$-cycloalkyl-C$_{1-6}$-alkyl-,
iv) heteroaryl-C$_{1-6}$-alkyl-, wherein the heteroaryl moiety can be optionally substituted by halogen,
v) heterocycloalkyl-C$_{1-6}$-alkyl-,
vi) C$_{1-6}$-alkyl-,
vii) C$_{2-6}$-alkenyl-CH$_2$— that is optionally substituted by halogen, (C$_{1-6}$-alkyl)$_3$SiO—, C$_{1-6}$-alkyl-COO— or C$_{1-6}$-alkyl-OOC—,
viii) C$_{1-6}$-alkoxy-CH$_2$—, and
ix) C$_{2-6}$-alkynyl-CH$_2$—;
or R$^4$ and R$^5$ together are selected from the group consisting of
i) C$_{3-10}$-cycloalkyl that is optionally substituted by C$_{1-6}$-alkyl, C$_{1-6}$-alkoxy, C$_{1-6}$-alkyl-OOC—, C$_{1-6}$-alkyl-COO—, halogen, halogen-C$_{1-6}$-alkyl, hydroxy-C$_{1-6}$-alkyl or oxo;
ii) heterocycloalkyl that is optionally substituted by benzyl, C$_{1-6}$-alkyl, C$_{1-6}$-alkyl-OOC—, halogen-C$_{1-6}$-alkyl or oxo; and
iii) C$_{3-10}$-cycloalkenyl that is optionally substituted by C$_{1-6}$-alkyl, C$_{1-6}$-alkyl-OOC—, halogen-C$_{1-6}$-alkyl, (C$_{1-6}$-alkyl)$_3$SiO—C$_{1-6}$-alkyl- or hydroxy-C$_{1-6}$-alkyl.

3. The compound of claim 1, wherein each R$^1$ is separately is selected from the group consisting of hydrogen, halogen, and C$_{1-6}$-alkoxy.

4. The compound of claim 1, wherein R$^1$ is hydrogen.

5. The compound of claim 1, wherein Y is O.

6. The compound of claim 1, wherein Y is SO$_2$.

7. The compound of claim 1, wherein R$^2$ is hydrogen.

8. The compound of claim 1, wherein R$^3$ is hydrogen.

9. The compound of claim 1, wherein R$^2$ and R$^3$ are =O.

10. The compound of claim 1, wherein R$^4$ is hydrogen or C$_{1-6}$-alkyl.

11. The compound of claim 1, wherein R$^5$ is benzyl or C$_{3-10}$-cycloalkyl-C$_{1-6}$-alkyl.

12. The compound of claim 1, wherein R$^4$ and R$^5$ together are
i) C$_{3-10}$-cycloalkyl that is optionally substituted by halogen;
ii) heterocycloalkyl that is optionally substituted by C$_{1-6}$-alkyl;
iii) C$_{3-10}$-cycloalkenyl that is optionally substituted by halogen-C$_{1-6}$-alkyl, and
iv) indanyl when Y is SO$_2$.

13. The compound of claim 1, selected from the group consisting of
(−)-(5S)-5-Benzyl-2-(1'H,3H-spiro[2-benzofuran-1,4'-piperidin]-1'-yl)-1,3-oxazol-4(5H)-one,
(+)-5-(Cyclopentylmethyl)-5-methyl-2-(1'H,3H-spiro[2-benzofuran-1,4'-piperidin]-1'-yl)-1,3-oxazol-4(5H)-one,
(+)-5-(Ethoxymethyl)-5-methyl-2-(1'H,3H-spiro[2-benzofuran-1,4'-piperidin]-1'-yl)-1,3-oxazol-4(5H)-one,
(−)-5-[(4-Chlorophenyl)(hydroxy)methyl]-2-(1'H,3H-spiro[2-benzofuran-1,4'-piperidin]-1'-yl)-1,3-oxazol-4(5H)-one diastereomer a,
(+)-5-[(4-Chlorophenyl)(hydroxy)methyl]-2-(1'H,3H-spiro[2-benzofuran-1,4'-piperidin]-1'-yl)-1,3-oxazol-4(5H)-one diastereomer b,
(+)-5-[(5-Chlorothiophen-2-yl)methyl]-5-methyl-2-(1'H,3H-spiro[2-benzofuran-1,4'-piperidin]-1'-yl)-1,3-oxazol-4(5H)-one,
(−)-5-[(6-Chloropyridin-3-yl)methyl]-5-methyl-2-(1'H,3H-spiro[2-benzofuran-1,4'-piperidin]-1'-yl)-1,3-oxazol-4(5H)-one,
(−)-5-Benzyl-5-methyl-2-(1'H,3H-spiro[2-benzofuran-1,4'-piperidin]-1'-yl)-1,3-oxazol-4(5H)-one,
(−)-5-Butyl-2-(1'H,3H-spiro[2-benzofuran-1,4'-piperidin]-1'-yl)-1,3-oxazol-4(5H)-one,
(−)-5-Butyl-5-methyl-2-(1'H,3H-spiro[2-benzofuran-1,4'-piperidin]-1'-yl)-1,3-oxazol-4(5H)-one,
(−)-5-Methyl-2-(1'H,3H-spiro[2-benzofuran-1,4'-piperidin]-1'-yl)-5-(tetrahydro-2H-pyran-3-ylmethyl)-1,3-oxazol-4(5H)-one diastereomer a,
(−)-5-Methyl-2-(1'H,3H-spiro[2-benzofuran-1,4'-piperidin]-1'-yl)-5-(tetrahydro-2H-pyran-3-ylmethyl)-1,3-oxazol-4(5H)-one diastereomer b,
(+)-5-Methyl-5-(1-phenylethyl)-2-(1'H,3H-spiro[2-benzofuran-1,4'-piperidin]-1'-yl)-1,3-oxazol-4(5H)-one diastereomer a,
(+)-5-Methyl-5-(1-phenylethyl)-2-(1'H,3H-spiro[2-benzofuran-1,4'-piperidin]-1'-yl)-1,3-oxazol-4(5H)-one diastereomer b,
(+)-(5R)-5-Benzyl-2-(1'H,3H-spiro[2-benzofuran-1,4'-piperidin]-1'-yl)-1,3-oxazol-4(5H)-one,
(+)-5-(Cyclopentylmethyl)-5-methyl-2-(1'H,3H-spiro[2-benzofuran-1,4'-piperidin]-1'-yl)-1,3-oxazol-4(5H)-one,
(+)-5-(Ethoxymethyl)-5-methyl-2-(1'H,3H-spiro[2-benzofuran-1,4'-piperidin]-1'-yl)-1,3-oxazol-4(5H)-one,
(+)-5-[(4-Chlorophenyl)(hydroxy)methyl]-2-(1'H,3H-spiro[2-benzofuran-1,4'-piperidin]-1'-yl)-1,3-oxazol-4(5H)-one diastereomer a,
(+)-5-[(4-Chlorophenyl)(hydroxy)methyl]-2-(1'H,3H-spiro[2-benzofuran-1,4'-piperidin]-1'-yl)-1,3-oxazol-4(5H)-one diastereomer b, (+)-5-[(5-Chlorothiophen-2-yl)methyl]-5-methyl-2-(1'H, 3H-spiro[2-benzofuran-1,4'-piperidin]-1'-yl)-1,3-oxazol-4(5H)-one,
(+)-5-[(6-Chloropyridin-3-yl)methyl]-5-methyl-2-(1'H, 3H-spiro[2-benzofuran-1,4'-piperidin]-1'-yl)-1,3-oxazol-4(5H)-one,
(+)-5-Benzyl-5-methyl-2-(1'H,3H-spiro[2-benzofuran-1, 4'-piperidin]-1'-yl)-1,3-oxazol-4(5H)-one,
(+)-5-Butyl-2-(1'H,3H-spiro[2-benzofuran-1,4'-piperidin]-1'-yl)-1,3-oxazol-4(5H)-one,
(+)-5-Butyl-5-methyl-2-(1'H,3H-spiro[2-benzofuran-1, 4'-piperidin]-1'-yl)-1,3-oxazol-4(5H)-one,
(+)-5-Methyl-2-(1'H,3H-spiro[2-benzofuran-1,4'-piperidin]-1'-yl)-5-(tetrahydro-2H-pyran-3-ylmethyl)-1,3-oxazol-4(5H)-one diastereomer a,
(+)-5-Methyl-2-(1'H,3H-spiro[2-benzofuran-1,4'-piperidin]-1'-yl)-5-(tetrahydro-2H-pyran-3-ylmethyl)-1,3-oxazol-4(5H)-one diastereomer b,
(+)-5-Methyl-5-(1-phenylethyl)-2-(1'H,3H-spiro[2-benzofuran-1,4'-piperidin]-1'-yl)-1,3-oxazol-4(5H)-one diastereomer a,
(+)-5-Methyl-5-(1-phenylethyl)-2-(1'H,3H-spiro[2-benzofuran-1,4'-piperidin]-1'-yl)-1,3-oxazol-4(5H)-one diastereomer b,
(4-Chlorophenyl)[4-oxo-2-(1'H,3H-spiro[2-benzofuran-1,4'-piperidin]-1'-yl)-4,5-dihydro-1,3-oxazol-5-yl]methylacetate,
1'-[5-Benzyl-4-oxo-4,5-dihydro-1,3-oxazol-2-yl]-3H-spiro[2-benzofuran-1,4'-piperidin]-3-one enantiomer A,
1'-[5-Benzyl-4-oxo-4,5-dihydro-1,3-oxazol-2-yl]-3H-spiro[2-benzofuran-1,4'-piperidin]-3-one enantiomer B,
1'-(4-Oxo-1-oxa-3-azaspiro[4.5]dec-2-en-2-yl)-3H-spiro[2-benzofuran-1,4'-piperidin]-3-one,
1'-(5-Benzyl-4-oxo-4,5-dihydro-1,3-oxazol-2-yl)-4-fluoro-3H-spiro[2-benzofuran-1,4'-piperidin]-3-one,
1'-(5-Benzyl-4-oxo-4,5-dihydro-1,3-oxazol-2-yl)-5-bromo-3H-spiro[2-benzofuran-1,4'-piperidin]-3-one,
1'-(5-Benzyl-4-oxo-4,5-dihydro-1,3-oxazol-2-yl)-5-fluoro-3H-spiro[2-benzofuran-1,4'-piperidin]-3-one,
1'-(5-Benzyl-4-oxo-4,5-dihydro-1,3-oxazol-2-yl)-5-methoxy-3H-spiro[2-benzofuran-1,4'-piperidin]-3-one,
1'-(5-Butyl-5-methyl-4-oxo-4,5-dihydro-1,3-oxazol-2-yl)-3H-spiro[2-benzofuran-1,4'-piperidin]-3-one,
1'-(8,8-Difluoro-4-oxo-1-oxa-3-azaspiro[4.5]dec-2-en-2-yl)-3H-spiro[2-benzofuran-1,4'-piperidin]-3-one,
1'-[4-Oxo-8-pentyl-1-oxa-3-azaspiro[4.5]dec-2-en-2-yl]-3H-spiro[2-benzofuran-1,4'-piperidin]-3-one diastereomer a,
1'-[4-Oxo-8-pentyl-1-oxa-3-azaspiro[4.5]dec-2-en-2-yl]-3H-spiro[2-benzofuran-1,4'-piperidin]-3-one diastereomer b,
1'-[5-(4-Chlorobenzyl)-5-methyl-4-oxo-4,5-dihydro-1,3-oxazol-2-yl]-3H-spiro[2-benzofuran-1,4'-piperidin]-3-one enantiomer A,
1'-[5-(4-Chlorobenzyl)-5-methyl-4-oxo-4,5-dihydro-1,3-oxazol-2-yl]-3H-spiro[2-benzofuran-1,4'-piperidin]-3-one enantiomer B,
1'-[5-(Cyclopentylmethyl)-4-oxo-4,5-dihydro-1,3-oxazol-2-yl]-3H-spiro[2-benzofuran-1,4'-piperidin]-3-one enantiomer A,
1'-[5-(Cyclopentylmethyl)-4-oxo-4,5-dihydro-1,3-oxazol-2-yl]-3H-spiro[2-benzofuran-1,4'-piperidin]-3-one enantiomer B,
1'-[5,5-Bis(4-chlorobenzyl)-4-oxo-4,5-dihydro-1,3-oxazol-2-yl]-3H-spiro[2-benzofuran-1,4'-piperidin]-3-one,
1'-[5-Benzyl-5-methyl-4-oxo-4,5-dihydro-1,3-oxazol-2-yl]-3H-spiro[2-benzofuran-1,4'-piperidin]-3-one enantiomer A,
1'-[5-Benzyl-5-methyl-4-oxo-4,5-dihydro-1,3-oxazol-2-yl]-3H-spiro[2-benzofuran-1,4'-piperidin]-3-one enantiomer B,
1'-[5-Butyl-4-oxo-4,5-dihydro-1,3-oxazol-2-yl]-3H-spiro[2-benzofuran-1,4'-piperidin]-3-one enantiomer A,
1'-[5-Butyl-4-oxo-4,5-dihydro-1,3-oxazol-2-yl]-3H-spiro[2-benzofuran-1,4'-piperidin]-3-one enantiomer B,
1'-{-5-[(4-Chlorophenyl)(hydroxy)methyl]-4-oxo-4, 5-dihydro-1,3-oxazol-2-yl}-3H-spiro[2-benzofuran-1,4'-piperidin]-3-one diastereomer a, enantiomer A,
1'-{-5-[(4-Chlorophenyl)(hydroxy)methyl]-4-oxo-4, 5-dihydro-1,3-oxazol-2-yl}-3H-spiro[2-benzofuran-1,4'-piperidin]-3-one diastereomer a, enantiomer B,
1'-{-5-[(4-Chlorophenyl)(hydroxy)methyl]-4-oxo-4, 5-dihydro-1,3-oxazol-2-yl}-3H-spiro[2-benzofuran-1,4'-piperidin]-3-one diastereomer b, enantiomer A,
1'-{-5-[(4-Chlorophenyl)(hydroxy)methyl]-4-oxo-4, 5-dihydro-1,3-oxazol-2-yl}-3H-spiro[2-benzofuran-1,4'-piperidin]-3-one diastereomer b, enantiomer B,
1'-{5-[(4-Chlorophenyl)(hydroxy)methyl]-5-methyl-4-oxo-4, 5-dihydro-1,3-oxazol-2-yl}-3H-spiro[2-benzofuran-1,4'-piperidin]-3-one,
2-(1'H,3H-Spiro[2-benzofuran-1,4'-piperidin]-1'-yl)-1,7-dioxa-3-azaspiro[4.5]dec-2-en-4-one,
2-(1'H,3H-Spiro[2-benzofuran-1,4'-piperidin]-1'-yl)-1-oxa-3-azaspiro[4.4]nona-2,7-dien-4-one,
2-(1'H,3H-Spiro[2-benzofuran-1,4'-piperidin]-1'-yl)-1-oxa-3-azaspiro[4.5]dec-2-en-4-one,
2-(1'H,3H-Spiro[2-benzofuran-1,4'-piperidin]-1'-yl)-1-oxa-8-thia-3-azaspiro[4.5]dec-2-en-4-one,
2-(1'H,3H-Spiro[2-benzofuran-1,4'-piperidin]-1'-yl)-3a',4',6',6a'-tetrahydro-1'H,4H-spiro[1,3-oxazole-5,2'-pentalene]-4,5'(3'H)-dione,
2-(1'H,3H-Spiro[2-benzofuran-1,4'-piperidin]-1'-yl)-3a',4'-dihydro-1'H,4H-spiro[1,3-oxazole-5,2'-pentalene]-4,5'(3'H)-dione,
2-(1'H,3H-Spiro[2-benzofuran-1,4'-piperidin]-1'-yl)-7-(trifluoromethyl)-1-oxa-3-azaspiro[4.4]nona-2,7-dien-4-one,
2'-(1'H,3H-Spiro[2-benzofuran-1,4'-piperidin]-1'-yl)-1,3,3a,4,5,6,7,7a-octahydro-4'H-spiro[indene-2,5'-[1,3]oxazol]-4'-one,
2-(1'H,3H-Spiro[2-benzofuran-1,4'-piperidin]-1'-yl)-1-oxa-8-thia-3-azaspiro[4.5]dec-2-en-4-one8,8-dioxide,
2'-(1'H,3H-Spiro[2-benzofuran-1,4'-piperidin]-1'-yl)-2,3,4a,5,7,7a-hexahydro-4'H-spiro[cyclopenta[b][1,4]dioxine-6,5'-[1,3]oxazol]-4'-one diastereomer b,
2'-(1'H,3H-Spiro[2-benzofuran-1,4'-piperidin]-1'-yl)-3,3a,4,5,6,7,8,8a-octahydro-1H,4'H-spiro[azulene-2,5'-[1,3]oxazol]-4'-one,
2'-(1'H,3H-Spiro[2-benzofuran-1,4'-piperidin]-1'-yl)-3a,4,6,6a-tetrahydro-1H,3H,4'H-spiro[cyclopenta[c]furan-5,5'-[1,3]oxazol]-4'-one,
2-(1'H,3H-Spiro[2-benzofuran-1,4'-piperidin]-1'-yl)-5-[2-(trifluoromethyl)prop-2-en-1-yl]-1,3-oxazol-4(5H)-one,
2'-(2,2-Dioxido-1'H,3H-spiro[2-benzothiophene-1,4'-piperidin]-1'-yl)-1,3-dihydro-4'H-spiro[indene-2,5'-[1,3]oxazol]-4'-one,
2-(3H-Spiro[isobenzofuran-1,4'-piperidine]-1'-yl)-1-oxa-3-azaspiro[4.4]non-2-en-4-one, 2-(3H-Spiro[isobenzofuran-1,4'-piperidine]-1'-yl)-5,5-bis (2-(trifluoromethyl)allyl)oxazol-4(5H)-one,
2'-(1'H,3H-Spiro[2-benzofuran-1,4'-piperidin]-1'-yl)-1,2,3,5-tetrahydro-4'H-spiro[2-benzazepine-4,5'-[1,3]oxazol]-4'-one,
2'-(1'H,3H-Spiro[2-benzofuran-1,4'-piperidin]-1'-yl)-3a,4,6,6a-tetrahydro-4'H-spiro[cyclopenta[d][1,3,2]dioxathiole-5,5'-[1,3]oxazol]-4'-one2-oxide,
2-Methyl-2'-(1'H,3H-spiro[2-benzofuran-1,4'-piperidin]-1'-yl)-1,2,3,5-tetrahydro-4'H-spiro[2-benzazepine-4,5'-[1,3]oxazol]-4'-one,
4-Oxo-2-(1'H,3H-spiro[2-benzofuran-1,4'-piperidin]-1'-yl)-1-oxa-3-azaspiro[4.4]non-2-ene-7,8-diyldiacetate diastereomer a,
4-Oxo-2-(1'H,3H-spiro[2-benzofuran-1,4'-piperidin]-1'-yl)-1-oxa-3-azaspiro[4.4]non-2-ene-7,8-diyldiacetate diastereomer b,
5-((4-Chlorophenyl)fluoromethyl)-2-(1'H,3H-spiro[2-benzofuran-1,4'-piperidin]-1'-yl)-1,3-oxazol-4(5H)-one diastereomer a, enantiomer A,
5-((4-Chlorophenyl)fluoromethyl)-2-(1'H,3H-spiro[2-benzofuran-1,4'-piperidin]-1'-yl)-1,3-oxazol-4(5H)-one diastereomer a, enantiomer B,
5-((4-Chlorophenyl)fluoromethyl)-2-(1'H,3H-spiro[2-benzofuran-1,4'-piperidin]-1'-yl)-1,3-oxazol-4(5H)-one diastereomer b, enantiomer A,
5-((4-Chlorophenyl)fluoromethyl)-2-(1'H,3H-spiro[2-benzofuran-1,4'-piperidin]-1'-yl)-1,3-oxazol-4(5H)-one diastereomer b, enantiomer B,
5-(2-Bromoprop-2-en-1-yl)-5-(prop-2-en-1-yl)-2-(1'H,3H-spiro[2-benzofuran-1,4'-piperidin]-1'-yl)-1,3-oxazol-4(5H)-one,
5-(2-Methylprop-2-en-1-yl)-2-(1'H,3H-spiro[2-benzofuran-1,4'-piperidin]-1'-yl)-1,3-oxazol-4(5H)-one,
5-(2-Methylpropyl)-2-(1'H,3H-spiro[2-benzofuran-1,4'-piperidin]-1'-yl)-1,3-oxazol-4(5H)-one,
5-(4-Chlorobenzyl)-2-(1'H,3H-spiro[2-benzofuran-1,4'-piperidin]-1'-yl)-1,3-oxazol-4(5H)-one,
5-(4-Chlorobenzyl)-5-methyl-2-(1'H,3H-spiro[2-benzofuran-1,4'-piperidin]-1'-yl)-1,3-oxazol-4(5H)-one,
5-(But-2-yn-1-yl)-2-(1'H,3H-spiro[2-benzofuran-1,4'-piperidin]-1'-yl)-1,3-oxazol-4(5H)-one,
5-(Cyclohexylmethyl)-5-methyl-2-(1'H,3H-spiro[2-benzofuran-1,4'-piperidin]-1'-yl)-1,3-oxazol-4(5H)-one,
5-(Cyclopentylmethyl)-2-(1'H,3H-spiro[2-benzofuran-1,4'-piperidin]-1'-yl)-1,3-oxazol-4(5H)-one enantiomer A,
5-(Cyclopentylmethyl)-2-(1'H,3H-spiro[2-benzofuran-1,4'-piperidin]-1'-yl)-1,3-oxazol-4(5H)-one enantiomer B,
5-(Cyclopentylmethyl)-5-methyl-2-(1'H,3H-spiro[2-benzofuran-1,4'-piperidin]-1'-yl)-1,3-oxazol-4(5H)-one,
5-(Hydroxy(phenyl)methyl)-2-(1'H,3H-spiro[2-benzofuran-1,4'-piperidin]-1'-yl)-1,3-oxazol-4(5H)-one diastereomer a, enantiomer A,
5-(Hydroxy(phenyl)methyl)-2-(1'H,3H-spiro[2-benzofuran-1,4'-piperidin]-1'-yl)-1,3-oxazol-4(5H)-one diastereomer a, enantiomer B,
5-(Hydroxy(phenyl)methyl)-2-(1'H,3H-spiro[2-benzofuran-1,4'-piperidin]-1'-yl)-1,3-oxazol-4(5H)-one diastereomer b, enantiomer A,
5-(Hydroxy(phenyl)methyl)-2-(1'H,3H-spiro[2-benzofuran-1,4'-piperidin]-1'-yl)-1,3-oxazol-4(5H)-one diastereomer b, enantiomer B,
5-(Prop-2-en-1-yl)-2-(1'H,3H-spiro[2-benzofuran-1,4'-piperidin]-1'-yl)-5-[2-(trifluoromethyl)prop-2-en-1-yl]-1,3-oxazol-4(5H)-one,
5-(Prop-2-en-1-yl)-2-(1'H,3H-spiro[2-benzofuran-1,4'-piperidin]-1'-yl)-1,3-oxazol-4(5H)-one,
5-(Prop-2-en-1-yl)-5-(prop-2-yn-1-yl)-2-(1'H,3H-spiro[2-benzofuran-1,4'-piperidin]-1'-yl)-1,3-oxazol-4(5H)-one,
5,5-bis(2-Methylprop-2-en-1-yl)-2-(1'H,3H-spiro[2-benzofuran-1,4'-piperidin]-1'-yl)-1,3-oxazol-4(5H)-one,
5,5-bis(4-Chlorobenzyl)-2-(1'H,3H-spiro[2-benzofuran-1,4'-piperidin]-1'-yl)-1,3-oxazol-4(5H)-one,
5,5-Di(but-2-ynyl)-2-(3H-spiro[isobenzofuran-1,4'-piperidine]-1'-yl)oxazol-4(5H)-one,
5,5-Di(prop-2-en-1-yl)-2-(1'H,3H-spiro[2-benzofuran-1,4'-piperidin]-1'-yl)-1,3-oxazol-4(5H)-one,
5-[(4-Chlorophenyl)(fluoro)methyl]-5-methyl-2-(1'H,3H-spiro[2-benzofuran-1,4'-piperidin]-1'-yl)-1,3-oxazol-4(5H)-one,
5-[(4-Chlorophenyl)(hydroxy)methyl]-2-(1'H,3H-spiro[2-benzofuran-1,4'-piperidin]-1'-yl)-1,3-oxazol-4(5H)-one,
5-[(4-Chlorophenyl)(hydroxy)methyl]-5-methyl-2-(1'H,3H-spiro[2-benzofuran-1,4'-piperidin]-1'-yl)-1,3-oxazol-4(5H)-one,
5-[(5-Chlorothiophen-2-yl)methyl]-5-methyl-2-(1'H,3H-spiro[2-benzofuran-1,4'-piperidin]-1'-yl)-1,3-oxazol-4(5H)-one,
5-[(6-Chloropyridin-3-yl)methyl]-5-methyl-2-(1'H,3H-spiro[2-benzofuran-1,4'-piperidin]-1'-yl)-1,3-oxazol-4(5H)-one,
5-[2-({[tert-Butyl(dimethyl)silyl]oxy}methyl)prop-2-en-1-yl]-5-(prop-2-en-1-yl)-2-(1'H,3H-spiro[2-benzofuran-1,4'-piperidin]-1'-yl)-1,3-oxazol-4(5H)-one,
5-[Hydroxy(phenyl)methyl]-5-methyl-2-(1'H,3H-spiro[2-benzofuran-1,4'-piperidin]-1'-yl)-1,3-oxazol-4(5H)-one,
5-{[4-(Difluoromethyl)phenyl](difluoro)methyl}-5-methyl-2-(1'H,3H-spiro[2-benzofuran-1,4'-piperidin]-1'-yl)-1,3-oxazol-4(5H)-one,
5',5'-Difluoro-2-(1'H,3H-spiro[2-benzofuran-1,4'-piperidin]-1'-yl)-3',3a',4',5',6',6a'-hexahydro-1'H,4H-spiro[1,3-oxazole-5,2'-pentalen]-4-one,
5-Allyl-5-(2-fluoroallyl)-2-(3H-spiro[isobenzofuran-1,4'-piperidine]-1'-yl)oxazol-4(5H)-one,
5-Allyl-5-(2-methylallyl)-2-(1'H,3H-spiro[2-benzofuran-1,4'-piperidin]-1'-yl)-1,3-oxazol-4(5H)-one,
5-Benzyl-2-(1'H,3H-spiro[2-benzofuran-1,4'-piperidin]-1'-yl)-1,3-oxazol-4(5H)-one,
5-Benzyl-2-(1'H,3H-spiro[2-benzothiophene-1,4'-piperidin]-1'-yl)-1,3-oxazol-4(5H)-one,
5-Benzyl-2-(1'H,5H-spiro[furo[3,4-b]pyridine-7,4'-piperidin]-1'-yl)-1,3-oxazol-4(5H)-one,
5-Benzyl-2-(1'H,7H-spiro[furo[3,4-b]pyridine-5,4'-piperidin]-1'-yl)-1,3-oxazol-4(5H)-one,
5-Benzyl-2-(2,2-dioxido-1'H,3H-spiro[2-benzothiophene-1,4'-piperidin]-1'-yl)-1,3-oxazol-4(5H)-one,
5-Benzyl-2-(3,3-dimethyl-1'H,3H-spiro[2-benzofuran-1,4'-piperidin]-1'-yl)-1,3-oxazol-4(5H)-one,
5-Benzyl-2-(3-methyl-1'H,3H-spiro[2-benzofuran-1,4'-piperidin]-1'-yl)-1,3-oxazol-4(5H)-one,
5-Benzyl-2-(4-fluoro-1'H,3H-spiro[2-benzofuran-1,4'-piperidin]-1'-yl)-1,3-oxazol-4(5H)-one,
5-Benzyl-2-(6-fluoro-1'H,3H-spiro[2-benzofuran-1,4'-piperidin]-1'-yl)-1,3-oxazol-4(5H)-one,
5-Benzyl-2-(7-fluoro-1'H,3H-spiro[2-benzofuran-1,4'-piperidin]-1'-yl)-1,3-oxazol-4(5H)-one,
5-Benzyl-5-ethyl-2-(1'H,3H-spiro[2-benzofuran-1,4'-piperidin]-1'-yl)-1,3-oxazol-4(5H)-one, 5-Butyl-2-(1'H,3H-spiro[2-benzofuran-1,4'-piperidin]-1'-yl)-1,3-oxazol-4(5H)-one,
5-Butyl-5-methyl-2-(1'H,3H-spiro[2-benzofuran-1,4'-piperidin]-1'-yl)-1,3-oxazol-4(5H)-one,
5-Methyl-2-(1'H,3H-spiro[2-benzofuran-1,4'-piperidin]-1'-yl)-5-(tetrahydrofuran-3-ylmethyl)-1,3-oxazol-4(5H)-one diastereomer a,
5-Methyl-2-(1'H,3H-spiro[2-benzofuran-1,4'-piperidin]-1'-yl)-5-(tetrahydrofuran-3-ylmethyl)-1,3-oxazol-4(5H)-one diastereomer b,
5-Methyl-2-(1'H,3H-spiro[2-benzofuran-1,4'-piperidin]-1'-yl)-5-(tetrahydrofuran-2-ylmethyl)-1,3-oxazol-4(5H)-one,
5-Methyl-5-(1-phenylethyl)-2-(1'H,3H-spiro[2-benzofuran-1,4'-piperidin]-1'-yl)-1,3-oxazol-4(5H)-one diastereomer a,
5-Methyl-5-(1-phenylethyl)-2-(1'H,3H-spiro[2-benzofuran-1,4'-piperidin]-1'-yl)-1,3-oxazol-4(5H)-one diastereomer b,
5-Methyl-5-(pentafluorobenzyl)-2-(1'H,3H-spiro[2-benzofuran-1,4'-piperidin]-1'-yl)-1,3-oxazol-4(5H)-one,
5-Methyl-5-(pyrrolidin-1-ylmethyl)-2-(1'H,3H-spiro[2-benzofuran-1,4'-piperidin]-1'-yl)-1,3-oxazol-4(5H)-one,
5-Phenyl-2-(1'H,3H-spiro[2-benzofuran-1,4'-piperidin]-1'-yl)-1,3-oxazol-4(5H)-one,
5-Propyl-2-(1'H,3H-spiro[2-benzofuran-1,4'-piperidin]-1'-yl)-1,3-oxazol-4(5H)-one,
7-({[tert-Butyl(dimethyl)silyl]oxy}methyl)-2-(1'H,3H-spiro[2-benzofuran-1,4'-piperidin]-1'-yl)-1-oxa-3-azaspiro[4.4]nona-2,7-dien-4-one,
7-(Hydroxymethyl)-2-(3H-spiro[isobenzofuran-1,4'-piperidine]-1'-yl)-1-oxa-3-azaspiro[4.4]nona-2,7-dien-4-one,
7,8-Dimethoxy-2-(1'H,3H-spiro[2-benzofuran-1,4'-piperidin]-1'-yl)-1-oxa-3-azaspiro[4.4]non-2-en-4-one diastereomer a,
7,8-Dimethyl-2-(1'H,3H-spiro[2-benzofuran-1,4'-piperidin]-1'-yl)-1-oxa-3-azaspiro[4.4]nona-2,7-dien-4-one,
7-Methyl-2-(1'H,3H-spiro[2-benzofuran-1,4'-piperidin]-1'-yl)-1-oxa-3-azaspiro[4.4]nona-2,7-dien-4-one,
8-(2,2-Difluoroethyl)-2-(1'H,3H-spiro[2-benzofuran-1,4'-piperidin]-1'-yl)-1-oxa-3,8-diazaspiro[4.5]dec-2-en-4-one,
8,8-Difluoro-2-(1'H,3H-spiro[2-benzofuran-1,4'-piperidin]-1'-yl)-1-oxa-3-azaspiro[4.5]dec-2-en-4-one,
8-Benzyl-2-(1'H,3H-spiro[2-benzofuran-1,4'-piperidin]-1'-yl)-1-oxa-3,8-diazaspiro[4.5]dec-2-en-4-one,
8-Pentyl-2-(1'H,3H-spiro[2-benzofuran-1,4'-piperidin]-1'-yl)-1-oxa-3-azaspiro[4.5]dec-2-en-4-one diastereomer a,
8-Pentyl-2-(1'H,3H-spiro[2-benzofuran-1,4'-piperidin]-1'-yl)-1-oxa-3-azaspiro[4.5]dec-2-en-4-one diastereomer b,
Ethyl2-((4-oxo-5-(prop-2-ynyl)-2-(3H-spiro[isobenzofuran-1,4'-piperidine]-1'-yl)-4,5-dihydrooxazol-5-yl)methyl)acrylate,
Ethyl2-{[4-oxo-5-(prop-2-en-1-yl)-2-(1'H,3H-spiro[2-benzofuran-1,4'-piperidin]-1'-yl)-4,5-dihydro-1,3-oxazol-5-yl]methyl}prop-2-enoate,
Ethyl4'-oxo-2'-(1'H,3H-spiro[2-benzofuran-1,4'-piperidin]-1'-yl)-4'H-spiro[bicyclo[3.1.0]hexane-3,5'-[1,3]oxazole]-6-carboxylate diastereomer a,
Ethyl4'-oxo-2'-(1'H,3H-spiro[2-benzofuran-1,4'-piperidin]-1'-yl)-4'H-spiro[bicyclo[3.1.0]hexane-3,5'-[1,3]oxazole]-6-carboxylate diastereomer b,
Ethyl4-oxo-2-(1'H,3H-spiro[2-benzofuran-1,4'-piperidin]-1'-yl)-1-oxa-3-azaspiro[4.4]nona-2,7-diene-7-carboxylate,
tert-Butyl4'-oxo-2'-(1'H,3H-spiro[2-benzofuran-1,4'-piperidin]-1'-yl)-1,5-dihydro-4'H-spiro[2-benzazepine-4,5'-[1,3]oxazole]-2(3H)-carboxylate, and
tert-Butyl4-oxo-2-(1'H,3H-spiro[2-benzofuran-1,4'-piperidin]-1'-yl)-1-oxa-3,8-diazaspiro[4.5]dec-2-ene-8-carboxylate,
or pharmaceutically acceptable salts thereof.

14. A pharmaceutical composition comprising a compound of claim 1 together with a pharmaceutically acceptable carrier.

* * * * *